(12) United States Patent
Cunningham

(10) Patent No.: US 8,987,432 B2
(45) Date of Patent: Mar. 24, 2015

(54) TARGETS FOR THE IDENTIFICATION OF ANTIBIOTICS THAT ARE NOT SUSCEPTIBLE TO ANTIBIOTIC RESISTANCE

(75) Inventor: Philip R. Cunningham, Troy, MI (US)

(73) Assignee: Wayne State University, Detroit, MI (US)

( * ) Notice: Subject to any disclaimer, the term of this patent is extended or adjusted under 35 U.S.C. 154(b) by 80 days.

(21) Appl. No.: 13/470,484

(22) Filed: May 14, 2012

(65) Prior Publication Data

US 2013/0331559 A1 Dec. 12, 2013

Related U.S. Application Data

(62) Division of application No. 11/914,077, filed as application No. PCT/US2006/018320 on May 11, 2006, now Pat. No. 8,178,659.

(60) Provisional application No. 60/711,492, filed on Aug. 25, 2005, provisional application No. 60/680,138, filed on May 11, 2005.

(51) Int. Cl.
  *C07H 21/02* (2006.01)
  *C07H 19/04* (2006.01)

(52) U.S. Cl.
  USPC ............................ 536/23.1; 536/26.6; 435/6.1

(58) Field of Classification Search
  USPC .................................. 536/23.1, 26.6; 435/6.1
  See application file for complete search history.

(56) References Cited

U.S. PATENT DOCUMENTS

| 4,772,555 | A | 9/1988 | De Boer |
| 4,873,316 | A | 10/1989 | Meade et al. |
| 5,821,058 | A | 10/1998 | Smith et al. |
| 5,981,280 | A | 11/1999 | Fang et al. |
| 7,081,341 | B2 | 7/2006 | Cunningham |
| 7,250,496 | B2 | 7/2007 | Bentwich |
| 2004/0014957 | A1 | 1/2004 | Eldrup et al. |

FOREIGN PATENT DOCUMENTS

| WO | 96/06106 | A | 2/1996 |
| WO | 96/06106 | A1 | 2/1996 |
| WO | 00/32619 | A1 | 6/2000 |
| WO | 01/42445 | A2 | 6/2001 |
| WO | 02/29019 | A2 | 4/2002 |
| WO | 03/029459 | A2 | 4/2003 |
| WO | 2004/003511 | A2 | 1/2004 |
| WO | 2006/115570 | A2 | 11/2006 |

OTHER PUBLICATIONS

Adachi, J. A., et al., "Natural History of Enteroaggregative and Enterotoxigenic *Escherichia coli* Infection Among US Travelers to Guadalajara, Mexico," The Journal of Infectious Diseases, May 17, 2002, pp. 1681-1683, vol. 185, No. 11.

Adang, A. E. P., et al., "Case Histories of Peptidomimetics: Progression from Peptides to Drugs"; Recueil des Travaux Chimiques des Pays-Bas, 1994, pp. 63-78, vol. 113, No. 2.

Agalarov, S. C., et al.,"Structure of the S15,S6,S18-rRNA Complex: Assembly of the 30S Ribosome Central Domain," Science, Apr. 7, 2000, pp. 107-113, vol. 288, No. 5463.

Ahn, J. M., et al., "Peptidonffimetics and Peptide Backbone Modifications"; Mini Reviews in Medicinal Chemistry, Oct. 2002, pp. 463-473, vol. 2, No. 5.

Andersson, D. I., et al., "Antibiotic Resistance Here to Stay? Compensatory Mutations Restore Virulence of Resistant Bacteria," Lakartidningen, Sep. 9, 1998, pp. 3940, 3943-3944, vol. 95, No. 37.

Ang, J. Y., et al., "Antibacterial Resistance," Indian Journal of Pediatrics, Mar. 2004, pp. 229-239, vol. 71, No. 3.

Aoki, H., et al., "Oxazolidinone Antibiotics Target the P Site on *Escherichia coli* Ribosomes," Antimicrobial Agents and Chemotherapy, Apr. 2002, pp. 1080-1085, vol. 46, No. 4.

Asai, T., et al., "Construction and Initial Characterization of *Escherichia coli* Strains With Few or No Intact Chromosomal rRNA Operons," Journal of Bacteriology, Jun. 1999, pp. 3803-3809, vol. 181, No. 12.

Baldari, C., et al., "A Novel Leader Peptide Which Allows Efficient Secretion of a Fragment of Human Interleukin 1 beta in *Saccharomyces cerevisiae*," The EMBO Journal, Jan. 1987, pp. 229-234, vol. 6, No. 1.

Banerji, J., et al., "A Lymphocyte-Specific Cellular Enhancer is Located Downstream of the Joining Region in Immunoglobulin Heavy Chain Genes," Cell, Jul. 1983, pp. 729-740, vol. 33, No. 3.

Barrick, J. E., et al., "Selection of RNA-Binding Peptides Using mRNA-Peptide Fusions," Methods, Mar. 2001, pp. 287-293, vol. 23, No. 3.

Barrick, J. E. et al., "Sequence Analysis of an Artificial Family of RNA-Binding Peptides," ; Protein Science, A Publication of the Protein Society, Nov. 2002, pp. 2688-2696, vol. 11, No. 11.

Batey, R. T., et al., "Preparation of Isotopically Labeled Ribonucleotides for Multidimensional NMR Spectroscopy of RNA," Nucleic Acids Research, Sep. 11, 1992, pp. 4515-4523, vol. 20, No. 17.

Batey, R. T. et al., "Interaction of the *Bacillus stearothermophilus* Ribosomal Protein S15 with 16 S rRNA: II. Specificity Determinants of RNA-Protein Recognition," Journal of Molecular Biology, Aug. 30, 1996, pp. 550-567, vol. 261, No. 4.

Bhattacharya, S. K., et al., "Multidrug-Resistant *Shigella dysenteriae* Type 1 in South Asia," The Lancet Infectious Diseases, Dec. 2003, p. 755, vol. 3, No. 12.

(Continued)

*Primary Examiner* — Jezia Riley
(74) *Attorney, Agent, or Firm* — Senniger Powers LLP

(57) ABSTRACT

To identify conserved and variable regions of the 16 S rRNA, an instant evolution experiment was performed on the entire 16 S rRNA. Analysis of these mutants identified regions that are required for function. These conserved sequences may be used as targets for pharmaceuticals that are taxonomically specific and which are refractory to the development of drug resistance.

21 Claims, 145 Drawing Sheets

(56) References Cited

OTHER PUBLICATIONS

Bjorkman, J., et al., "Effects of Environment on Compensatory Mutations to Ameliorate Costs of Antibiotic Resistance," Science, Feb. 25, 2000, pp. 1479-1482, vol. 287, No. 5457.

Bodhidatta, L., et al., "Bacterial Enteric Pathogens in Children With Acute Dysentery in Thailand: Increasing Importance of Quinolone-Resistant Campylobacter," The Southeast Asian Journal of Tropical Medicine and Public Health, Dec. 2002, pp. 752-757, vol. 33, No. 4.

Boettger, E. C., "Resistance to Drugs Targeting Protein Synthesis in Mycobacteria," Trends in Microbiology, Oct. 1994, pp. 416-421, vol. 2, No. 10.

Brodersen, D. E., et al., "Crystal Structure of the 30 S Ribosomal Subunit from *Thermus thermophilus*: Structure of the Proteins and Their Interactions With 16 S RNA," Journal of Molecular Biology, Feb. 22, 2002, pp. 725-768, vol. 316, No. 3.

Brosius, J., et al., "Construction and Fine Mapping of Recombinant Plasmids Containing the rrnB Ribosomal RNA operon of *E. coli*," Plasmid, Jul. 1981, pp. 112-118, vol. 6, No. 1.

Brow, D. A. et al. "Protection of Ribosomal RNA from Kethoxal in Polyribosomes. Implication of Specific Sites in Ribosome Function," Journal of Molecular Biology, Jan. 5, 1983, pp. 27-46, vol. 163, No. 1.

Bursavich, M. G., et al., "Designing Non-Peptide Peptidomimetics in the 21st Century: Inhibitors Targeting Conformational Ensembles," Journal of Medicinal Chemistry, Jan. 31, 2002, pp. 541-558, vol. 45, No. 3.

Byrne, G. W., et al., "Multiplex Gene Regulation: A Two-Tiered Approach to Transgene Regulation in Transgenic Mice," Proceedings of the National Academy of Sciences of the United States of America, Jul. 1989, pp. 5473-5477, vol. 86, No. 14.

Calame, K., et al., "Transcriptional Controlling Elements in the Immunoglobulin and T Cell Receptor Loci," Advances in Immunology, 1988, pp. 235-275, vol. 43.

Calos, M. P., "DNA Sequence for a Low-Level Promoter of the Lac Repressor Gene and an 'up' Promoter Mutation," Nature, Aug. 24, 1978, pp. 762-765, vol. 274, No. 5673.

Cannone, J. J., et al., "The Comparative RNA Web (CRW) Site: An Online Database of Comparative Sequence and Structure Information for Ribosomal, Intron, and Other RNAs: Correction," BMC Bioinformatics, Jul. 2002, p. 15, vol. 3, No. 1.

Capaldi, D. C. et al., "Use of the 1-(2-fluorophenyl)-4-methoxypiperidin-4-yl (Fpmp) and Related Protecting Groups in Oligoribonucleotide Synthesis: Stability of Internucleotide Linkages to Aqueous Acid," Nucleic Acids Research, Jun. 25, 1994, pp. 2209-2216, vol. 22, No. 12.

Carter, A. P., et al., "Crystal Structure of an Initiation Factor Bound to the 30S Ribosomal Subunit," Science, Jan. 19, 2001, pp. 498-501, vol. 291, No. 5503.

Carter, A. P., et al., "Functional Insights from the Structure of the 30S Ribosomal Subunit and its Interactions With Antibiotics," Nature, Sep. 21, 2000, pp. 340-348, vol. 407, No. 6802.

Carter-Muenchau, P., et al., "Growth-Rate Dependent Regulation of 6-phosphogluconate Dehydrogenase Level Mediated by an Anti-Shine-Dalgarno Sequence Located Within the *Escherichia coli* gnd Structural Gene," Proceedings of the National Academy of Sciences of the United States of America, Feb. 1989, pp. 1138-1142, vol. 86, No. 4.

Castagnoli, L., et al., "Alternative Bacteriophage Display Systems," Combinatorial Chemistry and High Throughput Screening, Apr. 2001, pp. 121-133, vol. 4, No. 2.

Cha, J., et al., "New Vectors for Direct Cloning of PCR Products," Gene, Dec. 1993, pp. 369-370, vol. 136, Nos. 1-2.

Chen, H., et al., "Determination of the Optimal Aligned Spacing Between the Shine-Dalgarno Sequence and the Translation Initiation Codon of *Escherichia coli* mRNAs," Nucleic Acids Research, Nov. 25, 1994, pp. 4953-4957, vol. 22, No. 23.

Chopra, I., et al., "The Role of Mutators in the Emergence of Antibiotic-Resistant Bacteria," Drug Resistance Updates, Jun. 2003, pp. 137-145, vol. 6, No. 3.

Chow, C. S. et al., "A Structural Basis for RNA-Ligand Interactions," Chemical Reviews, Aug. 5, 1997, pp. 1489-1514, vol. 97, No. 5.

Clarke, S. C., et al., "Virulence of Enteropathogenic *Escherichia coli*, A Global Pathogen." Clinical Microbiology Reviews, Jul. 2003, pp. 365-378, vol. 16, No. 3.

Clarke, S. C., et al., "Enteropathogenic *Escherichia coli* Infection: History and Clinical Aspects," British Journal of Biomedical Science, 2002, pp. 123-127, vol. 59, No. 2.

Collins, M. et a l., "Methicillin-Resistant *Staphylococcus aureus* (MRSA) in the Practice of Otolaryngology—An Emerging Community Acquired Organism?," Current Opinion in Otolaryngology and Head and Neck Surgery, Jun. 2003, pp. 179-183, vol. 11, No. 3.

Cunningham, P., et al., "Functional Effects of Base Changes Which Further Define the Decoding Center of *Escherichia coli* 16S Ribosomal RNA: Mutation of C1404, G1405, C1496, G1497, and U1498," Biochemistry, Jul. 20, 1993, pp. 7172-7180, vol. 32, No. 28.

Cunningham, P. R., et al., "The Role of 16S RNA in Ribosome Function: Single Base Alterations and Their Effect on in vitro Protein Synthesis," Archivos de Biologia y Medicina Experimentales (Santiago), Dec. 1988, pp. 393-401, vol. 21, Nos. 3-4.

Danner, S. et al., "T7 Phage Display: A Novel Genetic Selection System for Cloning RNA-Binding Proteins from cDNA Libraries," Proceedings of the National Academy of Sciences of the United States of America, Nov. 6, 2001, pp. 12954-12959, vol. 98, No. 23.

de Boer, H. A., et al., "The tac Promoter: A Functional Hybrid Derived from the trp and lac Promoters," Proceedings of the National Academy of Sciences of the United States of America, Jan. 1983, pp. 21-25, vol. 80, No. 1.

De Stasio, E. A., et al., "Mutations in 16S Ribosomal RNA Disrupt Antibiotic—RNA Interactions," The EMBO Journal, Apr. 1989, pp. 1213-1216, vol. 8, No. 4.

Denman, R. et al., "In vitro Assembly of 30S and 70S Bacterial Ribosomes from 16S RNA Containing Single Base Substitutions, Insertions, and Deletions Around the Decoding Site (C1400)," Biochemistry, Feb. 7, 1989, pp. 1002-1011, vol. 28, No. 3.

Depardieu, F., et al., "VanD-Type Vancomycin-Resistant *Enterococcus faecium* 10196A," Antimicrobial Agents and Chemotherapy, Jan. 2003, pp. 7-18, vol. 47, No. 1.

Dessen, A., et al., "Molecular Mechanisms of Antibiotic Resistance in Gram-Positive Pathogens," Current Drug Targets Infectious Disorders, May 2001, pp. 63-77, vol. 1, No. 1.

Dower, W. J., et al., "High Efficiency Transformation of *E. coli* by High Voltage electroporation," Nucleic Acids Research, Jul. 11, 1988, pp. 6127-6145, vol. 16, No. 13.

Edlund, T., et al., "Cell-Specific Expression of the Rat Insulin Gene: Evidence for Role of Two Distinct 5' Flanking Elements," Science, Nov. 22, 1985, vol. 230, No. 4728.

Enright, M. C., "The Evolution of a Resistant Pathogen—The Case of MRSA," Current Opinion in Pharmacology, Oct. 2003, pp. 474-479, vol. 3, No. 5.

European Search Report for EP Application No. 06759609.8, mailed Jan. 13, 2009.

Sirinavin, S., et al., "Antibiotics for Treating Salmonella Gut Infections," Cochrane Database of Systematic Reviews, 2000, CD001167, No. 2.

Smith, D. B., et al., "Single-Step Purification of Polypeptides Expressed in *Escherichia coli* as Fusions with Glutathione S-Transferase," Gene, Jul. 15, 1988, pp. 31-40, vol. 67, No. 1.

Stormo, G. D., et al., "Characterization of Translational Initiation Sites in *E. coli*," Nucleic Acids Research, May 11, 1982, pp. 2971-2996, vol. 10, No. 9.

Tapprich, W. E., et al., "Mutation at Position 791 *Escherichia coli* 16S Ribosomal RNA Affects Processes Involved in the Initiation of Protein Synthesis," Proceedings of the National Academy of Sciences of the United States of America, Jul. 1989, pp. 4927-4931, vol. 86, No. 13.

Tapprich, W. E., et al., "Involvement of Bases 787-795 of *Escherichia coli* 16S Ribosomal RNA in Ribosomal Subunit Sssociation," Proceedings of the National Academy of Sciences of the United States of America, Feb. 1986, pp. 556-560, vol. 83, No. 3.

Tok, J. B., et al., "RNA Apatamers that Specifically Bind to a 16S Ribosomal RNA Decoding Region Construct," Nucleic Acids Research, Aug. 1, 2000, pp. 5902-5910, vol. 28, No. 15.

(56) References Cited

OTHER PUBLICATIONS

Triman, K., et al., "Isolation of Temperature-Sensitive Mutants of 16S rRNA in *Escherichia coli*," Journal of Molecular Biology, Oct. 20, 1989, pp. 645-653, vol. 209, No. 4.

Tsiodras, S., et al., "Linezolid Resistance in a Clinical Isolate of *Staphylococcus aureus*," Lancet, Jul. 21, 2001, pp. 207-208, vol. 358, No. 9277.

Vicens, Q., et al., "Crystal Structure of Geneticin Bound to a Bacterial 16S Ribosomal RNA a Site Oligonucleotide," Journal of Molecular Biology, Feb. 28, 2003, pp. 1175-1188, vol. 326, No. 4.

Vicens, Q., et al., "Crystal Structure of Paromomycin Docked into the Eubacterial Ribosomal Decoding a Site," Structure, Aug. 2001, pp. 647-658, vol. 9, No. 8.

Vila-Sanjurjo, A. et al., "Mutational Analysis of the Conserved Bases C1402 and A1500 in the Center of the Decoding Domain of *Escherichia coli* 16S rRNA Reveals an Important Tertiary Interaction," Journal of Molecular Biology, May 4, 2001, pp. 457-463, vol. 308, No. 3.

Vila-Sanjurjo, A., et al., "Isolation of Kasugamycin Resistant Mutants in the 16 S Ribosomal RNA of *Escherichia coli*," Journal of Molecular Biology, Oct. 15, 1999, pp. 1-8, vol. 293, No. 1.

Voulgaris, J., et al., "Increased rrn Gene Dosage Causes Intermittent Transcription of rRNA in *Escherichia coli*," Journal of Bacteriology, Jul. 1999, pp. 4170-4175, vol. 181, No. 14.

Wada, K., et al., "Codon Usage Tabulated from the GenBank Genetic Sequence Data," Nucleic Acids Research, May 11, 1992, pp. 2111-2118, Supplement 20.

Wallace, C. K., et al., "Optimal Antibiotic Therapy in Cholera," Bulletin of the World Health Organization, 1968, pp. 239-245, vol. 39, No. 2.

Wang, Y., et al., "Specificity of Aminoglycoside Binding to RNA Constructs Derived from the 16S rRNA Decoding Region and the HIV-RRE Activator Region," Biochemistry, Jan. 28, 1997, pp. 768-779, vol. 36, No. 4.

Wanke, C. A., "To know *Escherichia coli* is to Know Bacterial Diarrheal Disease," Clinical Infectious Diseases, 2001, pp. 1710-1712, vol. 32, No. 12.

Wilson, K. S., et al., "Mapping the Position of Translational Elongation Factor EF-G in the Ribosome by Directed Hydroxyl Radical Probing," Cell, Jan. 9, 1998, pp. 131-139, vol. 92, No. 1.

Wimberly, B. T., et al., "Structure of the 30S Ribosomal Subunit," Nature, Sep. 21, 2000, pp. 327-339, vol. 407, No. 6802.

Winkler, F. K., et al., "Structure-Based Approaches in Modern Drug Discovery Research," Ernst Schering Research Foundation Workshop, 2001, pp. 123-142, vol. 34.

Winoto, A., et al., "A Novel, Inducible and T Cell-Specific Enhancer Located at the 3' End of the T Cell Receptor Alpha Locus," The EMBO Journal, Mar. 1989, pp. 729-733, vol. 8, No. 3.

Xiong, L., et al., "Oxazolidinone Resistance Mutations in 23S rRNA of *Escherichia coli* Reveal the Central Region of Domain V as the Primary Site of Drug Action," Journal of Bacteriology, Oct. 2000, pp. 5325-5331, vol. 182, No. 19.

Yanisch-Perron, C., et al., "Improved M13 Phage Cloning Vectors and Host Strains: Nucleotide Sequences of the M13mp18 and pUC19 Vectors," Gene, 1985, pp. 103-119, vol. 33, No. 1.

Yoshizawa, S., et al., "Structural Origins of Gentamicin Antibiotic Action," The EMBO Journal, Nov. 16, 1998, pp. 6437-6448, vol. 17, No. 22.

Yusupov, M. M., et al., "Crystal Structure of the Ribosome at 5.5 A Resolution," Science, 2001, pp. 883-896, vol. 292, No. 5518.

Yusupova, G. Z., et al., "The Path of Messenger RNA Through the Ribosome," Cell, Jul. 27, 2001, pp. 233-241, vol. 106, No. 2.

Zhang, K., et al., "Assessing Reliability of Gene Clusters from Gene Expression Data," Functional & Integrative Genomics, Nov. 2000, pp. 156-173, vol. 1, No. 3.

Zhang, X., et al., "Quinolone Antibiotics Induce Shiga Toxin-Encoding Bacteriophages, Toxin Production, and Death in Mice," The Journal of Infectious Diseases, Feb. 2000, pp. 664-670, vol. 181, No. 2.

Evans, G. A., "The Oxazolidinones," Current Infectious Disease Reports, Feb. 2002, pp. 17-27, vol. 4, No. 1.

Fauci, A. S., et al., "Emerging Infectious Diseases: A 10-Year Perspective From the National Institute of Allergy and Infectious Diseases," Emerging Infectious Diseases, Apr. 2005, pp. 519-525, vol. 11, No. 4.

Fourmy, D., et al., "Structure of the a Site of *Escherichia coli* 16S Ribosomal RNA Complexed with an Aminoglycoside Antibiotic," Science, Nov. 22, 1996, pp. 1367-1371, vol. 274, No. 5291.

Gabashvili, I. S., et al., "Major Rearrangements in the 70S Ribosomal 3D Structure Caused by a Conformational Switch in 16S Ribosomal RNA," The EMBO Journal, Nov. 15, 1999, pp. 6501-6507. vol. 18, No. 22.

Gallego, J., et al., "Targeting RNA with Small-Molecule Drugs: Therapeutic Promise and Chemical Challenges," Accounts of Chemical Research, Oct. 2001, pp. 836-843, vol. 34, No. 10.

Goeddel, D. V., "Systems for Heterologous Gene Expression," Methods in Enzymology, 1990, pp. 3-7, vol. 185.

Gomi, H., et al., "In vitro Antimicrobial Susceptibility Testing of Bacterial Enteropathogens Causing Traveler's Diarrhea in Four Geographic Regions," Antimicrobial Agents and Chemotherapy, Jan. 2001, pp. 212-216, vol. 45, No. 1.

Gonzales, R. D., et al., "Infections Due to Vancomycin-Resistant *Enterococcus faecium* Resistant to Linezolid," Lancet, Apr. 14, 2001, p. 1179, vol. 357, No. 9263.

Gottesman, S., "Minimizing Proteolysis in *Escherichia coli*: Genetic Solutions," Methods in Enzymology, 1990, pp. 119-129, vol. 185.

Govantes, F., et al., "Mechanism of Translational Coupling in the nifLA Operon of *Klebsiella pneumoniae*," The EMBO Journal, Apr. 15, 1998, pp. 2368-2377, vol. 17, No. 8.

Guerrant, R. L., et al., "Magnitude and Impact of Diarrheal Diseases," Archives of Medical Research, Jul.-Aug. 2002, pp. 351-355, vol. 33, No. 4.

Gutell, R. R., "Collection of Small Subunit (16S- and 16S-like) Ribosomal RNA Structures," Nucleic Acids Research, Sep. 1994, pp. 3502-3507, vol. 22, No. 17.

Gutell, R. R., et al., "Identifying Constraints on the Higher-Order Structure of RNA: Continued Development and Application of Comparative Sequence Analysis Methods," Nucleic Acids Research, Nov. 11, 1992, pp. 5785-5795, vol. 20, No. 21.

Haddad, J., et al., "Design of Novel Antibiotics that Bind to the Ribosomal Acyltransfer Site," Journal of the American Chemical Society, Apr. 3, 2002, pp. 3229-3237, vol. 124, No. 13.

Hanahan, D., "Studies on Transformation of *Escherichia coli* with Plasmids," Journal of Molecular Biology, Jun. 5, 1983, pp. 557-580, vol. 166, No. 4.

Hancock, R. E., et al., "Peptide Antibiotics," Antimicrobial Agents and Chemotherapy, Jun. 1999, pp. 1317-1323, vol. 43, No. 6.

Harms, J., et al., "High Resolution Structure of the Large Ribosomal Subunit from a Mesophilic Eubacterium," Cell, Nov. 30, 2001, pp. 679-688, vol. 107, No. 5.

Hartman, A. B., et al., "Epidemiology of Tetracycline Resistance Determinants in *Shigella spp.* and Enteroinvasive *Escherichia coli*: Characterization and Dissemination of tet(A)-1," Journal of Clinical Microbiology, Mar. 2003, pp. 1023-1032, vol. 41, No. 3.

Herr, W., et al., "Mechanism of Ribosomal Subunit Association: Discrimination of Specific Sites in 16S RNA Essential for Association Activity," Journal of Molecular Biology, Jun. 5, 1979, pp. 433-449, vol. 130, No. 4.

Herrero, I. A., et al., "Nosocomial Spread of Linezolid-Resistant, Vancomycin-Resistant *Enterococcus faecium*," The New England Journal of Medicine, Mar. 14, 2002, pp. 867-869, vol. 346, No. 11.

Higuchi, R., "Using PCR to Engineer DNA," PCR Technology, 1989, pp. 61-70.

Hui, A., et al., "Specialized Ribosome System: Preferential Translation of a Single mRNA Species by a Subpopulation of Mutated Ribosomes in *Escherichia coli*," Proceedings of the National Academy of Sciences of the United States of America, Jul. 1987, pp. 4762-4766, vol. 84, No. 14.

Hui, A., et al., "Directing Ribosomes to a Single mRNA Species: A Method to Study Ribosomal RNA Mutations and Their Effects on Translation of a Single Messenger in *Escherichia coli*," Methods in Enzymology, 1987, pp. 432-452, vol. 153.

(56) References Cited

OTHER PUBLICATIONS

Hwang, S., et al., "Inhibition of Gene Expression in Human Cells Through Small Molecule-RNA Interactions," Proceedings of the National Academy of Sciences of the United States of America, Nov. 9, 1999, pp. 12997-13002, vol. 96, No. 23.

International Search Report dated Nov. 28, 2007.

John, T. J., "Emerging & Re-Emerging Bacterial Pathogens in India," The Indian Journal of Medical Research, Jan. 1996, pp. 4-18, vol. 103.

Jones, R. N., et al., "Linezolid-Resistant *Enterococcus faecium* Isolated From a Patient Without Prior Exposure to an Oxazolidinone: Report From the Sentry Antimicrobial Surveillance Program," Diagnostic Microbiology and Infectious Disease, Feb. 2002, pp. 137-139, vol. 42, No. 2.

Kaufman, R. J., et al., "Translation Efficiency of Polycistronic mRNAs and Their Utilization to Express Heterologous Genes in Mammalian Cells," The EMBO Journal, Jan. 1987, pp. 187-195, vol. 6, No. 1.

Keller, W., et al., "Cleavage and Polyadenylation Factor CPF Specifically Interacts with the Pre-mRNA 38 Processing Signal AAUAAA," The EMBO Journal, Dec. 1991, pp. 4241-4249, vol. 10, No. 13.

Keren-Zur, M., et al., "Localization of the Decoding Region on the 30S *Escherichia coli* Ribosomal Subunit by Affinity Immunoelectron Microscopy," Proceedings of the National Academy of Sciences of the United States of America, Mar. 1979, pp. 1054-1058, vol. 76, No. 3.

Kessel, M., et al., "Murine Developmental Control Genes," Science, Jul. 27, 1990, pp. 374-379, vol. 249, No. 4967.

Khan, W. A., et al., "Randomised Controlled Comparison of Single-Dose Ciprofloxacin and Doxycycline for Cholera Caused by Vibrio Cholerae 01 or 0139," Lancet, Aug. 3, 1996, pp. 296-300, vol. 348, No. 9023.

Kieber-Emmons, T., et al., "Therapeutic Peptides and Peptidomimetics," Current Opinion in Biotechnology, Aug. 1997, pp. 435-441, vol. 8, No. 4.

Kloss, P., et al., "Resistance Mutations in 23 S rRNA Identify the Site of Action of the Protein Synthesis Inhibitor Linezolid in the Ribosomal Peptidyl Transferase Center," Journal of Molecular Biology, Nov. 19, 1999, pp. 93-101, vol. 294, No. 1.

Klostermeier, D., et al., "A Three-Fluorophore Fret Assay for High-Throughput Screening of Small-Molecule Inhibitors of Ribosome Assembly," Nucleic Acids Research, May 17, 2004, pp. 2707-2715, vol. 32, No. 9.

Ko, J.-H., et al., "Probing the Functional Motifs of *Escherichia coli* 5S rRNA in Relation to 16S rRNA Using a SELEX Experiment," The Bulletin of the Korean Chemical Society, 1999, pp. 1335-1339, vol. 20, No. 11.

Koosha, H., et al., "Alterations in the Peptidyltransferase and Decoding Domains of Ribosomal RNA Suppress Mutations in the Elongation Factor G Gene," RNA, Aug. 2000, pp. 1166-1173, vol. 6, No. 8.

Kozak, M., "Regulation of Translation via mRNA Structure in Prokaryotes and Eukaryotes," Gene, 2005, pp. 13-37, vol. 361.

Krzyzosiak, W., et al., "In Vitro Synthesis of 16S Ribosomal RNA Containing Single Base Changes and Assembly Into a Functional 30S Ribosome," Biochemistry, Apr. 21, 1987, pp. 2353-2364, vol. 26, No. 8.

Kurjan, J., et al., "Structure of a Yeast Pheromone Gene (MF Alpha): A Putative Alpha-Factor Precursor Contains Four Tandem Copies of Mature Alpha-Factor," Cell, Oct. 1982, pp. 933-943, vol. 30, No. 3.

Laios, E., et al., "Combinatorial Genetic Technology for the Development of New Anti-Infectives," Archives of Pathology & Laboratory Medicine, Dec. 2004, pp. 1351-1359, vol. 128, No. 12.

Lam, K. S. et al., "Application of a Dual Color Detection Scheme in the Screening of a Random Combinatorial Peptide Library," Journal of Immunological Methods, Mar. 27, 1995, pp. 219-223, vol. 180, No. 2.

Lee, K., et al., "Genetic Approaches to Studying Protein Synthesis: Effects of Mutations at Psi516 and A535 in *Escherichia coli* 16S rRNA," The Journal of Nutrition, Nov. 2001, pp. 2994S-3004S, vol. 131, No. 11.

Lee, K., et al., "Genetic Approaches to Studying Protein Synthesis: Effects of Mutations at Pseudouridine 516 and A535 in *Escherichia coli* 16S rRNA," Symposium: Translational Control: A Mechanistic Perspective at the Experimental Biology 2001 Meeting, 2001.

Lee, K., et al., "In Vivo Determination of RNA Structure-Function Relationships: Analysis of the 790 Loop in Ribosomal RNA," Journal of Molecular Biology, Jun. 27, 1997, pp. 732-743, vol. 269, No. 5.

Lee, K., et al., "Genetic Analysis of the Shine-Dalgarno Interaction: Selection of Alternative Functional mRNA-rRNA Combinations," RNA, Dec. 1996, pp. 1270-1285, vol. 2, No. 12.

Lesley, S. A., et al., "Use of in Vitro Protein Synthesis From Polymerase Chain Reaction-Generated Templates to Study Interaction of *Escherichia coli* Transcription Factors with Core RNA Polymerase and for Epitope Mapping of Monoclonal Antibodies," The Journal of Biological Chemistry, Feb. 5, 1991, pp. 2632-2638, vol. 266, No. 4.

Levy, S. B., et al., "Antibacterial Resistance Worldwide: Causes, Challenges and Responses," Nature Medicine, 2004, pp. S122-S129, vol. 10.

Levy, S. B., "Antibiotic Resistance: Consequences of Inaction," Clinical Infectious Diseases 33, Supplement 3, 2001, pp. S124-S129.

Lin-Goerke, J. L., et al., "PCR-Based Random Mutagenesis Using Manganese and Reduced dNTP Concentration," BioTechniques, Sep. 1997, pp. 409-412, vol. 23, No. 3.

Lind, K. E., et al., "Structure-Based Computational Database Screening, in Vitro Assay, and NMR Assessment of Compunds that Target TAR RNA," Chemistry & Biology, Feb. 2002, pp. 185-193, vol. 9, No. 2.

Lindenbaum, J., et al., "Antibiotic Therapy of Cholera in Children," Bulletin of the World Health Organization, 1967, pp. 529-538, vol. 37, No. 4.

Llano-Sotelo, B., et al., "Aminoglycosides Modified by Resistance Enzymes Display Diminished Binding to the Bacterial Ribosomal Aminoacyl-tRNA Site," Chemistry & Biology, Apr. 2002, pp. 455-463, vol. 9, No. 4.

Lodmell, J. S., et al., "A Conformational Switch in *Escherichia coli* 16S Ribosomal RNA During Decoding of Messenger RNA," Science, Aug. 29, 1997, pp. 1262-1267, vol. 277, No. 5330.

Luria, S. E., et al., "Hybridization Between *Escherichia coli* and *Shigella*," Journal of Bacteriology, Oct. 1957, pp. 461-476, vol. 74, No. 4.

Lynch, S. R., et al., "Comparison of X-Ray Crystal Structure of the 30S Subunit-Antibiotic Complex with NMR Structure of Decoding Site Oligonucleotide-Paromomycin Complex," Structure, Jan. 2003, pp. 43-53, vol. 11, No. 1.

Maden, B. E., "The Numerous Modified Nucleotides in Eukaryotic Ribosomal RNA," Progress in Nucleic Acid Research and Molecular Biology, 1990, pp. 241-303, vol. 39.

Magnet, S., et al., "Molecular Insights into Aminoglycoside Action and Resistance," Chemical Reviews, Feb. 2005, pp. 477-498, vol. 105, No. 2.

Maidak, B. L., et al., "The Ribosomal Database Project (RDP)," Nucleic Acids Research, Jan. 1, 1996, pp. 82-85, vol. 24, No. 1.

Makosky, P. C., et al., "Spectinomycin Resistance at Site 1192 in 16S Ribosomal RNA of *E. coli*: An Analysis of Three Mutants," Biochimie, Aug. 1987, pp. 885-889, vol. 69, No. 8.

McManus, M. C., "Mechanisms of Bacterial Resistance to Antimicrobial Agents," American Journal of Health-System Pharmacy, Jun. 15, 1997, pp. 1420-1433, quiz pp. 1444-1446, vol. 54, No. 12.

Miller, B. T., et al., "Peptide Biotinylation with Amine-Reactive Esters: Differential Side Chain Reactivity," Peptides, 1997, pp. 1585-1595, vol. 18, No. 10.

Miller, J. H., A Short Course in Bacterial Genetics: A Laboratory Manual and Handbook for *Escherichia coli* and Related Bacterial, 1992, pp. 71-80, Cold Spring Harbor Laboratory Press, Cold Spring Harbor, NY.

Mirza, S. H., et al., "Multi-Drug Resistant Typhoid: A Global Problem," Journal of Medical Microbiology, May 1996, pp. 317-319, vol. 44, No. 5.

(56) References Cited

OTHER PUBLICATIONS

Moazed, D., et al., "Interconversion of Active and Inactive 30S Ribosomal Subunits is Accompanied by a Conformation Change in the Decoding Region of 16S rRNA," Journal of Molecular Biology, Oct. 5, 1986, pp. 483-493, vol. 191, No. 3.
Morosyuk, S. V., et al., "Structure and Function of the Conserved 690 Hairpin in *Escherichia coli* 16S Ribosomal RNA. II. NMR Solution Structure," Journal of Molecular Biology, Mar. 16, 2001, pp. 197-211, vol. 307, No. 1.
Morosyuk, S. V., et al., "Structure and Function of the Conserved 690 Hairpin in *Escherichia coli* 16S Ribosomal RNA. III. Functional Analysis of the 690 Loop," Journal of Molecular Biology, Mar. 16, 2001, pp. 213-228, vol. 307, No. 1.
Morosyuk, S. V., et al., "Structure and Function of the Conserved 690 Hairpin in *Escherichia coli* 16S Ribosomal RNA: Analysis of the Stem Nucleotides," Journal of Molecular Biology, Jun. 30, 2000, pp. 113-126, vol. 300, No. 1.
Mucha, P., et al., "Interaction of RNA with Phage Display Selected Peptides Analyzed by Capillary Electrophoresis Mobility Shift Assay," RNA, May 2002, pp. 698-704, vol. 8, No. 5.
Mucha, P., et al., "Anticodon Domain Methylated Nucleosides of Yeast tRNA(Phe) are Significant Recognition Determinants in the Building of a Phage Display Selected Peptide," Biochemistry, Nov. 27, 2001, pp. 14191-14199, vol. 40, No. 47.
Nandi, S., et al., "Gram-Positive Bacteria are a Major Reservoir of Class 1 Antibiotic Resistance Integrons in Poultry Litter," Proceedings of the National Academy of Sciences of the United States of America, 2004, pp. 7118-7122, vol. 101, No. 18.
Nataro, J. P., et al., "Diarrheagenic *Escherichia coli*," Clinical Microbiology Reviews, Jan. 1998, pp. 142-201, vol. 11, No. 1.
Nielsen, D. A., et al., "A Highly Sensitive, Mixed-Phase Assay for Chloramphenicol Acetyltransferase Activity in Transfected Cells," Analytical Biochemistry, May 15, 1989, pp. 19-23, vol. 179, No. 1.
Nikonowicz, E. P., et al., "Preparation of 13C and 15N Labelled RNAs for Heteronuclear Multi-Dimensional NMR Studies," Nucleic Acids Research, Sep. 11, 1992, pp. 4507-4513, vol. 20, No. 17.
O'Connor, M., et al., "Enhancement of Translation by the Epsilon Element is Independent of the Sequence of the 460 Region of 16S IRNA," Nucleic Acids Research, Apr. 1, 2001, pp. 1420-1425, vol. 29, No. 7.
O'Connor, M., et al., "Mutagenesis of the Peptidyltransferase Center of 23S rRNA: The Invariant U2449 is Dispensable," Nucleic Acids Research, Feb. 1, 2001, pp. 710-715, vol. 29, No. 3.
Ogle, J. M., et al., "Recognition of Cognate Transfer RNA by the 30S Ribosomal Subunit," Science, May 4, 2001, pp. 897-902, vol. 292, No. 5518.
Oldfield, E. C., 3rd, et al., "The Role of Antibiotics in the Treatment of Infectious Diarrhea," Gastroenterology Clinics of North America, Sep. 2001, pp. 817-836, vol. 30, No. 3.
Orr, J. W., et al., "Protein and Mg(2+)-Induced Conformational Changes in the S15 Binding Site of 16 S Ribosomal RNA," Journal of Molecular Biology, Jan. 23, 1998, pp. 453-464, vol. 275, No. 3.
Papich, M. G., "Antimicrobial Therapy for Gastrointestinal Diseases," The Veterinary Clinics of North America, Equine Practice, Dec. 2003, pp. 645-663, vol. 19, No. 3.
Pelham, H. R., et al., " an Efficient mRNA-Dependent Translation System from Reticulocyte Lysates," European Journal of Biochemistry, Aug. 1, 1976, pp. 247-256, vol. 67, No. 1.
Peske, F., et al., "Conformational Changes of the Small Ribosomal Subunit During Elongation Factor G-Dependent tRNA-mRNA Translocation," Journal of Molecular Biology, Nov. 5, 2004, pp. 1183-1194, vol. 343, No. 5.

Pinkert, C. A., et al., "An Albumin Enhancer Located 10 kb Upstream Functions Along with its Promoter to Direct Efficient, Liver-Specific Expression in Transgenic Mice," Genes & Development, May 1987, pp. 268-277, vol. 1, No. 3.
Pioletti, M., et al., "Crystal Structures of Complexes of the Small Ribosomal Subunit with Tetracycline, Edeine and IF3," The EMBO Journal, Apr. 17, 2001, pp. 1829-1839, vol. 20, No. 8.
Powers, T., et al., "A Functional Pseudoknot in 16S Ribosomal RNA," The EMBO Journal, Aug. 1991, pp. 2203-2214, vol. 10, No. 8.
Prince, J. B., et al., "Covalent Crosslinking of tRNA 1 Val to 16S RNA at the Ribosomal P Site: Identification of Crosslinked Residues," Proceedings of the National Academy of Sciences of the United States of America, Sep. 1982, pp. 5450-5454, vol. 79, No. 18.
Queen, C., et al., "Immunoglobulin Gene Transcription is Activated by Downstream Sequence Elements," Cell, Jul. 1983, pp. 741-748, vol. 33, No. 3.
Recht, M. I., et al., "Effect of Mutations in the A Site of 16 S rRNA on Aminoglycoside Antibiotic-Ribosome Interaction," Journal of Molecular Biology, Feb. 12, 1999, pp. 33-43, vol. 286, No. 1.
Rodriguez-Correa, D., et al., "Genetic Evidence Against the 16S Ribosomal RNA Helix 27 Conformational Switch Model," RNA, Jan. 2004, pp. 28-33, vol. 10, No. 1.
Rothman, J. H., et al., "Peptide-Binding Antibiotics: A Solid-Phase Assay for Screening Libraries of Vancomycin Mimics for Selective d-Aia-d-Aia Binding," Bioorganic & Medicinal Chemistry Letters, 1997, pp. 3159-3164; vol. 7, No. 24.
Sander, P., et al., "Ribosomal and Non-Ribosomal Resistance to Oxazolidinones: Species-Specific Idiosyncrasy of Ribosomal Alterations," Molecular Microbiology, Dec. 2002, pp. 1295-1304, vol. 46, No. 5.
Schottel, J. L., et al., "Effects of Alterations in the Translational Control Region on Bacterial Gene Expression: Use of Cat Gene Constructs Transcribed from the lac Promoter as a Model System," Gene, May 1984, pp. 177-193, vol. 28, No. 2.
Schultz, L. D., et al., "Expression and Secretion in Yeast of a 400-kDa Envelope Glycoprotein Derived From Epstein-Barr Virus," Gene, 1987, pp. 113-123, vol. 54, No. 1.
Seed, B., "An LFA-3 cDNA Encodes a Phospholipid-Linked Membrane Protein Homologous to its Receptor CD2," Nature, Oct. 29-Nov. 4, 1987, pp. 840-842, vol. 329, No. 6142.
Serganov, A. A., et al., "The 16S rRNA Binding Site of *Thermus thermophilus* Ribosomal Protein S15: Comparison with *Escherichia coli* S15, Minimum Site and Structure," RNA, Nov. 1996, pp. 1124-1138, vol. 2, No. 11.
Sergiev, P. V., et al., "Mutations at Position A960 of *E. coli* 23S Ribosomal RNA Influence the Structure of 5S Ribosomal RNA and the Peptidyltransferase Region of 23 S Ribosomal RNA," Journal of Molecular Biology, Jun. 2, 2000, pp. 379-389, vol. 299, No. 2.
Shine, J., et al., "The 3'-Terminal Sequence of *Escherichia coli* 16S Ribosomal RNA: Complementarity to Nonsense Triplets and Ribosome Binding Sites," Proceedings of the National Academy of Sciences of the United States of America, Apr. 1974, pp. 1342-1346, vol. 71, No. 4.
Sigmund, C. D., et al., "Antibiotic Resistance Mutations in Ribosomal RNA Genes of *Escherichia coli*," Methods in Enzymology, 1988, pp. 673-690, vol. 164.
Sigmund, C. D., et al., "Antibiotic Resistance in 16S and 23S Ribosomal RNA Genes of *Escherichia coli*," Nucleic Acids Research, Jun. 11, 1984, pp. 4653-4663, vol. 12, No. 11.
Sigmund, C. D., et al., "Erythromycin Resistance Due to a Mutation in a Ribosomal RNA Operon of *Escherichia coli*," Proceedings of the National Academy of Sciences of the United States of America, Sep. 1982, pp. 5602-5606, vol. 79, No. 18.

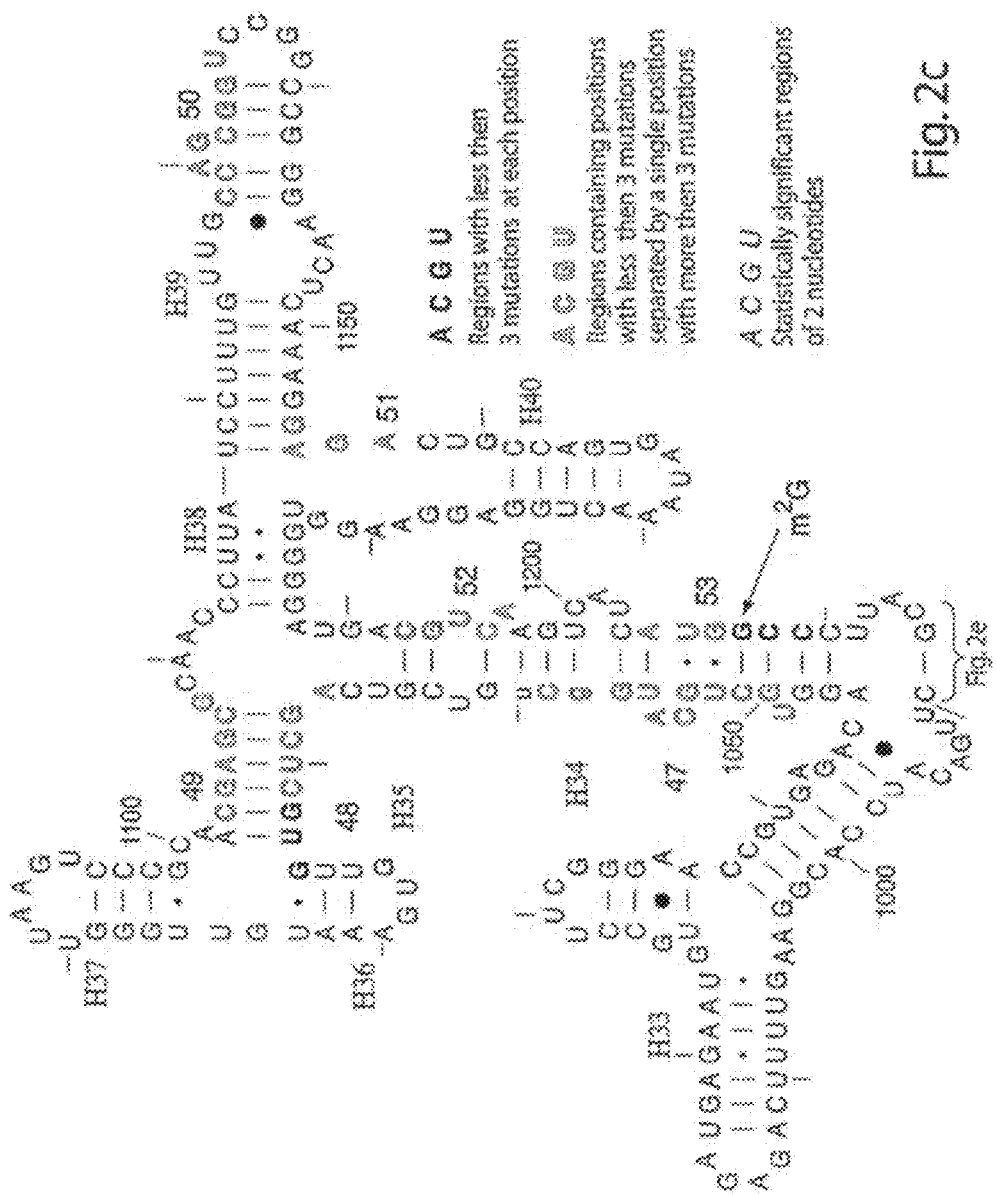

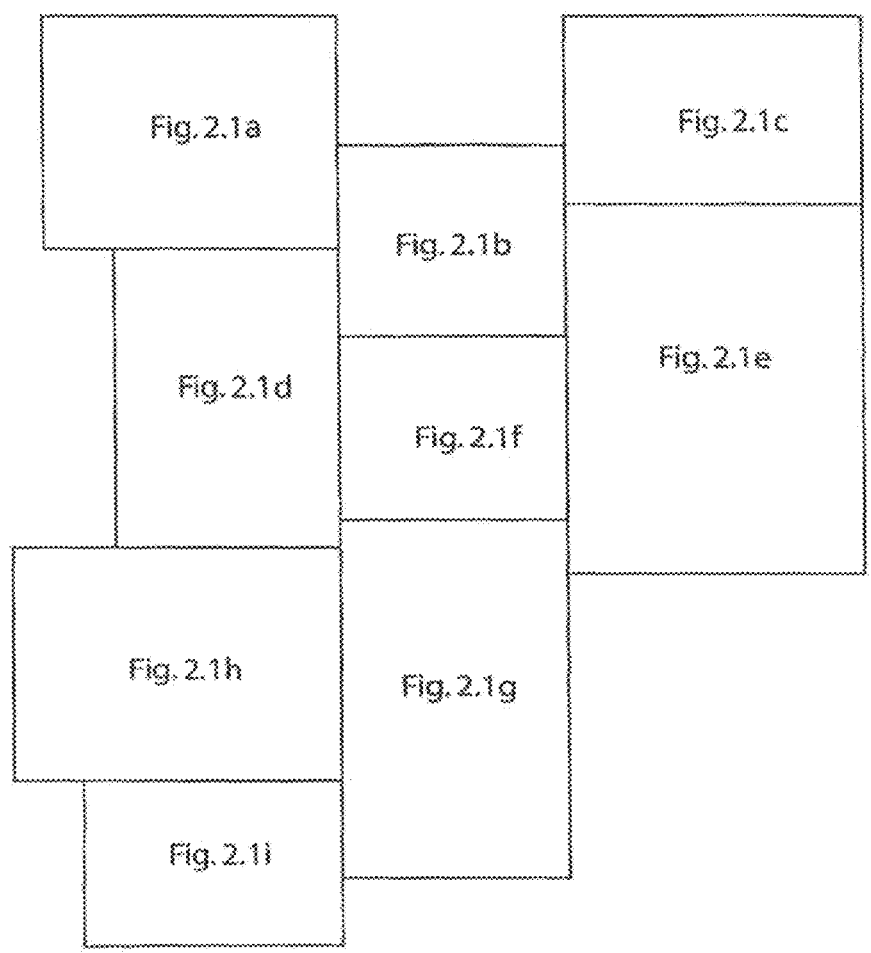
Fig. 2.1

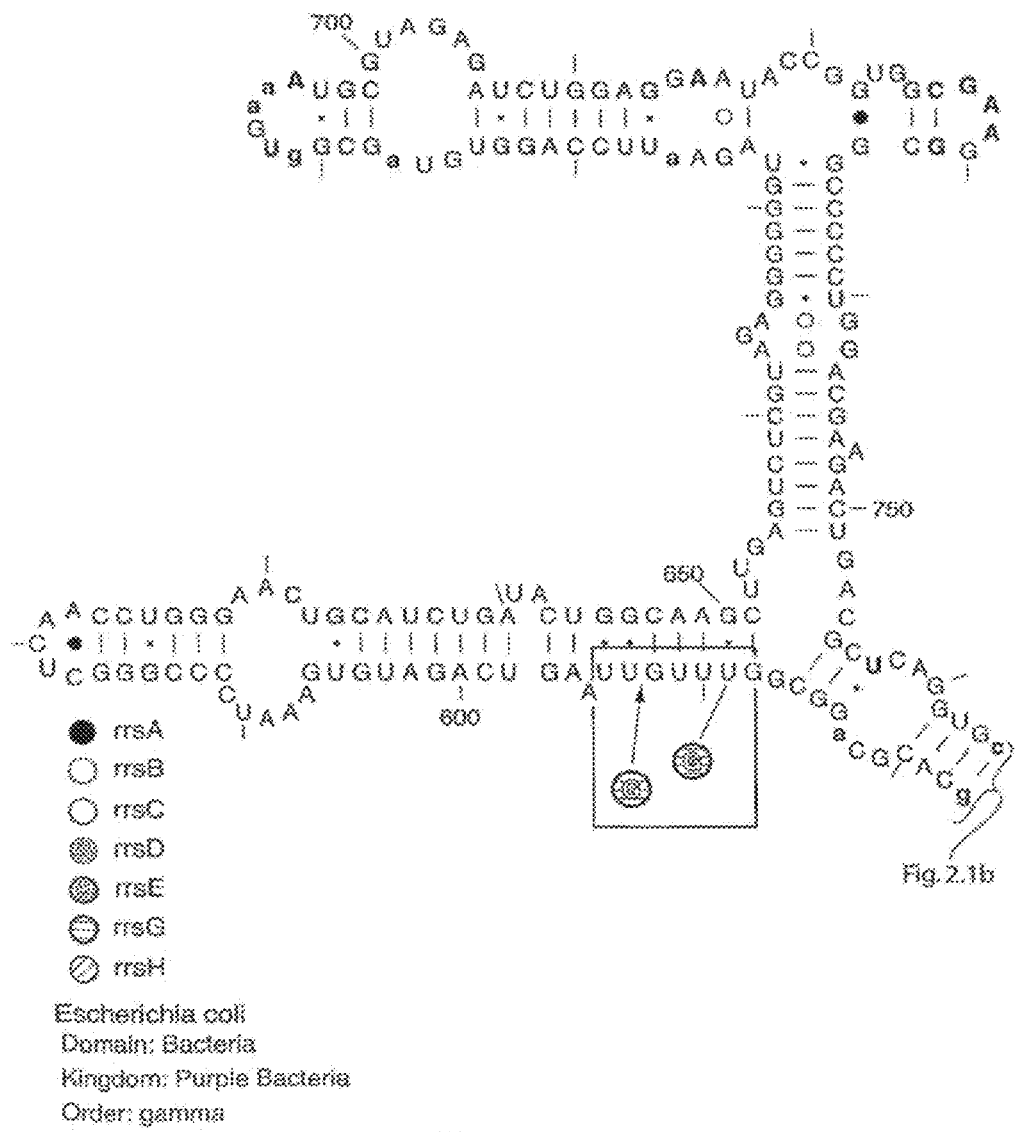
Fig. 2.1a

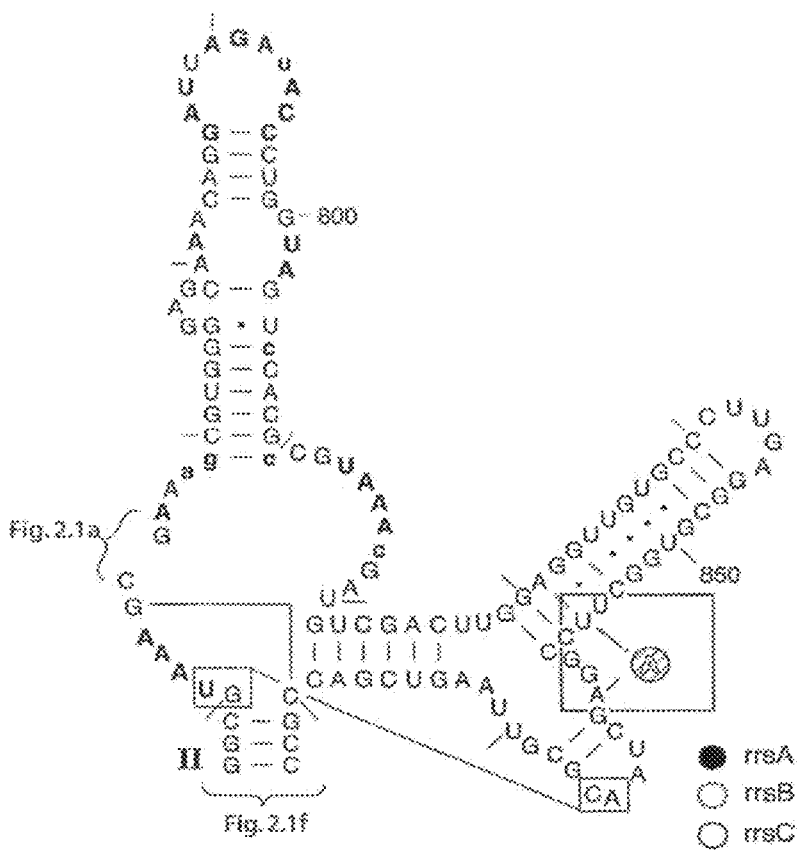
Fig. 2.1b

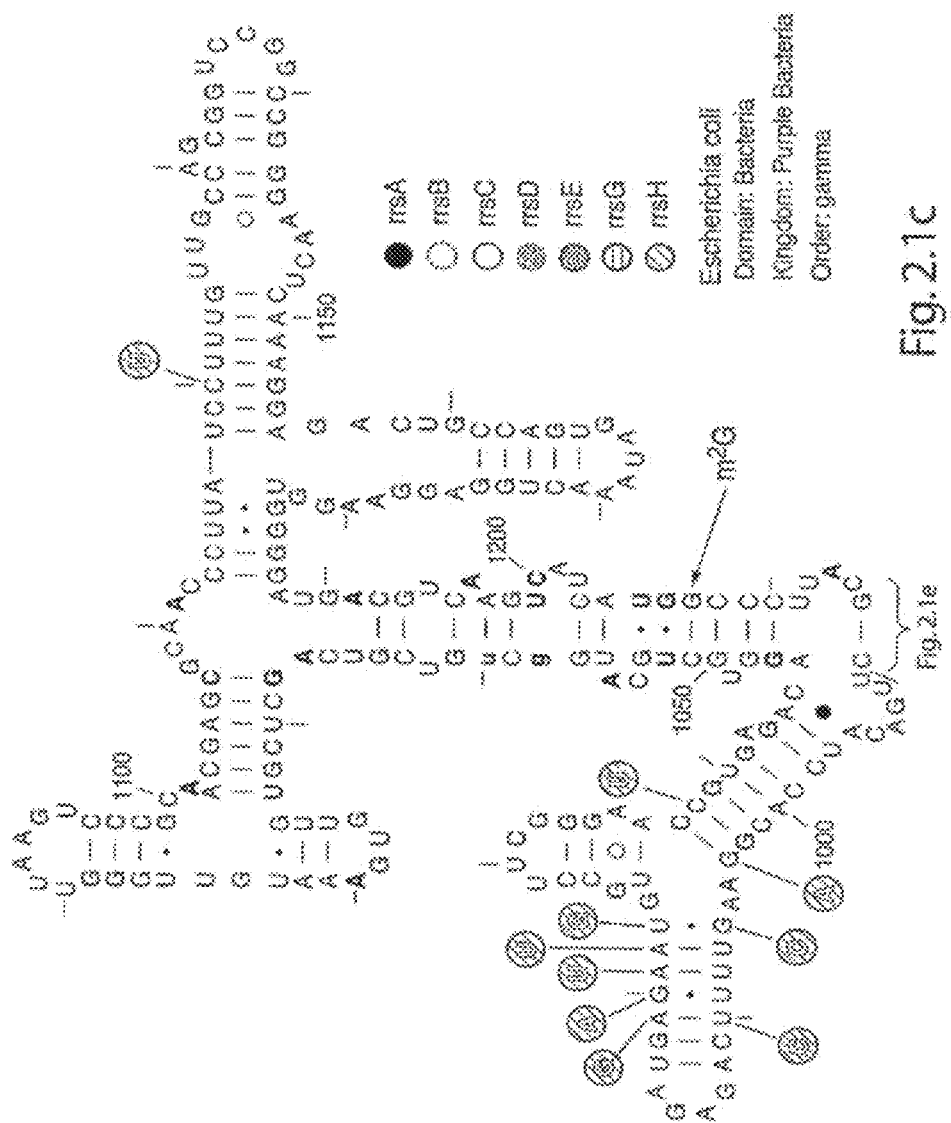
Fig. 2.1c

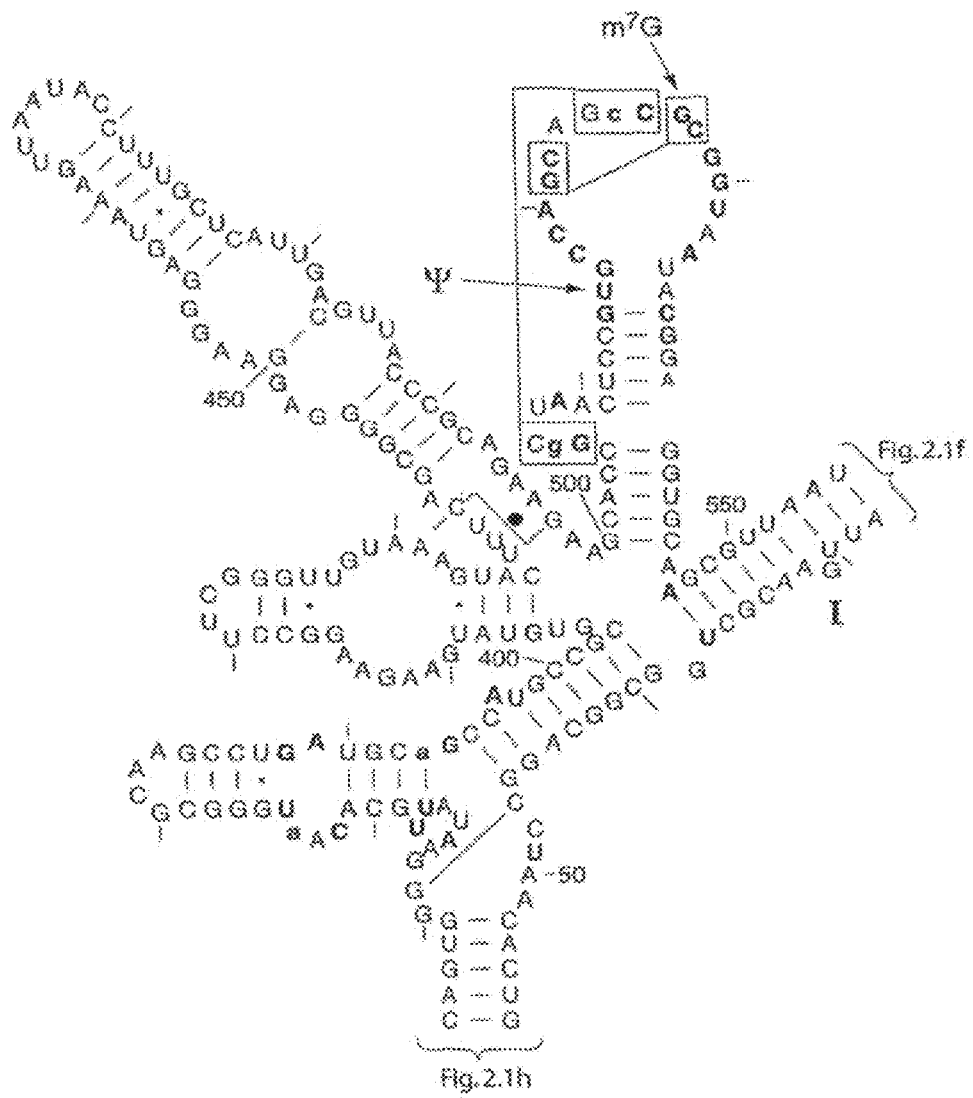
Fig. 2.1d

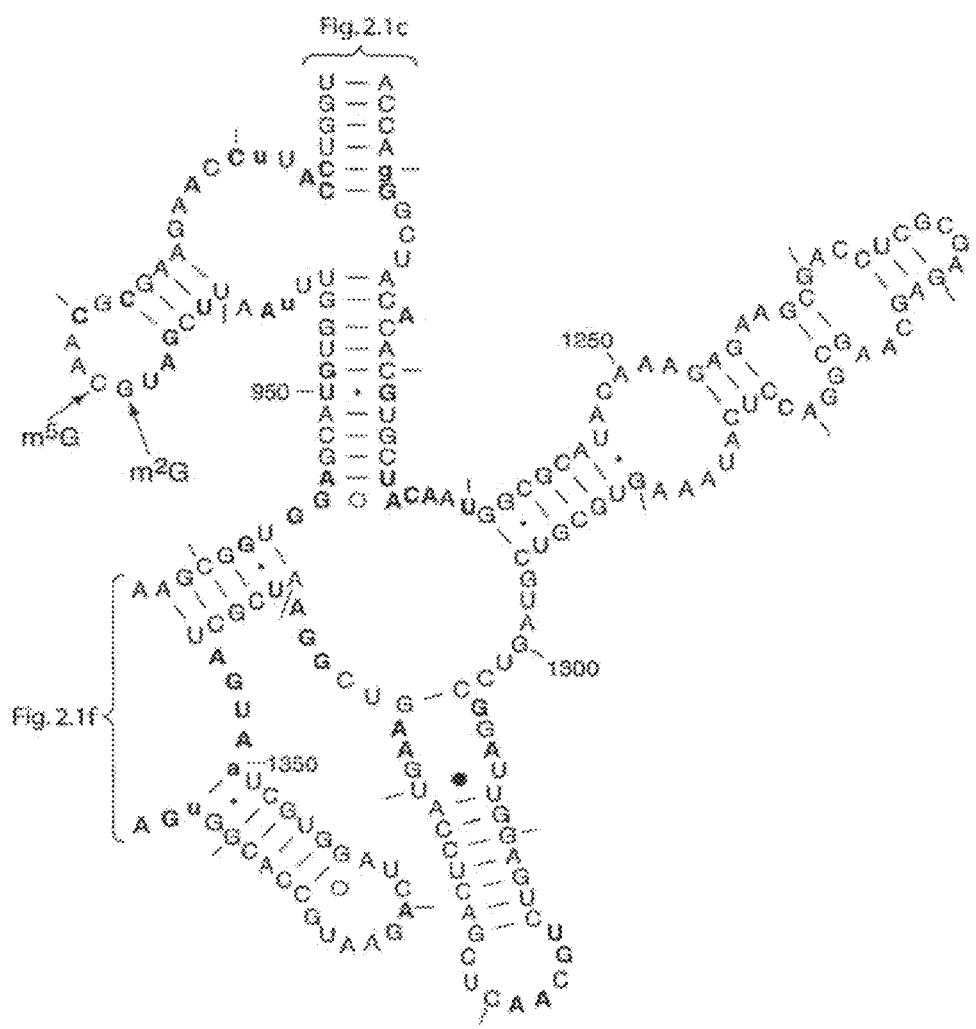
Fig. 2.1e

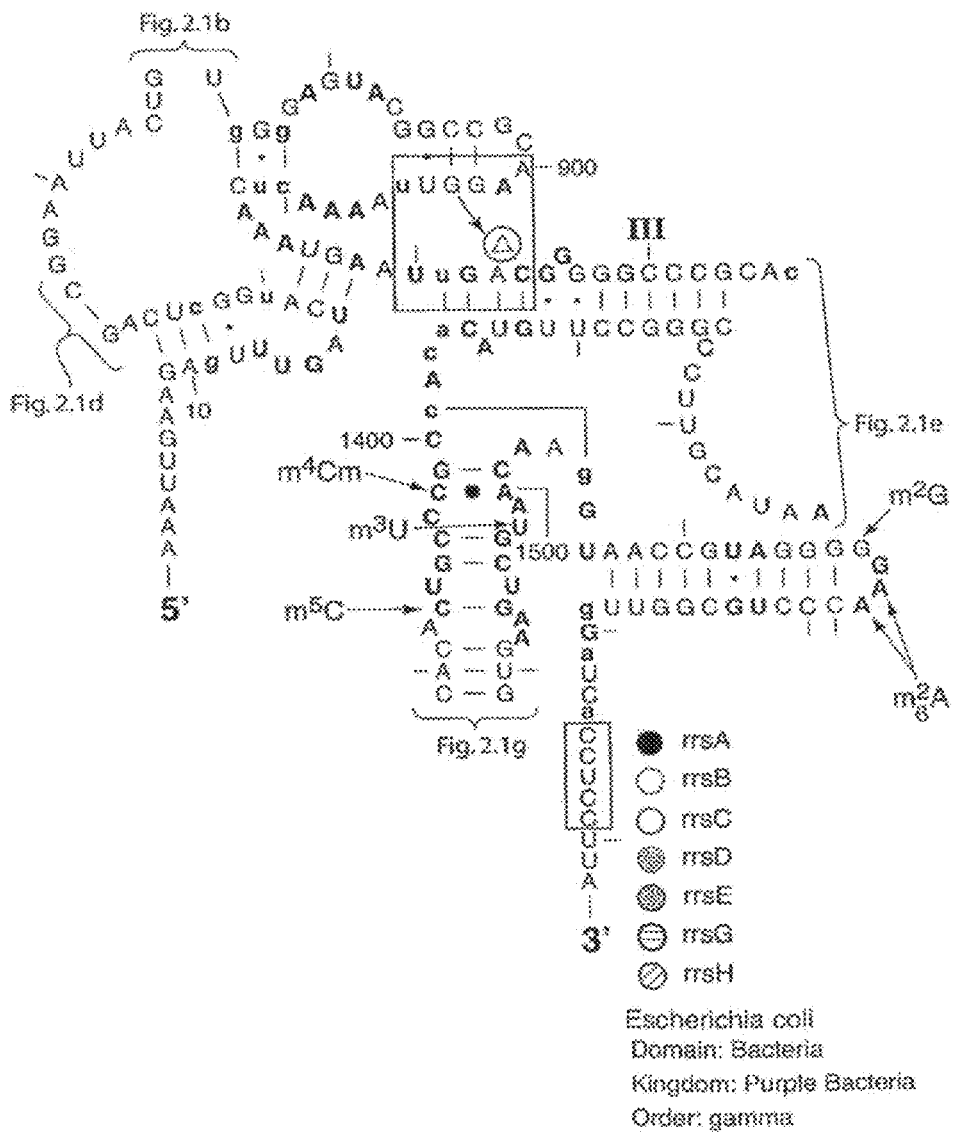
Fig. 2.1f

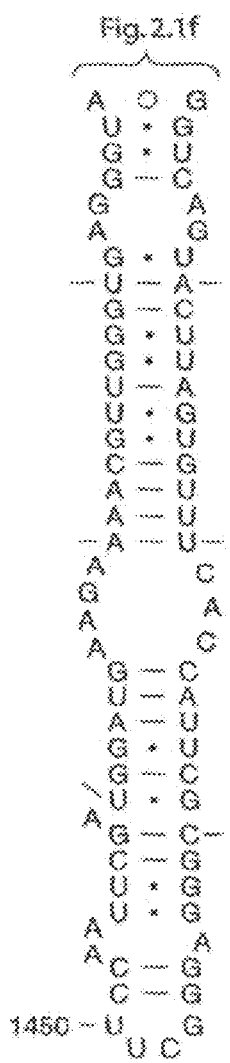
Fig. 2.1g

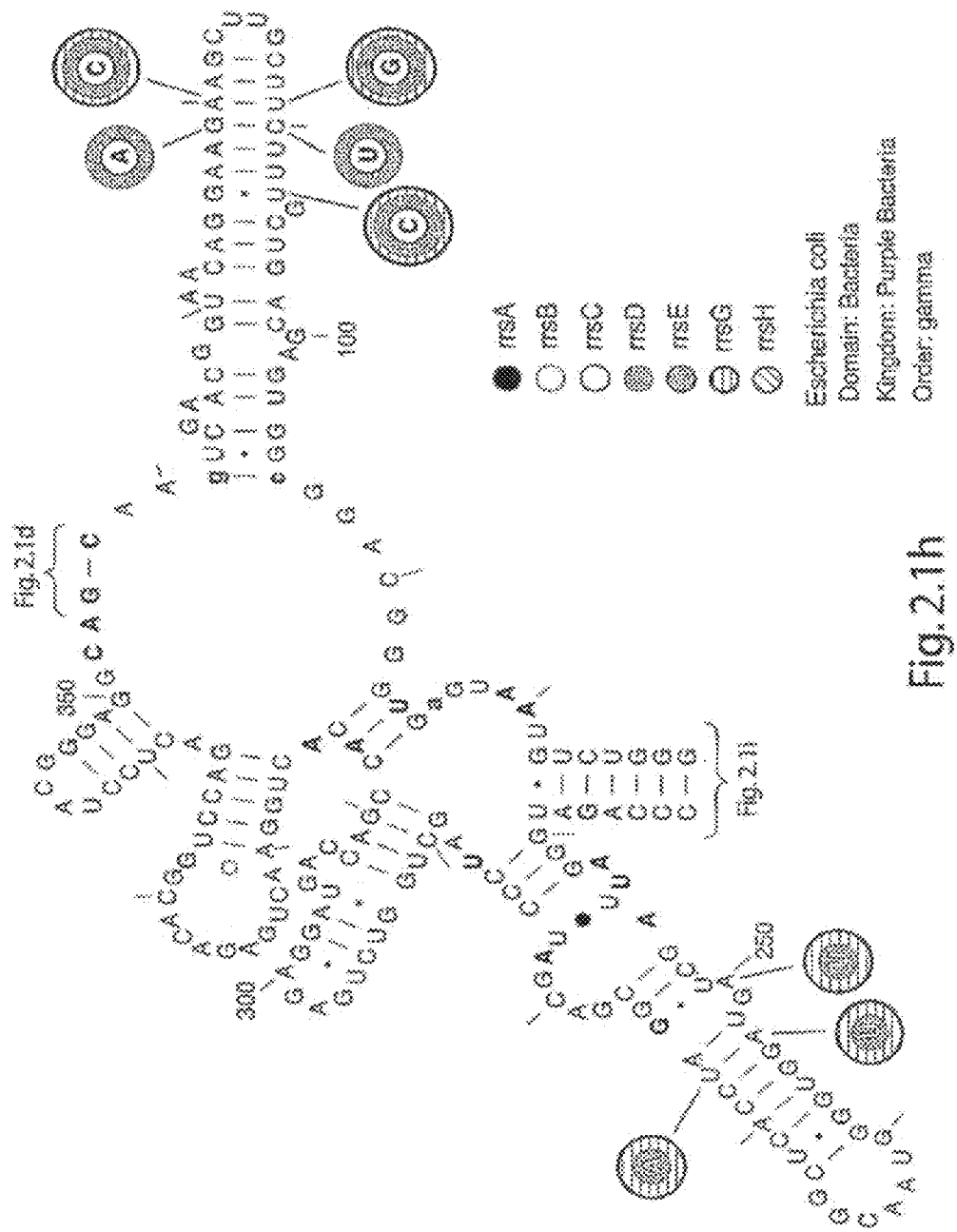
Fig.2.1h

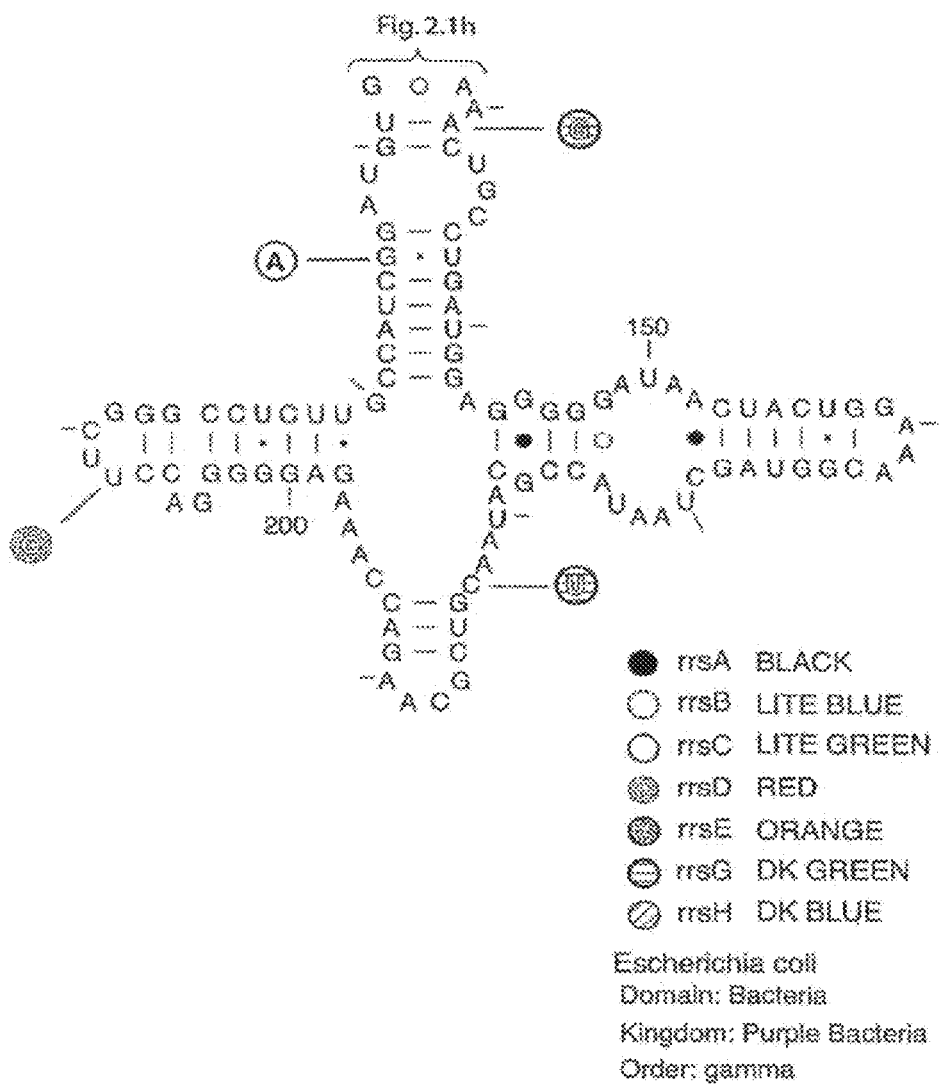
Fig. 2.1i

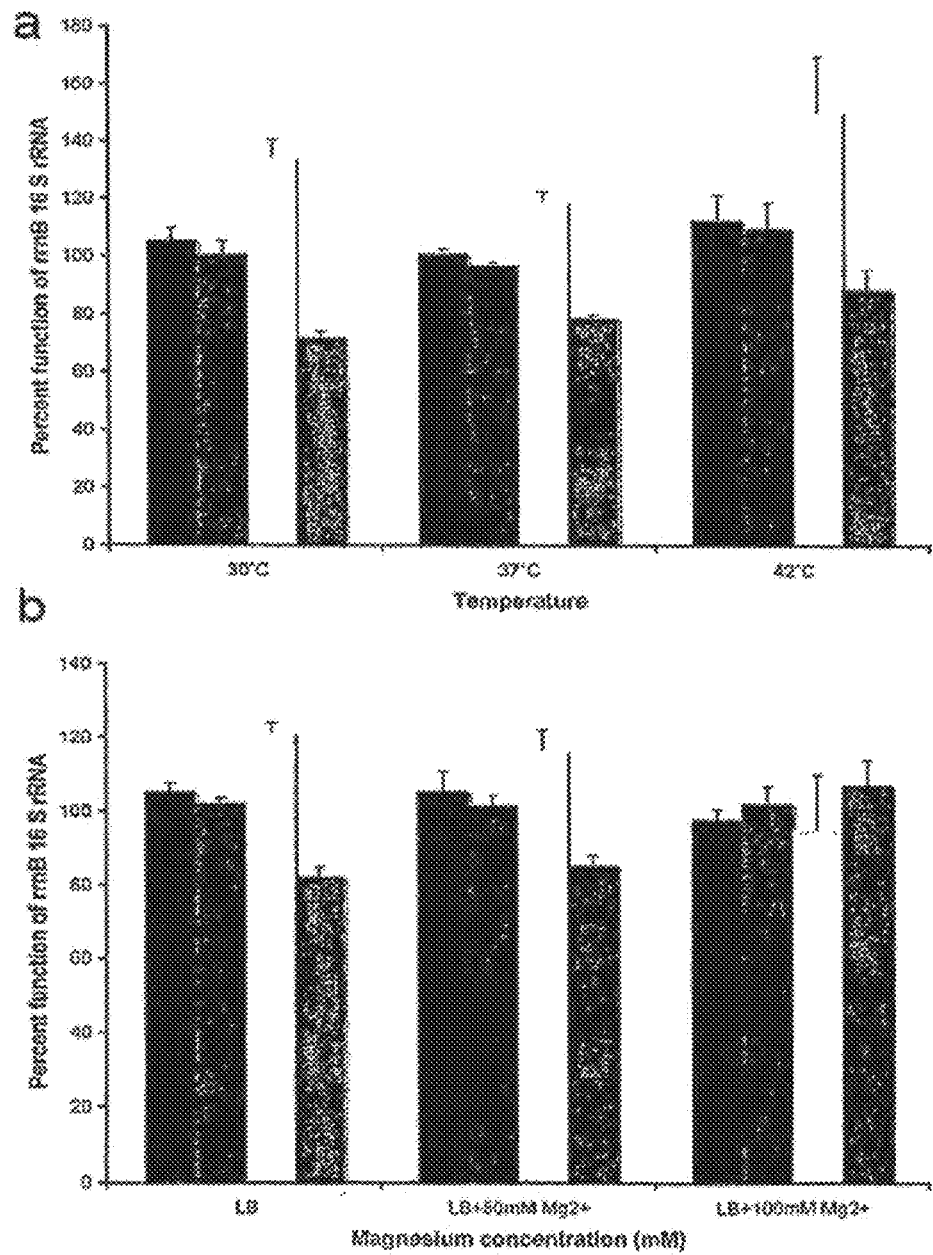
Fig. 2.2i

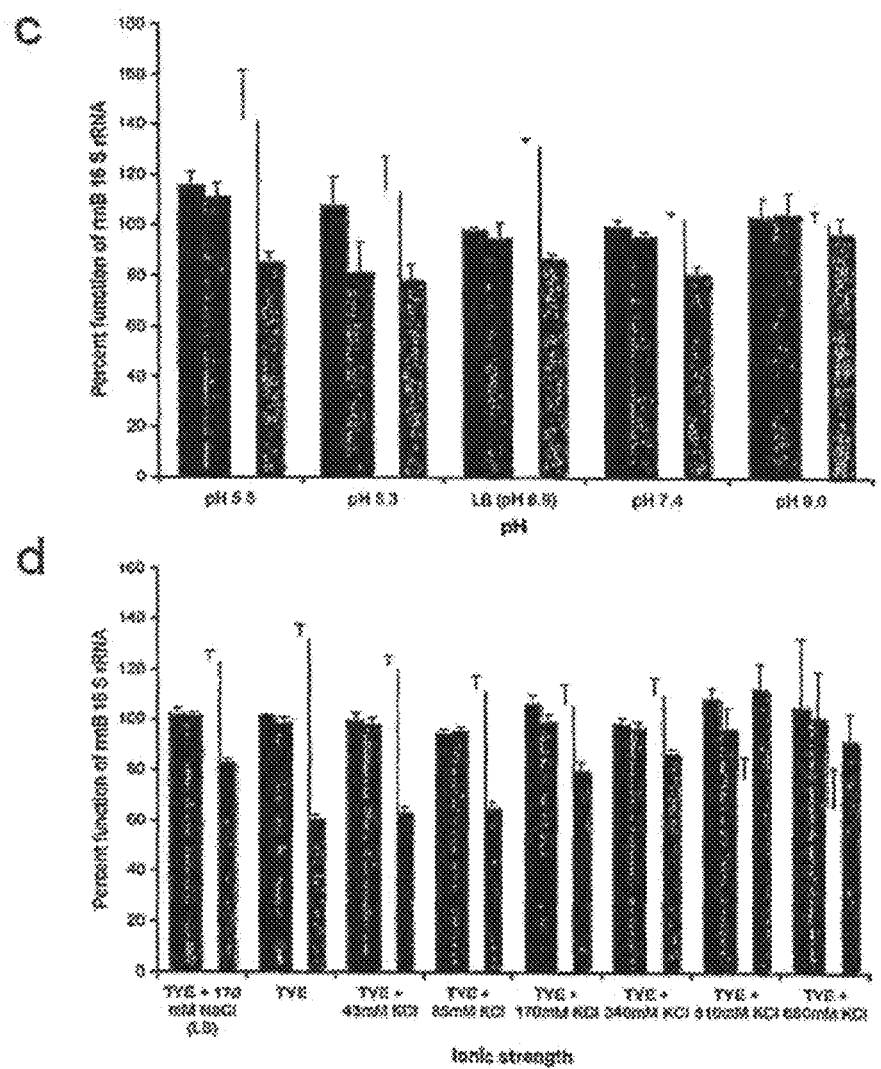
Fig. 2.2ii

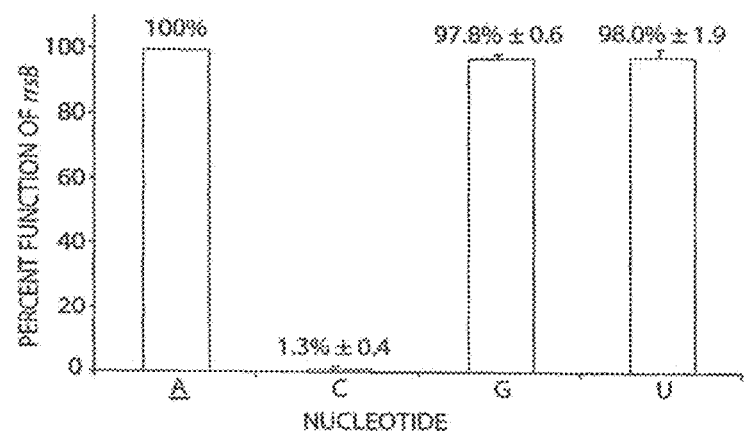
Fig. 2.3a
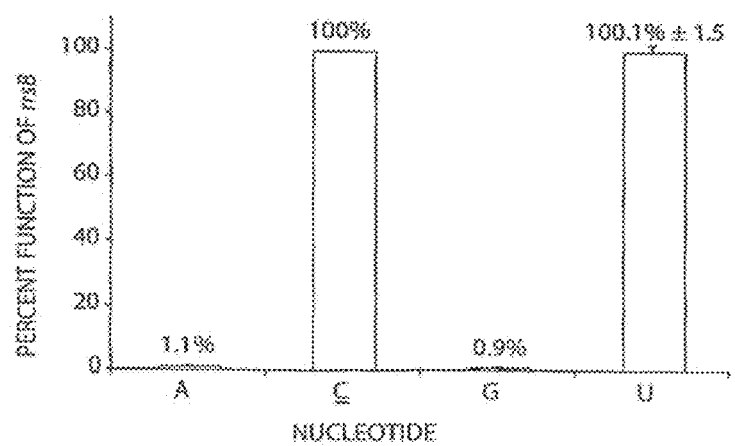
Fig. 2.3b

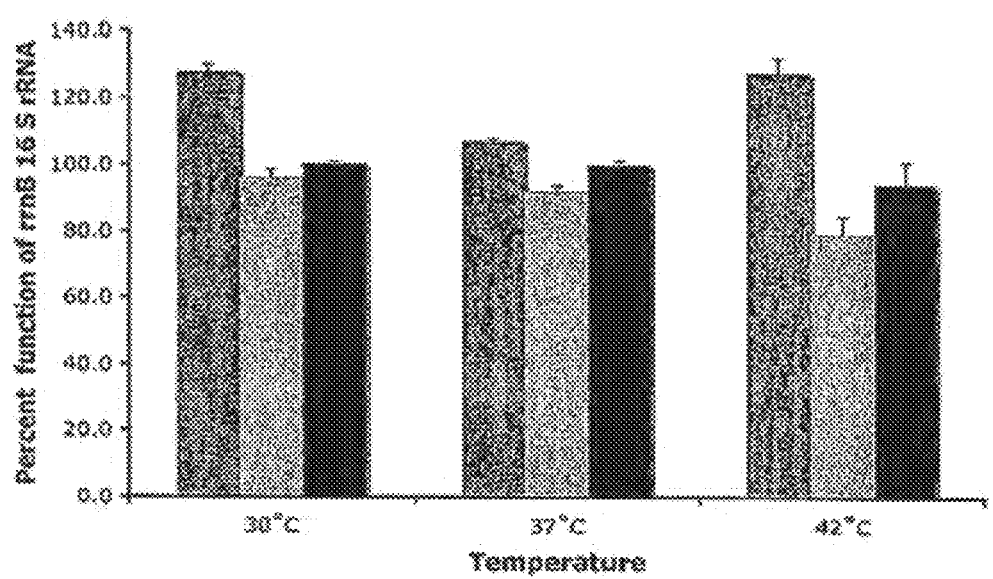
Fig. 2.4

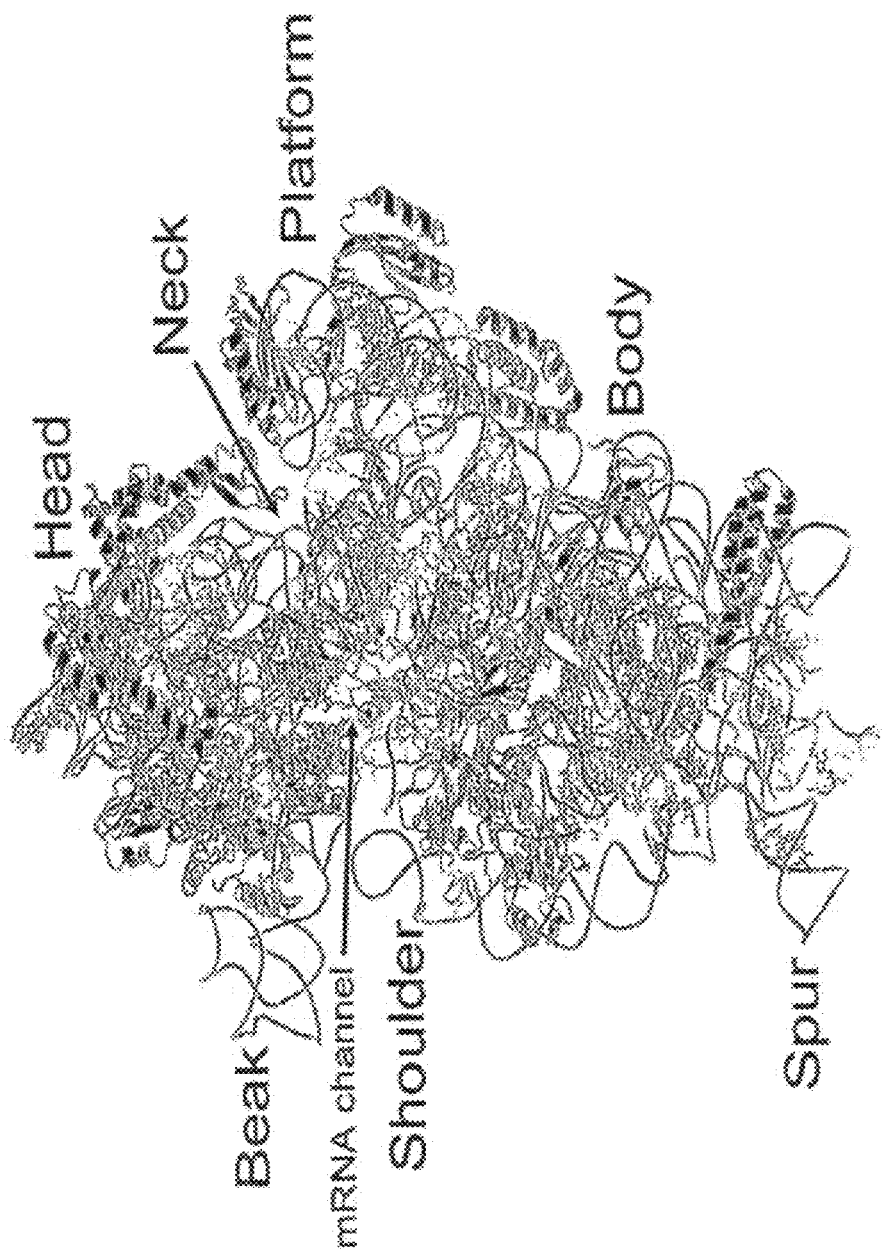

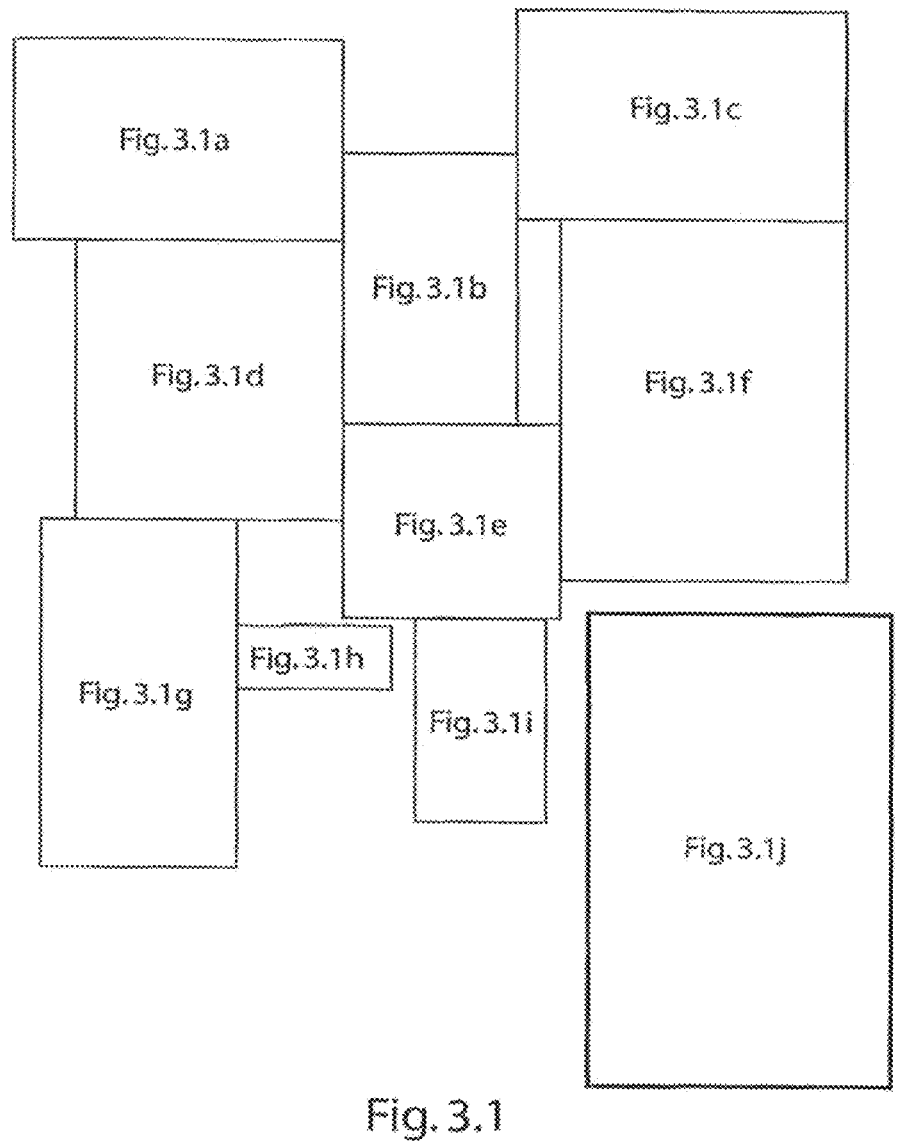
Fig. 3.1

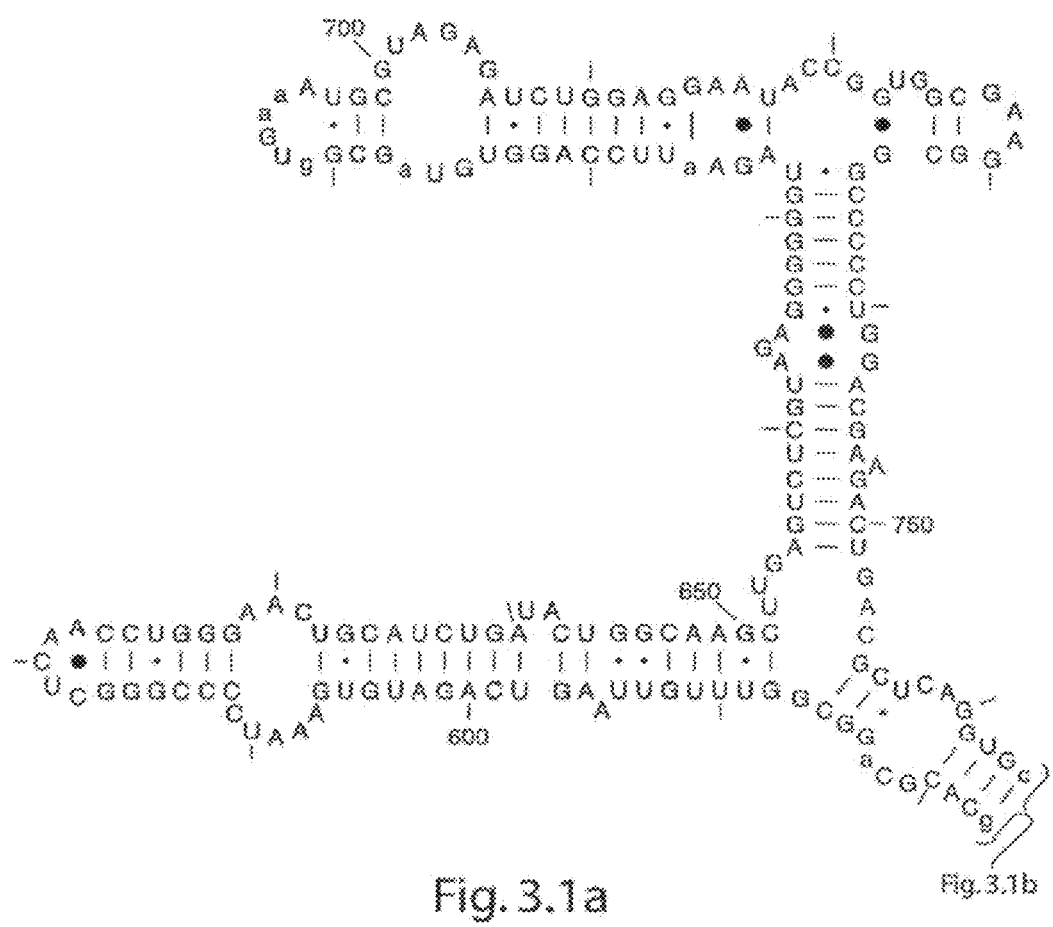
Fig. 3.1a  Fig. 3.1b

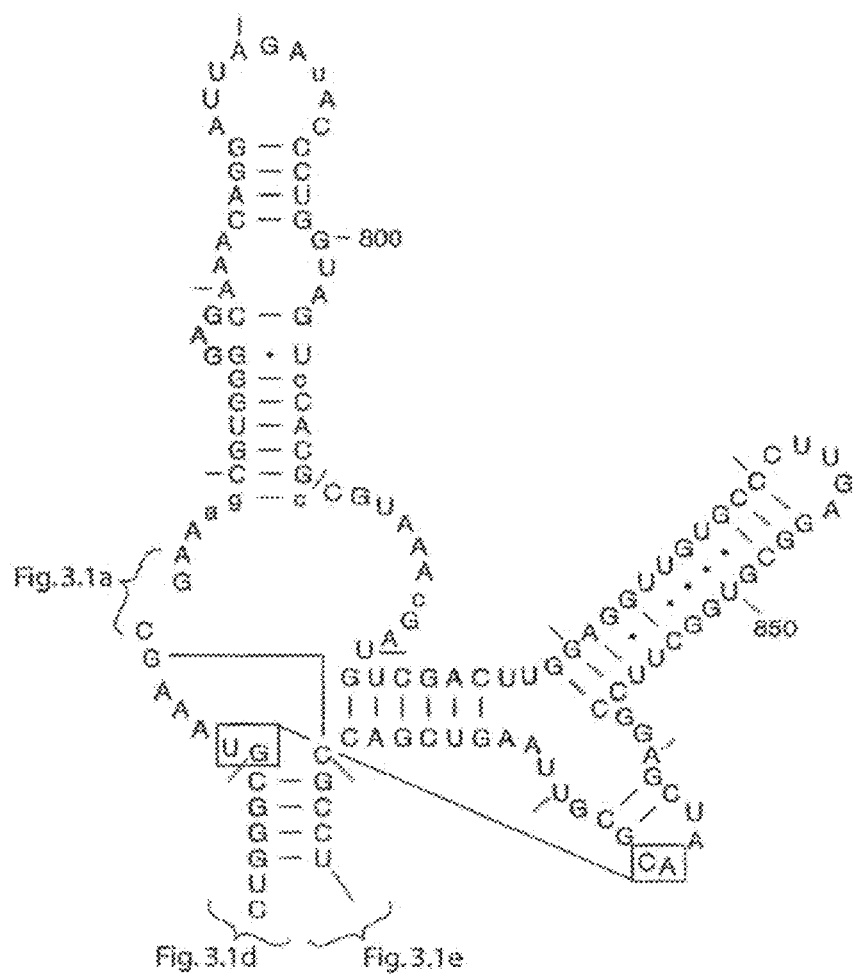
Fig. 3.1b

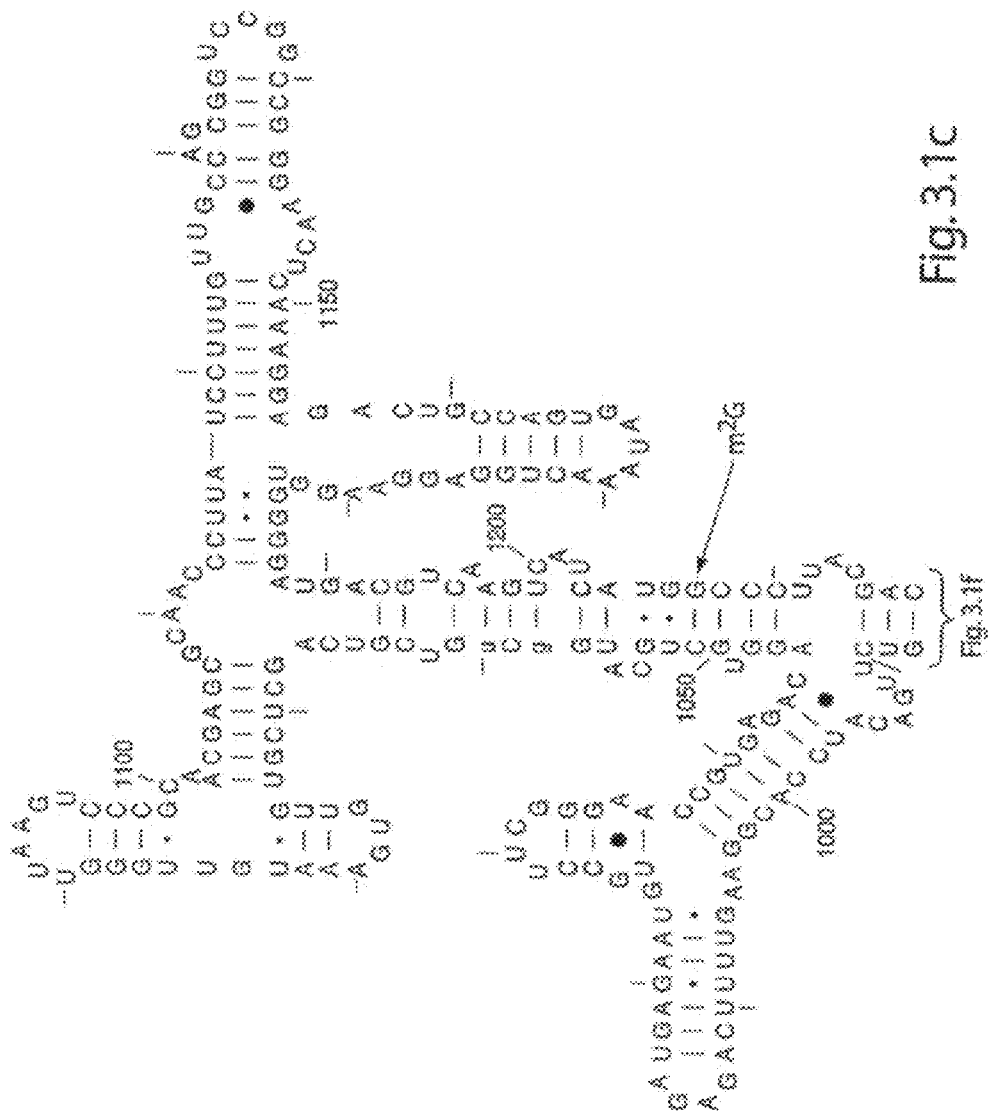
Fig.3.1c

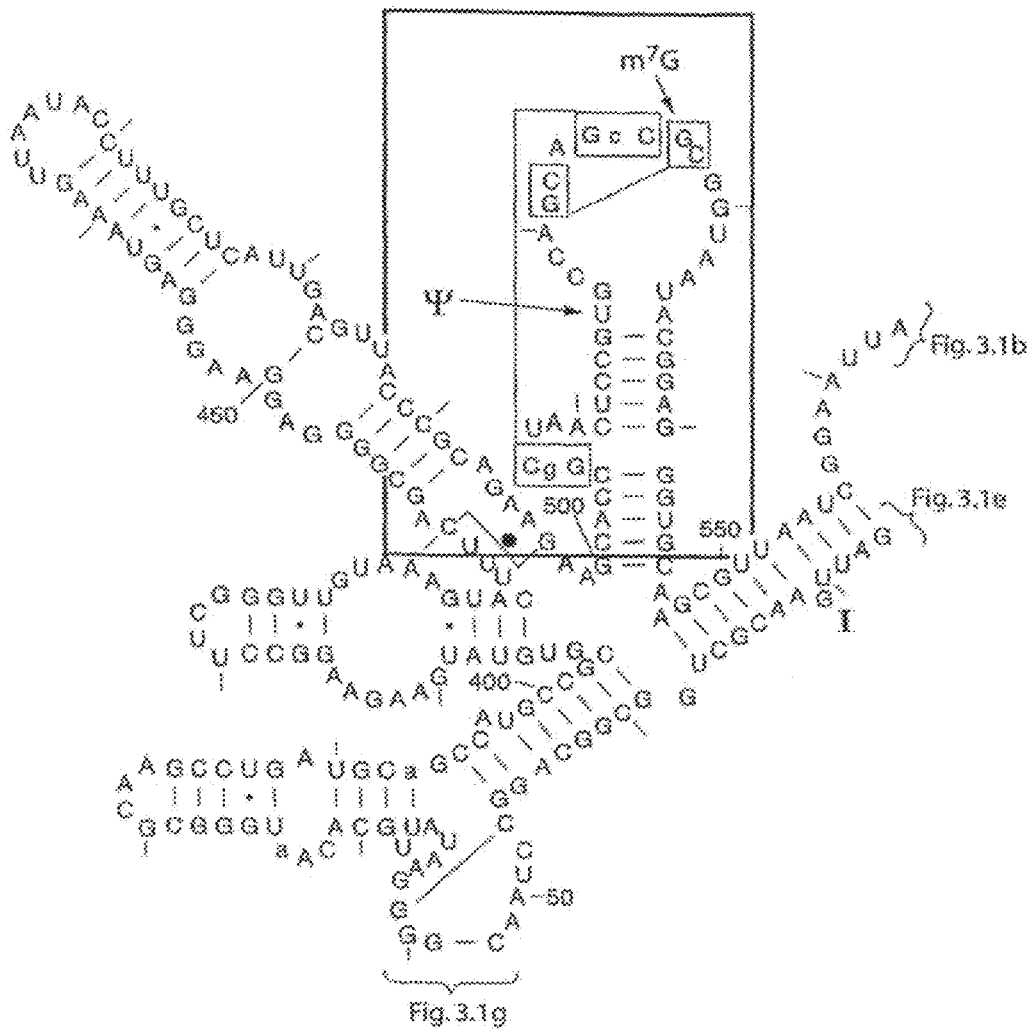
Fig. 3.1d

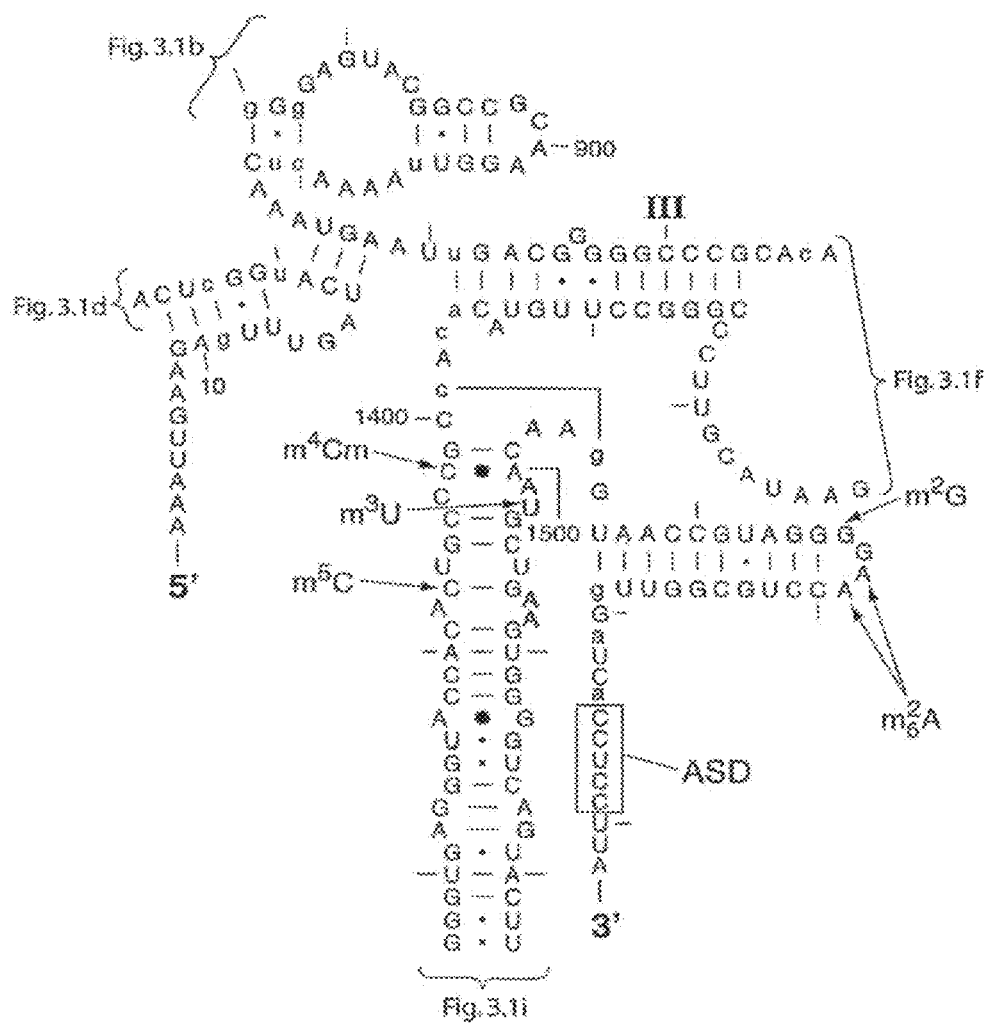
Fig. 3.1e

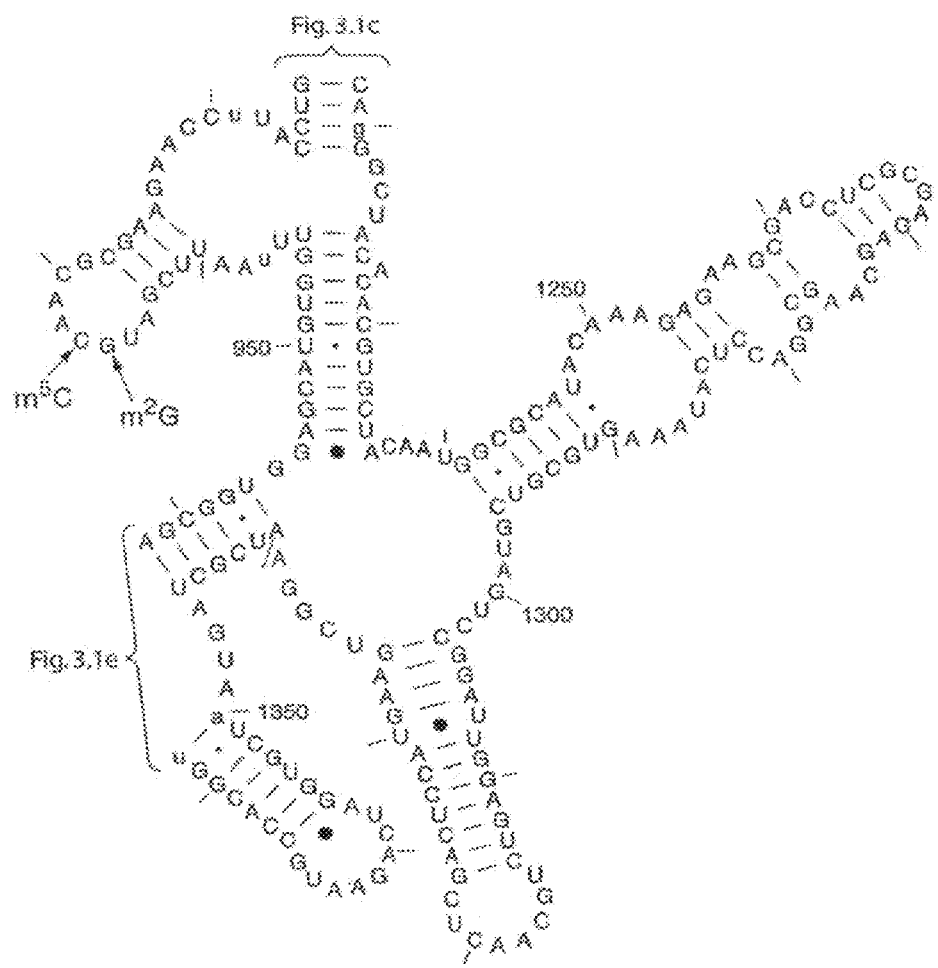
Fig.3.1f

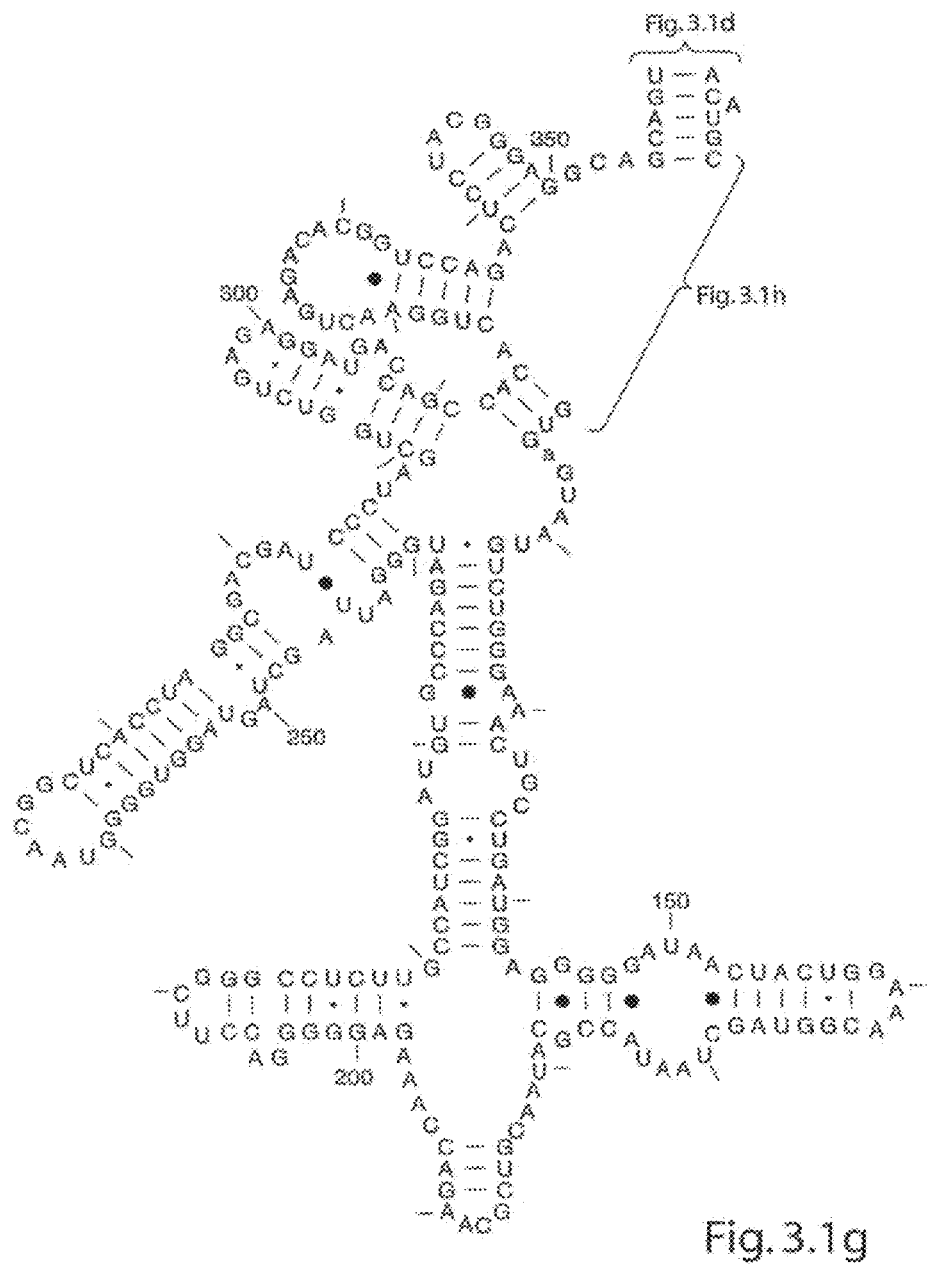
Fig. 3.1g

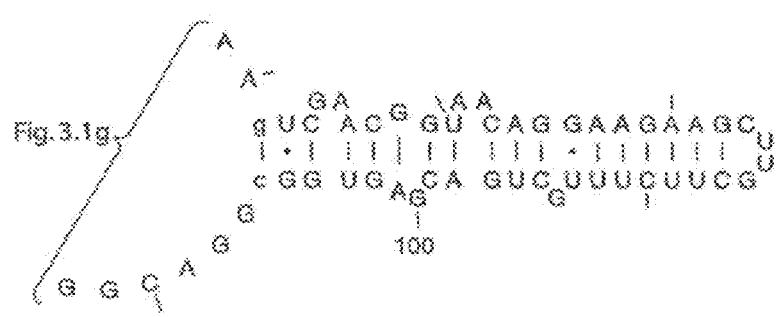
Fig. 3.1h

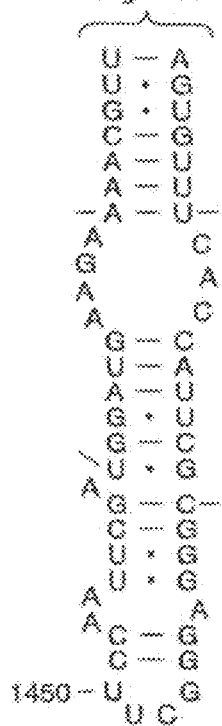
Fig.3.1i

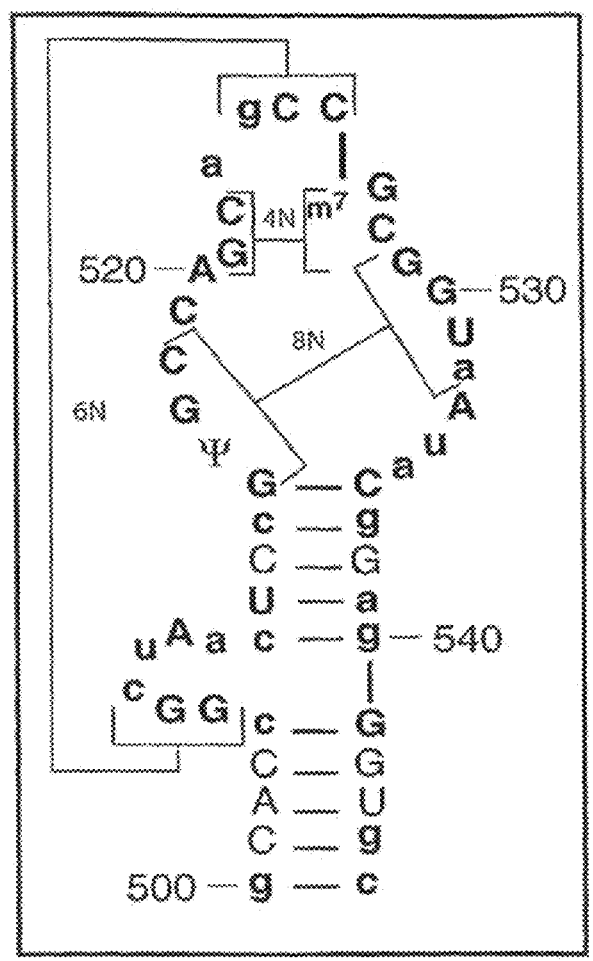
Fig.3.1j

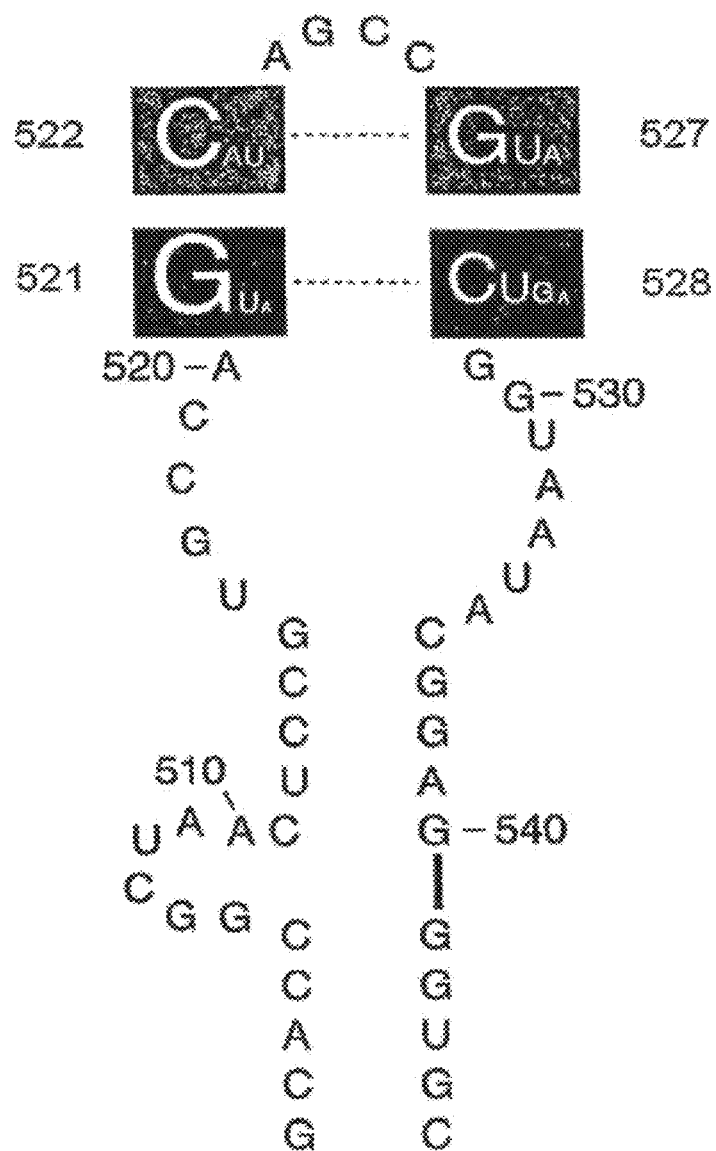
Fig. 3.2

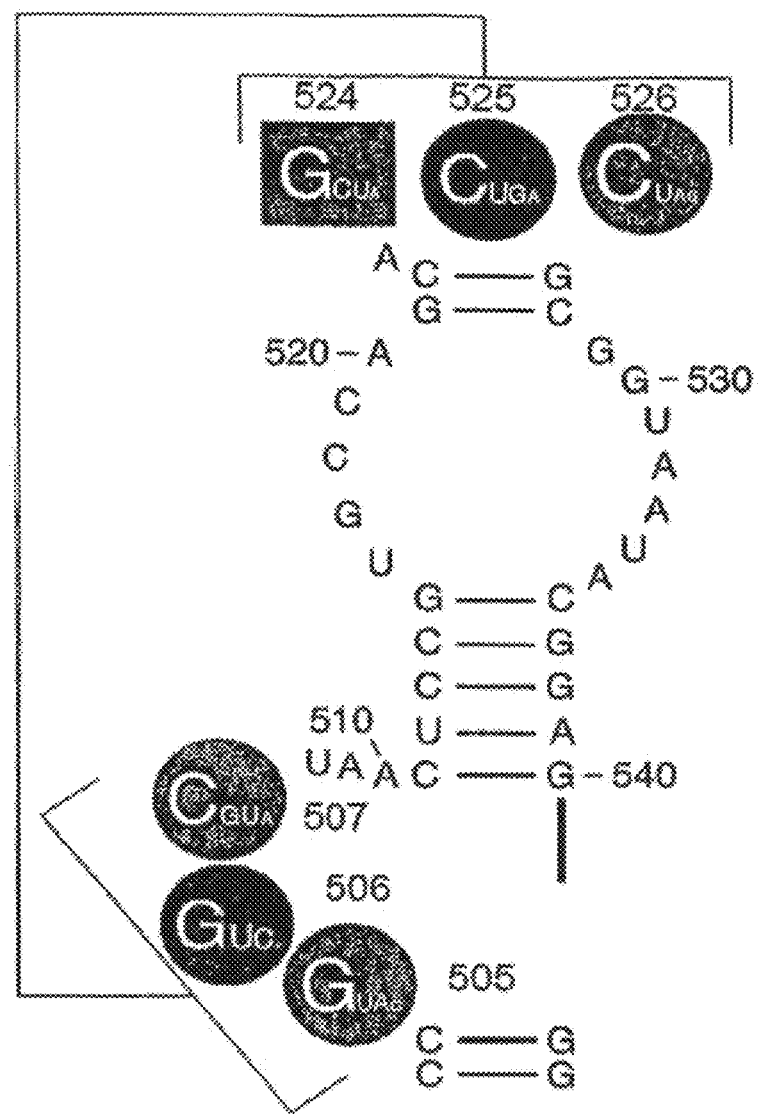
Fig. 3.3

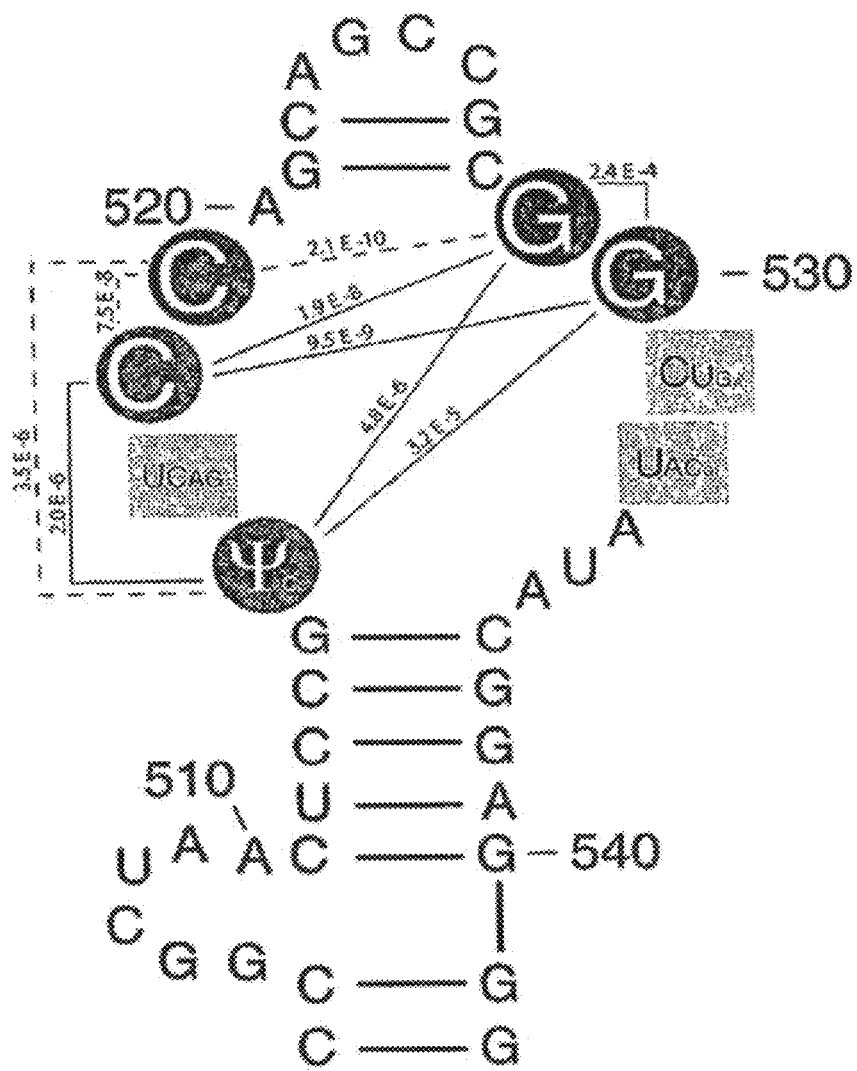
Fig. 3.4

Table 3.1a. Sequence and function of the functional 530 loop 4N mutants

| Sequence number | Nucleotide sequence[a] | | | | Number of mutations[b] | MIC[c] |
|---|---|---|---|---|---|---|
| | 521 | 522 | 527 | 528 | | |
| WT[d] | G | C | m$^7$G | C | | 700 |
| 1 | G | A | U | U | 3 | 750 |
| 2 | G | U | A | C | 2 | 750 |
| 3 | G | A | U | C | 2 | 700 |
| 4 | U | C | m$^7$G | A | 2 | 700 |
| 5 | G | U | m$^7$G | C | 1 | 700 |
| 6 | A | C | m$^7$G | U | 2 | 700 |
| 7 | G | C | m$^7$G | G | 1 | 600 |
| 8 | G | C | m$^7$G | U | 1 | 400 |
| 9 | U | C | A | G | 3 | 400 |
| 10 | G | C | U | C | 1 | 200 | a Sequence of isolated 4N mutants. Mutations are bold and underlined.
b The number of muatations in each sequence.
c The minimum inhibitory concentration of chloramphenicol in μg/ml.
d The wild-type sequence.

Fig. 3.5a

Table 3.1b. Sequence and function of the 530 loop 6N mutants

| Sequence number | Nucleotide sequence[a] | | | | | | Number of mutations[b] | MIC[c] |
|---|---|---|---|---|---|---|---|---|
| | 505 | 506 | 507 | 524 | 525 | 526 | | |
| WT[d] | G | G | C | G | C | C | | 750 |
| 1 | G | G | C | U | C | C | 1 | 750 |
| 2 | G | G | A | G | C | C | 1 | 750 |
| 3 | U | U | C | G | A | A | 4 | 750 |
| 4 | G | C | C | G | G | C | 2 | 750 |
| 5 | A | G | C | G | C | C | 1 | 700 |
| 6 | G | C | G | C | G | C | 4 | 700 |
| 7 | G | U | A | U | A | C | 4 | 700 |
| 8 | G | U | C | G | U | C | 2 | 700 |
| 9 | G | C | A | U | G | C | 4 | 700 |
| 10 | G | G | U | U | C | C | 2 | 700 |
| 11 | G | U | U | G | C | C | 1 | 650 |
| 12 | G | G | C | G | C | A | 1 | 650 |
| 13 | A | G | G | G | C | C | 2 | 650 |
| 14 | G | G | C | G | G | C | 1 | 600 |
| 15 | G | G | C | U | C | C | 1 | 600 |
| 16 | U | C | C | G | G | A | 4 | 600 |
| 17 | G | U | G | U | U | C | 4 | 600 |
| 18 | G | G | U | G | C | C | 1 | 600 |
| 19 | U | G | C | G | C | C | 1 | 550 |
| 20 | C | G | G | C | C | G | 4 | 550 |
| 21 | A | G | G | U | C | U | 4 | 550 |
| 22 | G | A | A | U | U | C | 4 | 550 |
| 23 | G | C | U | G | C | C | 2 | 500 |
| 24 | G | G | C | C | U | U | 3 | 500 |
| 25 | G | C | G | U | G | C | 4 | 500 |
| 26 | C | G | C | G | C | U | 2 | 500 |
| 27 | C | G | C | G | C | A | 2 | 450 |
| 28 | A | U | C | G | A | U | 4 | 450 |
| 29 | A | C | G | C | G | U | 6 | 450 |
| 30 | U | U | C | G | C | C | 2 | 450 |
| 31 | C | G | A | G | C | G | 3 | 400 |
| 32 | A | G | U | A | C | U | 4 | 400 |
| 33 | U | U | C | A | A | G | 5 | 400 |
| 34 | G | C | C | G | U | C | 2 | 400 |
| 35 | G | G | G | U | U | C | 3 | 300 |
| 36 | G | A | U | U | U | C | 4 | 200 |
| 37 | U | C | U | A | G | A | 6 | 200 |
| 38 | A | U | C | A | U | G | 5 | 200 |
| 39 | U | G | C | G | C | U | 2 | 200 |

[a–d] Same as in Table 3.1a

Fig. 3.5b

Table 3.1c. Sequence and function of 530 loop 8N mutants

| Sequence number | Nucleotide Sequence[a] | | | | | | | | Number of mutations[b] | Number of replicants[c] | MIC[d] |
|---|---|---|---|---|---|---|---|---|---|---|---|
| | 516 | 517 | 518 | 519 | ... 528 | 530 | 531 | 532 | | | |
| WT[d] | U | G | C | C | G | G | U | A | | 1 | 700 |
| 1 | U | U | C | C | G | G | A | U | 3 | | 800 |
| 2 | U | G | C | C | G | G | U | G | 1 | | 800 |
| 3 | U | G | C | C | G | C | G | A | 2 | | 800 |
| 4 | C | U | C | C | G | G | U | A | 2 | | 750 |
| 5 | U | G | C | C | G | U | U | C | 2 | | 750 |
| 6 | U | U | C | C | G | G | C | U | 3 | 2 | 750 |
| 7 | U | G | C | C | G | G | C | A | 1 | | 750 |
| 8 | U | U | C | C | G | G | U | C | 2 | 3 | 750 |
| 9 | U | C | C | C | G | G | U | A | 1 | 2 | 750 |
| 10 | U | G | C | C | G | G | U | U | 1 | | 750 |
| 11 | U | C | C | C | G | G | A | A | 2 | | 700 |
| 12 | C | U | C | C | G | G | U | G | 3 | 1 | 700 |
| 13 | U | G | C | C | G | G | A | C | 2 | | 700 |
| 14 | U | A | C | C | G | G | U | A | 1 | | 700 |
| 15 | U | C | C | C | G | G | C | G | 3 | 1 | 700 |
| 16 | U | U | C | C | G | G | C | G | 3 | | 700 |
| 17 | U | A | C | C | G | G | C | A | 2 | | 700 |
| 18 | C | G | C | C | G | G | U | U | 2 | | 700 |
| 19 | C | U | C | C | G | G | C | G | 4 | | 700 |
| 20 | U | G | C | C | G | C | U | A | 1 | | 700 |
| 21 | U | A | C | C | C | G | G | A | 3 | | 650 |
| 22 | U | C | C | C | G | G | A | U | 3 | 1 | 650 |
| 23 | U | U | C | C | G | G | U | U | 2 | | 650 |
| 24 | C | C | C | C | G | G | C | U | 4 | | 650 |
| 25 | U | G | C | C | G | G | C | G | 2 | | 650 |
| 26 | U | A | C | C | G | G | G | A | 2 | 1 | 650 |
| 27 | U | A | C | C | G | G | G | G | 3 | | 600 |
| 28 | U | A | C | C | G | G | C | G | 3 | | 600 |
| 29 | U | U | C | C | G | G | U | A | 1 | | 600 |
| 30 | G | C | C | C | G | G | U | A | 2 | | 600 |
| 31 | U | G | A | C | G | G | U | A | 1 | | 600 |
| 32 | U | A | C | C | G | G | C | U | 3 | 4 | 600 |
| 33 | U | A | C | C | G | C | U | C | 3 | | 600 | continued

Fig. 3.5c-1 continued

| Sequence number | Nucleotide Sequence[a] | | | | | | | | Number of mutations[b] | Number of replicants[e] | MIC[c] |
|---|---|---|---|---|---|---|---|---|---|---|---|
| | 516 | 517 | 518 | 519 | ... | 529 | 530 | 531 | 532 | | | |
| 34 | U | A | C | C | G | G | G | C | 3 | | 600 |
| 35 | U | G | G | C | C | U | C | U | 5 | | 600 |
| 36 | U | U | C | C | G | G | G | G | 3 | | 600 |
| 37 | C | U | C | C | G | G | G | U | 4 | 1 | 550 |
| 38 | C | G | C | C | G | G | G | C | 3 | | 550 |
| 39 | C | G | C | C | G | G | A | A | 2 | | 550 |
| 40 | U | C | C | C | G | G | G | A | 2 | | 500 |
| 41 | U | C | C | C | G | G | U | U | 2 | | 500 |
| 42 | C | U | C | C | G | G | U | C | 3 | | 500 |
| 43 | U | G | C | C | G | G | G | A | 1 | 1 | 500 |
| 44 | U | C | C | C | G | G | C | U | 3 | 3 | 500 |
| 45 | C | U | C | C | G | G | G | C | 4 | | 500 |
| 46 | C | U | C | C | G | G | C | U | 4 | 1 | 500 |
| 47 | U | A | C | C | G | G | U | U | 2 | | 450 |
| 48 | U | C | C | C | G | C | A | C | 4 | | 450 |
| 49 | U | C | C | C | G | C | C | U | 4 | | 450 |
| 50 | C | U | C | C | G | G | G | A | 3 | | 400 |
| 51 | C | G | C | C | G | G | C | U | 3 | | 400 |
| 52 | G | U | C | C | G | G | C | A | 3 | | 400 |
| 53 | U | A | C | C | G | G | G | U | 3 | | 400 |
| 54 | U | U | C | C | G | G | G | C | 3 | | 350 |
| 55 | U | C | C | C | G | G | C | C | 3 | 2 | 350 |
| 56 | U | C | C | C | G | G | U | C | 2 | | 350 |
| 57 | G | G | C | C | G | G | U | A | 1 | | 200 |
| 57 | G | G | C | C | G | G | U | A | 1 | | 200 |
| 58 | A | A | G | G | U | U | C | U | 8 | | 100 |
| 59 | A | A | U | G | C | U | C | U | 8 | | 100 |
| 60 | U | A | C | C | C | C | A | C | 5 | | 100 |
| 61 | A | A | C | G | A | G | C | U | 6 | | 100 |
| 62 | U | G | C | G | G | G | G | C | 3 | | 100 |
| 63 | A | C | G | C | C | U | A | C | 7 | | 100 |
| 64 | C | C | A | U | U | G | A | G | 7 | | 100 |
| 65 | C | U | C | C | G | A | C | U | 5 | | 100 |
| 66 | G | U | A | G | G | G | C | U | 6 | | 100 |

[a-d] Same as in Table 3.1a
[e] Number of times the sample was identified during the selection.

Fig. 3.5c-2

Table 3.2 Importance of base pairing in the 4N interaction.

| BASE PAIR / MISMATCH | | 521/528 | 522/527 |
|---|---|---|---|
| AU | # occurrence | 2 | 3 |
|  | percent | 18.2 | 27.3 |
| CG | # occurrence | 5 | 5 |
|  | percent | 45.5 | 45.5 |
| GU | # occurrence | 3 | 1 |
|  | percent | 27.3 | 9.1 |
| MISMATCH | # occurrence | 1 | 2 |
|  | percent | 9.1 | 18.2 |
| Chi-Squared P | | 0.036 * | 0.054 * |

Fig. 3.6

Table 3.3 Importance of base pairing in the 6N interaction

| COVARIATION[a] | | 505/526 | 506/525 | 507/524 |
|---|---|---|---|---|
| Chi-squaredP | | 1.19E-04 *** | 4.38E-08 *** | 5.85E-04 *** |

| base pair[b] | | 505/526 | 506/525 | 507/524 |
|---|---|---|---|---|
| AU | # occurrence[c] | 7 | 7 | 5 |
|  | % | 17.5 | 17.5 | 12.5 |
| CG | # occurrence | 22 | 23 | 22 |
|  | % | 55.0 | 57.5 | 55 |
| GU | # occurrence | 2 | 2 | 3 |
|  | % | 5.0 | 5.0 | 7.5 |
| MISMATCH | # occurrence | 9 | 8 | 10 |
|  | % | 22.5 | 20.0 | 25 |
| Chi-SquaredP | | 3.73E-11 *** | 3.73E-11 *** | 3.06E-02 *** |

[a] Covariation analysis between interacting positions
[b] Base pairs indentified between interacting positions in the selected pool
[c] Number of times the indicated base pair occurs between the two positions in the selected pool

Fig. 3.7

Table 3.5. Description and use of oligodeoxynucleotides

| Oligo | Sequence (5' to 3') | Used for |
|---|---|---|
| lac-L | TTGGATCCGGACACCATCGAATTGGTGCAAAACCT | Primer lac-L, 4N mutagenesis PCR outside upper primer |
| 16s-AvrII | ACGTCCAAGACCAAAGAGG | Primer 16s rRNA, 6N & 8N mutagenesis PCR outside upper primer |
| 16s- BglII | CTCTCAAATTTTCGCAACAC | Primer 16s rRNA, all mutagenesis PCR outside lower primer |
| 16s-537F | GGAAGGGTGCAAGCGTTAATCGGAA | Primer 16s rRNA, mutagenesis PCR inside |
| 530-4N | TTCCGATTAACGCTTGCACGTCCGTCGTATTACCNNGGCTNNNTGGCACGGAGTTAGCCGGTG | 530 region,4N mutagenesis PCR inside primer |
| 530-6N | TTCCGATTAACGCTTGCACCCTCCGTATTACCGCNNNTGCRGGCACGGAGTTANNNGGTGCTTCT | 530 region, 6N mutagenesis PCR inside primer |
| 530-8N | TTCCGATTAACGCTTGCACCCTCCGTATTACCGCGGCTGCTNNNNCGGAGTTAGCCGGTGCTTCTCTGCTTT | 530 region, 8N mutagenesis PCR inside primer |
| 16S 416F | GGGCCTTCGGGTTGTAAAGTA | Sequencing primer |
| 16S N527 | CTTGCACCCTCCGTATTACCGNGGCTGCTGGC | Mutation of position 527 |
| 16S N528 | CTTGCACCCTCCGTATTACCNCGGCTGCTGGC | Mutation of position 528 |
| 16S N530 | TTGCACCCTCCGTATTANCGCGGCTGCTGGCA | Mutation of position 530 |

Fig. 3.8

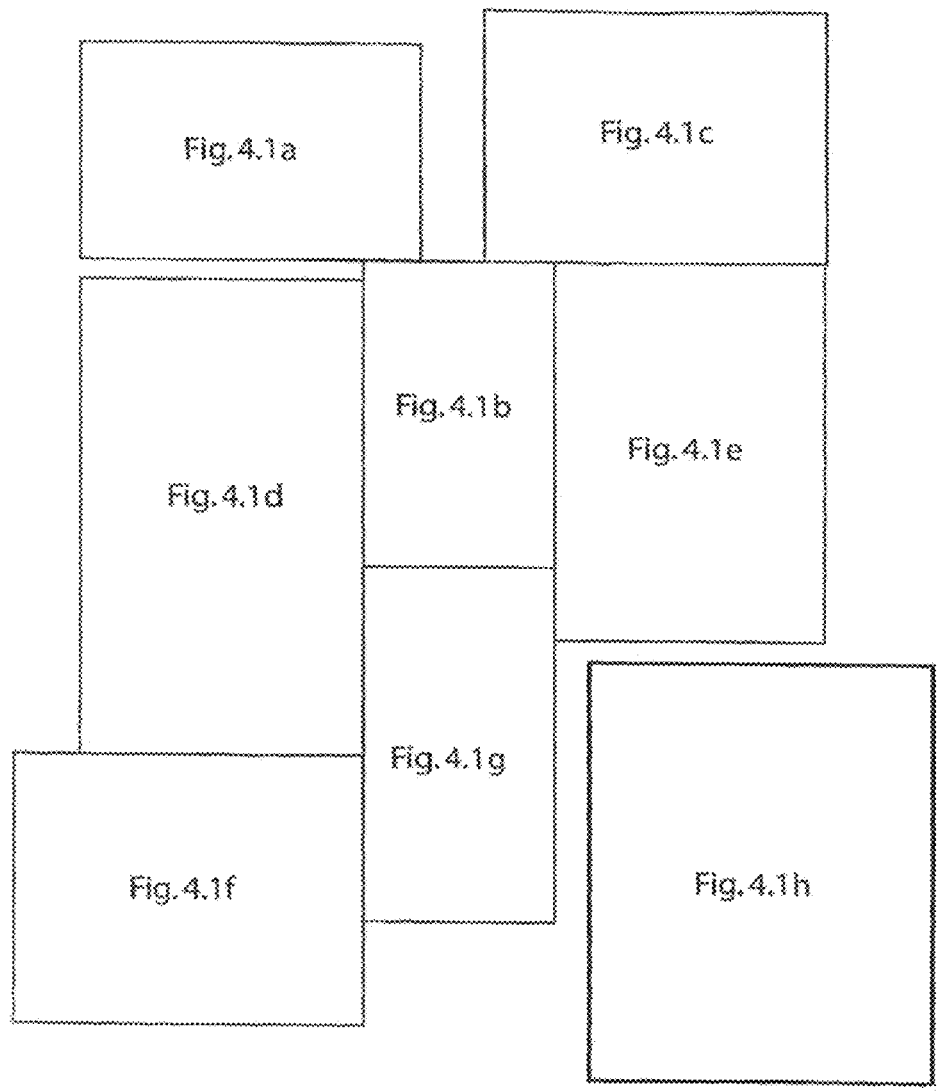
Fig. 4.1

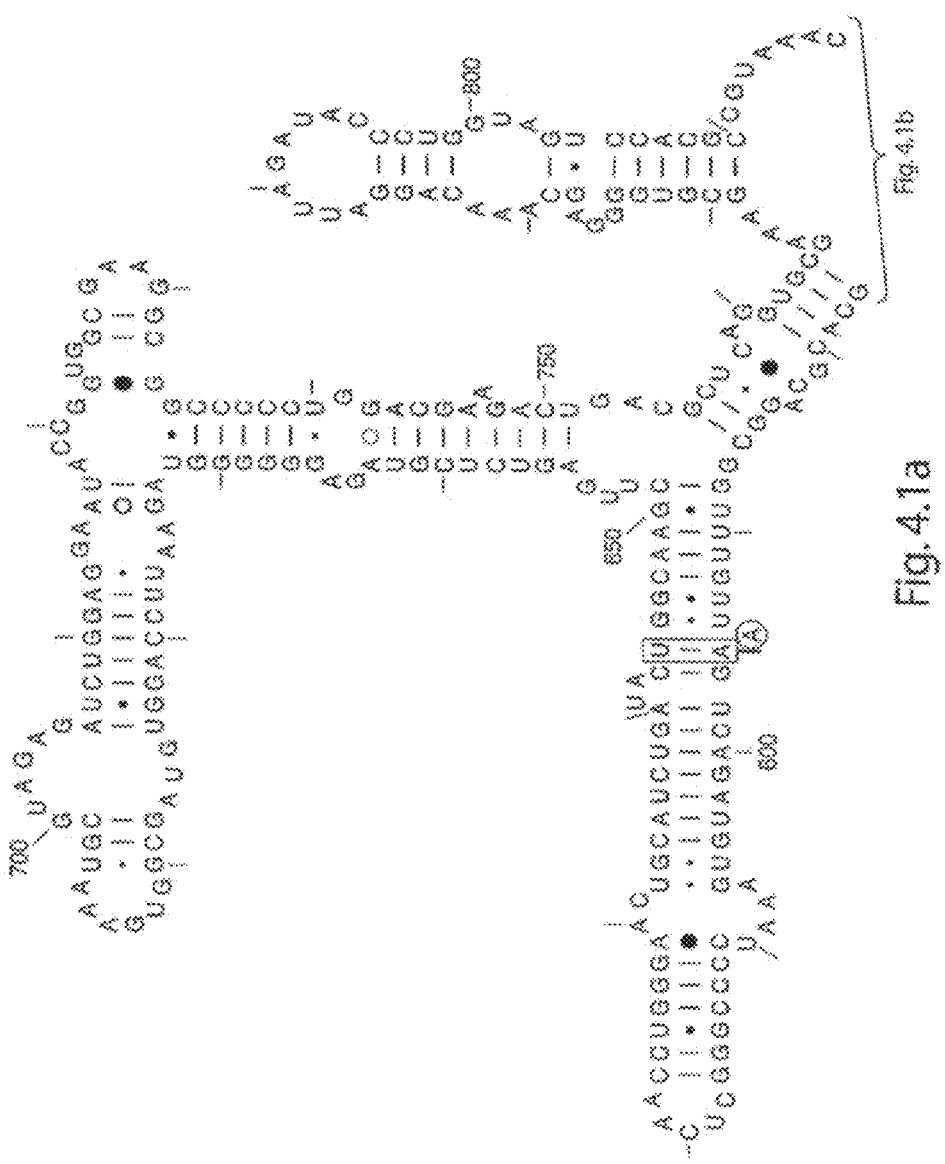

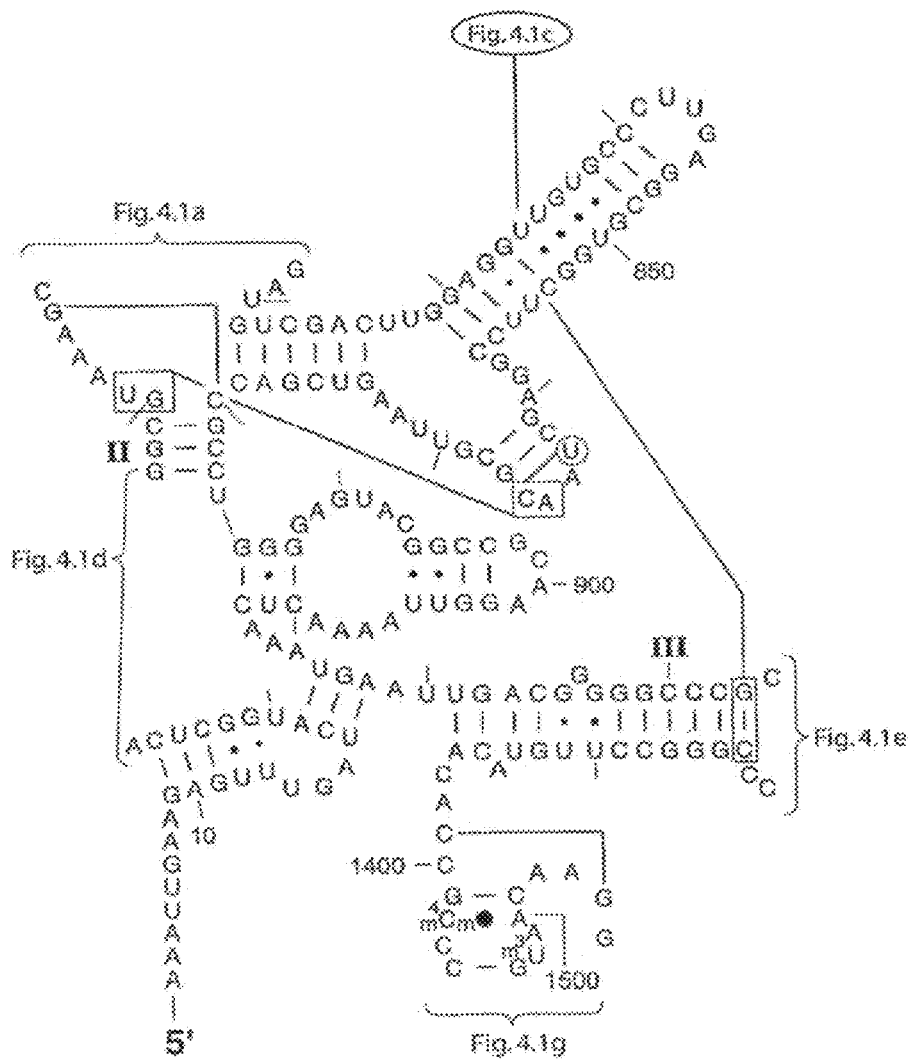
Fig. 4.1b

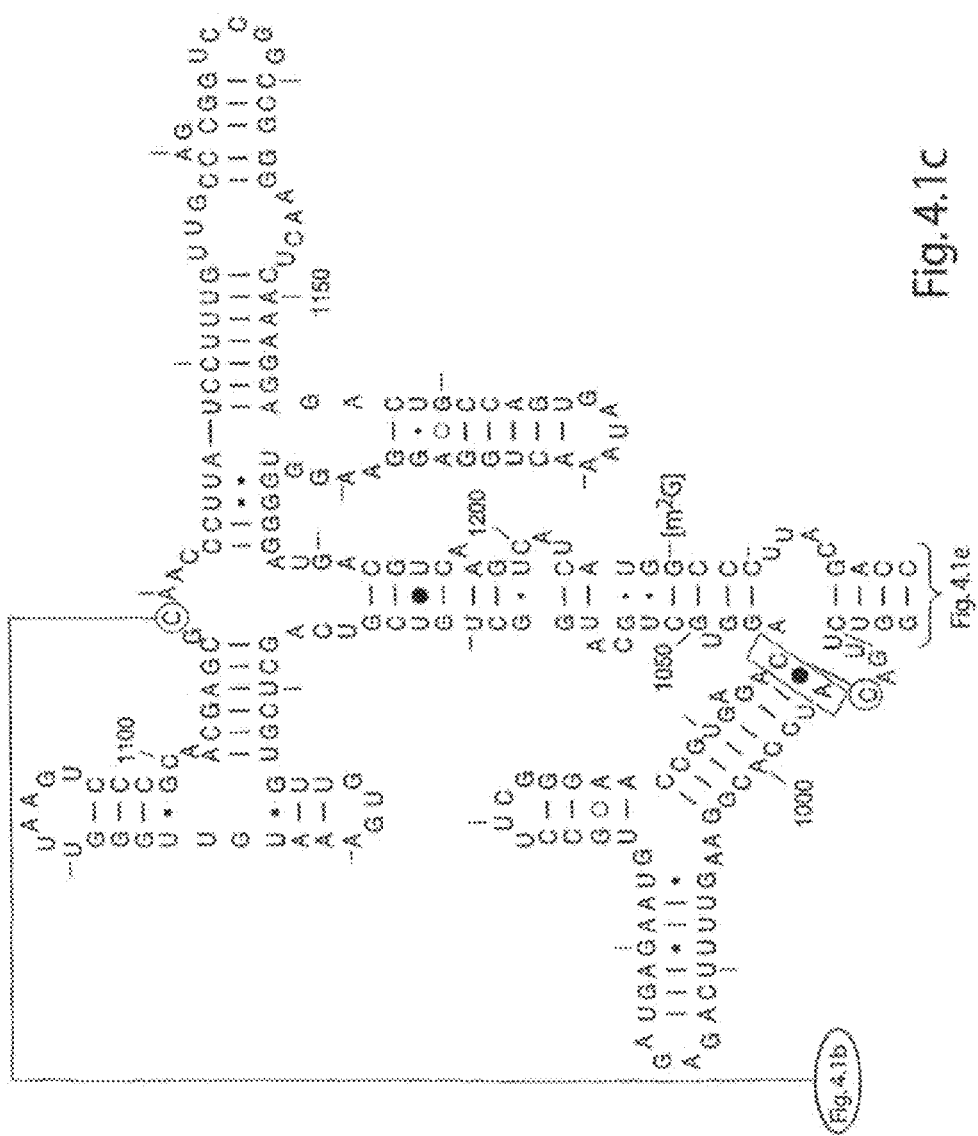
Fig.4.1c

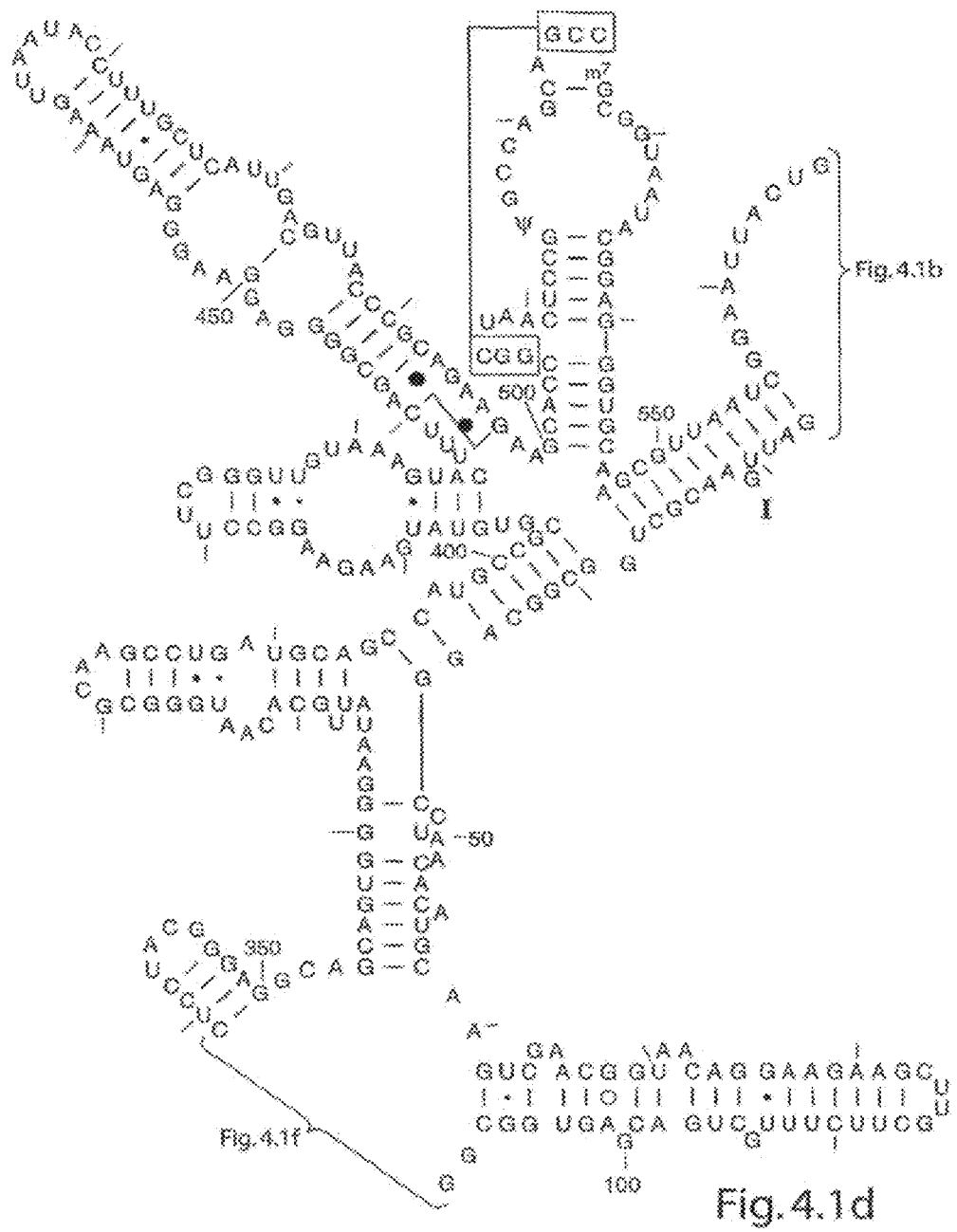
Fig. 4.1d

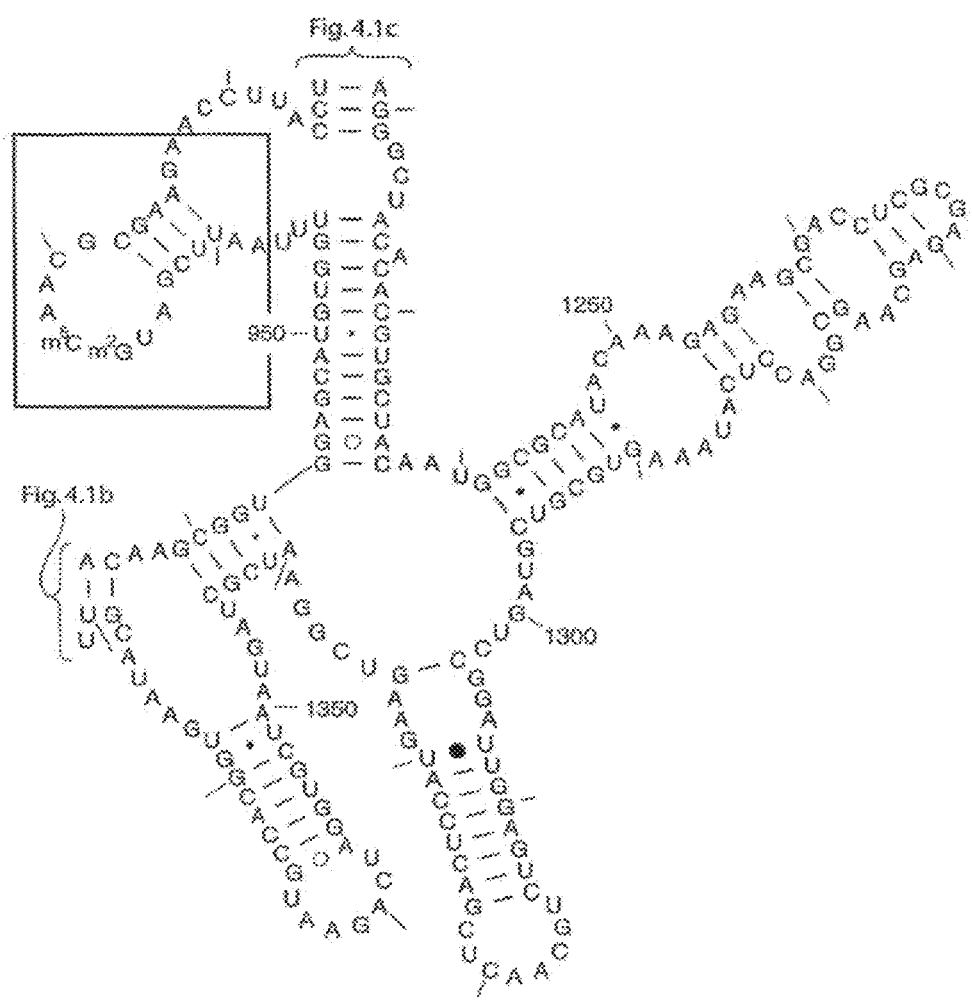
Fig.4.1e

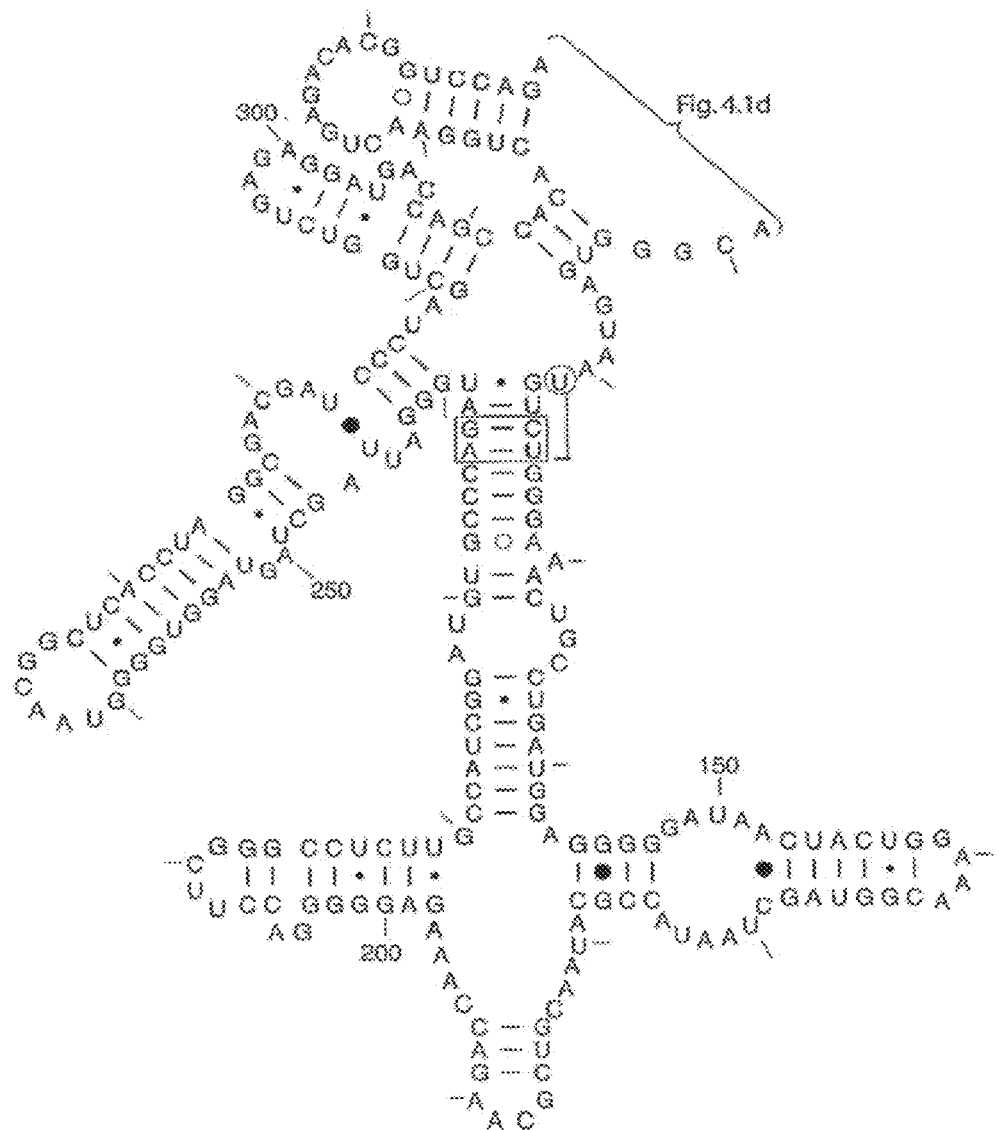
Fig.4.1f

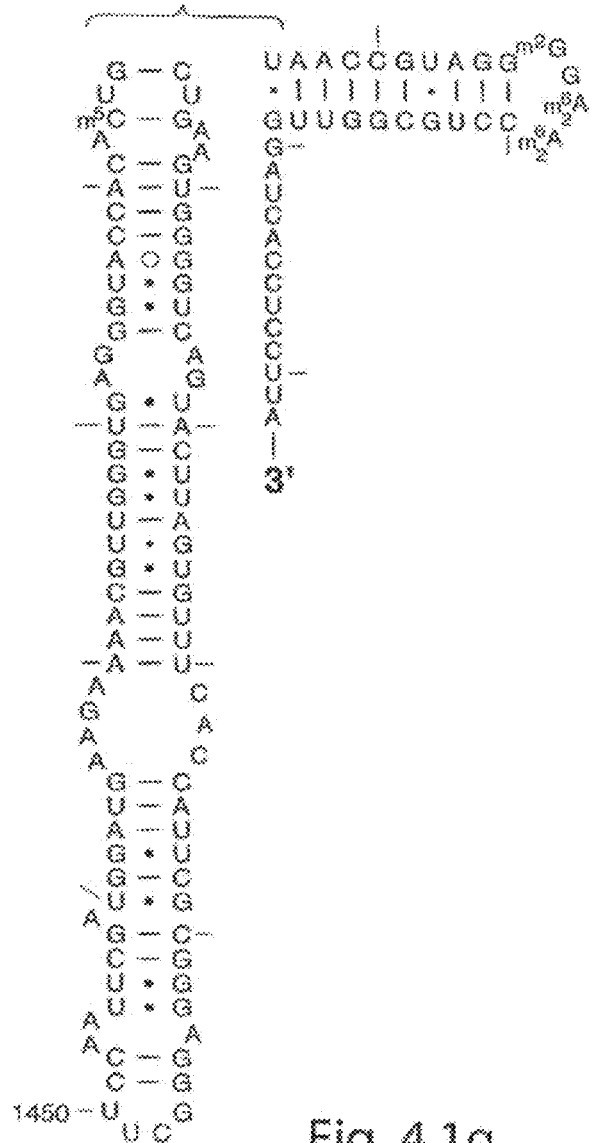
Fig. 4.1g

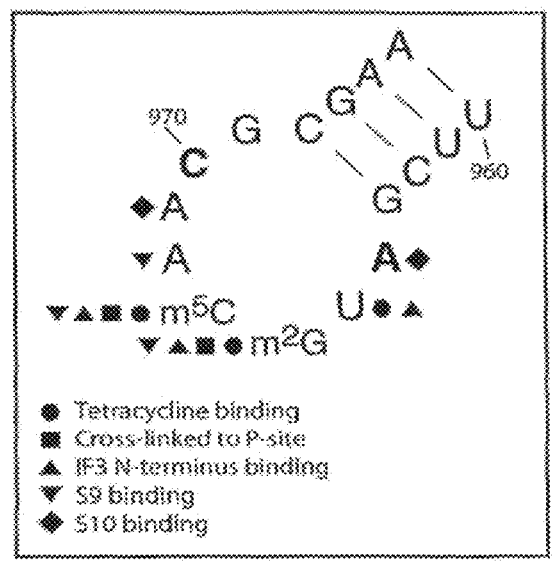
Fig.4.1h

| | A | C | G | U | Chi Test | Consensus |
|---|---|---|---|---|---|---|
| 964 | ● | · | | · | 1.5 x 10⁻⁵⁶ | A |
| 965 | · | ● | · | ● | 7.6 x 10⁻⁴⁰ | H |
| 966 | ● | · | ● | · | 5.2 x 10⁻²⁰ | R |
| 967 | ● | ● | · | · | 2.8 x 10⁻⁶ | M |
| 968 | · | · | · | ● | 3.4 x 10⁻³⁵ | H |
| 969 | ● | · | ● | · | 6.6 x 10⁻²³ | R |
| 970 | · | ● | · | · | 3.4 x 10⁻²⁰ | M |
| 971 | ● | ● | ● | · | 1.4 x 10⁻⁶ | V |

Fig. 4.2

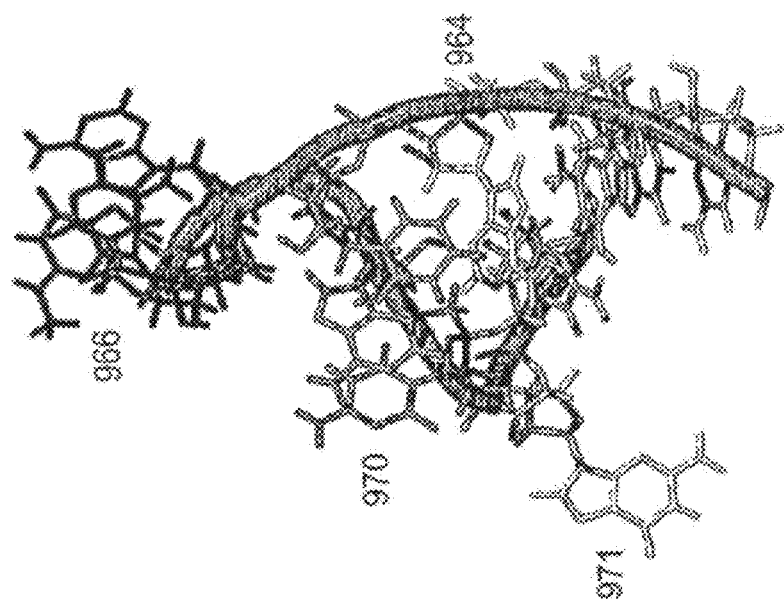
Fig. 4.3b
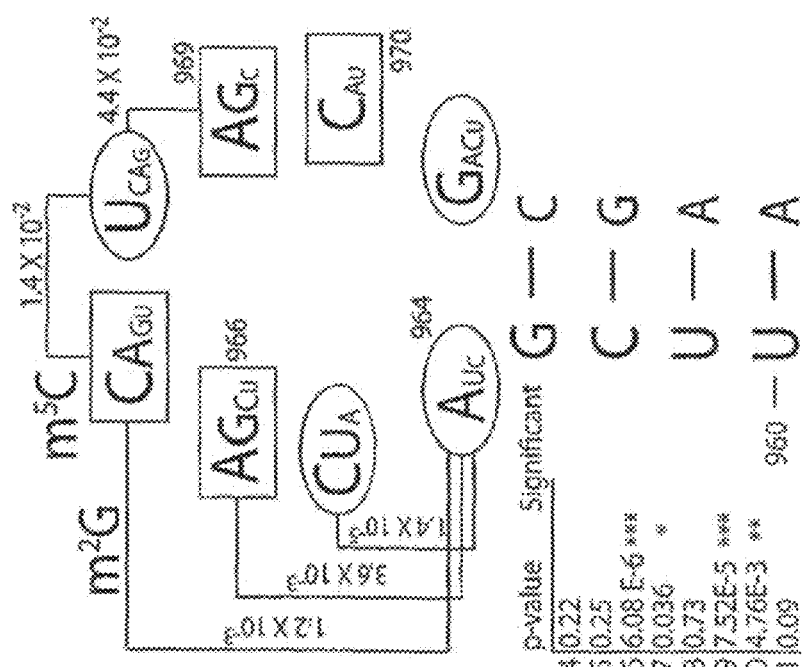
Fig. 4.3a

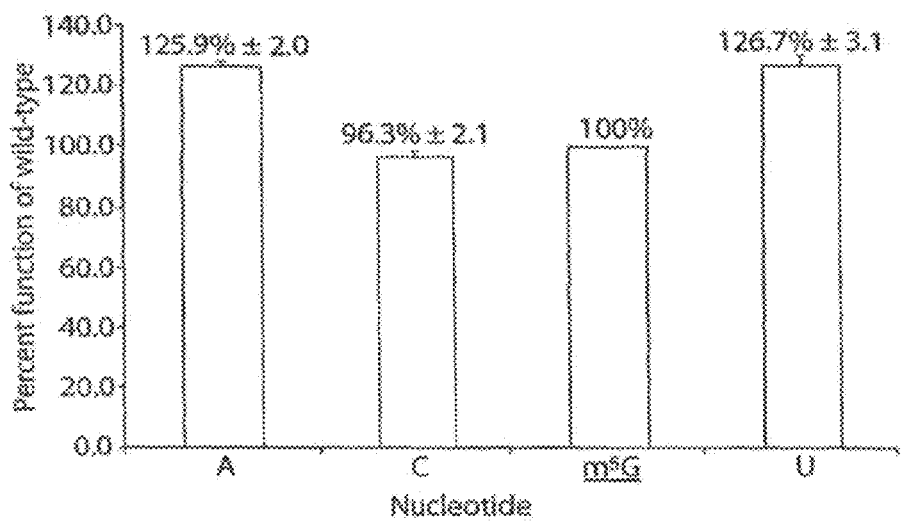
Fig. 4.4a
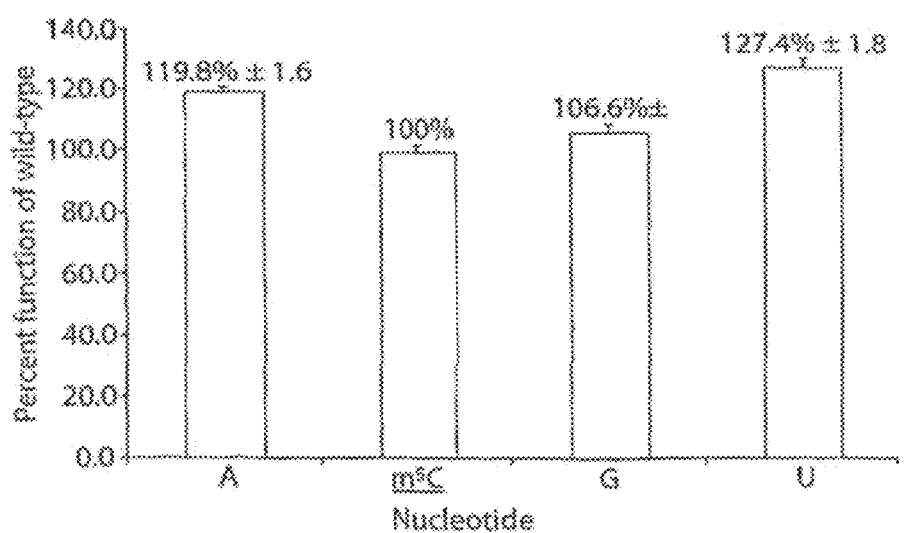
Fig. 4.4b

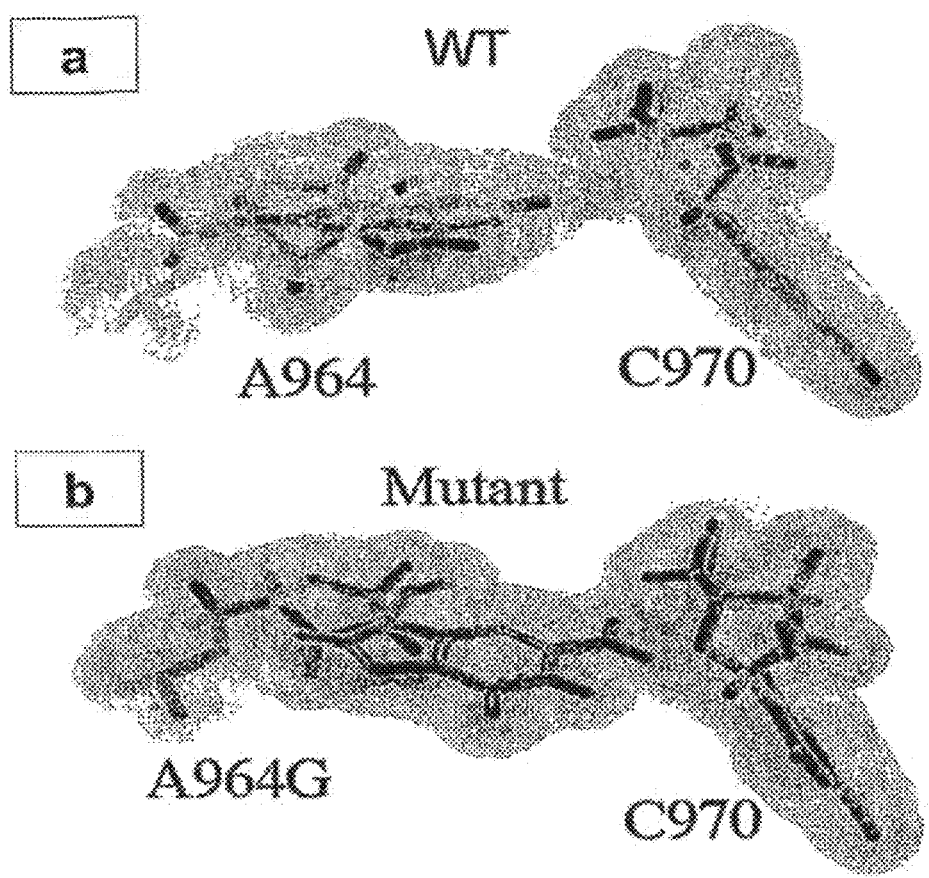
Fig. 4.5

Table 4.1. Sequences of functional 970 loop mutants.

| Samples | \multicolumn{8}{c|}{Sequences[b]} | Number of mutations[c] | Percent function[d] |
|---|---|---|---|---|---|---|---|---|---|
|  | 964 | 965 | 966 | 967 | 968 | 969 | 970 | 971 | | |
| WT[a] | A | U | G | C | A | A | C | G | 0 | 100 |
| 1 | A | U | G | A | A | A | C | G | 1 | 119.8 |
| 2 | A | U | G | C | A | A | C | U | 1 | 94.3 |
| 3 | A | C | G | A | U | A | C | G | 3 | 54.3 |
| 4 | U | C | G | C | U | A | A | C | 5 | 39.8 |
| 5 | A | U | G | C | U | A | A | C | 3 | 39.7 |
| 6 | A | U | G | A | U | A | C | G | 2 | 39.2 |
| 7 | A | U | G | C | G | G | C | G | 2 | 38.1 |
| 8 | A | U | C | A | C | A | C | G | 3 | 37.3 |
| 9 | A | C | G | A | A | A | C | A | 3 | 36.1 |
| 10 | A | U | A | A | U | G | C | G | 4 | 34.9 |
| 11 | A | U | G | C | C | A | C | A | 2 | 34.4 |
| 12 | A | G | G | G | A | G | A | A | 5 | 34.3 |
| 13 | A | U | G | C | C | A | C | C | 2 | 34.3 |
| 14 | A | U | C | G | A | G | G | G | 4 | 34.2 |
| 15 | A | C | G | C | G | A | C | G | 2 | 33.7 |
| 16 | A | U | A | A | U | G | C | C | 5 | 32.2 |
| 17 | A | C | G | C | C | G | C | G | 3 | 32.0 |
| 18 | A | A | G | C | G | G | C | G | 3 | 31.6 |
| 19 | A | A | A | C | U | A | C | G | 3 | 31.5 |
| 20 | A | C | A | A | U | A | C | C | 5 | 31.4 |
| 21 | U | C | G | U | U | A | C | A | 5 | 30.7 |
| 22 | U | C | G | C | U | A | C | C | 4 | 30.0 | continued

Fig. 4.6a-1 continued

| Samples | Sequences[b] | | | | | | | | Number of mutations[c] | Percent function[d] |
|---|---|---|---|---|---|---|---|---|---|---|
| | 964 | 965 | 966 | 967 | 968 | 969 | 970 | 971 | | |
| 23 | A | C | G | A | U | A | C | U | 4 | 29.8 |
| 24 | A | C | A | A | U | A | C | C | 5 | 29.7 |
| 25 | A | A | G | G | U | G | C | G | 4 | 29.7 |
| 26 | A | A | G | U | U | A | C | C | 4 | 28.9 |
| 27 | A | C | G | G | U | A | C | C | 4 | 28.7 |
| 28 | A | U | A | A | U | A | C | A | 4 | 28.5 |
| 29 | A | C | A | A | C | A | C | G | 4 | 28.3 |
| 30 | A | C | A | A | U | A | A | G | 5 | 28.1 |
| 31 | A | C | A | G | U | A | A | G | 5 | 27.8 |
| 32 | U | A | G | C | U | A | C | A | 4 | 27.3 |
| 33 | A | G | A | G | U | A | C | G | 4 | 27.1 |
| 34 | C | A | C | A | C | A | C | A | 6 | 26.9 |
| 35 | A | U | A | G | U | A | A | G | 4 | 26.8 |
| 36 | A | C | G | C | U | G | C | C | 4 | 26.7 |
| 37 | A | C | A | C | C | A | C | A | 4 | 26.5 |
| 38 | U | C | G | C | U | A | A | G | 4 | 26.4 |
| 39 | A | U | G | C | U | A | A | A | 3 | 26.3 |
| 40 | A | U | A | A | U | A | A | G | 4 | 26.1 |
| 41 | A | C | G | A | U | G | A | G | 5 | 26.1 |
| 42 | A | U | A | C | C | A | C | G | 2 | 26.0 |
| 43 | A | C | A | C | G | A | C | G | 3 | 25.8 |
| 44 | A | A | G | C | U | A | A | A | 4 | 25.7 |
| 45 | A | C | A | A | U | A | C | U | 5 | 25.0 |
| 46 | A | C | A | A | U | A | A | C | 6 | 24.7 |
| 47 | A | U | G | C | C | G | C | A | 3 | 24.5 | continued

Fig.4.6a-2 continued

| Samples | Sequences[a] | | | | | | | | Number of mutations[b] | Percent function[c] |
|---|---|---|---|---|---|---|---|---|---|---|
| | 964 | 965 | 966 | 967 | 968 | 969 | 970 | 971 | | |
| 48 | C | A | A | A | U | A | C | A | 6 | 24.5 |
| 49 | A | A | A | C | U | A | C | A | 4 | 24.5 |
| 50 | A | C | A | C | U | A | A | C | 5 | 24.4 |
| 51 | A | U | A | A | C | A | C | C | 4 | 23.8 |
| 52 | A | G | G | C | U | A | A | C | 4 | 23.6 |
| 53 | A | C | U | C | A | A | C | G | 2 | 23.4 |
| 54 | C | C | G | U | U | A | C | A | 5 | 23.4 |
| 55 | U | C | A | A | U | A | A | C | 7 | 23.1 |
| 56 | A | C | A | G | U | A | A | C | 6 | 23.0 |
| 57 | A | A | U | C | C | A | C | G | 3 | 22.6 |
| 58 | A | C | A | C | U | G | C | C | 5 | 22.4 |
| 59 | A | U | A | A | U | A | A | C | 5 | 22.0 |
| 60 | A | U | G | G | C | G | C | A | 4 | 21.6 |
| 61 | A | A | G | C | G | A | A | C | 4 | 21.6 |
| 62 | A | C | A | A | C | A | C | C | 5 | 21.1 |
| 63 | A | A | G | C | A | G | U | G | 3 | 20.9 |
| 64 | A | C | A | A | U | G | A | C | 7 | 20.8 |
| 65 | A | U | A | C | G | A | C | G | 2 | 20.5 |
| 66 | A | C | A | A | C | C | C | G | 5 | 19.9 |
| 67 | A | U | G | A | U | G | A | C | 5 | 19.7 |
| 68 | A | C | A | A | U | A | A | A | 6 | 19.2 |
| 69 | A | A | G | G | A | G | G | U | 5 | 19.2 |
| 70 | A | C | A | C | A | A | A | G | 3 | 18.8 |
| 71 | A | U | A | C | U | A | A | A | 4 | 18.3 | continued

Fig.4.6b-1 continued

| Samples | Sequences[b] | | | | | | | | Number of mutations[c] | Percent function[d] |
|---|---|---|---|---|---|---|---|---|---|---|
| | 964 | 965 | 966 | 967 | 968 | 969 | 970 | 971 | | |
| 72 | A | A | G | C | U | G | U | C | 5 | 18.1 |
| 73 | A | U | A | A | C | A | A | A | 5 | 18.1 |
| 74 | A | U | A | A | U | C | C | C | 5 | 18.0 |
| 75 | C | A | C | A | U | A | C | G | 6 | 17.7 |
| 76 | A | U | G | C | A | A | G | A | 2 | 17.6 |
| 77 | A | C | C | C | U | A | C | G | 3 | 17.5 |
| 78 | A | C | G | C | A | A | U | G | 2 | 16.9 |
| 79 | A | U | C | A | A | G | C | G | 3 | 16.2 |
| 80 | A | C | A | A | A | G | C | C | 6 | 16.1 |
| 81 | A | U | A | U | U | C | C | A | 5 | 15.8 |
| 82 | A | C | A | A | A | A | C | A | 4 | 15.0 |
| 83 | A | U | A | G | C | A | A | G | 4 | 15.0 |
| 84 | A | U | A | U | C | G | A | G | 5 | 14.8 |
| 85 | A | C | A | U | C | A | A | C | 6 | 13.9 |
| 86 | A | U | A | C | U | G | U | G | 4 | 13.6 |
| 87 | A | C | A | A | A | G | A | A | 6 | 13.6 |
| 88 | A | C | G | C | U | G | C | G | 3 | 12.9 |
| 89 | A | U | U | A | C | G | C | G | 4 | 12.5 |
| 90 | C | A | C | U | C | A | C | G | 5 | 12.4 |
| 91 | A | C | A | U | C | A | C | U | 5 | 12.3 |
| 92 | A | C | A | G | U | G | A | A | 7 | 12.2 |
| 93 | A | C | C | C | U | G | C | A | 5 | 11.8 |
| 94 | A | A | A | C | A | G | C | A | 4 | 11.5 |
| 95 | A | U | C | A | G | C | U | A | 6 | 11.4 |
| 96 | C | A | C | A | C | G | A | G | 7 | 11.4 |
| 97 | A | U | U | C | U | A | C | C | 3 | 11.4 | continued

Fig. 4.6b-2 continued

| Samples | Sequences[b] | | | | | | | | Number of mutations[c] | Percent function[d] |
|---|---|---|---|---|---|---|---|---|---|---|
| | 964 | 965 | 966 | 967 | 968 | 969 | 970 | 971 | | |
| 98 | A | C | U | A | U | U | C | G | 5 | 11.0 |
| 99 | U | C | U | C | U | A | A | C | 6 | 10.9 |
| 100 | A | U | G | A | A | G | C | C | 3 | 10.4 |
| 101 | U | C | G | G | C | C | G | A | 7 | 10.2 |
| 102 | C | A | C | U | U | G | C | A | 7 | 10.1 |
| 103 | A | C | U | A | U | G | C | C | 6 | 10.0 |
| 104 | A | C | C | C | U | A | C | C | 4 | 10.0 |
| 105 | A | U | C | G | U | G | C | G | 4 | 9.8 |
| 106 | A | C | C | U | U | A | C | C | 5 | 9.5 |
| 107 | A | A | A | A | U | G | A | C | 7 | 9.5 |
| 108 | A | A | A | G | U | G | A | G | 6 | 9.3 |
| 109 | A | U | A | U | U | U | C | G | 4 | 8.7 |
| 110 | A | A | G | A | U | G | U | A | 5 | 8.6 |
| 111 | A | U | A | G | C | A | A | A | 5 | 8.2 |
| 112 | A | U | G | U | C | A | G | A | 4 | 7.9 |
| 113 | A | U | C | G | U | G | C | A | 5 | 7.6 |
| 114 | A | U | G | C | C | G | U | G | 3 | 7.1 |
| 115 | A | C | U | A | C | A | C | A | 5 | 6.5 |
| 116 | A | U | A | C | A | G | U | A | 4 | 6.0 |
| 117 | A | A | C | C | C | G | C | A | 5 | 5.6 |
| 118 | U | C | A | C | U | A | A | C | 6 | 5.3 |
| 119 | U | C | G | C | G | G | C | U | 5 | 5.2 |
| 120 | A | A | A | G | U | A | U | G | 5 | 4.7 |
| 121 | U | U | C | C | A | C | U | A | 5 | 3.1 |
| 122 | A | A | C | U | U | G | C | A | 6 | 3.0 |
| 123 | U | C | A | C | U | C | C | G | 5 | 2.7 |
| 124 | C | A | A | U | U | G | G | A | 8 | 2.5 |

[a] Sequence and function of the unmutated construct (WT, wild type).
[b] The 970 loop sequences selected from the pool of functional mutants. Mutations are underlined.
[c] The number of mutations in each sequence.
[d] The level of function for each mutant. The function is an average based on at least three independent assays.

Fig. 4.6c

Table 4.2 Analysis of 967-1400 crosslink.

| 1400[a] | 967 | Observed[b] | Expected[c] |
|---|---|---|---|
| C | C | 100 | |
| A | C | 17.1 | |
| C | A | 119.8 | |
| A | A | 22.2 | 20.49 |
| G | C | 15.5 | |
| C | A | 119.8 | |
| G | A | 13.3 | 18.57 |
| U | C | 129.5 | |
| C | A | 119.8 | |
| U | A | 120.5 | 155.14 |
| A | C | 17.1 | |
| C | G | 106.6 | |
| A | G | 17.1 | 18.23 |
| G | C | 15.5 | |
| C | G | 106.6 | |
| G | G | 7.5 | 16.52 |
| U | C | 129.5 | |
| C | G | 106.6 | |
| U | G | 88.7 | 138.05 |
| A | C | 17.1 | |
| C | U | 127.4 | |
| A | U | 14.1 | 21.79 |
| G | C | 15.5 | |
| C | U | 127.4 | |
| G | U | 6.9 | 19.75 |
| U | C | 129.5 | |
| C | U | 127.4 | |
| U | U | 113.2 | 164.98 | a - Positions 1400 or 967. Mutations are underlined and colored red
b - The percent function of each mutant as compared to the wild type.
c - The expected function of the double mutant is the product of the corresponding single mutants. Functional interactions between positions are indicated by different observed and predicted values in the double mutants.

Fig. 4.7

Table 4.3. Conservation of the 970 loop.

| | Prokaryote [a] | | | | | | | |
|---|---|---|---|---|---|---|---|---|
| | 964 | 965 | 966 | 967 | 968 | 969 | 970 | 971 |
| A | 11812 | 3499 | 140 | 1356 | 9853 | 11794 | 274 | 376 |
| C | 6 | 1542 | 60 | 10300 | 51 | 28 | 11557 | 189 |
| G | 8 | 397 | 10903 | 220 | 43 | 16 | 11 | 11210 |
| U | 19 | 6407 | 742 | 69 | 1898 | 7 | 3 | 70 |

| | Eukaryote [b] | | | | | | | |
|---|---|---|---|---|---|---|---|---|
| | 964 | 965 | 966 | 967 | 968 | 969 | 970 | 971 |
| A | 4571 | 48 | 7 | 0 | 4567 | 4578 | 7 | 4397 |
| C | 2 | 4499 | 11 | 4578 | 6 | 0 | 4574 | 7 |
| G | 5 | 8 | 6 | 1 | 3 | 4 | 0 | 172 |
| U | 4 | 27 | 4558 | 3 | 6 | 0 | 1 | 6 |

| | Mitochondria [c] | | | | | | | |
|---|---|---|---|---|---|---|---|---|
| | 964 | 965 | 966 | 967 | 968 | 969 | 970 | 971 |
| A | 1289 | 14 | 1192 | 1049 | 444 | 72 | 1 | 482 |
| C | 1 | 85 | 0 | 149 | 299 | 1226 | 1298 | 650 |
| G | 3 | 2 | 91 | 67 | 6 | 0 | 1 | 123 |
| U | 7 | 1198 | 17 | 35 | 551 | 2 | 0 | 45 |

| | Instant evolution [d] | | | | | | | |
|---|---|---|---|---|---|---|---|---|
| | 964 | 965 | 966 | 967 | 968 | 969 | 970 | 971 |
| A | 104 | 26 | 54 | 43 | 19 | 72 | 35 | 38 |
| C | 8 | 52 | 18 | 49 | 28 | 7 | 73 | 34 |
| G | 0 | 3 | 44 | 18 | 8 | 43 | 6 | 46 |
| U | 12 | 43 | 8 | 14 | 69 | 2 | 10 | 6 |

[a] Nucleotide distribution of the 970 loop in Bacterial and Archaeal rRNA sequences
[b] Nucleotide distribution of the 970 loop in Eukaryotic rRNA sequences
[c] Nucleotide distribution of the 970 loop in mitochondrial rRNA sequences
[d] Nucleotide distribution of the mutants pool from the saturation mutagenesis

Fig. 4.8

Table 4.4 Effect of initiation factor overexpression

| Mutant | Percent function [a] | |
|---|---|---|
| | pRNA123 | + IF3 |
| Wild-type | 100 | 100 |
| m$^2$G966U | 127 ± 3.1 | 100 ± 0.9 |
| m$^5$C967U | 127 ± 3.0 | 98 ± 7.3 |
| G693U | 141 ± 6.9 | 134 ± 8.9 |

[a] Percent function of mutants with and without the overexpression of IF3.

Fig. 4.9

Table 4.5 Nucleoside requirements for the 970 loop

| Loop position | Nt under-represented[a] | Base pairing[b] A/U vs. G/C | Purine vs. Pyrimidine[b] | Charge preference:[c] N6/N4 (+) vs. (−) | Charge preference:[c] N2 (+) vs. (−)[d] | Factor binding |
|---|---|---|---|---|---|---|
| 964 | C/G/U | A/U | Purine | (+) | (−) | Hydroxyl radical probing with RF1 shows medium cleavage (Wilson et al. (2000)) |
| 965 | G | no preference | Pyrimidine | (+) | (−) | |
| 966 | C/U | no preference | Purine | no preference | (+) | Modeled N-terminal domain of IF3 (Pioletti et al. (2001))/ P-site tRNA (Yusupov et al. (2001)) |
| 967 | G/U | no preference | no preference | (+) | (+) | Modeled N-terminal domain of IF3 (Pioletti et al. (2001))/ P-site tRNA (Yusupov et al. (2001))/ (s)U cross-link to 1400 (Wims et al. (1997)) |
| 968 | A/G | A/U | Pyrimidine | (−) | (+) | Modeled N-terminal domain of IF3 (Pioletti et al. (2001))/ P-site tRNA (Yusupov et al. (2001)) |
| 969 | C/U | A/U | Purine | (+) | (+) | |
| 970 | G/U | G/C | Pyrimidine | (+) | (−) | |
| 971 | U | G/C | Purine | no preference | (+) | |

[a] Nucleotides under represented in the selected mutant pool at each mutated position.
[b] Nucleotide preference at each position based on Chi squared analysis.
[c] Charge preference at each position based on Chi squared analysis.
[d] Charge preference at the N2 position of the base. Adenosine does not possess a charged group at the N2 position. Adenosine mutations were found at all nucleotide positions but were over represented at positions 964, 966, 967, and 969. They were under represented at position 968 and displayed a random distribution at positions 965, 970, and 971.

Fig. 4.10

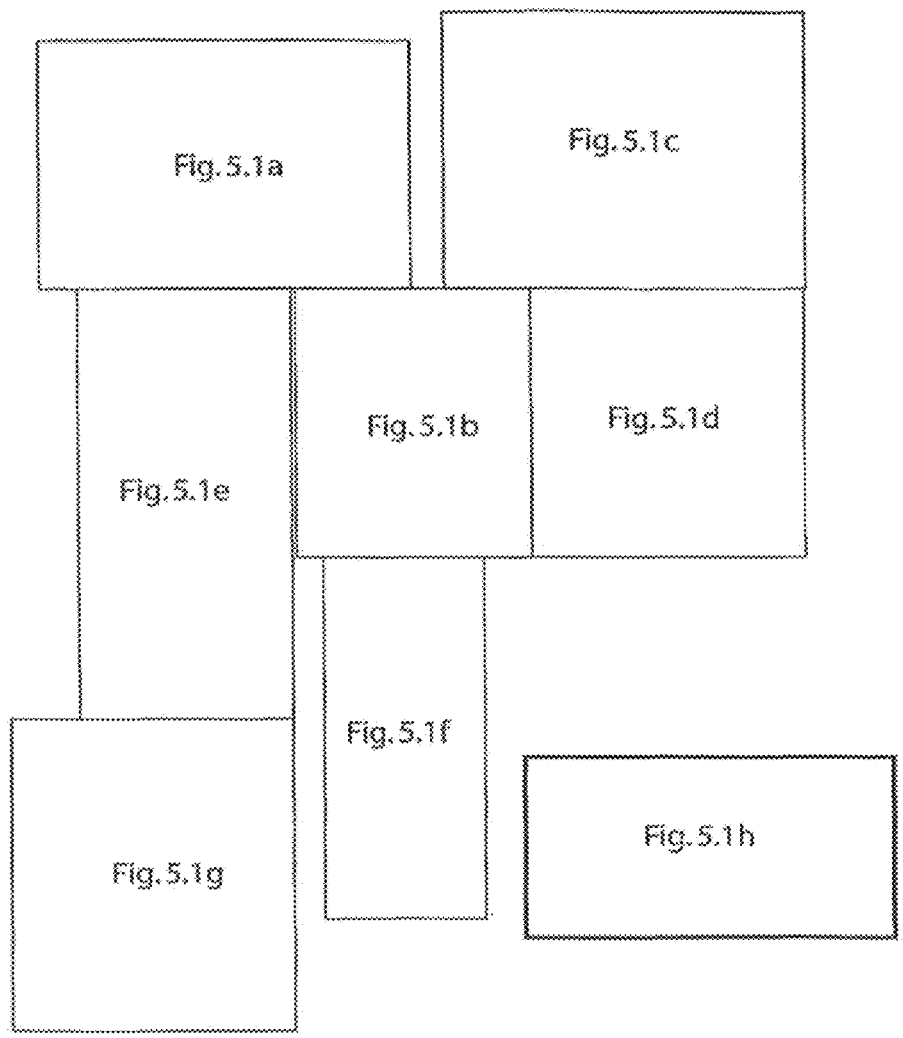
Fig.5.1

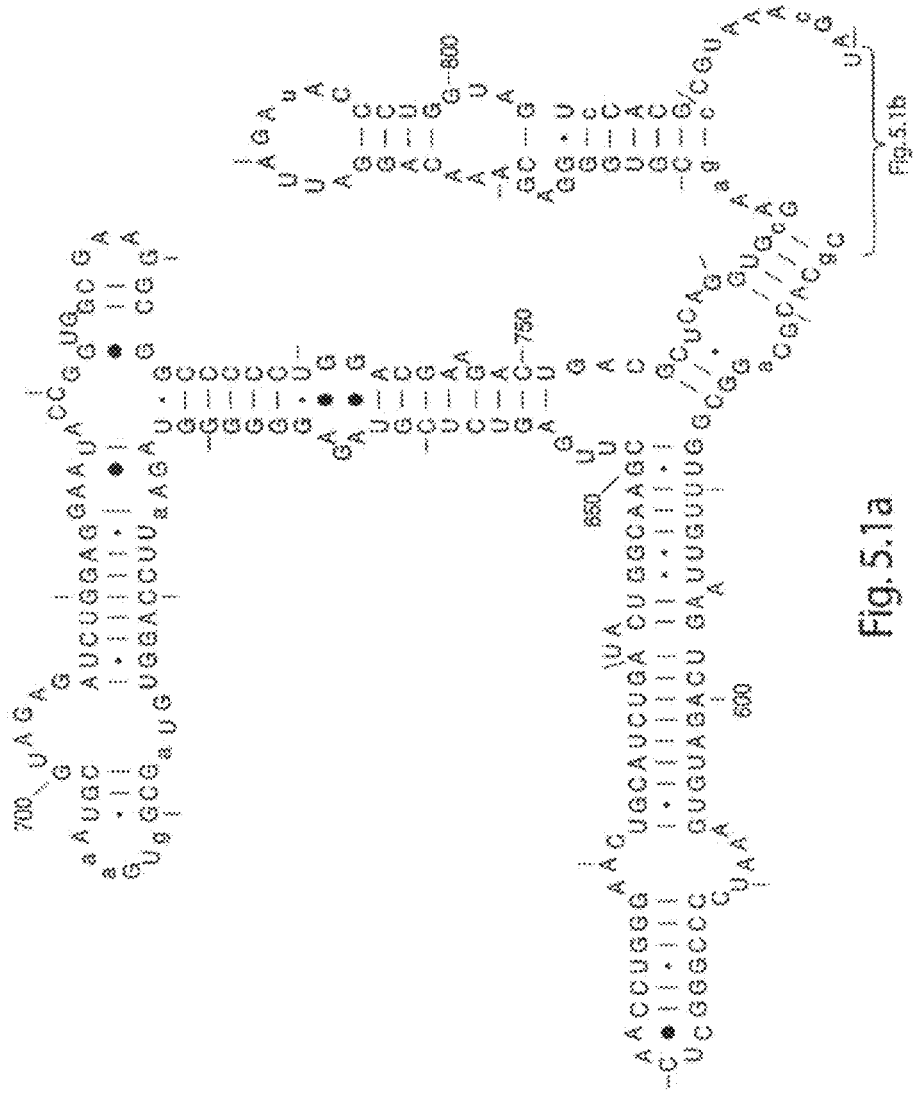

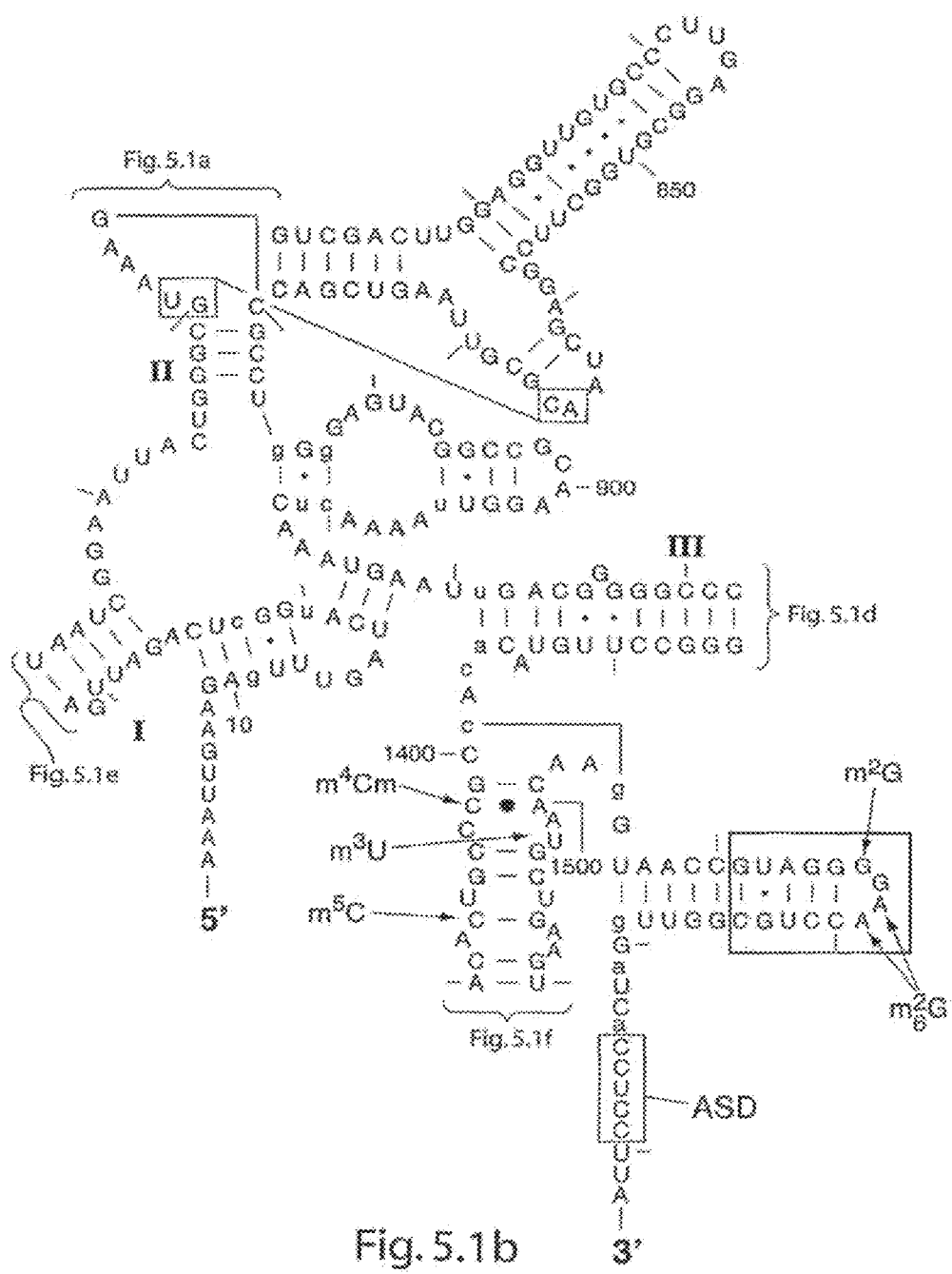
Fig. 5.1b

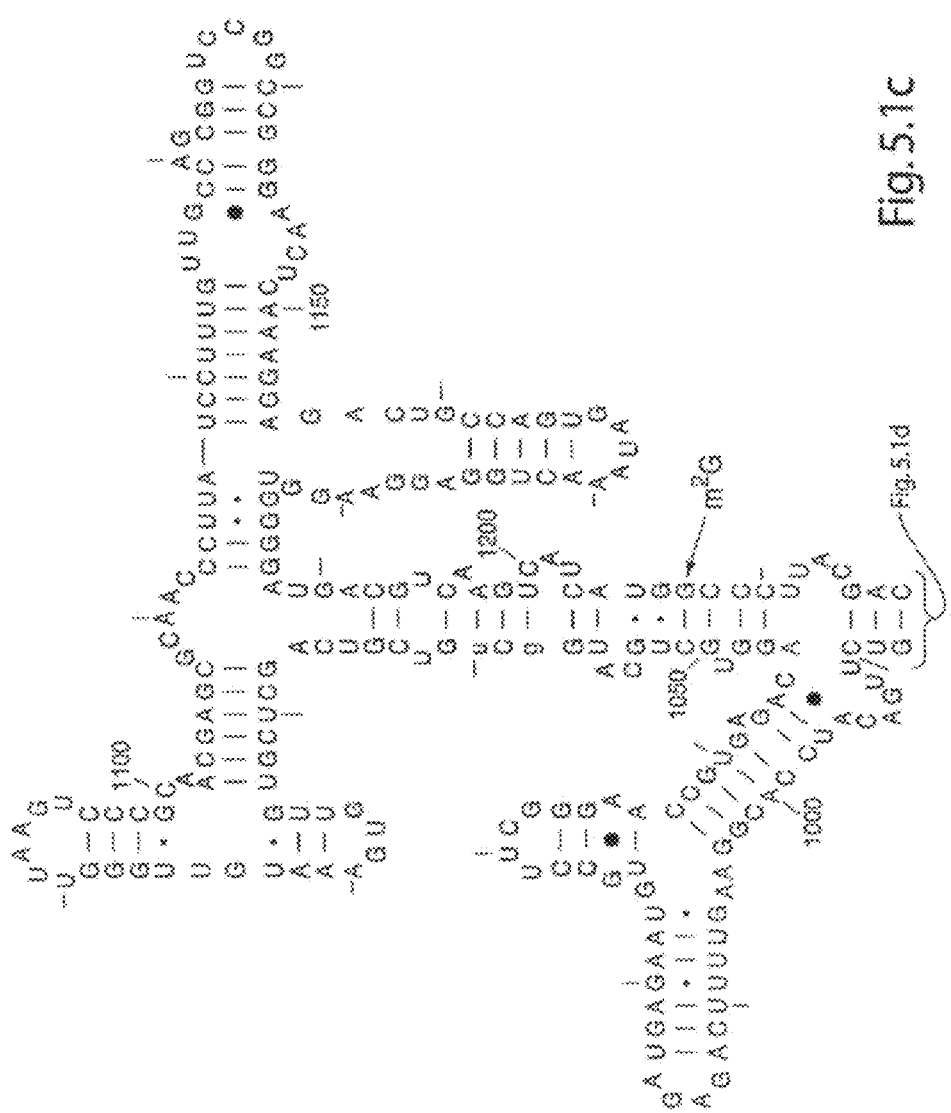

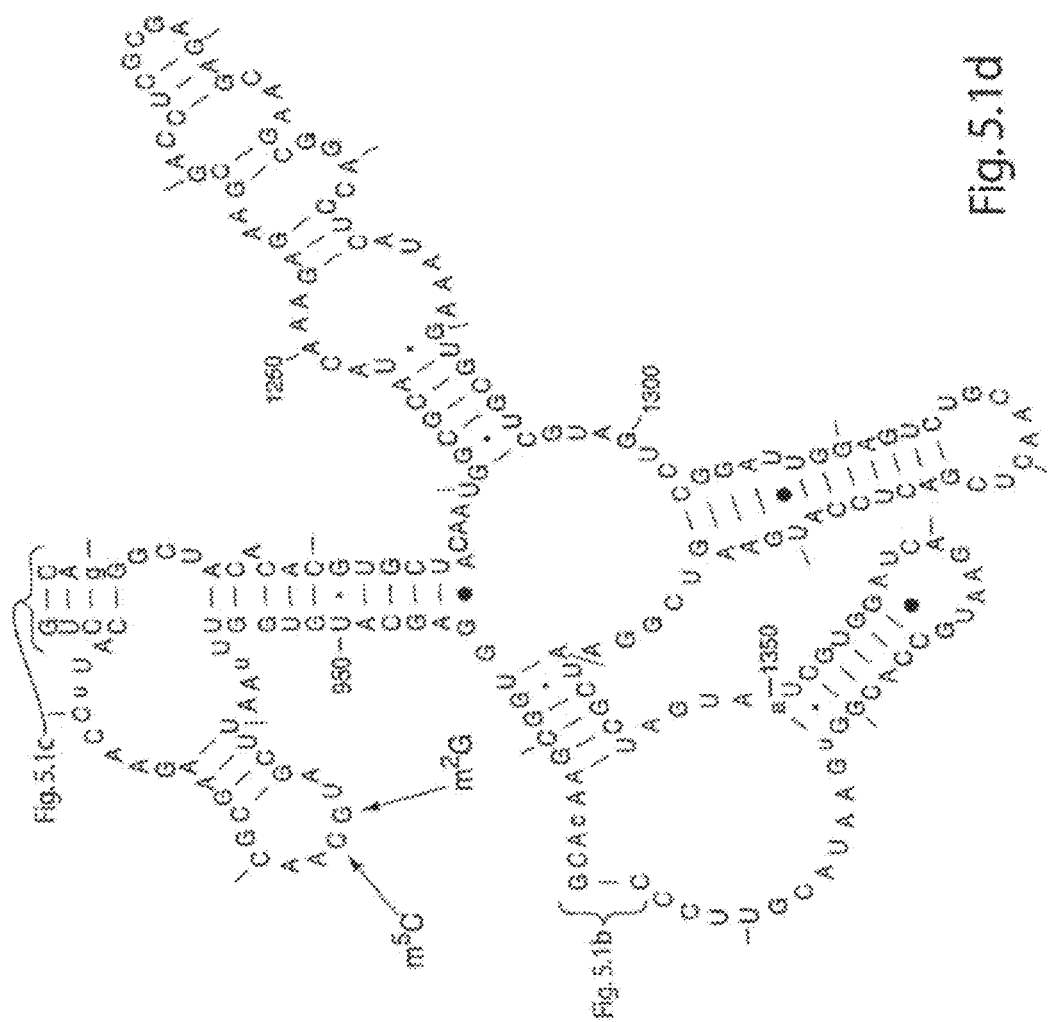

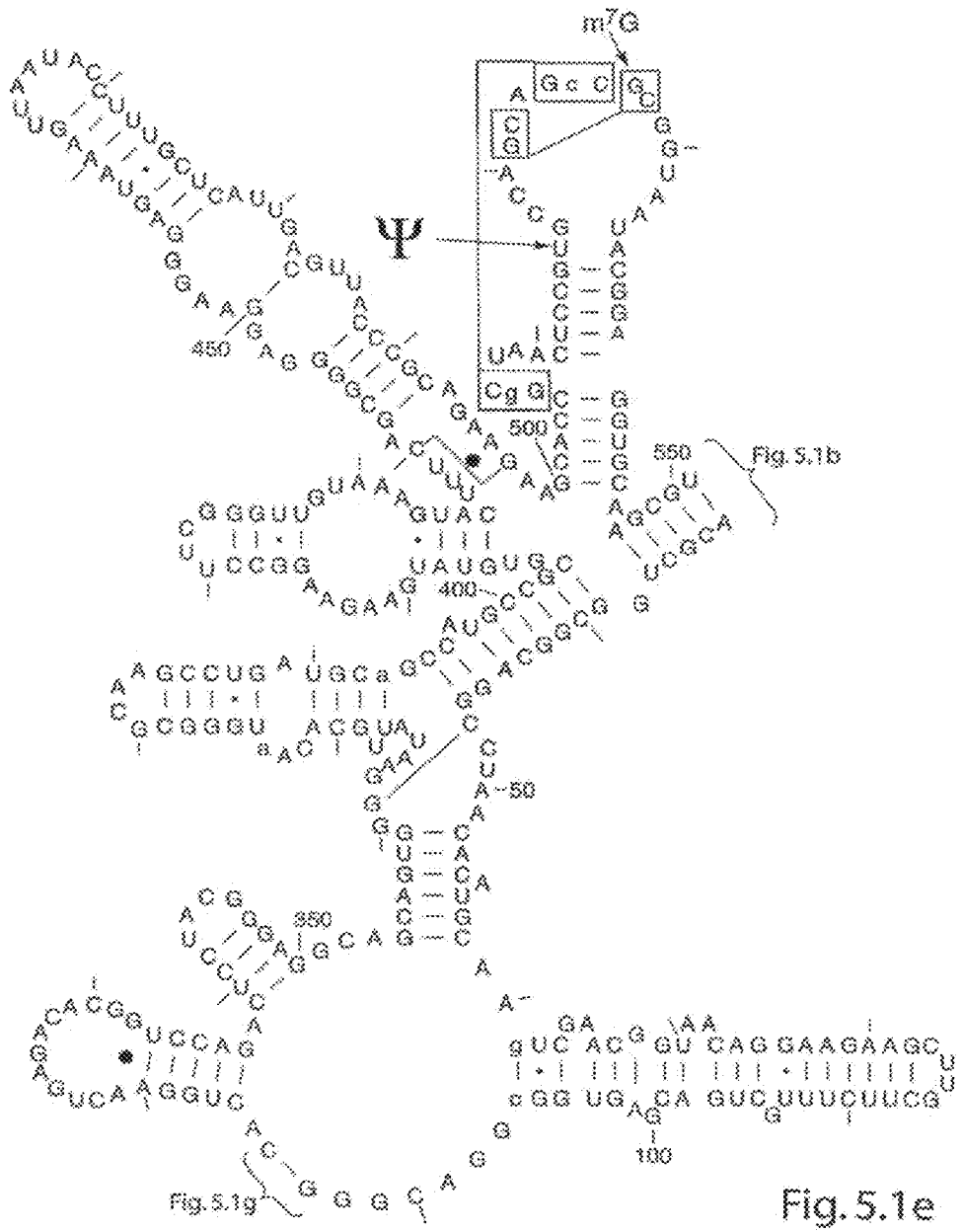
Fig.5.1e

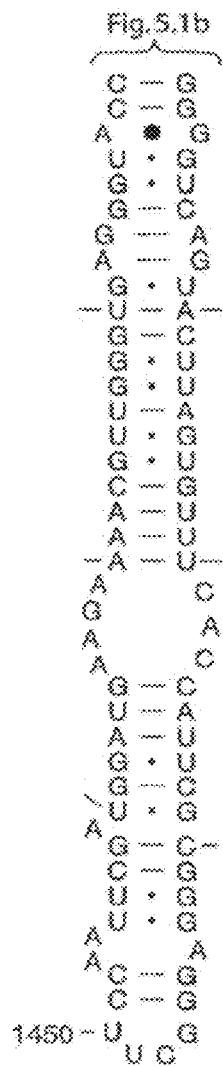
Fig.5.1f

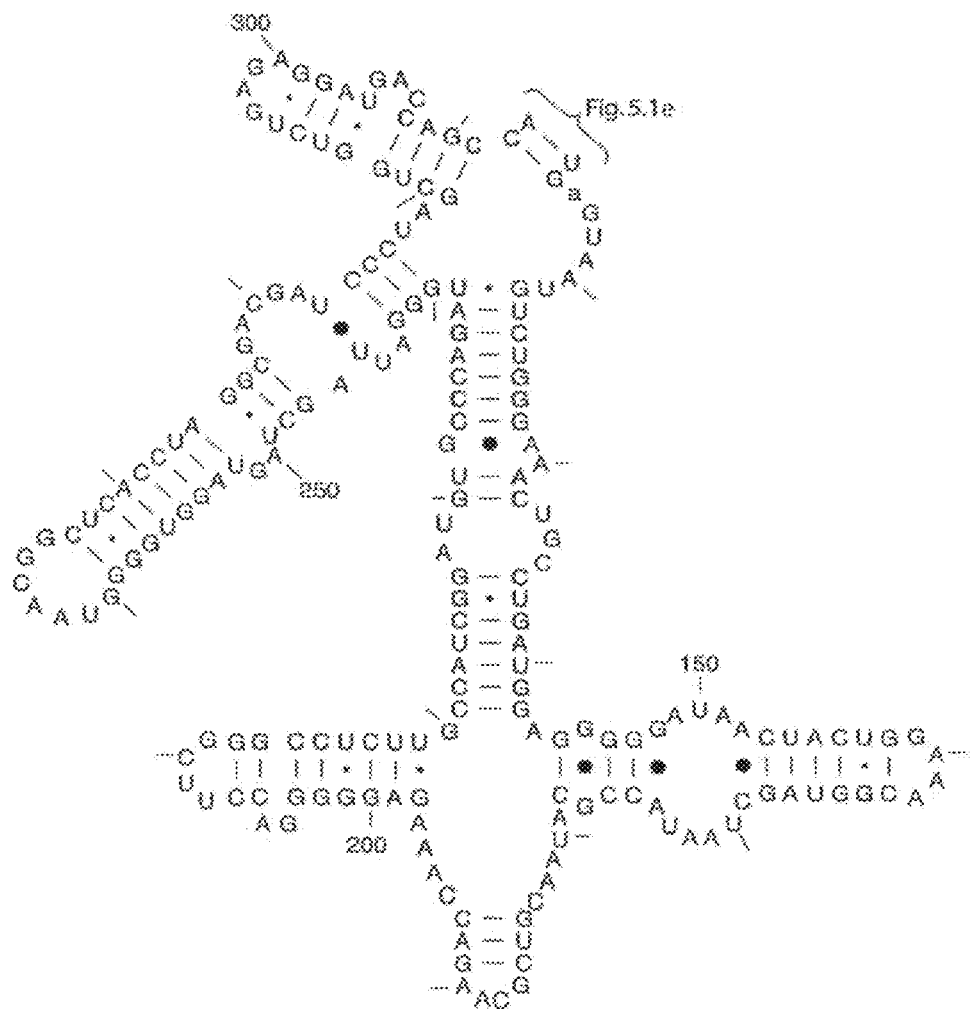
Fig. 5.1g

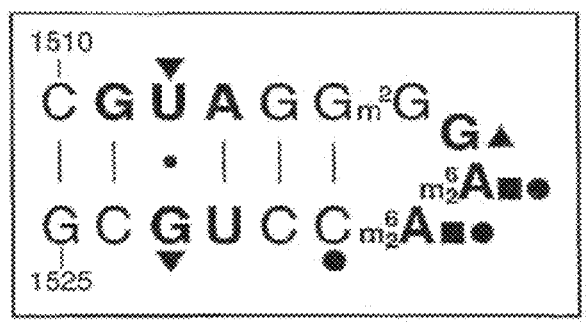
Fig. 5.1h

|   | 1519 | | | |
|---|---|---|---|---|
|   | A | C | G | U |
| A | 100 | 2.3±0.3 | 4.5±0.4 | 7.5±0.7 |
| C | 7.5±0.5 | 1.2±0.2 | 1.1±0.1 | 1.5±0.3 |
| G | 6.8±0.7 | 1.3±0.3 | 0.9±0.2 | 1.1±0.2 |
| U | 3.8±0.3 | 1.1±0.1 | 1.0±0.1 | 1.3±0.1 |

|      | 1523 |  |  |  |
|------|------|------|------|------|
|      | A | C | G | U |
| A    | 1.8 ± 0.1 | 7.6 ± 0.8 | 32.6 ± 1.5 | 32.8 ± 0.5 |
| C    | 54.7 ± 2.3 | 50.6 ± 0.8 | 80.3 ± 3.2 | 50.0 ± 3.6 |
| G    | 23.1 ± 0.8 | 62.3 ± 1.0 | 35.6 ± 0.3 | 13.1 ± 0.6 |
| U    | 53.1 ± 1.4 | 42.9 ± 0.6 | 100 | 57.1 ± 0.4 |

| | A | C | G | U | Consensus* | Chi-test |
|---|---|---|---|---|---|---|
| 1512 | | · | · | ● | Y | $3 \times 10^{-40}$ |
| 1513 | ● | · | · | ● | D | $1 \times 10^{-12}$ |
| 1514 | · | ● | ● | · | N | $4 \times 10^{-6}$ |
| 1515 | · | ● | ● | ● | N | 0.09 |
| 1516 | · | · | ● | · | D | $9 \times 10^{-15}$ |
| 1517 | · | | ● | | R | $5 \times 10^{-31}$ |
| 1518 | ● | | · | | A | $2 \times 10^{-68}$ |
| 1519 | ● | | | | A | $1 \times 10^{-71}$ |
| 1520 | · | · | ● | · | N | 0.12 |
| 1521 | · | ● | ● | ● | N | $2 \times 10^{-2}$ |
| 1522 | · | · | · | ● | W | $4 \times 10^{-18}$ |
| 1523 | · | · | ● | · | G | $4 \times 10^{-38}$ |

* At least a 10% prevalence in the pool

Fig. 5.4

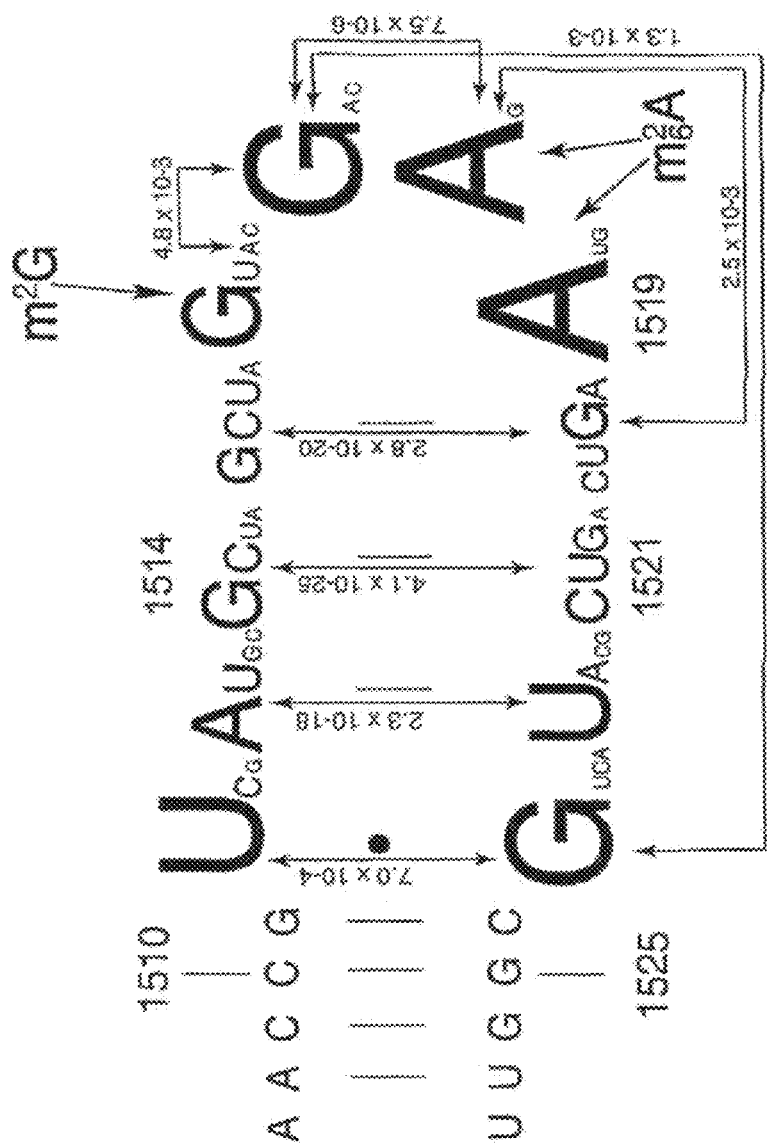
Fig. 5.5

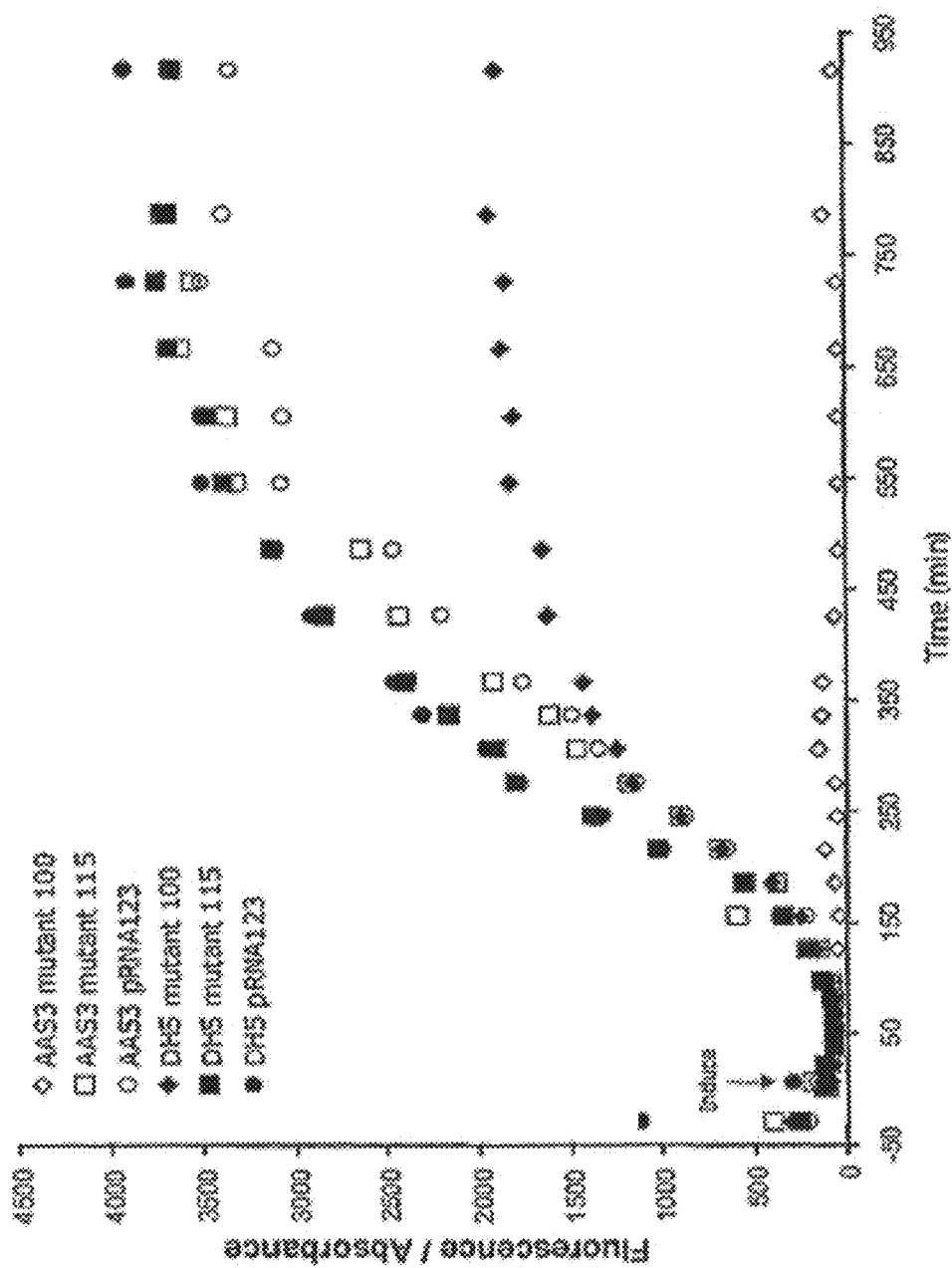
Fig. 5.6

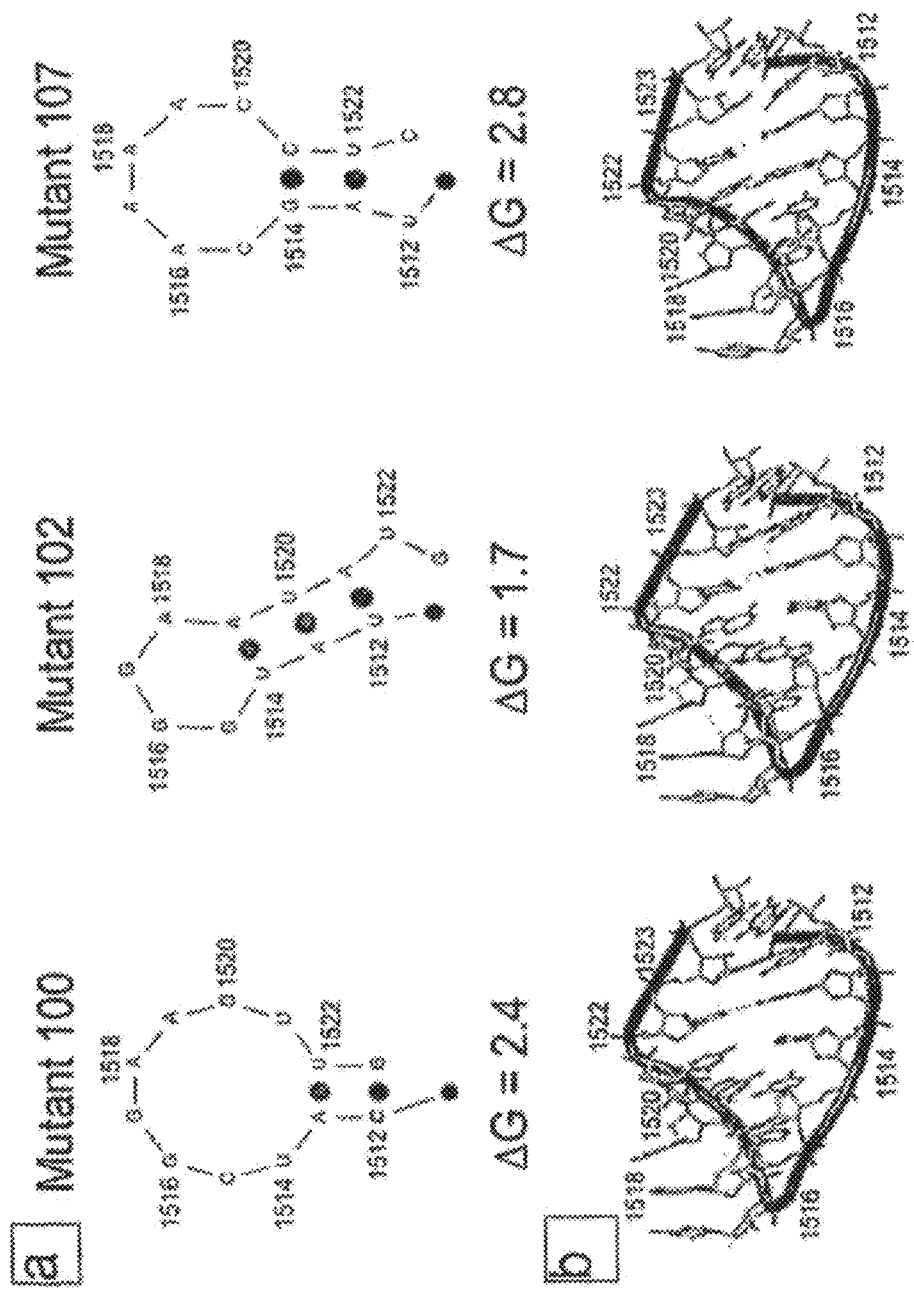
Fig. 5.7

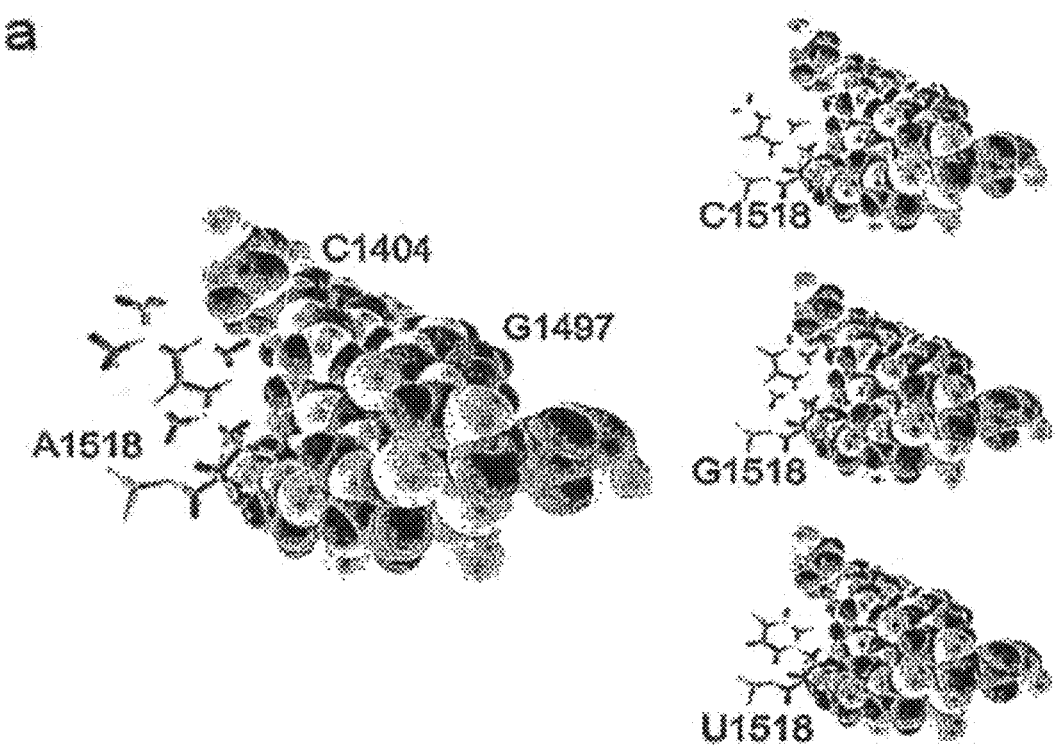
Fig. 5.8a

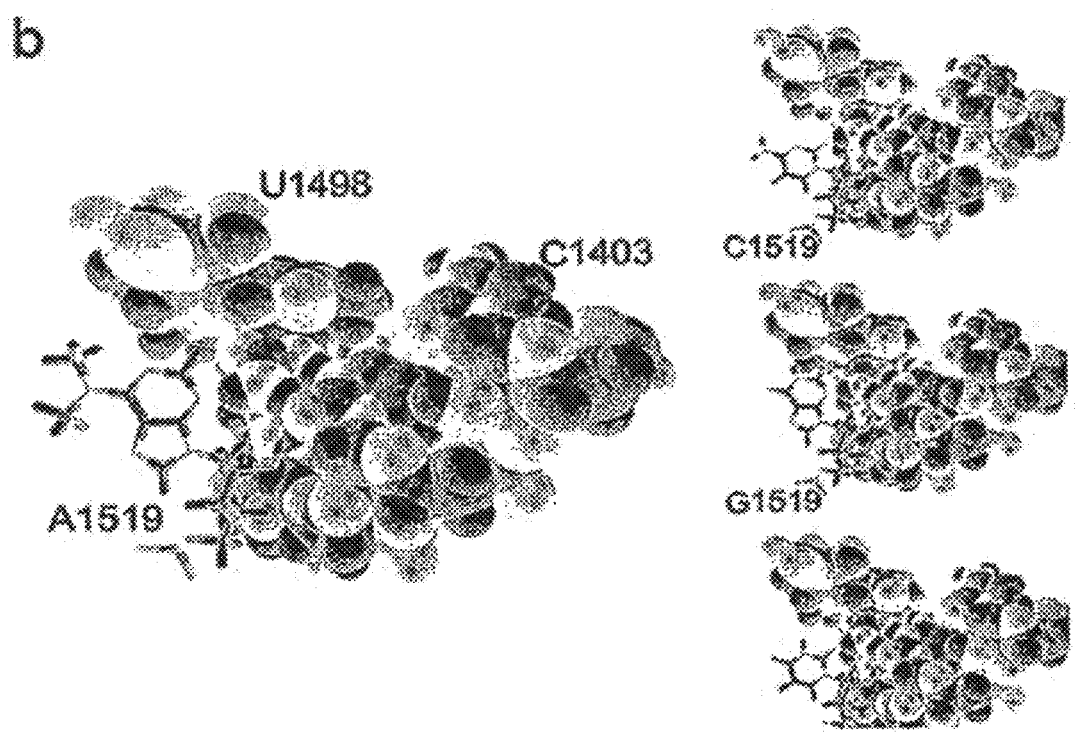
Fig. 5.8b

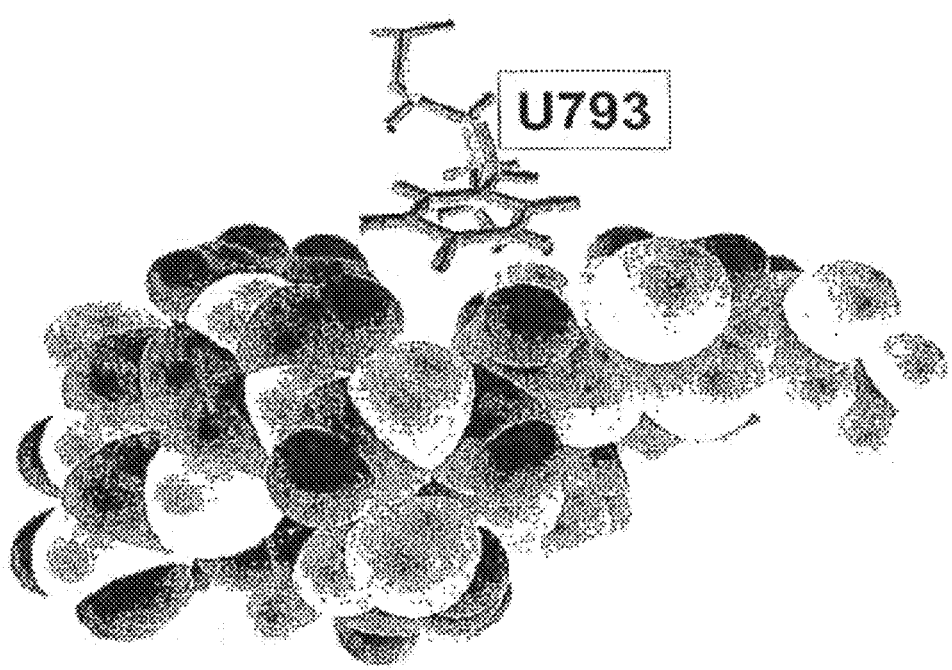
Fig. 5.9

Table S.1. Sequences of functional helix 46 mutants.

| Samples | \_ | \_ | \_ | \_ | Sequences[a] | \_ | \_ | \_ | \_ | \_ | \_ | \_ | Number of mutations[c] | Percent function[d] |
|---|---|---|---|---|---|---|---|---|---|---|---|---|---|---|
| | 1512 | 1513 | 1514 | 1515 | 1516 | 1517 | 1518 | 1519 | 1520 | 1521 | 1522 | 1523 | | |
| WT[b] | U | A | G | G | G | G | A | A | C | C | U | G | 0 | 100 |
| 1 | C | A | G | C | U | G | A | A | G | C | U | G | 4 | 10.2 ± 1.00 |
| 2 | C | A | G | G | G | G | A | A | U | C | U | U | 3 | 11.2 ± 4.2 |
| 3 | U | U | U | C | G | G | A | A | G | G | A | G | 6 | 11.3 ± 0.29 |
| 4 | U | U | U | C | G | G | A | A | G | G | A | U | 7 | 11.3 ± 0.36 |
| 5 | U | A | G | C | G | G | A | U | U | C | U | G | 3 | 11.9 ± 0.47 |
| 6 | U | U | A | G | U | G | A | A | C | U | G | G | 5 | 12.1 ± 0.48 |
| 7 | U | A | U | G | G | G | A | A | A | A | U | G | 3 | 12.3 ± 8.1 |
| 8 | U | U | G | C | U | G | A | A | G | C | A | U | 6 | 12.3 ± 2.27 |
| 9 | U | C | C | C | G | G | A | A | G | A | G | G | 6 | 13.3 ± 0.46 |
| 10 | C | U | C | U | G | G | A | A | G | G | A | C | 8 | 14.0 ± 0.32 |
| 11 | U | A | A | G | G | G | A | A | A | U | U | G | 3 | 14.6 ± 0.46 |
| 12 | U | G | G | G | A | G | A | A | C | C | U | G | 2 | 15.0 ± 2.94 |
| 13 | U | G | U | C | G | G | A | A | G | A | U | A | 6 | 15.5 ± 0.54 |
| 14 | U | A | A | C | U | G | A | A | U | U | U | G | 5 | 15.5 ± 0.98 |
| 15 | U | C | C | C | A | G | A | A | G | G | G | C | 8 | 15.5 ± 0.46 |
| 16 | C | A | G | G | C | G | A | A | C | C | U | A | 3 | 15.8 ± 3.16 |
| 17 | C | A | C | U | G | G | A | A | G | G | U | G | 5 | 15.9 ± 0.27 |
| 18 | U | A | C | G | G | G | A | A | G | G | U | G | 3 | 16.0 ± 0.57 |
| 19 | C | A | C | A | A | G | A | A | U | G | U | A | 7 | 16.1 ± 1.79 |
| 20 | C | U | C | A | G | A | A | A | U | G | A | A | 9 | 16.2 ± 3.32 |
| 21 | U | U | A | C | U | G | A | A | G | U | C | G | 7 | 16.3 ± 0.5 |
| 22 | U | U | G | C | G | G | A | A | C | C | A | G | 3 | 16.4 ± 1.56 |
| 23 | U | U | G | U | G | A | A | A | A | C | C | G | 5 | 16.7 ± 1.08 |
| 24 | U | U | C | U | G | G | A | A | A | A | A | G | 8 | 16.8 ± 0.82 |
| 25 | U | U | G | C | U | G | A | A | G | U | A | G | 6 | 17.2 ± 4.09 |
| 26 | U | A | A | U | C | G | A | A | A | U | U | G | 6 | 17.5 ± 0.3 |
| 27 | U | A | A | U | A | G | A | A | A | U | U | G | 6 | 17.5 ± 0.46 |
| 28 | C | A | G | G | U | G | A | A | C | U | U | G | 3 | 17.5 ± 0.78 |
| 29 | U | A | G | U | G | A | A | A | G | C | U | G | 3 | 17.8 ± 0.58 |
| 30 | U | U | G | G | G | G | A | A | G | C | A | G | 3 | 17.8 ± 0.48 | continued

Fig. 5.10a-1 continued

| Samples | Sequence[a] | | | | | | | | | | | | Number of mutations[b] | Percent function[c] |
|---|---|---|---|---|---|---|---|---|---|---|---|---|---|---|
| | 1512 | 1513 | 1514 | 1515 | 1516 | 1517 | 1518 | 1519 | 1520 | 1521 | 1522 | 1523 | | |
| 31 | U | C | A | U | A | G | A | A | A | U | U | G | 6 | 17.8 ± 0.58 |
| 32 | C | A | C | A | G | G | A | A | U | G | U | U | 8 | 17.8 ± 3.76 |
| 33 | C | A | C | U | A | G | A | A | A | G | U | C | 7 | 18.2 ± 0.53 |
| 34 | U | C | G | G | G | G | A | A | C | U | G | G | 3 | 18.4 ± 0.77 |
| 35 | U | C | G | C | U | G | A | A | G | C | U | G | 4 | 18.8 ± 0.58 |
| 36 | G | C | G | G | U | G | A | A | C | C | U | C | 4 | 18.9 ± 0.59 |
| 37 | C | C | U | G | G | G | A | A | U | G | U | G | 5 | 20.0 ± 0.48 |
| 38 | U | U | C | U | G | G | A | A | A | G | C | G | 6 | 20.7 ± 0.5 |
| 39 | U | A | A | A | C | G | A | A | U | U | U | G | 5 | 21.2 ± 0.58 |
| 40 | U | U | U | U | G | G | A | A | A | U | A | G | 6 | 21.2 ± 0.72 |
| 41 | U | U | C | U | U | G | A | A | G | A | A | G | 7 | 21.4 ± 0.51 |
| 42 | U | G | A | C | C | G | A | A | G | U | U | G | 6 | 22.5 ± 0.23 |
| 43 | U | U | U | G | U | G | A | A | C | A | C | G | 5 | 22.8 ± 0.11 |
| 44 | U | C | U | C | C | G | A | A | C | A | U | G | 6 | 23.1 ± 0.14 |
| 45 | U | A | G | U | U | G | A | A | G | C | U | G | 3 | 23.4 ± 1.38 |
| 46 | U | A | G | G | U | G | A | A | C | U | U | G | 2 | 23.5 ± 2.52 |
| 47 | U | A | G | U | G | G | A | A | G | C | U | U | 3 | 23.7 ± 0.46 |
| 48 | U | C | G | C | G | G | A | A | G | C | G | U | 5 | 24.5 ± 0.49 |
| 49 | U | A | U | A | U | G | A | A | U | G | U | G | 5 | 24.9 ± 0.87 |
| 50 | U | U | C | U | G | G | A | A | U | G | A | G | 6 | 24.9 ± 1.27 |
| 51 | U | A | U | A | C | G | A | A | U | A | U | G | 5 | 26.3 ± 0.41 |
| 52 | C | U | G | U | G | A | A | A | C | A | U | G | 6 | 26.7 ± 2.37 |
| 53 | C | G | G | U | G | A | A | A | A | C | C | U | 7 | 26.9 ± 0.48 |
| 54 | U | A | C | A | G | G | A | A | U | A | U | G | 4 | 27.0 ± 0.53 |
| 55 | C | U | C | C | A | G | A | A | G | G | A | U | 8 | 27.1 ± 0.93 |
| 56 | U | G | G | A | G | G | A | A | U | U | C | G | 5 | 27.5 ± 0.45 |
| 57 | U | A | G | C | G | G | A | A | U | U | U | G | 3 | 27.7 ± 0.5 |
| 58 | U | A | A | U | G | G | A | A | U | U | U | G | 4 | 28.5 ± 0.31 |
| 59 | U | A | C | U | U | G | A | A | A | G | U | G | 5 | 29.7 ± 1.03 |
| 60 | U | A | A | A | G | A | A | A | G | U | U | G | 5 | 30.0 ± 1.39 |
| 61 | U | G | G | A | G | G | A | A | U | C | A | G | 4 | 30.3 ± 1.44 | continued

| Samples | \multicolumn{12}{c|}{Sequences} | Number of mutations | Percent function |
|---|---|---|---|---|---|---|---|---|---|---|---|---|---|---|
| | 1512 | 1513 | 1514 | 1515 | 1516 | 1517 | 1518 | 1519 | 1520 | 1521 | 1522 | 1523 | | |
| 62 | U | A | G | A | C | G | A | A | U | C | U | G | 3 | 30.5±2.41 |
| 63 | U | A | G | U | A | G | A | A | C | C | U | G | 3 | 30.7±2.36 |
| 64 | C | U | G | U | G | G | A | A | A | C | A | U | 6 | 31.4±0.69 |
| 65 | U | A | C | G | G | G | A | A | C | G | U | C | 3 | 31.5±2.58 |
| 66 | U | U | G | A | U | G | A | A | U | C | A | G | 5 | 31.5±1.26 |
| 67 | U | A | A | A | A | G | A | A | U | U | U | G | 5 | 32.3±2.89 |
| 68 | U | A | G | C | U | G | A | A | C | U | U | G | 4 | 32.5±2.44 |
| 69 | U | U | U | C | U | G | A | A | G | A | A | G | 7 | 32.5±1.7 |
| 70 | U | C | G | G | G | A | A | A | U | C | G | A | 5 | 32.8±0.1 |
| 71 | U | C | G | G | A | G | A | A | C | U | G | C | 5 | 34.0±1.91 |
| 72 | U | U | G | C | G | A | A | A | C | A | U | G | 4 | 34.5±0.27 |
| 73 | U | U | G | C | G | A | A | A | G | C | A | U | 6 | 34.6±0.12 |
| 74 | C | U | C | A | G | A | A | A | U | G | U | G | 7 | 35.0±0.17 |
| 75 | U | U | C | G | G | C | A | A | C | U | A | G | 4 | 35.3±0.97 |
| 76 | C | A | U | G | G | G | A | A | A | C | U | G | 3 | 35.3±0.62 |
| 77 | C | A | G | G | C | C | G | A | C | U | A | G | 6 | 35.4±1.05 |
| 78 | U | U | C | G | G | A | A | A | C | U | A | G | 5 | 35.5±0.79 |
| 79 | U | A | C | G | U | G | A | A | C | G | U | U | 4 | 35.7±0.43 |
| 80 | U | G | C | U | G | G | A | A | A | G | A | G | 6 | 36.1±1.53 |
| 81 | U | G | G | G | A | G | G | A | A | C | U | G | 4 | 36.7±1.49 |
| 82 | C | A | G | G | G | G | A | A | C | U | U | G | 2 | 38.8±0.88 |
| 83 | C | A | C | C | G | G | A | A | G | G | U | C | 6 | 38.2±1.87 |
| 84 | U | A | G | A | U | G | A | A | U | C | U | G | 3 | 38.4±3.80 |
| 85 | U | U | C | C | C | G | A | A | G | A | A | G | 7 | 38.4±2.28 |
| 86 | U | U | A | U | G | G | A | A | A | U | A | G | 6 | 39.8±3.86 |
| 87 | U | C | C | C | C | G | A | A | G | G | A | G | 7 | 40.5±1.79 |
| 88 | U | U | G | U | G | G | A | A | A | U | A | G | 5 | 42.1±3.73 |
| 89 | C | A | G | G | G | G | A | A | C | C | C | G | 2 | 42.3±1.38 |
| 90 | U | A | U | G | U | G | A | A | C | A | U | G | 3 | 42.6±3.02 |

| Sample | Sequences<sup>b</sup> 1512 | 1513 | 1514 | 1515 | 1516 | 1517 | 1518 | 1519 | 1520 | 1521 | 1522 | 1523 | Number of mutations<sup>c</sup> | Percent function<sup>d</sup> |
|---|---|---|---|---|---|---|---|---|---|---|---|---|---|---|
| 91 | U | G | C | U | G | G | A | A | A | C | U | G | 5 | 43.2 ± 1.22 |
| 92 | U | U | G | U | G | G | A | A | C | U | A | G | 5 | 43.3 ± 1.63 |
| 93 | C | A | C | G | G | G | A | A | U | C | U | G | 4 | 43.4 ± 2.19 |
| 94 | U | G | A | C | G | G | A | A | U | U | C | G | 6 | 44.2 ± 3.2 |
| 95 | U | U | C | C | C | G | A | A | G | G | A | G | 7 | 45.4 ± 1.82 |
| 96 | U | A | U | G | G | G | A | A | U | G | U | G | 3 | 48.1 ± 2.63 |
| 97 | U | A | G | C | A | G | A | A | C | C | U | G | 3 | 51.8 ± 3.35 |
| 98 | U | A | U | G | G | A | A | A | U | U | U | G | 4 | 52.2 ± 1.09 |
| 99 | U | A | G | U | G | G | A | A | A | U | U | G | 3 | 52.9 ± 3.46 |
| 100 | C | A | U | C | G | G | A | A | C | U | U | G | 5 | 53.4 ± 2.11 |
| 101 | U | A | C | U | G | G | A | A | G | G | C | G | 5 | 55.3 ± 2.93 |
| 102 | U | A | U | G | G | G | A | A | U | A | U | G | 3 | 55.3 ± 1.94 |
| 103 | C | A | U | G | G | G | A | A | G | U | U | G | 4 | 58.7 ± 0.76 |
| 104 | U | A | G | A | A | G | A | A | G | C | U | G | 3 | 55.8 ± 5.43 |
| 105 | U | A | C | C | U | G | A | A | G | G | U | G | 5 | 55.9 ± 3.91 |
| 106 | U | A | G | U | A | G | A | A | A | C | U | G | 3 | 56.5 ± 1.64 |
| 107 | U | A | G | C | A | A | A | A | C | C | U | C | 4 | 57.8 ± 3.86 |
| 108 | U | A | C | U | G | G | A | A | G | C | C | G | 4 | 58.0 ± 2.9 |
| 109 | U | A | C | A | G | A | A | A | U | G | U | G | 5 | 65.9 ± 5.43 |
| 110 | U | A | G | G | G | G | A | A | A | C | U | G | 1 | 77.3 ± 6.52 |
| 111 | U | A | G | G | G | G | A | G | A | C | U | G | 2 | 73.1 ± 2.86 |
| 112 | U | A | G | A | A | G | A | A | C | U | G | G | 4 | 76.7 ± 2.88 |
| 113 | U | A | G | C | G | G | A | A | C | U | U | G | 1 | 78.2 ± 4.09 |
| 114 | U | A | G | G | G | A | G | A | A | C | U | G | 3 | 78.9 ± 5.3 |
| 115 | U | G | A | G | G | G | A | A | C | U | G | G | 4 | 80.5 ± 2.72 |
| 116 | U | A | G | G | G | G | A | A | C | U | G | G | 2 | 91.5 ± 4.39 |

<sup>a</sup> Sequence and function of the unmutated construct (WT, wild type).
<sup>b</sup> The helix 45 mutant sequences selected from the pool of functional mutants. Mutations are bold and underlined.
<sup>c</sup> The number of mutations in each clone.
<sup>d</sup> The level of function for each clone. The function is an average based on at least three independent assays.

Fig. 5.10b-2

Table 5.2. Functional analysis of helix 45 mutants selected in DH5.

| Mutant[a] | In AAS3[b] | In DH5[c] | % difference[d] |
|---|---|---|---|
| 97 | 59.8 | 51.8 | 15.36 |
| 100 | 2.0 | 53.4 | -96.28 |
| 102 | 7.6 | 55.3 | -86.28 |
| 104 | 62.3 | 55.8 | 11.59 |
| 105 | 94.7 | 55.9 | 69.48 |
| 107 | 1.3 | 57.8 | -97.69 |
| 109 | 73.4 | 65.9 | 11.38 |
| 110 | 99.1 | 72.3 | 37.05 |
| 112 | 72.6 | 74.7 | -2.83 |
| 113 | 110.1 | 78.2 | 40.77 |
| 114 | 98.4 | 78.9 | 24.76 |
| 115 | 100.3 | 80.5 | 24.54 |

[a] Mutant number corresponds to mutant sequence in Table 1
[b] Percent function of ksgA* selected mutants in a ksgA strain
[c] Percent function of ksgA* selected mutants in a ksgA* strain
[d] Percent difference in function from the ksgA* strain

Fig. 5.11

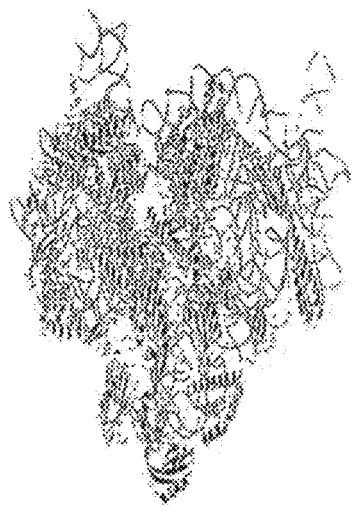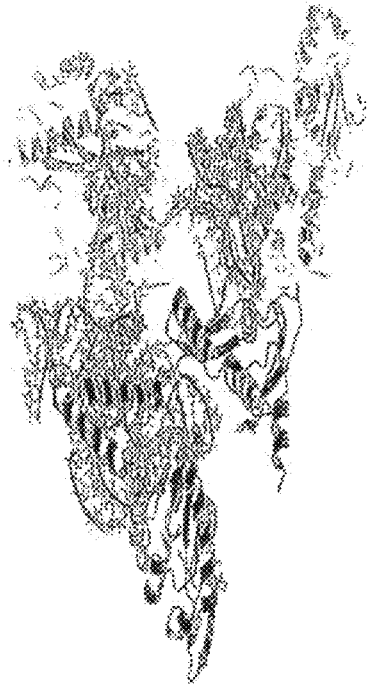
(Front) (Back) Fig. 6f

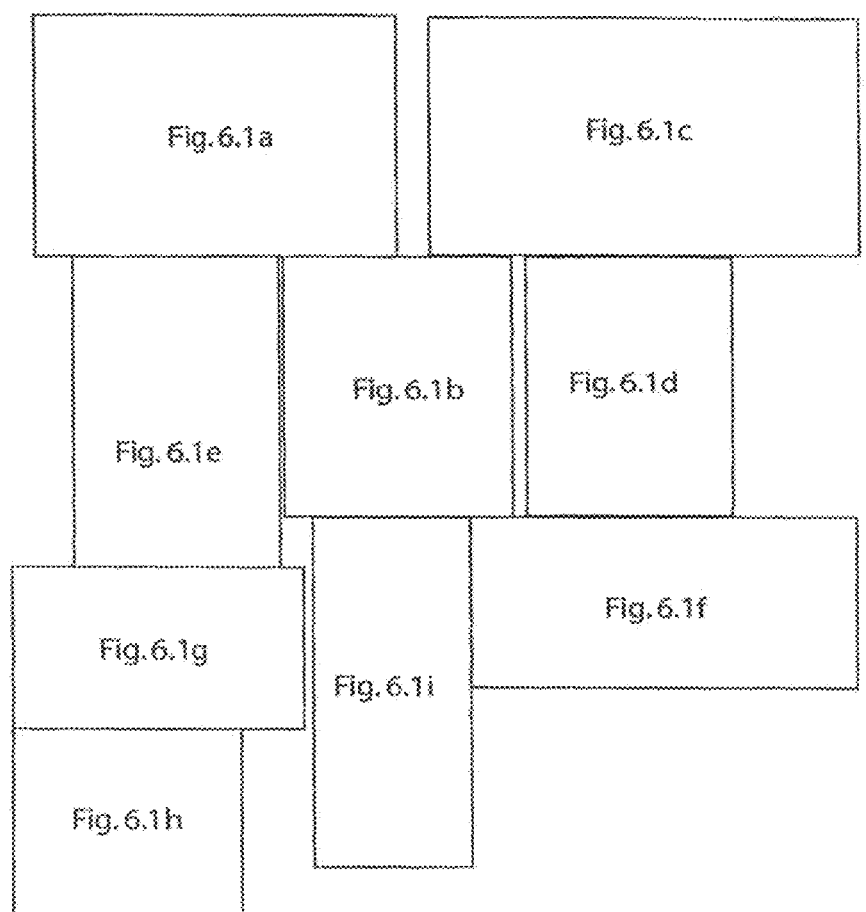
Fig.6.1

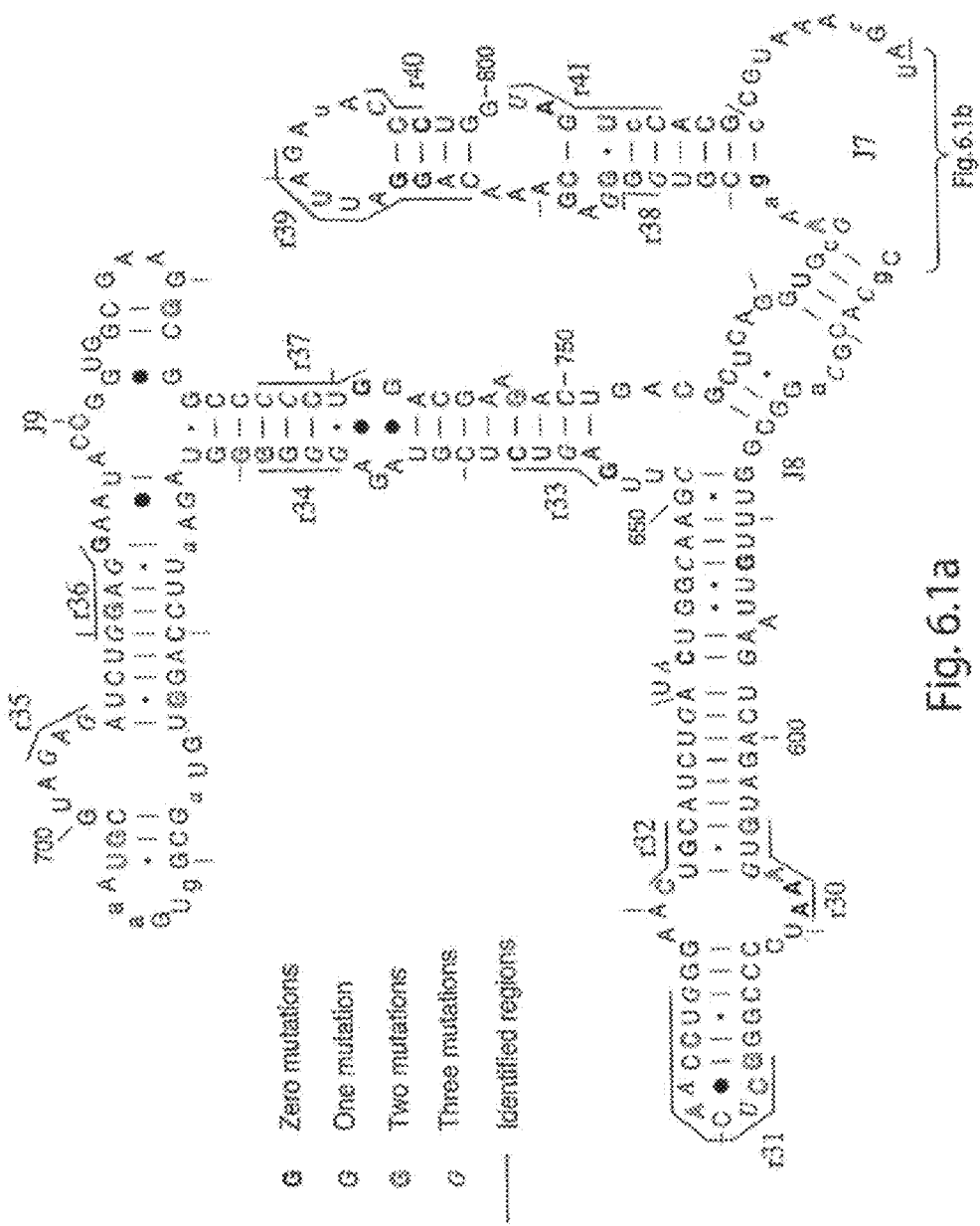
Fig. 6.1a

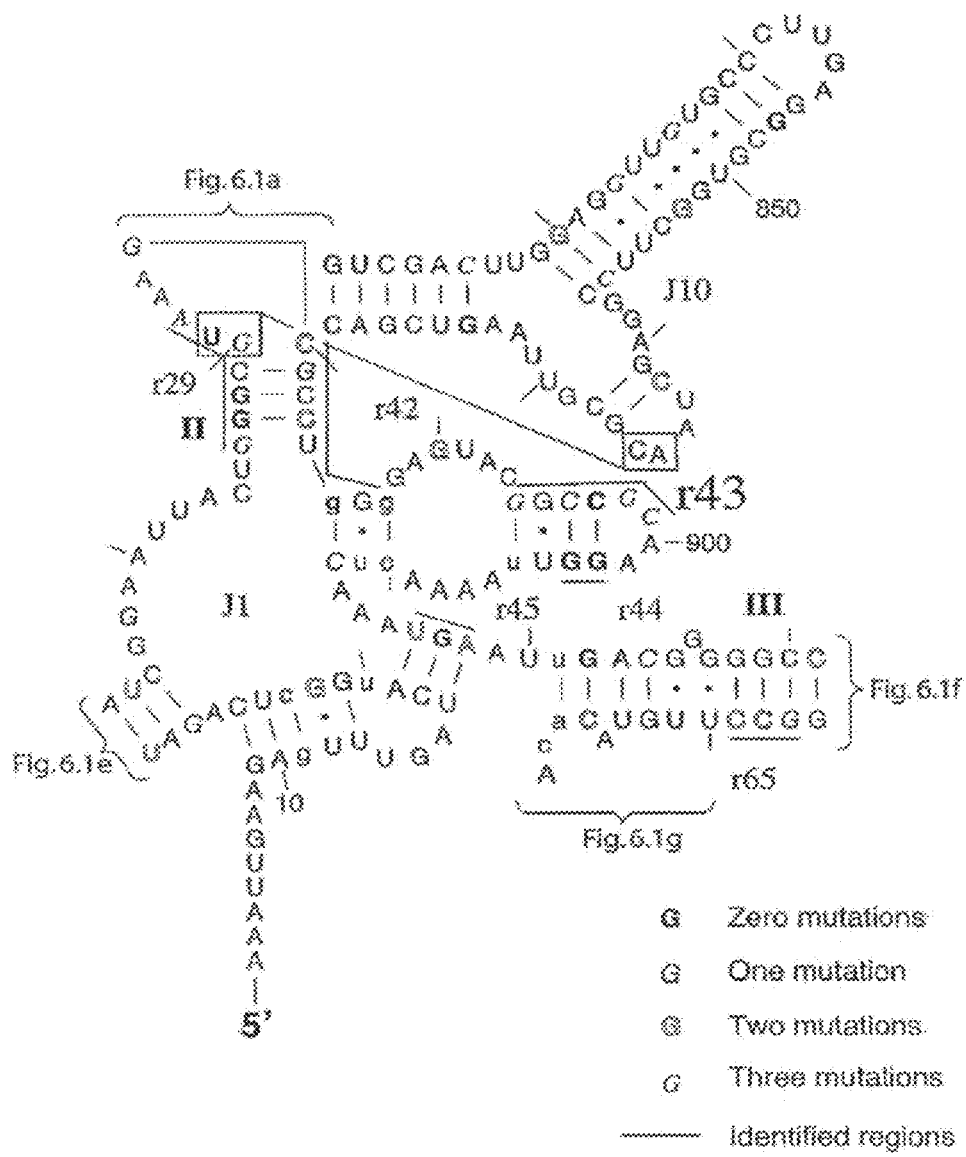
Fig. 6.1b

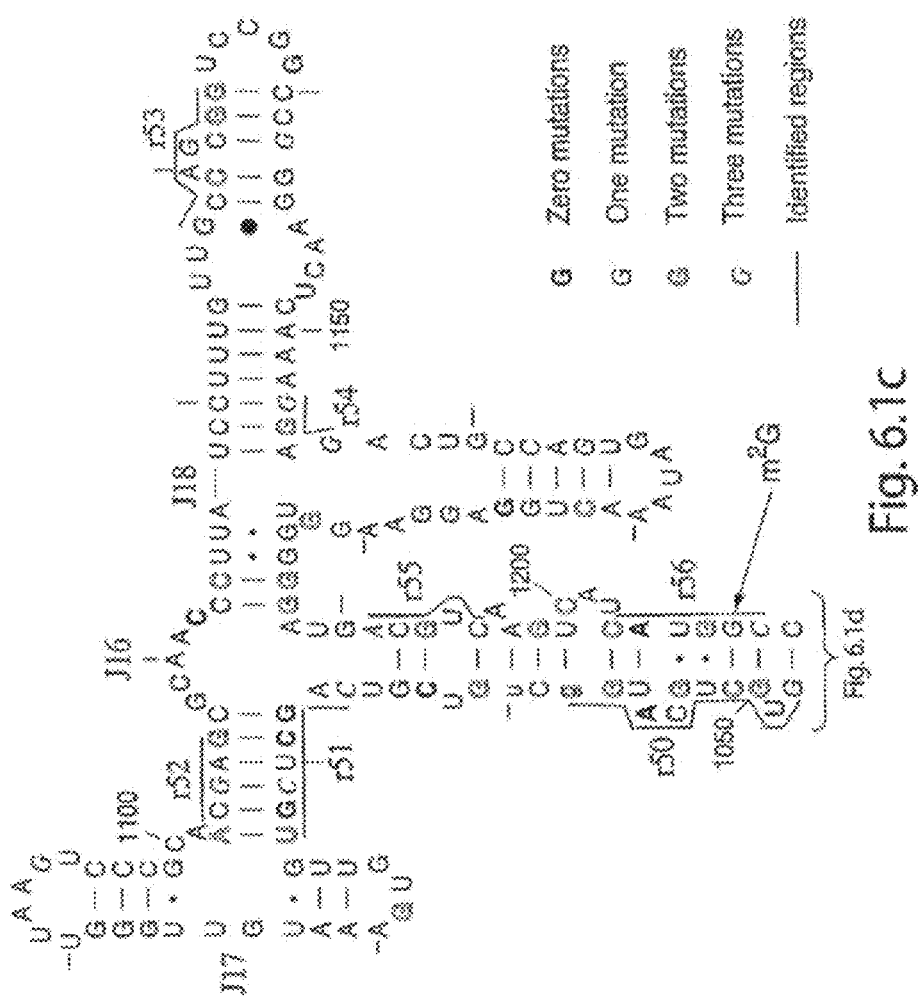

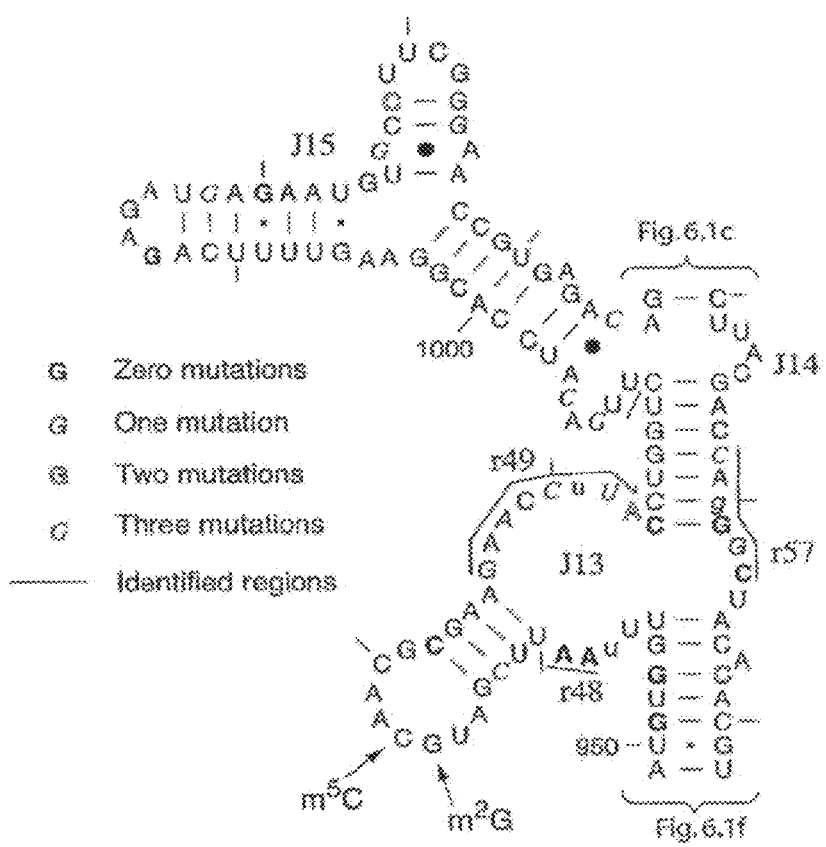
Fig. 6.1d

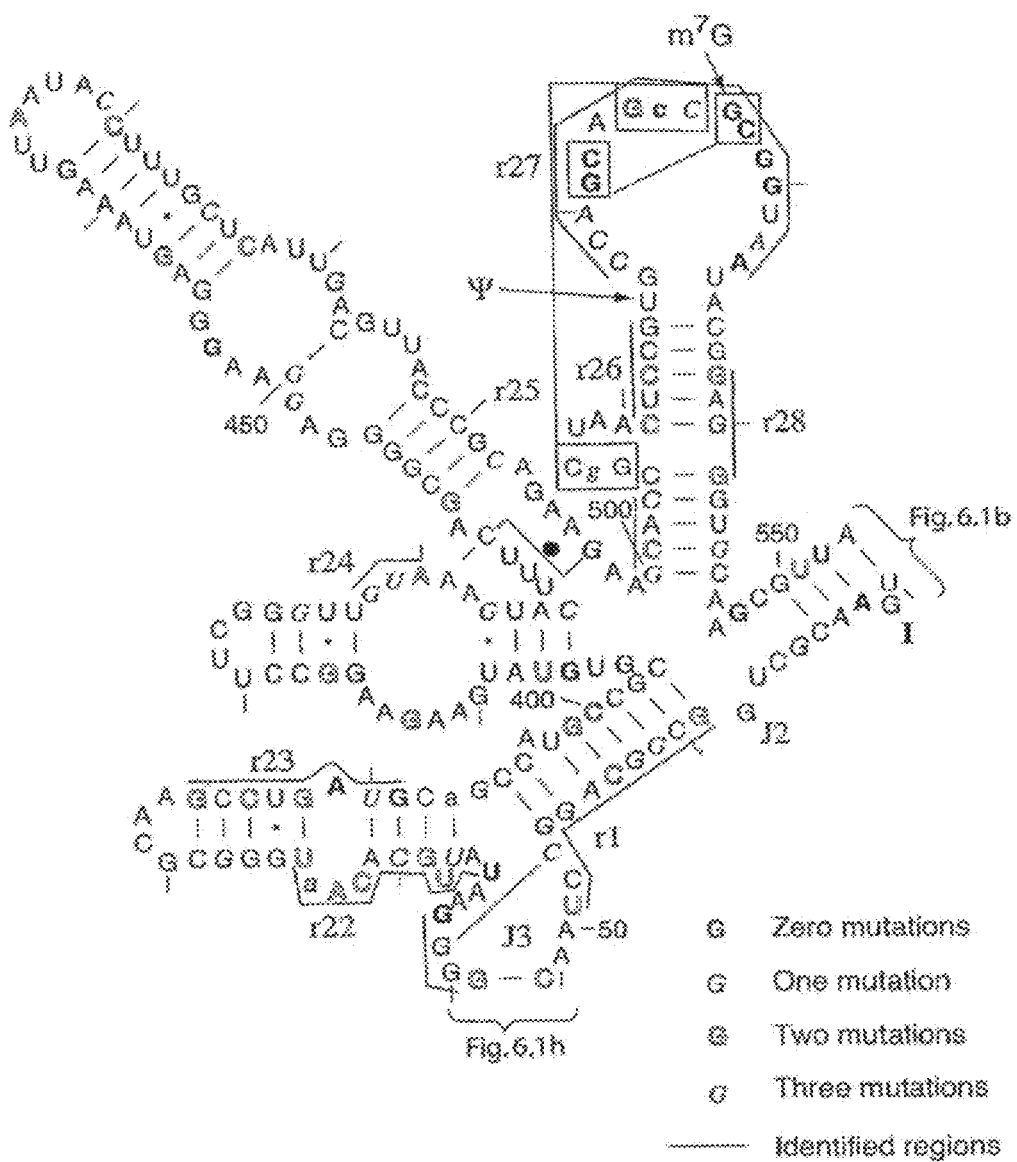
Fig. 6.1e

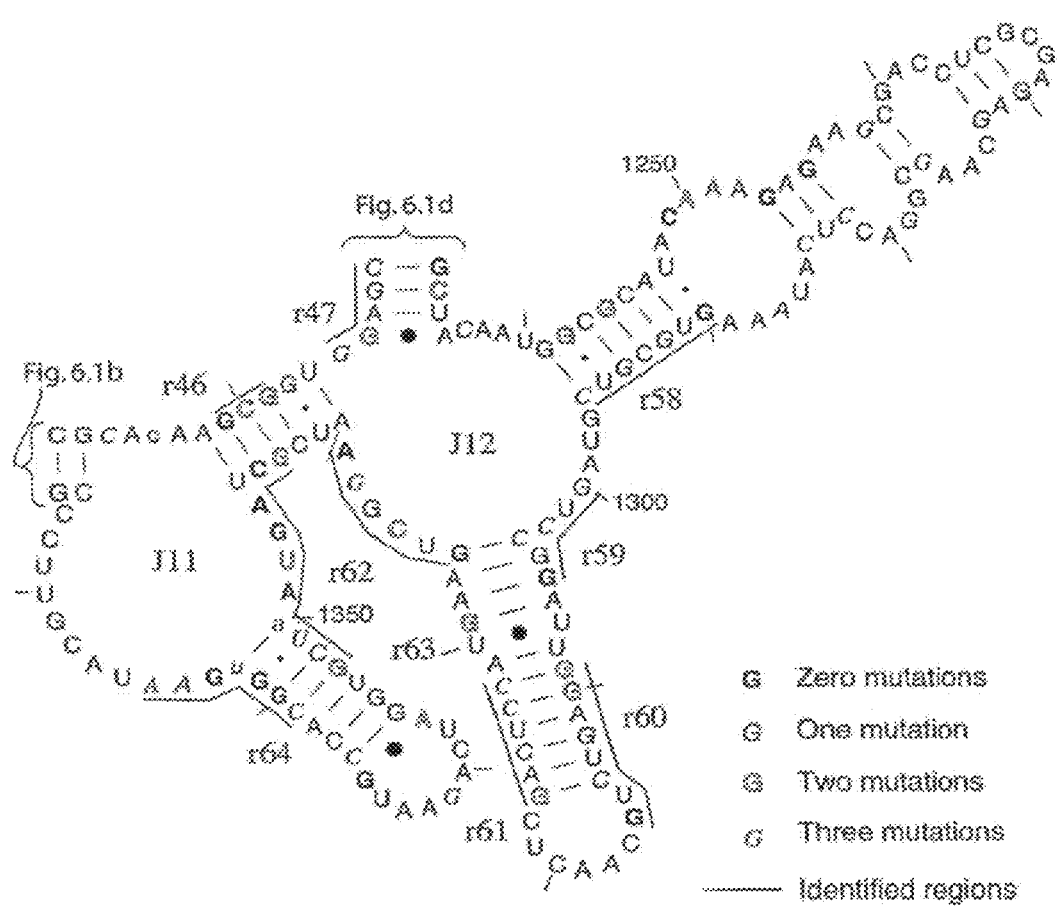
Fig. 6.1f

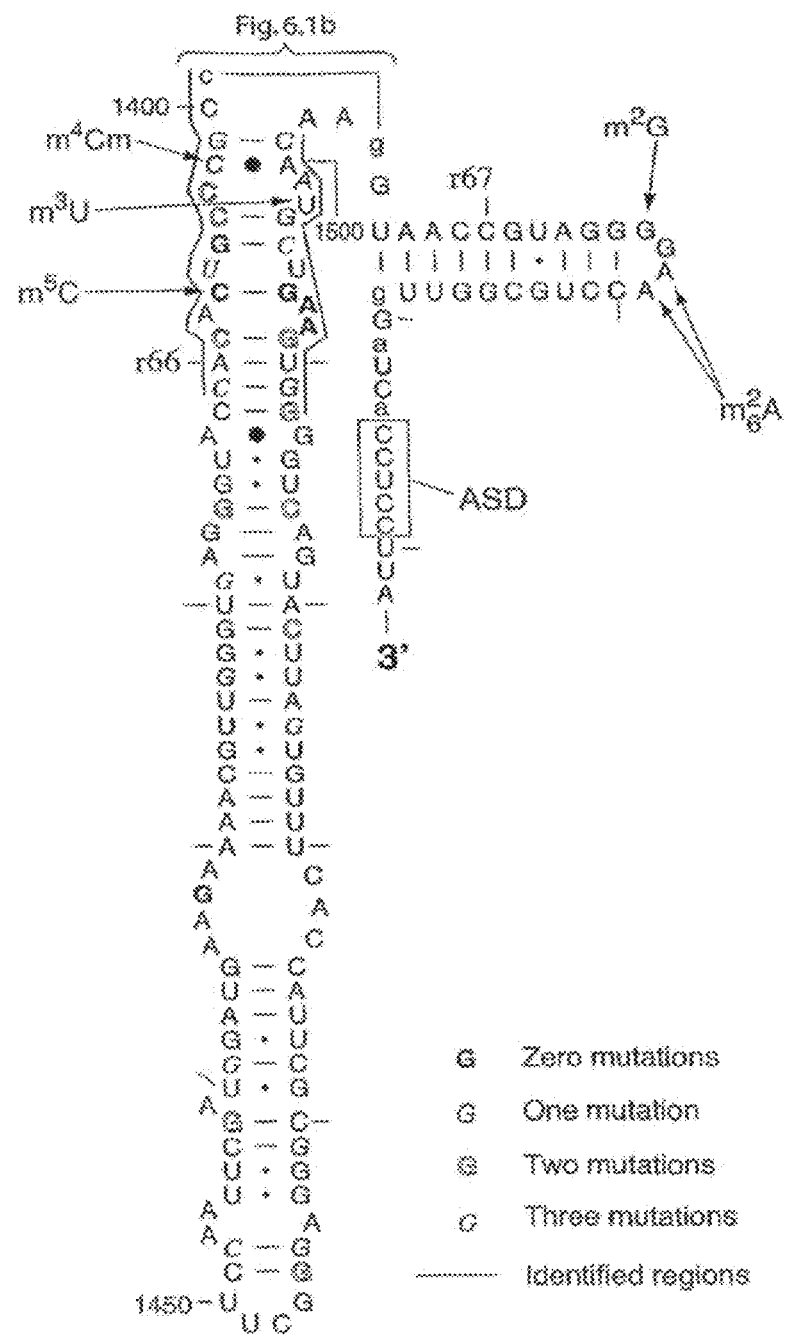
Fig. 6.1g

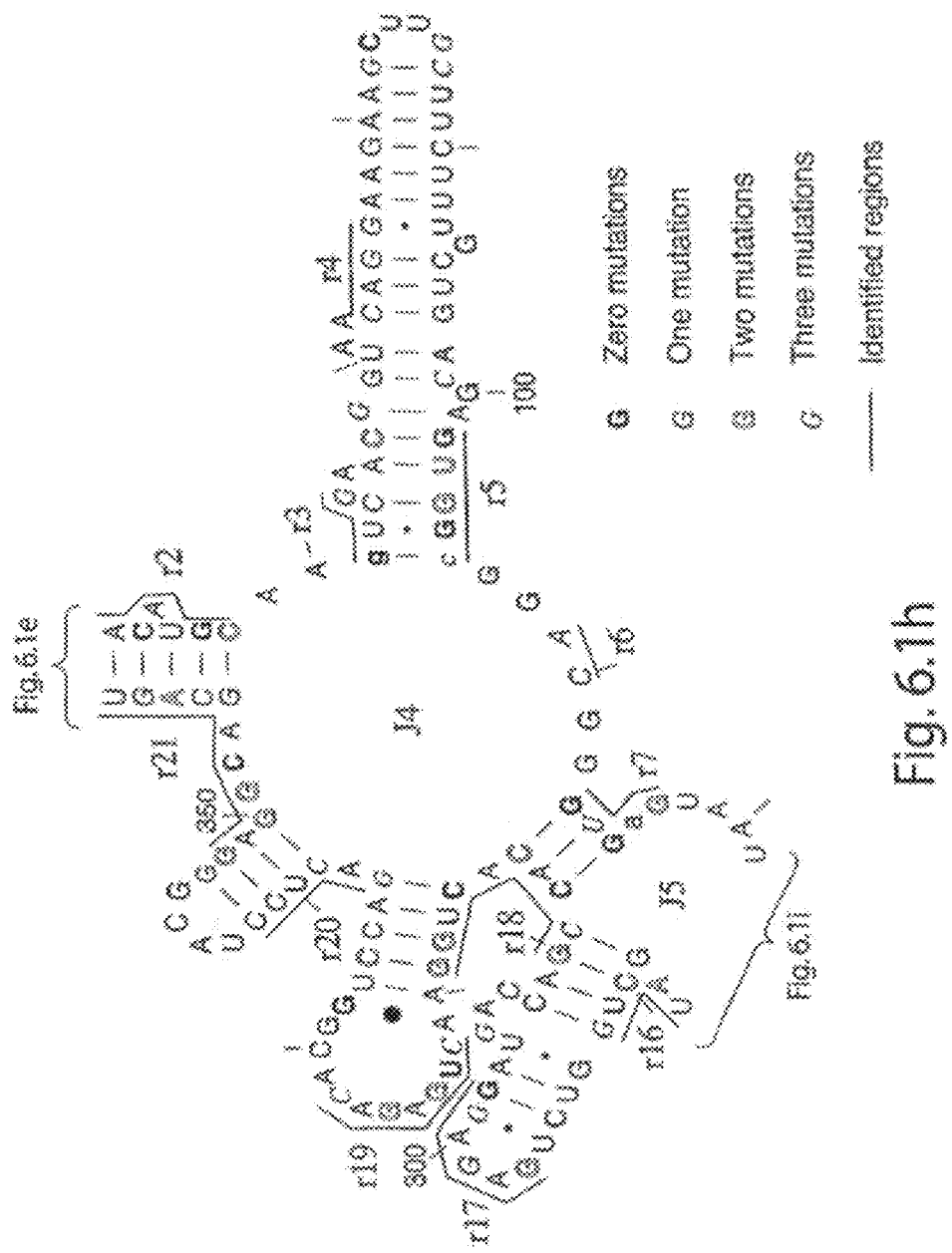
Fig. 6.1h

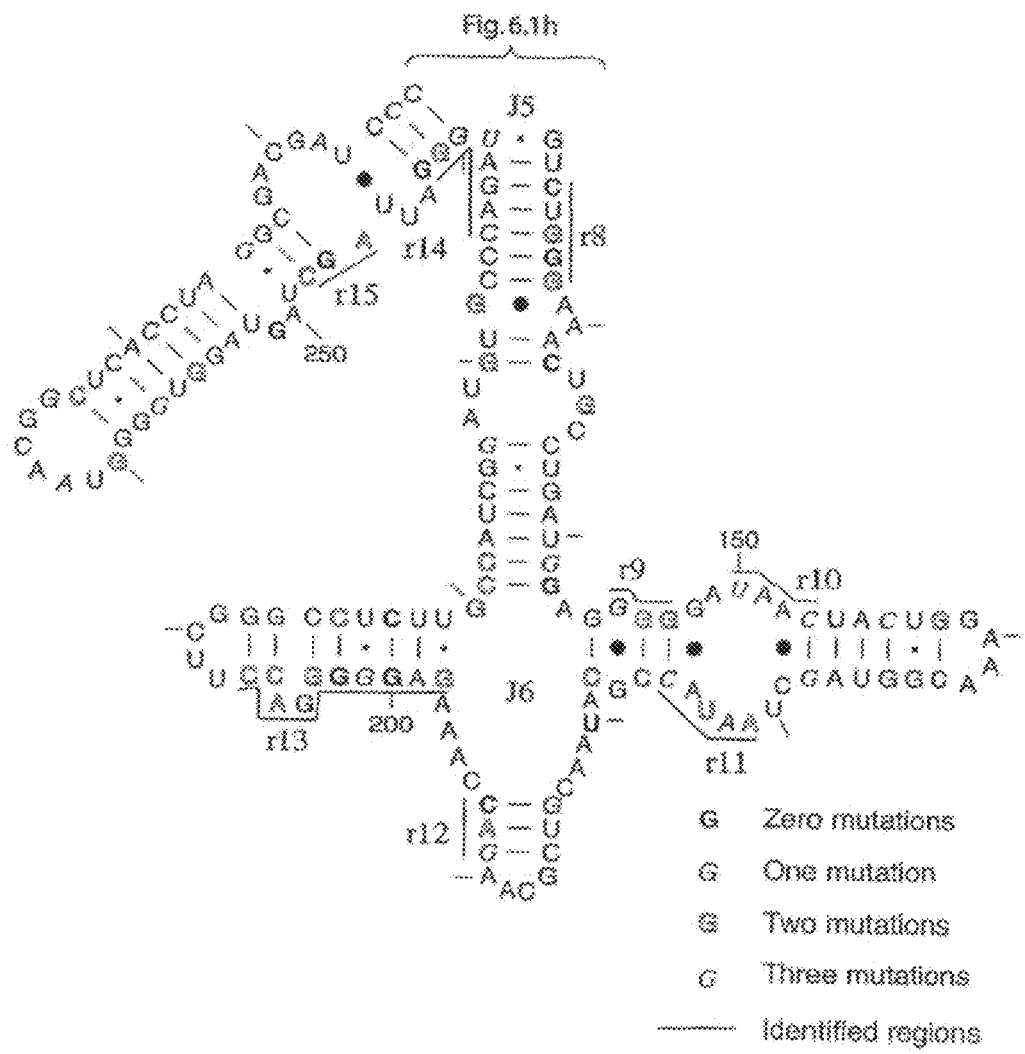
Fig. 6.1i

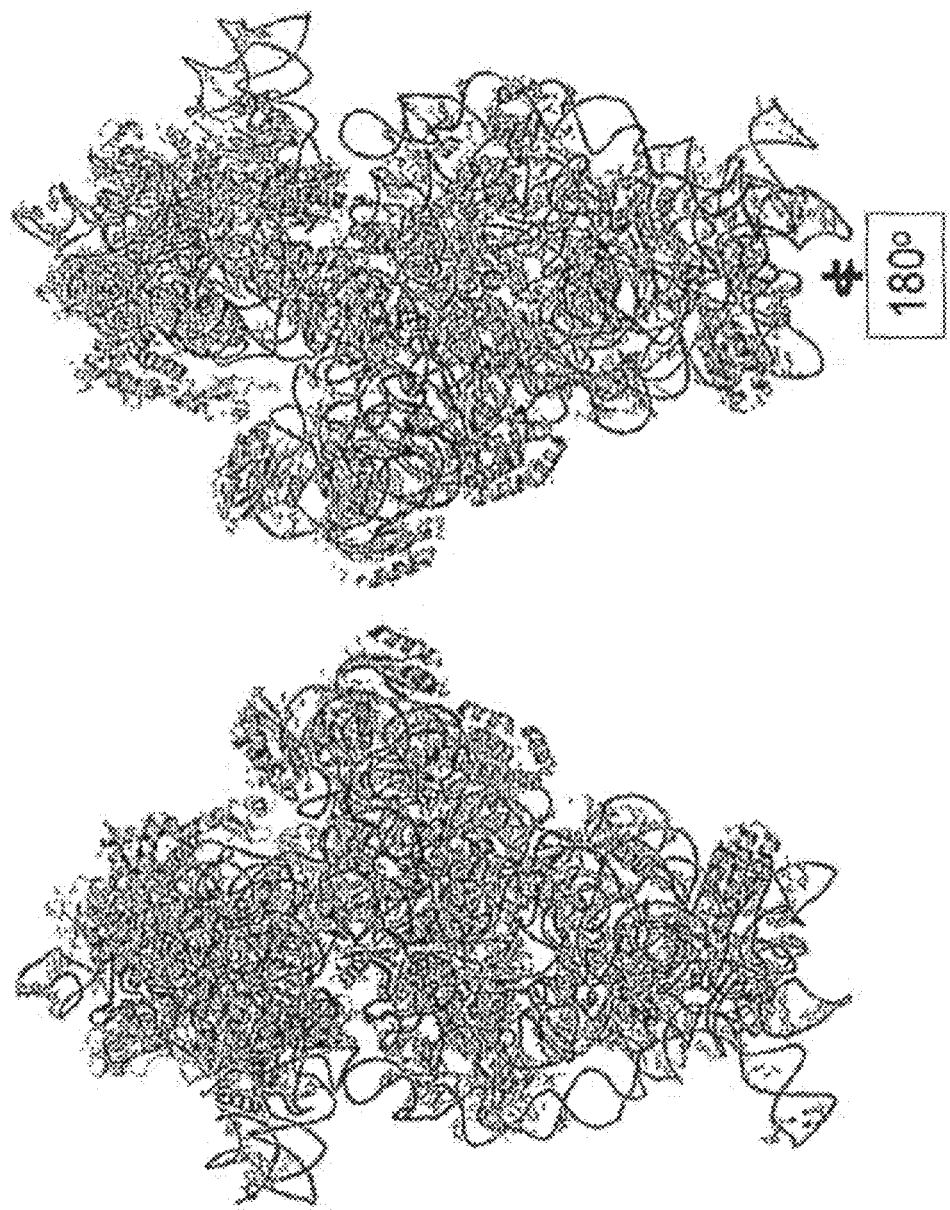
Fig. 6.2

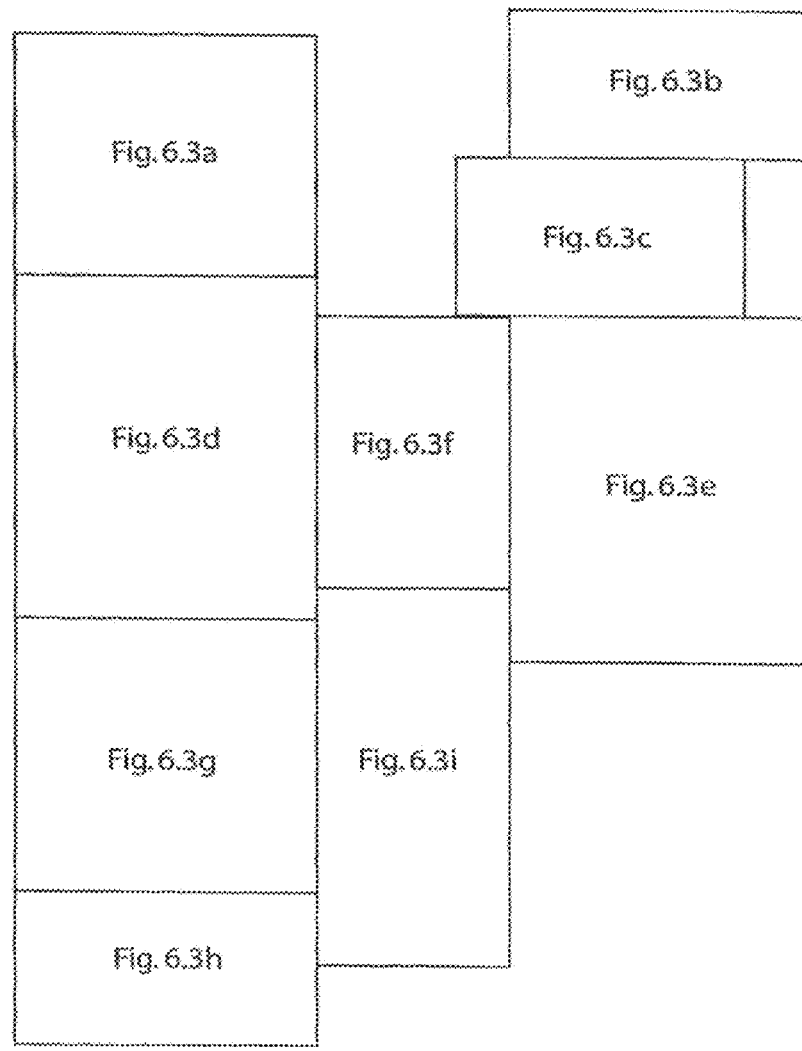
Fig.6.3

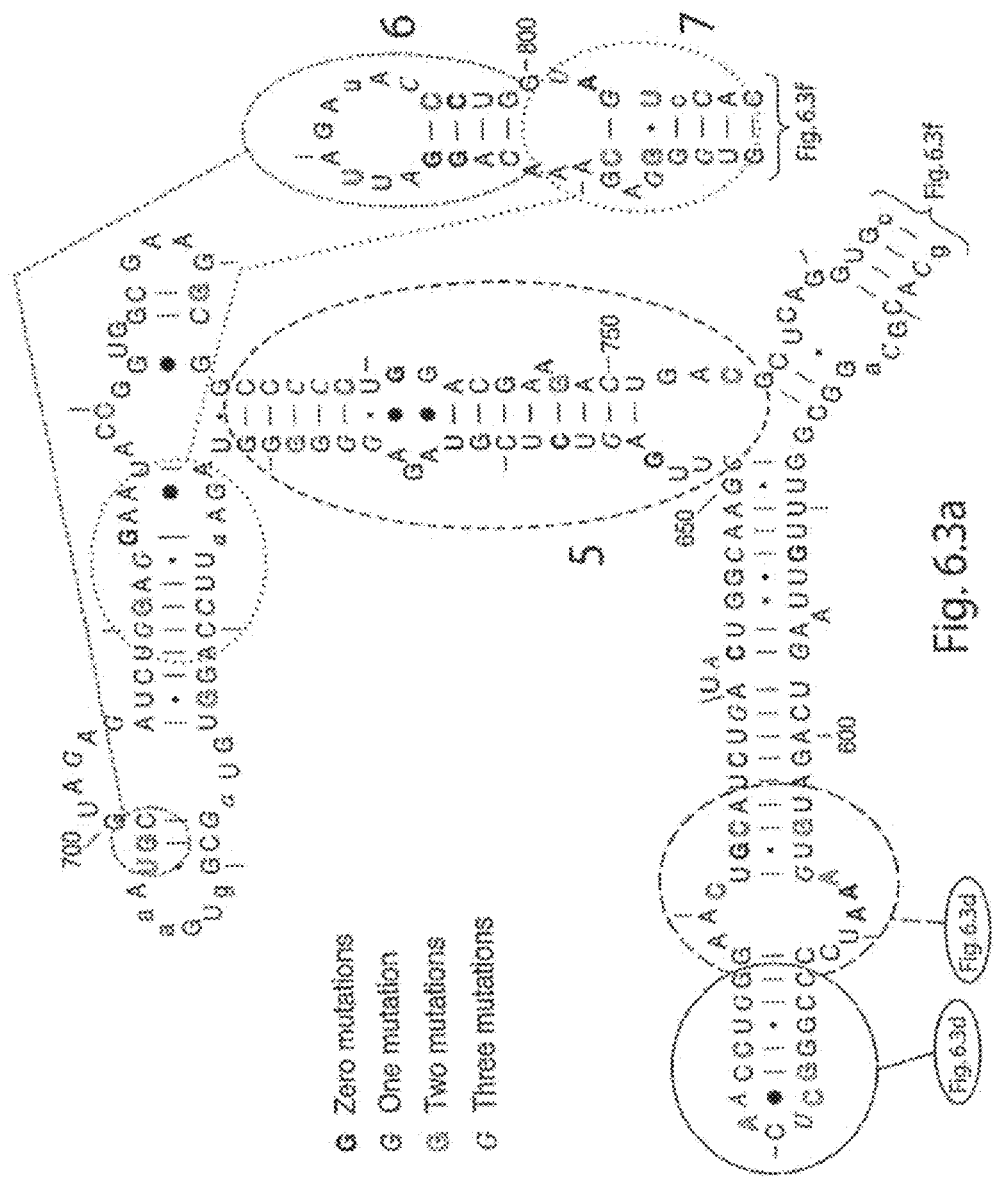
Fig. 6.3a

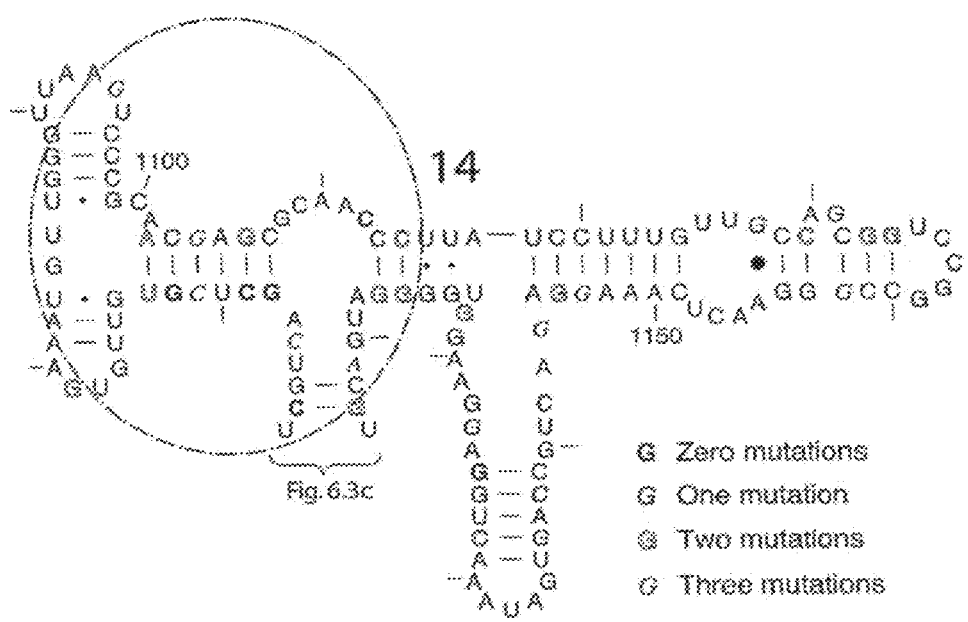
Fig. 6.3b

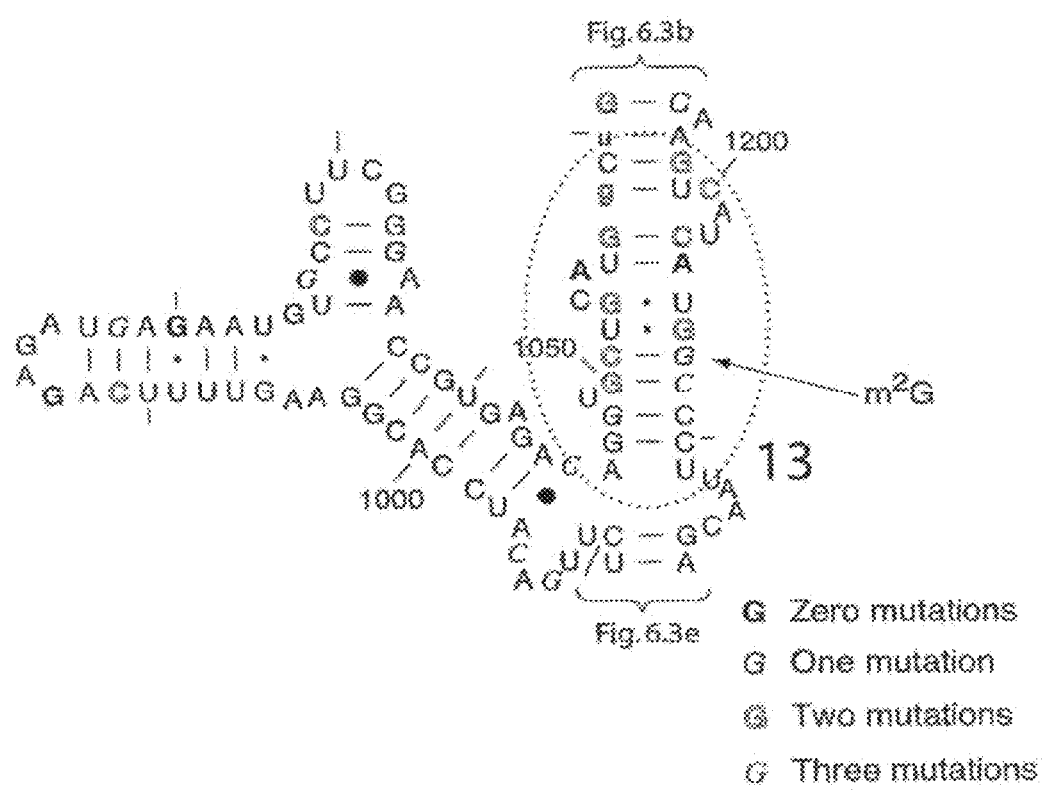
Fig. 6.3c

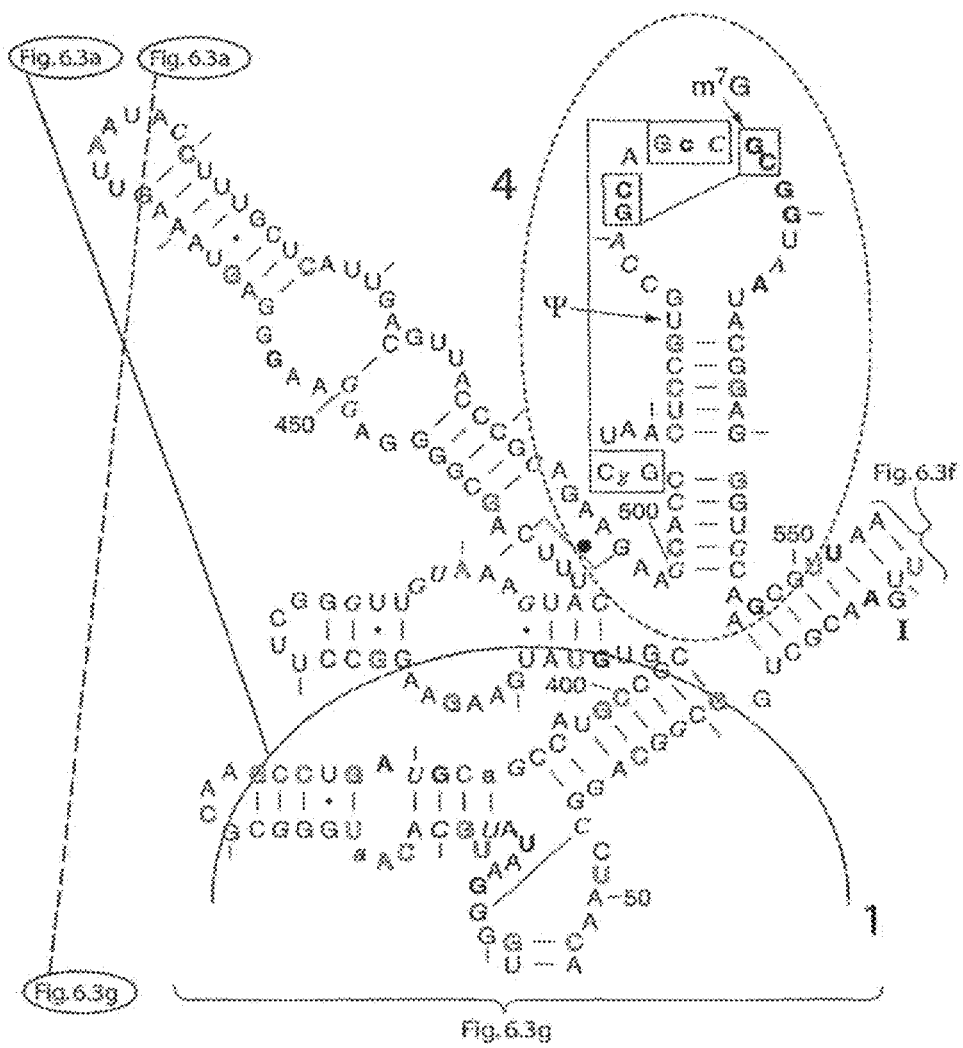
Fig. 6.3d
G Zero mutations
G One mutation
G Two mutations
G Three mutations

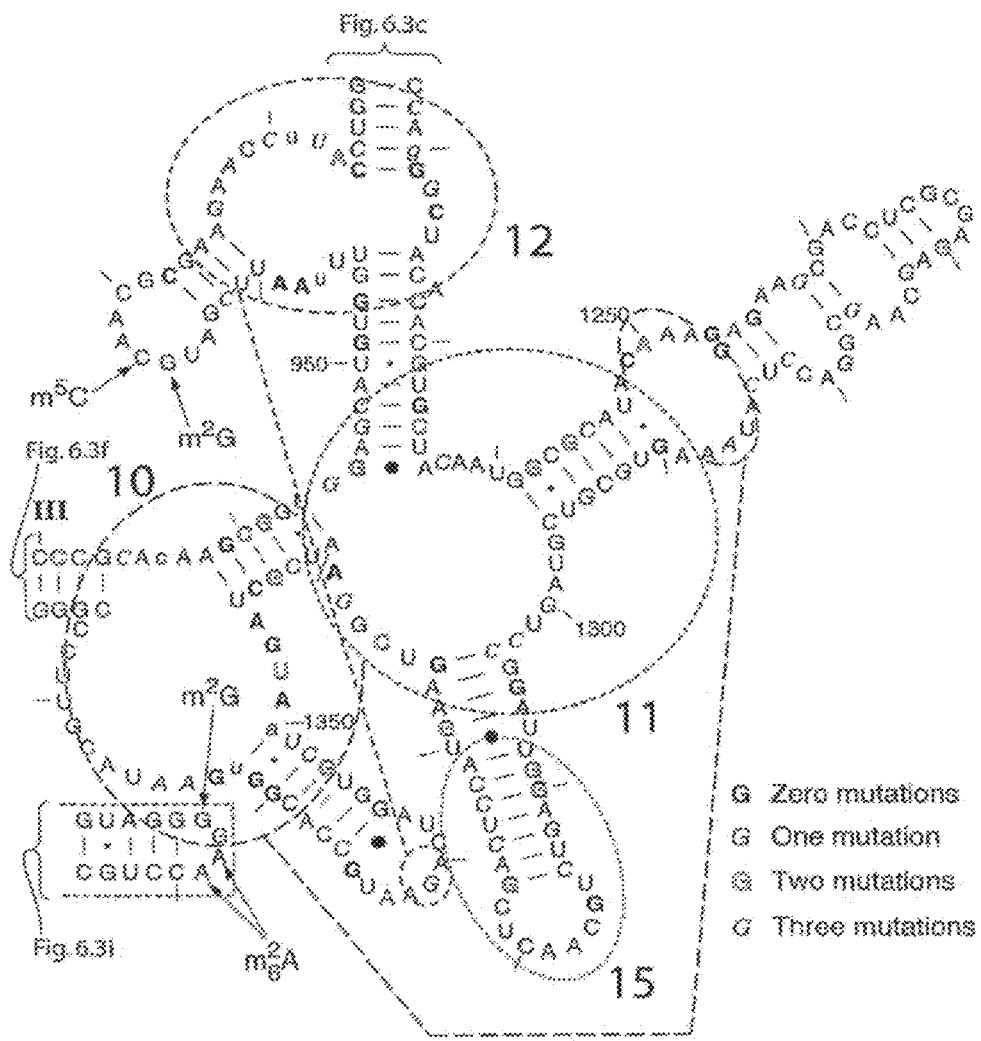
Fig. 6.3e

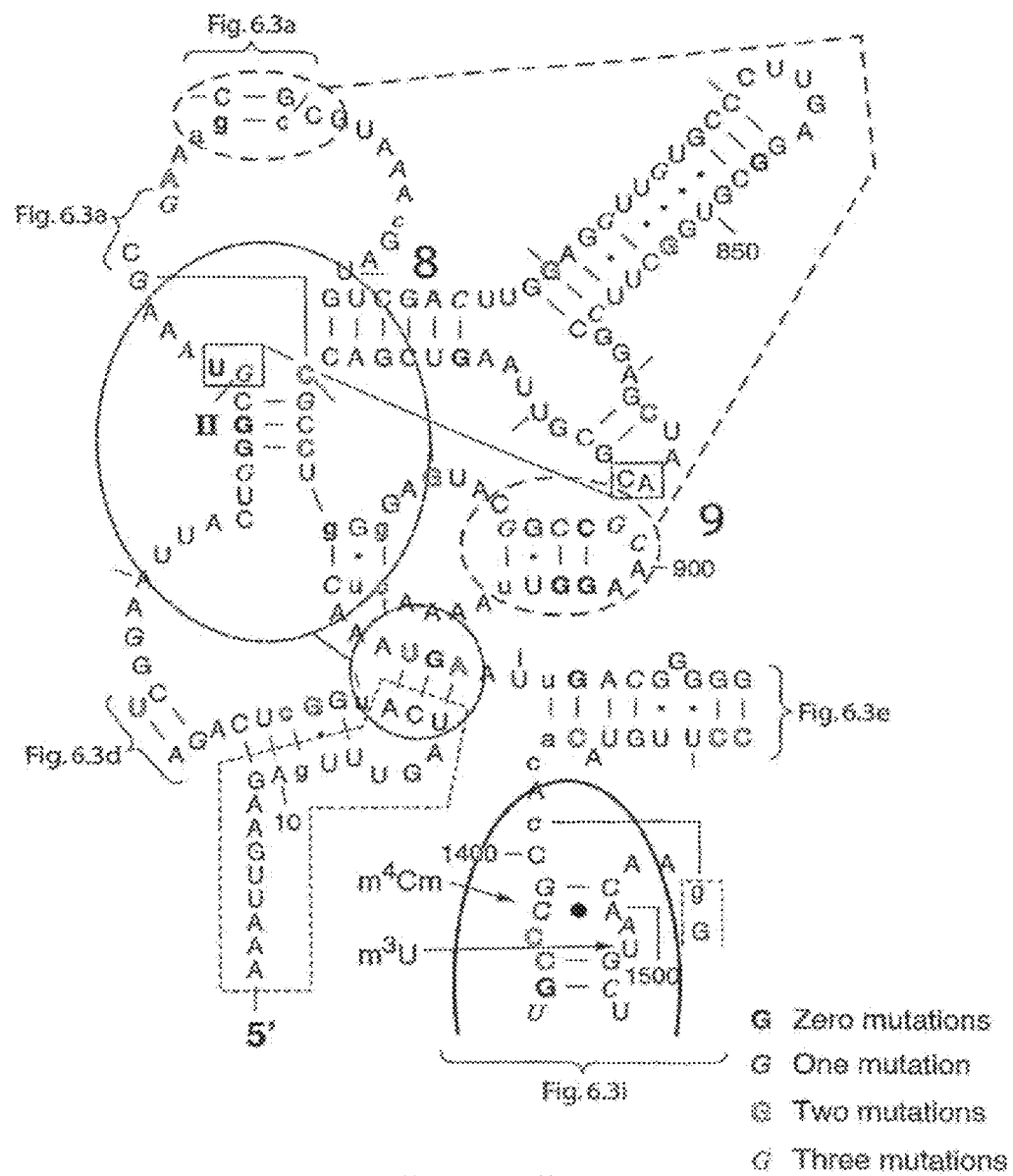
Fig. 6.3f

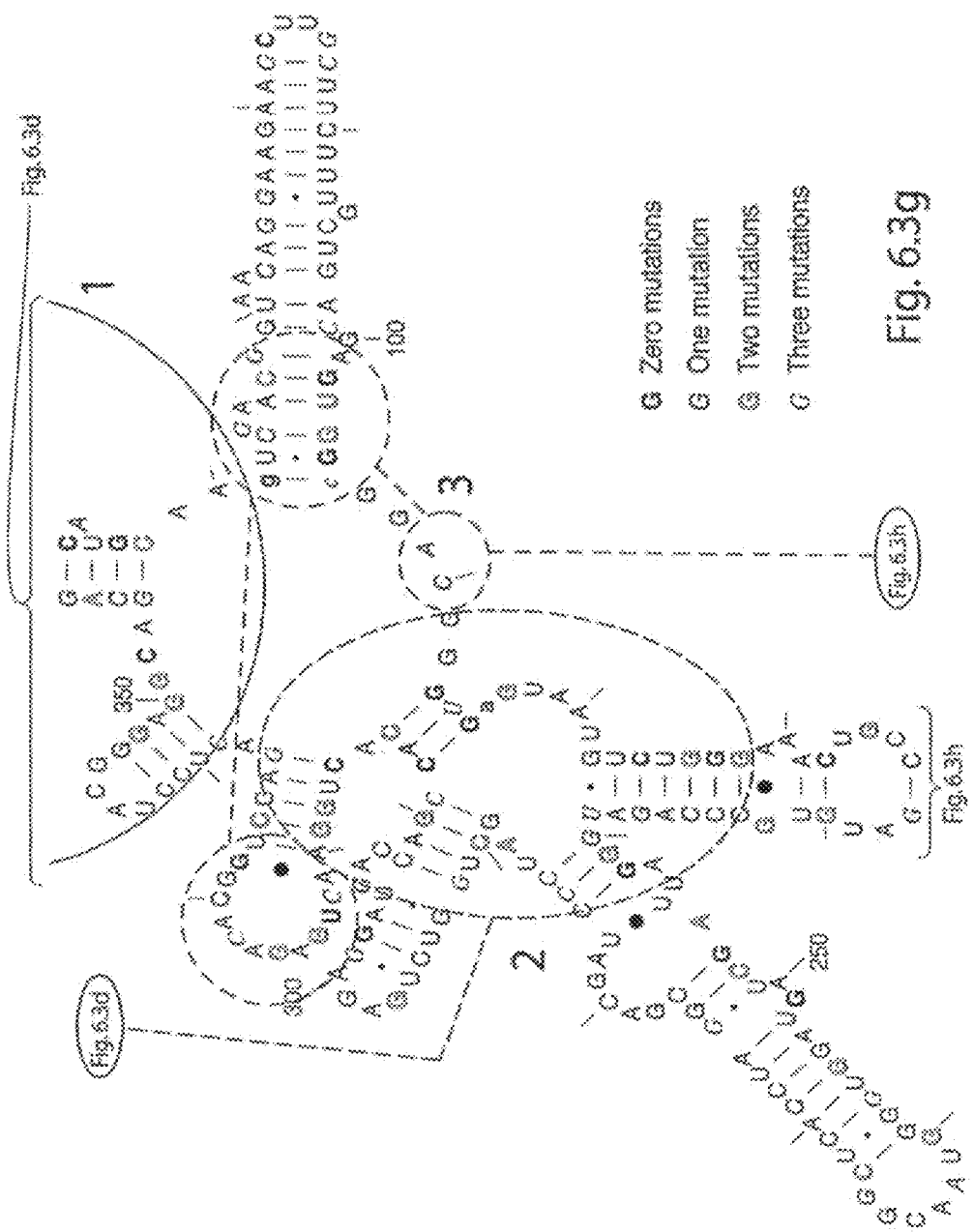

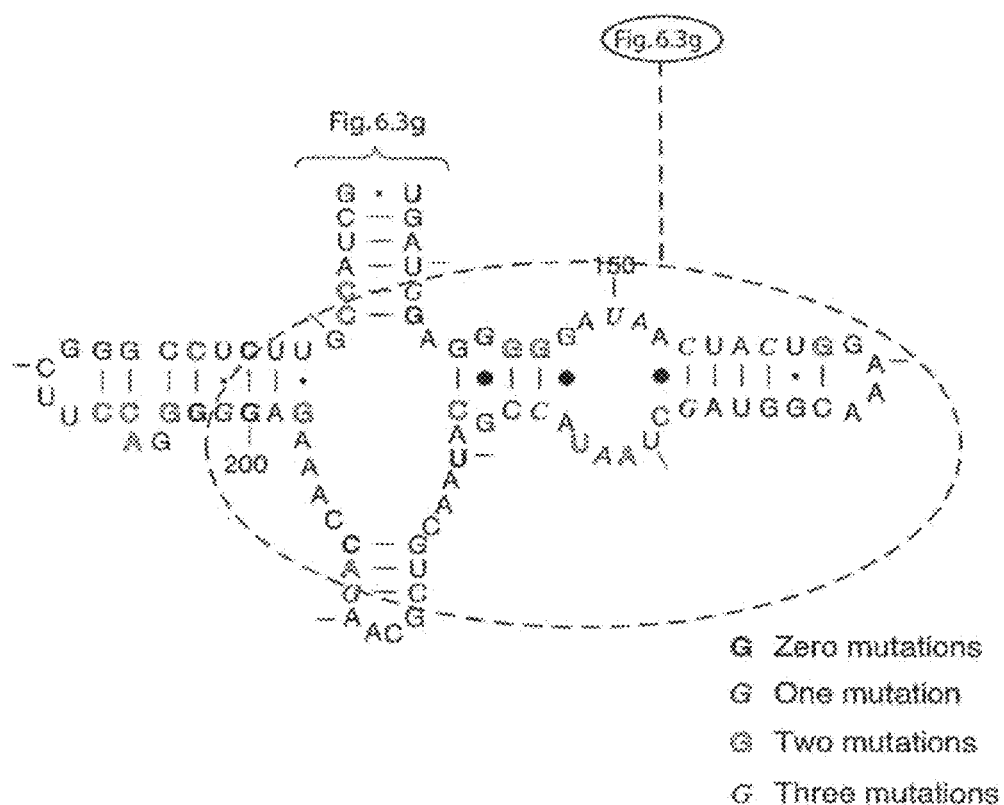
Fig. 6.3h

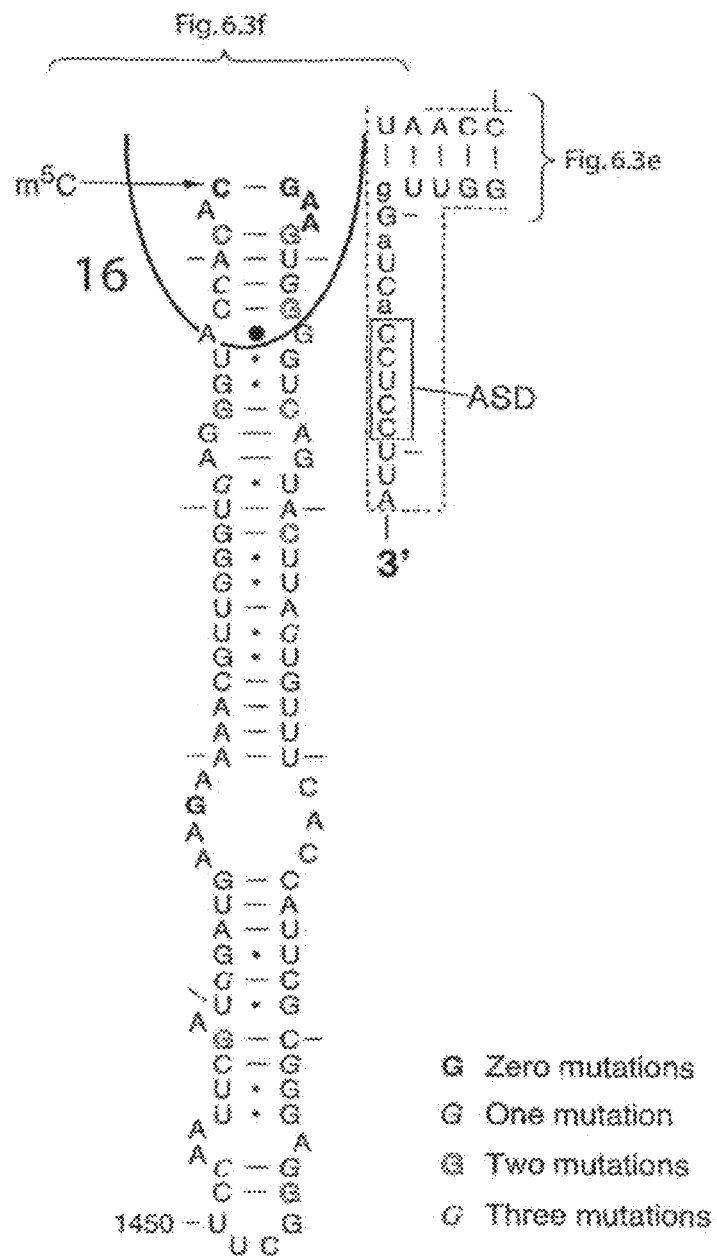
Fig. 6.3i

Table 6.1 Regions identified in the mutation library

| Region | Nucleotides | Functions |
|---|---|---|
| 1 | 39 - 49 | 1 |
| 2 | 52 - 58 | |
| 3 | 61 - 64 | |
| 4 | 73 - 76 | |
| 5 | 102 - 106 | 1 |
| 6 | 109 - 110 | 1 |
| 7 | 113 - 117 | |
| 8 | 124 - 128 | 1 |
| 9 | 145 - 147 | |
| 10 | 150 - 153 | |
| 11 | 171 - 175 | |
| 12 | 191 - 193 | 1 |
| 13 | 198 - 207 | |
| 14 | 235 - 242 | 1 |
| 15 | 246 - 248 | 1 |
| 16 | 285 - 292 | |
| 17 | 297 - 302 | |
| 18 | 310 - 319 | 1 |
| 19 | 322 - 328 | 1 |
| 20 | 337 - 342 | |
| 21 | 348 - 363 | 1 |
| 22 | 365 - 375 | 1 |
| 23 | 384 - 391 | 1 |
| 24 | 428 - 430 | 1 |
| 25 | 500 - 503 | 1 |
| 26 | 511 - 515 | 1 |
| 27 | 518 - 533 | 1, 2a, 4a, 5 |
| 28 | 538 - 541 | 1 |
| 29 | 566 - 572 | 1 |
| 30 | 604 - 609 | 1 |
| 31 | 617 - 626 | 1 |
| 32 | 631 - 634 | |
| 33 | 654 - 658 | 1 |
| 34 | 666 - 669 | 1 | continued

Fig. 6.4a continued

| Region | Nucleotides | Functions |
|---|---|---|
| 35 | 703 - 705 | 1 |
| 36 | 710 - 714 | 1, 3 |
| 37 | 737 - 741 | 1 |
| 38 | 773 - 776 | 3 |
| 39 | 783 - 791 | 2b, 2g, 3, 5 |
| 40 | 795 - 797 | 1, 2b |
| 41 | 801 - 806 | |
| 42 | 880 - 887 | 1 |
| 43 | 894 - 899 | 1 |
| 44 | 902 - 903 | |
| 45 | 916 - 918 | |
| 46 | 939 - 941 | 1 |
| 47 | 944 - 948 | 1 |
| 48 | 958 - 959 | 1 |
| 49 | 976 - 985 | 1 |
| 50 | 1048 - 1058 | 1, 2a, 5 |
| 51 | 1066 - 1073 | 1, 2d |
| 52 | 1102 - 1106 | 1 |
| 53 | 1127 - 1134 | 1 |
| 54 | 1153 - 1156 | 1 |
| 55 | 1191 - 1195 | 1, 2d |
| 56 | 1203 - 1208 | 1 |
| 57 | 1218 - 1223 | 1 |
| 58 | 1290 - 1296 | 1 |
| 59 | 1300 - 1305 | 1 |
| 60 | 1309 - 1316 | 1 |
| 61 | 1323 - 1328 | 1 |
| 62 | 1334 - 1339 | 5 |
| 63 | 1343 - 1353 | 1 |
| 64 | 1369 - 1375 | 1 |
| 65 | 1387 - 1389 | |
| 66 | 1399 - 1411 | 2c, 2f, 3, 4a, 5 |
| 67 | 1488 - 1591 | 1, 2c, 2e, 2f, 2g, 3, 4a, 5 |

1-Protein binding
2-Antibiotic binding (2a Tetracycline, 2b Pactamycin, 2c Hygromycin B, 2d Spectinomycin, 2e Streptomycin, 2f Paromomycin, 2g Edeine)
3-Intersubunit bridges
4-Factor binding (4a IF1, 4b IF3)
5-tRNA binding

Fig. 6.4b

Table 6.2 Clusters identified in the mutational library

| Cluster | Positions | Region(s) | Helix(ces) | Protein(s) |
|---|---|---|---|---|
| 1 | 39-49, 52-58, 337-342, 348-362, 365-375, 384-391, 617-626 | 1, 2, 20, 21, 22, 23, 31 | 4, 5, 15, 21 | S4 (D), S16 (P) |
| 2 | 113-117, 124-128, 239-242, 285-292, 310-319, 604-609, 631-634, 305 | 7, 8, 14, 16, 18, 30, 32 | 7, 11, 12, 21 | S16 (P), S17 (Q) |
| 3 | 61-64, 102-106, 109-110, 322-328, 145-147, 150-153, 171-175, 191-193, 168, 184 | 3, 5, 6, 9, 10, 11, 12, 19 | 6, 8, 9, 13 | S20 (T) |
| 4 | 500-503, 511-515, 518-533, 538-541, 506, 544, 548 | 25, 26, 27, 28 | 18 | S4 (D), S12 (L) |
| 5 | 654-658, 666-669, 737-741, 732, 746, 750, 754 | 33, 34, 37 | 22, 23 | S6 (F), S15 (O) |
| 6 | 783-791, 795-797, 697 | 39, 40 | 23, 24 | |
| 7 | 710-714, 773-776, 801-806, 676, 679 | 36, 38, 41 | 23, 24 | S6 (F) |
| 8 | 566-572, 880-887, 916-918, 575, 910, 912 | 29, 42, 45 | 2, 19 | S12 (L) |
| 9 | 894-899, 902-903 | 43, 44 | 27 | |
| 10 | 939-941, 1343-1353, 1369-1375, 994, 1250, 1287 | 46, 63, 64 | 28, 29, 41, 43 | S7 (G), S9 (I) |
| 11 | 944-948, 1290-1296, 1300-1305, 1334-1339, 1233, 1234, 1237, 1242, 1244 | 47, 58, 59, 62 | 30, 41, 42 | S9 (I), S13 (M) |
| 12 | 958-959, 976-985, 1218-1223, 1361 | 48, 49, 57 | 31, 32, 43 | S14 (N), S19 (S) |
| 13 | 1048-1058, 1203-1208, 1200 | 50, 56 | 34 | S3 (C), S14 (N) |
| 14 | 1066-1073, 1102-1106, 1191-1195, 1061, 1063, 1066, 1094 | 51, 52, 55 | 34, 35 | S2 (B), S5 (E) |
| 15 | 1309-1316, 1323-1328 | 60, 61 | 42 | S13 (M), S14 (N), S19 (S) |
| 16 | 1387-1389, 1399-1411, 1488-1501 | 65, 66, 67 | 28, 44 | S12 (L) |

Fig. 6.5

| Region | Nucleotides | Functions | Region | Nucleotides | Functions |
|---|---|---|---|---|---|
| 1 | 39 - 49 | 1 | 33 | 710 - 714 | 1, 3 |
| 2 | 52 - 58 |  | 34 | 737 - 741 | 1 |
| 3 | 73 - 76 |  | 35 | 773 - 776 | 3 |
| 4 | 102 - 106 | 1 | 36 | 783 - 791 | 2b, 2g, 3, 5 |
| 5 | 109 - 110 | 1 | 37 | 795 - 797 | 1, 2b |
| 6 | 113 - 117 |  | 38 | 801 - 806 |  |
| 7 | 124 - 128 | 1 | 39 | 880 - 887 | 1 |
| 8 | 145 - 147 |  | 40 | 894 - 899 | 1 |
| 9 | 150 - 153 |  | 41 | 902 - 903 |  |
| 10 | 171 - 175 |  | 42 | 916 - 918 |  |
| 11 | 191 - 193 | 1 | 43 | 939 - 941 | 1 |
| 12 | 198 - 207 |  | 44 | 944 - 948 | 1 |
| 13 | 235 - 242 | 1 | 45 | 958 - 959 | 1 |
| 14 | 246 - 248 | 1 | 46 | 976 - 985 | 1 |
| 15 | 285 - 292 |  | 47 | 1048 - 1058 | 1, 2a, 5 |
| 16 | 297 - 302 |  | 48 | 1066 - 1073 | 1, 2d |
| 17 | 310 - 319 | 1 | 49 | 1102 - 1106 | 1 |
| 18 | 322 - 328 | 1 | 50 | 1127 - 1134 | 1 |
| 19 | 337 - 342 |  | 51 | 1153 - 1156 | 1 |
| 20 | 348 - 362 | 1 | 52 | 1191 - 1195 | 1, 2d |
| 21 | 365 - 375 | 1 | 53 | 1203 - 1208 | 1 |
| 22 | 384 - 391 | 1 | 54 | 1218 - 1223 | 1 |
| 23 | 428 - 430 | 1 | 55 | 1233 - 1234 | 1 |
| 24 | 447 - 450 | 1 | 56 | 1290 - 1296 | 1 |
| 25 | 500 - 503 | 1 | 57 | 1300 - 1305 | 1 |
| 26 | 518 - 530 | 1, 2e, 4a, 5 | 58 | 1309 - 1316 | 1 |
| 27 | 538 - 541 | 1 | 59 | 1323 - 1328 | 1 |
| 28 | 566 - 572 | 1 | 60 | 1343 - 1353 | 1 |
| 29 | 604 - 609 | 1 | 61 | 1369 - 1375 | 1 |
| 30 | 617 - 626 | 1 | 62 | 1387 - 1389 |  |
| 31 | 631 - 634 |  | 63 | 1399 - 1411 | 2c, 2f, 3, 4a, 5 |
| 32 | 703 - 705 | 1 | 64 | 1488 - 1501 | 1, 2c, 2e, 2f, 2g, 3, 4a, 5 |

1 Protein binding; 2 Antibiotic binding (2a Tetracycline, 2b Pactamycin, 2c Hygromycin B, 2d Spectinomycin, 2e Streptomycin, 2f Paromomycin, 2g Edeine); 3 Intersubunit bridges; 4 Factor binding (4a IF1, 4b IF3); 5 tRNA binding

Fig. 8

| SEQ ID NO | Nucleotides |
|---|---|
| 1 | 39 - 49 |
| 2 | 52 - 58 |
| 3 | 73 - 76 |
| 4 | 102 - 106 |
| 5 | 109 - 110 |
| 6 | 113 - 117 |
| 7 | 124 - 128 |
| 8 | 145 - 147 |
| 9 | 150 - 153 |
| 10 | 171 - 175 |
| 11 | 191 - 193 |
| 12 | 198 - 207 |
| 13 | 235 - 242 |
| 14 | 246 - 248 |
| 15 | 285 - 292 |
| 16 | 297 - 302 |
| 17 | 310 - 319 |
| 18 | 322 - 328 |
| 19 | 337 - 342 |
| 20 | 348 - 362 |
| 21 | 365 - 375 |
| 22 | 384 - 391 |
| 23 | 428 - 430 |
| 24 | 447 - 450 |
| 25 | 500 - 503 |
| 26 | 518 - 530 |
| 27 | 538 - 541 |
| 28 | 566 - 572 |
| 29 | 604 - 609 |
| 30 | 617 - 626 |
| 31 | 631 - 634 |
| 32 | 703 - 705 |
| 33 | 710 - 714 |
| 34 | 737 - 741 |
| 35 | 773 - 776 |
| 36 | 783 - 791 |
| 37 | 795 - 797 |
| 38 | 801 - 806 |
| 39 | 880 - 887 |
| 40 | 894 - 899 |
| 41 | 902 - 903 |
| 42 | 916 - 918 |
| 43 | 939 - 941 |
| 44 | 944 - 948 |
| 45 | 958 - 959 |
| 46 | 976 - 985 |
| 47 | 1048 - 1058 |
| 48 | 1066 - 1073 |
| 49 | 1102 - 1106 |
| 50 | 1127 - 1134 |
| 51 | 1153 - 1156 |
| 52 | 1191 - 1195 |
| 53 | 1203 - 1208 |
| 54 | 1218 - 1223 |
| 55 | 1233 - 1234 |
| 56 | 1290 - 1296 |
| 57 | 1300 - 1305 |
| 58 | 1309 - 1316 |
| 59 | 1323 - 1328 |
| 60 | 1343 - 1353 |
| 61 | 1369 - 1375 |
| 62 | 1387 - 1389 |
| 63 | 1399 - 1411 |
| 64 | 1488 - 1501 |

Fig. 9

| Cluster | Positions | Region(s) | Helix(ces) | Protein(s) |
|---|---|---|---|---|
| 1 | 73-76 | 3 | 6 | |
| 2 | 198-207 | 12 | 10 | |
| 3 | 428-430 | 23 | 16 | S4 (D) |
| 4 | 500-503, 518-530, 538-541 | 25, 26, 27 | 18 | S4 (D), S12 (L) |
| 5 | 285-292, 297-302 | 15, 16 | 11a, 12 | |
| 6 | 102-106, 145-147, 150-153, 171-175, 191-193 | 4, 8, 9, 10, 11 | 6, 8, 9 | S20 (T) |
| 7 | 124-128, 235-242, 246-248 | 7, 13, 14 | 7, 11 | S17 (Q) |
| 8 | 39-49, 52-58, 109-110, 113-117, 310-319, 322-328, 337-342, 348-362, 365-375, 384-391, 447-450 | 1, 2, 5, 6, 17, 18, 19, 20, 21, 23, 24 | 4, 5, 6a, 13, 14, 15, 17 | S12 (L), S16 (P), S20 (T) |
| 9 | 703-705, 737-741 | 32, 34 | 22, 23 | S6 (F), S11 (K), S15 (O) |
| 10 | 604-609, 617-626, 631-634 | 29, 30, 31 | 21 | S4 (D), S16 (P) |
| 11 | 763-791, 795-797 | 36, 37 | 24 | S11 (K) |
| 12 | 894-899, 902-903 | 40, 41 | 27 | S17 (Q) |
| 13 | 566-573, 880-887, 916-918 | 28, 39, 42 | 2, 19 | S12 (L) |
| 14 | 710-714, 773-776, 801-806 | 33, 35, 38 | 23, 24 | S6 (F), S11 (K), S15 (O) |
| 15 | 1127-1134 | 50 | 39 | S9 (I) |
| 16 | 1153-1156 | 51 | 40 | |
| 17 | 939-941, 944-948, 1233-1234, 1290-1296, 1300-1305 | 43, 44, 55, 56, 57 | 29, 30, 41, 42 | S7 (G), S9 (I), S13 (M) |
| 18 | 1343-1353, 1369-1375 | 60, 61 | 43 | S7 (G), S9 (I) |
| 19 | 958-959, 976-985, 1218-1223, 1309-1316, 1323-1328 | 45, 46, 54, 58, 59 | 31, 32, 42 | S13 (M), S14 (N), S19 (S) |
| 20 | 1048-1058, 1066-1073, 1102-1106, 1191-1195, 1203-1208 | 47, 48, 49, 52, 53 | 34, 35 | S2 (B), S3 (C), S4 (D), S5 (E) |
| 21 | 1387-1399, 1399-1411, 1488-1501 | 62, 63, 64 | 28, 44 | S12 (L) |

Fig. 10

SEQUENCE LISTING

```
<160> NUMBER OF SEQ ID NOS: 95

<210> SEQ ID NO 1
<211> LENGTH: 11
<212> TYPE: RNA
<213> ORGANISM: Escherichia coli

<400> SEQUENCE: 1
gcggcaggcc u                                                            11

<210> SEQ ID NO 2
<211> LENGTH: 7
<212> TYPE: RNA
<213> ORGANISM: Escherichia coli

<400> SEQUENCE: 2
```

```
cacaugc                                                              7

<210> SEQ ID NO 3
<211> LENGTH: 4
<212> TYPE: RNA
<213> ORGANISM: Escherichia coli

<400> SEQUENCE: 3 cagg                                                                 4

<210> SEQ ID NO 4
<211> LENGTH: 5
<212> TYPE: RNA
<213> ORGANISM: Escherichia coli

<400> SEQUENCE: 4 guggc                                                                5

<210> SEQ ID NO 5
<211> LENGTH: 2
<212> TYPE: RNA
<213> ORGANISM: Escherichia coli

<400> SEQUENCE: 5 ac                                                                   2

<210> SEQ ID NO 6
<211> LENGTH: 5
<212> TYPE: RNA
<213> ORGANISM: Escherichia coli

<400> SEQUENCE: 6 gugag                                                                5

<210> SEQ ID NO 7
<211> LENGTH: 5
<212> TYPE: RNA
<213> ORGANISM: Escherichia coli

<400> SEQUENCE: 7 cuggg                                                                5

<210> SEQ ID NO 8
<211> LENGTH: 3
<212> TYPE: RNA
<213> ORGANISM: Escherichia coli

<400> SEQUENCE: 8 ggg                                                                  3

<210> SEQ ID NO 9
<211> LENGTH: 4
<212> TYPE: RNA
<213> ORGANISM: Escherichia coli

<400> SEQUENCE: 9 uaac                                                                 4

<210> SEQ ID NO 10
<211> LENGTH: 5
<212> TYPE: RNA
<213> ORGANISM: Escherichia coli
```

```
<400> SEQUENCE: 10 aauac                                                              5

<210> SEQ ID NO 11
<211> LENGTH: 3
<212> TYPE: RNA
<213> ORGANISM: Escherichia coli

<400> SEQUENCE: 11 gac                                                                3

<210> SEQ ID NO 12
<211> LENGTH: 10
<212> TYPE: RNA
<213> ORGANISM: Escherichia coli

<400> SEQUENCE: 12
gaggggacc                                                         10

<210> SEQ ID NO 13
<211> LENGTH: 8
<212> TYPE: RNA
<213> ORGANISM: Escherichia coli

<400> SEQUENCE: 13 cagauggg                                                           8

<210> SEQ ID NO 14
<211> LENGTH: 3
<212> TYPE: RNA
<213> ORGANISM: Escherichia coli

<400> SEQUENCE: 14 agc                                                                3

<210> SEQ ID NO 15
<211> LENGTH: 8
<212> TYPE: RNA
<213> ORGANISM: Escherichia coli

<400> SEQUENCE: 15 ccuagcug                                                           8

<210> SEQ ID NO 16
<211> LENGTH: 6
<212> TYPE: RNA
<213> ORGANISM: Escherichia coli

<400> SEQUENCE: 16 gagagg                                                             6

<210> SEQ ID NO 17
<211> LENGTH: 10
<212> TYPE: RNA
<213> ORGANISM: Escherichia coli

<400> SEQUENCE: 17
gccacacugg                                                        10

<210> SEQ ID NO 18
<211> LENGTH: 7
<212> TYPE: RNA
<213> ORGANISM: Escherichia coli
```

```
<400> SEQUENCE: 18 cugagac                                                              7

<210> SEQ ID NO 19
<211> LENGTH: 6
<212> TYPE: RNA
<213> ORGANISM: Escherichia coli

<400> SEQUENCE: 19 gacucc                                                               6

<210> SEQ ID NO 20
<211> LENGTH: 15
<212> TYPE: RNA
<213> ORGANISM: Escherichia coli

<400> SEQUENCE: 20
gaggcagcag ugggg                                                    15

<210> SEQ ID NO 21
<211> LENGTH: 11
<212> TYPE: RNA
<213> ORGANISM: Escherichia coli

<400> SEQUENCE: 21
uauugcacaa u                                                        11

<210> SEQ ID NO 22
<211> LENGTH: 8
<212> TYPE: RNA
<213> ORGANISM: Escherichia coli

<400> SEQUENCE: 22 gccugaug                                                             8

<210> SEQ ID NO 23
<211> LENGTH: 3
<212> TYPE: RNA
<213> ORGANISM: Escherichia coli

<400> SEQUENCE: 23 gua                                                                  3

<210> SEQ ID NO 24
<211> LENGTH: 4
<212> TYPE: RNA
<213> ORGANISM: Escherichia coli

<400> SEQUENCE: 24 gagg                                                                 4

<210> SEQ ID NO 25
<211> LENGTH: 4
<212> TYPE: RNA
<213> ORGANISM: Escherichia coli

<400> SEQUENCE: 25 gcac                                                                 4

<210> SEQ ID NO 26
<211> LENGTH: 13
<212> TYPE: RNA
```

```
<213> ORGANISM: Escherichia coli

<400> SEQUENCE: 26
ccagcagccg cgg                                                          13

<210> SEQ ID NO 27
<211> LENGTH: 4
<212> TYPE: RNA
<213> ORGANISM: Escherichia coli

<400> SEQUENCE: 27 gagg                                                                     4

<210> SEQ ID NO 28
<211> LENGTH: 7
<212> TYPE: RNA
<213> ORGANISM: Escherichia coli

<400> SEQUENCE: 28 gggcgua                                                                  7

<210> SEQ ID NO 29
<211> LENGTH: 6
<212> TYPE: RNA
<213> ORGANISM: Escherichia coli

<400> SEQUENCE: 29 gugaaa                                                                   6

<210> SEQ ID NO 30
<211> LENGTH: 10
<212> TYPE: RNA
<213> ORGANISM: Escherichia coli

<400> SEQUENCE: 30
gcucaaccug                                                              10

<210> SEQ ID NO 31
<211> LENGTH: 4
<212> TYPE: RNA
<213> ORGANISM: Escherichia coli

<400> SEQUENCE: 31 cugc                                                                     4

<210> SEQ ID NO 32
<211> LENGTH: 3
<212> TYPE: RNA
<213> ORGANISM: Escherichia coli

<400> SEQUENCE: 32 gag                                                                      3

<210> SEQ ID NO 33
<211> LENGTH: 5
<212> TYPE: RNA
<213> ORGANISM: Escherichia coli

<400> SEQUENCE: 33 ggagg                                                                    5

<210> SEQ ID NO 34
<211> LENGTH: 5
```

```
<212> TYPE: RNA
<213> ORGANISM: Escherichia coli

<400> SEQUENCE: 34 cccug                                                                    5

<210> SEQ ID NO 35
<211> LENGTH: 4
<212> TYPE: RNA
<213> ORGANISM: Escherichia coli

<400> SEQUENCE: 35 gggg                                                                     4

<210> SEQ ID NO 36
<211> LENGTH: 9
<212> TYPE: RNA
<213> ORGANISM: Escherichia coli

<400> SEQUENCE: 36 caggauuag                                                                9

<210> SEQ ID NO 37
<211> LENGTH: 3
<212> TYPE: RNA
<213> ORGANISM: Escherichia coli

<400> SEQUENCE: 37 ccc                                                                      3

<210> SEQ ID NO 38
<211> LENGTH: 6
<212> TYPE: RNA
<213> ORGANISM: Escherichia coli

<400> SEQUENCE: 38 uagucc                                                                   6

<210> SEQ ID NO 39
<211> LENGTH: 8
<212> TYPE: RNA
<213> ORGANISM: Escherichia coli

<400> SEQUENCE: 39 cgccuggg                                                                 8

<210> SEQ ID NO 40
<211> LENGTH: 6
<212> TYPE: RNA
<213> ORGANISM: Escherichia coli

<400> SEQUENCE: 40 ggccgc                                                                   6

<210> SEQ ID NO 41
<211> LENGTH: 2
<212> TYPE: RNA
<213> ORGANISM: Escherichia coli

<400> SEQUENCE: 41 gg                                                                       2

<210> SEQ ID NO 42
```

```
<211> LENGTH: 3
<212> TYPE: RNA
<213> ORGANISM: Escherichia coli

<400> SEQUENCE: 42 uga                                                                        3

<210> SEQ ID NO 43
<211> LENGTH: 3
<212> TYPE: RNA
<213> ORGANISM: Escherichia coli

<400> SEQUENCE: 43 gcg                                                                        3

<210> SEQ ID NO 44
<211> LENGTH: 5
<212> TYPE: RNA
<213> ORGANISM: Escherichia coli

<400> SEQUENCE: 44 ggagc                                                                      5

<210> SEQ ID NO 45
<211> LENGTH: 2
<212> TYPE: RNA
<213> ORGANISM: Escherichia coli

<400> SEQUENCE: 45 aa                                                                         2

<210> SEQ ID NO 46
<211> LENGTH: 10
<212> TYPE: RNA
<213> ORGANISM: Escherichia coli

<400> SEQUENCE: 46
gaaccuuacc                                                                10

<210> SEQ ID NO 47
<211> LENGTH: 11
<212> TYPE: RNA
<213> ORGANISM: Escherichia coli

<400> SEQUENCE: 47
gugcugcaug g                                                              11

<210> SEQ ID NO 48
<211> LENGTH: 8
<212> TYPE: RNA
<213> ORGANISM: Escherichia coli

<400> SEQUENCE: 48 cagcucgu                                                                   8

<210> SEQ ID NO 49
<211> LENGTH: 5
<212> TYPE: RNA
<213> ORGANISM: Escherichia coli

<400> SEQUENCE: 49 acgag                                                                      5
```

```
<210> SEQ ID NO 50
<211> LENGTH: 8
<212> TYPE: RNA
<213> ORGANISM: Escherichia coli

<400> SEQUENCE: 50 gccagcgg                                                                   8

<210> SEQ ID NO 51
<211> LENGTH: 4
<212> TYPE: RNA
<213> ORGANISM: Escherichia coli

<400> SEQUENCE: 51 ggag                                                                       4

<210> SEQ ID NO 52
<211> LENGTH: 5
<212> TYPE: RNA
<213> ORGANISM: Escherichia coli

<400> SEQUENCE: 52 acguc                                                                      5

<210> SEQ ID NO 53
<211> LENGTH: 6
<212> TYPE: RNA
<213> ORGANISM: Escherichia coli

<400> SEQUENCE: 53 cauggc                                                                     6

<210> SEQ ID NO 54
<211> LENGTH: 6
<212> TYPE: RNA
<213> ORGANISM: Escherichia coli

<400> SEQUENCE: 54 cagggc                                                                     6

<210> SEQ ID NO 55
<211> LENGTH: 2
<212> TYPE: RNA
<213> ORGANISM: Escherichia coli

<400> SEQUENCE: 55 gc                                                                         2

<210> SEQ ID NO 56
<211> LENGTH: 7
<212> TYPE: RNA
<213> ORGANISM: Escherichia coli

<400> SEQUENCE: 56 gugcguc                                                                    7

<210> SEQ ID NO 57
<211> LENGTH: 6
<212> TYPE: RNA
<213> ORGANISM: Escherichia coli

<400> SEQUENCE: 57 guccgg                                                                     6
```

```
<210> SEQ ID NO 58
<211> LENGTH: 8
<212> TYPE: RNA
<213> ORGANISM: Escherichia coli

<400> SEQUENCE: 58 ggagucug                                                                    8

<210> SEQ ID NO 59
<211> LENGTH: 6
<212> TYPE: RNA
<213> ORGANISM: Escherichia coli

<400> SEQUENCE: 59 gacucc                                                                      6

<210> SEQ ID NO 60
<211> LENGTH: 11
<212> TYPE: RNA
<213> ORGANISM: Escherichia coli

<400> SEQUENCE: 60
gcuaguaauc g                                                               11

<210> SEQ ID NO 61
<211> LENGTH: 7
<212> TYPE: RNA
<213> ORGANISM: Escherichia coli

<400> SEQUENCE: 61 cggugaa                                                                     7

<210> SEQ ID NO 62
<211> LENGTH: 3
<212> TYPE: RNA
<213> ORGANISM: Escherichia coli

<400> SEQUENCE: 62 gcc                                                                         3

<210> SEQ ID NO 63
<211> LENGTH: 13
<212> TYPE: RNA
<213> ORGANISM: Escherichia coli

<400> SEQUENCE: 63
ccgcccguca cac                                                             13

<210> SEQ ID NO 64
<211> LENGTH: 14
<212> TYPE: RNA
<213> ORGANISM: Escherichia coli

<400> SEQUENCE: 64
ggugaagucg uaac                                                            14

<210> SEQ ID NO 65
<211> LENGTH: 1542
<212> TYPE: RNA
<213> ORGANISM: Escherichia coli

<400> SEQUENCE: 65
aaauugaaga guuugaucau ggcucagauu gaacgcuggc ggcaggccua acacaugcaa          60
```

| | |
|---|---|
| gucgaacggu aacaggaaga agcuugcuuc uuugcugacg aguggcggac gggugaguaa | 120 |
| ugucugggaa acugccugau ggaggggau aacuacugga aacgguagcu aauaccgcau | 180 |
| aacgucgcaa gaccaaagag ggggaccuuc gggccucuug ccaucggaug ugcccagaug | 240 |
| ggauuagcua uaggugggg uaacggcuca ccuaggcgac gaucccuagc uggucugaga | 300 |
| ggaugaccag ccacacugga acugagacac gguccagacu ccuacgggag gcagcagugg | 360 |
| ggaauauugc acaauggcg caagccugau gcagccaugc cgcguguaug aagaaggccu | 420 |
| ucggguugua aaguacuuuc agcggggagg aagggaguaa aguuaauacc uuugcucauu | 480 |
| gacguuaccc gcagaagaag caccggcuaa cuccgugcca gcagccgcgg uaauacggag | 540 |
| ggugcaagcg uuaaucggaa uuacugggcg uaaagcgcac gcaggcgguu guuaagucag | 600 |
| gaugugaaau ccccgggcuc aaccggaa cugcaucuga uacugcaag cuugagcucu | 660 |
| guagagggg guagaauucc aggguagcg gugaaaugcg uagagaucug gaggaauacc | 720 |
| gguggcgaag gcggccccu ggacgaagac ugacgcucag gugcgaaagc gggggagca | 780 |
| aacaggauua gauacccugg uaguccacgc cguaaacgau gucgacuugg agguugugcc | 840 |
| cuugaggcgu ggcuuccgga gcuaacgcgu uaagucgacc gccuggggag uacggccgca | 900 |
| agguuaaaac ucaaaugaau ugacggggc ccgcacaagc gguggagcau gguguuaau | 960 |
| ucgaugcaac gcgaagaacc uuaccuggc uugacaucca cggaaguuu cagagaugag | 1020 |
| aaugugccuu cgggaaccgu gagacaggug cugcauggcu gucucagcu cguguuguga | 1080 |
| aauguugggu uaagucccgc aacgagcgca acccuuaucc uuuguugcca gcggccggc | 1140 |
| cgggaacuca aaggagacug ccagugauaa acuggaggaa ggugggaug acgucaaguc | 1200 |
| aucauggcc uuacgaccag ggcuacacac gugcuacaau ggcgcauaca aagagaagcg | 1260 |
| accucgcgag agcaagcgga ccucauaaag ugcgucuag uccggauugg agucugcaac | 1320 |
| ucgacuccau gaagucggaa ucgcuaguaa ucguggauca gaaugccacg gugaauacgu | 1380 |
| ucccgggccu uguacacacc gcccgucaca ccaugggagu ggguugcaaa agaaguaggu | 1440 |
| agcuuaaccu ucggagggc gcuuaccacu uugugauuca ugacuggggu gaagucguaa | 1500 |
| caagguaacc guaggggaac cugcgguugg aucaccuccu ua | 1542 |

<210> SEQ ID NO 66
<211> LENGTH: 19
<212> TYPE: DNA
<213> ORGANISM: Artificial Sequence
<220> FEATURE:
<223> OTHER INFORMATION: synthetic primer

<400> SEQUENCE: 66
aaattgaaga gtttgatca                                                19

<210> SEQ ID NO 67
<211> LENGTH: 20
<212> TYPE: DNA
<213> ORGANISM: Artificial Sequence
<220> FEATURE:
<223> OTHER INFORMATION: synthetic primer

<400> SEQUENCE: 67
cgcgtaaacg ccttgctttt                                               20

<210> SEQ ID NO 68
<211> LENGTH: 43
<212> TYPE: DNA

```
<213> ORGANISM: Artificial Sequence
<220> FEATURE:
<223> OTHER INFORMATION: synthetic primer
<220> FEATURE:
<221> NAME/KEY: misc_feature
<222> LOCATION: (33)..(33)
<223> OTHER INFORMATION: n is a, c, g, or t

<400> SEQUENCE: 68
gtttccagta gttatccccc tccatcaggc agnttcccag aca                 43

<210> SEQ ID NO 69
<211> LENGTH: 17
<212> TYPE: DNA
<213> ORGANISM: Artificial Sequence
<220> FEATURE:
<223> OTHER INFORMATION: synthetic primer

<400> SEQUENCE: 69
gcagtgagcg caacgca                                              17

<210> SEQ ID NO 70
<211> LENGTH: 45
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (35)..(35)
<223> OTHER INFORMATION: n is a, c, g, or t

<400> SEQUENCE: 70
ataactactg gaaacggtag ctaataccgc ataangtcgc aagac               45

<210> SEQ ID NO 71
<211> LENGTH: 50
<212> TYPE: DNA
<213> ORGANISM: Artificial Sequence
<220> FEATURE:
<223> OTHER INFORMATION: synthetic primer

<400> SEQUENCE: 71
cggtattcct ccagatctct acgcatttha ccgctacacc tggaattcta          50

<210> SEQ ID NO 72
<211> LENGTH: 20
<212> TYPE: DNA
<213> ORGANISM: Artificial Sequence
<220> FEATURE:
<223> OTHER INFORMATION: synthetic primer

<400> SEQUENCE: 72
agttcccgaa ggcaccaatc                                           20

<210> SEQ ID NO 73
<211> LENGTH: 20
<212> TYPE: DNA
<213> ORGANISM: Artificial Sequence
<220> FEATURE:
<223> OTHER INFORMATION: synthetic primer

<400> SEQUENCE: 73
acgtcgcaag accaaagagg                                           20

<210> SEQ ID NO 74
<211> LENGTH: 60
```

```
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (29)..(36)
<223> OTHER INFORMATION: n is a, c, g, or t

<400> SEQUENCE: 74
ggatgtcaag accaggtaag gttcttcgnn nnnnnncgaa ttaaaccaca tgctccaccg    60

<210> SEQ ID NO 75
<211> LENGTH: 20
<212> TYPE: DNA
<213> ORGANISM: Artificial Sequence
<220> FEATURE:
<223> OTHER INFORMATION: synthetic primer

<400> SEQUENCE: 75
acgtcgcaag accaaagagg                                                20

<210> SEQ ID NO 76
<211> LENGTH: 20
<212> TYPE: DNA
<213> ORGANISM: Artificial Sequence
<220> FEATURE:
<223> OTHER INFORMATION: synthetic prmer

<400> SEQUENCE: 76
cctggtcttg acatccacgg                                                20

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
ggtcggcgac tttcactcac                                                20

<210> SEQ ID NO 78
<211> LENGTH: 60
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (30)..(41)
<223> OTHER INFORMATION: n is a, c, g, or t

<400> SEQUENCE: 78
actggggtga agtcgtaaca aggtaaccgn nnnnnnnnnn ncggttggat catgggatta    60

<210> SEQ ID NO 79
<211> LENGTH: 20
<212> TYPE: DNA
<213> ORGANISM: Artificial Sequence
<220> FEATURE:
<223> OTHER INFORMATION: synthetic primer

<400> SEQUENCE: 79
ggtcggcgac tttcactcac                                                20

<210> SEQ ID NO 80
```

```
<211> LENGTH: 60
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 80
actggggtga agtcgtaaca aggtaaccgn aggggaacct ncggttggat catgggatta      60

<210> SEQ ID NO 81
<211> LENGTH: 60
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (36)..(37)
<223> OTHER INFORMATION: n is a, c, g, or t

<400> SEQUENCE: 81
actggggtga agtcgtaaca aggtaaccgt aggggnncct gcggttggat catgggatta      60

<210> SEQ ID NO 82
<211> LENGTH: 17
<212> TYPE: DNA
<213> ORGANISM: Artificial Sequence
<220> FEATURE:
<223> OTHER INFORMATION: synthetic primer

<400> SEQUENCE: 82
gcagtgagcg caacgca                                                    17

<210> SEQ ID NO 83
<211> LENGTH: 20
<212> TYPE: DNA
<213> ORGANISM: Artificial Sequence
<220> FEATURE:
<223> OTHER INFORMATION: synthetic primer

<400> SEQUENCE: 83
gtacgcttag tcgcttaacc                                                 20

<210> SEQ ID NO 84
<211> LENGTH: 67
<212> TYPE: RNA
<213> ORGANISM: Artificial Sequence
<220> FEATURE:
<223> OTHER INFORMATION: synthetic primer

<400> SEQUENCE: 84
ggguuuguuu ggaccgaugu gaaaucsccu ggcucaaccu gggaacugca ucugucacag      60
gcaagcc                                                               67

<210> SEQ ID NO 85
<211> LENGTH: 34
<212> TYPE: DNA
<213> ORGANISM: Artificial Sequence
<220> FEATURE:
<223> OTHER INFORMATION: lac-L primer
```

```
<400> SEQUENCE: 85
ttggatccga caccatcgaa ttggtgcaaa acct                              34

<210> SEQ ID NO 86
<211> LENGTH: 20
<212> TYPE: DNA
<213> ORGANISM: Artificial Sequence
<220> FEATURE:
<223> OTHER INFORMATION: 16s-Avr II primer

<400> SEQUENCE: 86
acgtcgcaag accaaagagg                                              20

<210> SEQ ID NO 87
<211> LENGTH: 19
<212> TYPE: DNA
<213> ORGANISM: Artificial Sequence
<220> FEATURE:
<223> OTHER INFORMATION: 16s-Bgl II primer

<400> SEQUENCE: 87
ctgcaaattt tcgcaacac                                               19

<210> SEQ ID NO 88
<211> LENGTH: 24
<212> TYPE: DNA
<213> ORGANISM: Artificial Sequence
<220> FEATURE:
<223> OTHER INFORMATION: 16s-537F primer

<400> SEQUENCE: 88
ggagggtgca agcgttaatc ggaa                                         24

<210> SEQ ID NO 89
<211> LENGTH: 60
<212> TYPE: DNA
<213> ORGANISM: Artificial Sequence
<220> FEATURE:
<223> OTHER INFORMATION: 530_4n primer
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 89
ttccgattaa cgcttgcacc gtccgtatta ccnnggctnn tggcacggag ttagccggtg   60

<210> SEQ ID NO 90
<211> LENGTH: 64
<212> TYPE: DNA
<213> ORGANISM: Artificial Sequence
<220> FEATURE:
<223> OTHER INFORMATION: 530-6N primer
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (53)..(55)
<223> OTHER INFORMATION: n is a, c, g, or t

<400> SEQUENCE: 90
```
ttccgattaa cgctgcaccc tccgtattac cgcnnntgct ggcacggagt tannngtgc    60 ttct                                                               64

<210> SEQ ID NO 91
<211> LENGTH: 71
<212> TYPE: DNA
<213> ORGANISM: Artificial Sequence
<220> FEATURE:
<223> OTHER INFORMATION: 530BN primer
<220> FEATURE:
<221> NAME/KEY: misc_feature
<222> LOCATION: (28)..(31)
<223> OTHER INFORMATION: n is a, c, g, or t
<220> FEATURE:
<221> NAME/KEY: misc_feature
<222> LOCATION: (41)..(44)
<223> OTHER INFORMATION: n is a, c, g, or t

<400> SEQUENCE: 91
ttccgattaa cgctgcaccc tccgtatnnn ngcggctgct nnnncggagt tagccggtgc    60
ttctctgctt t                                                       71

<210> SEQ ID NO 92
<211> LENGTH: 20
<212> TYPE: DNA
<213> ORGANISM: Artificial Sequence
<220> FEATURE:
<223> OTHER INFORMATION: 416F primer

<400> SEQUENCE: 92
ggccttcggg ttgtaaagta                                              20

<210> SEQ ID NO 93
<211> LENGTH: 32
<212> TYPE: DNA
<213> ORGANISM: Artificial Sequence
<220> FEATURE:
<223> OTHER INFORMATION: N527 primer
<220> FEATURE:
<221> NAME/KEY: misc_feature
<222> LOCATION: (22)..(22)
<223> OTHER INFORMATION: n is a, c, g, or t

<400> SEQUENCE: 93
cttgcaccct ccgtattacc gnggctgctg gc                                32

<210> SEQ ID NO 94
<211> LENGTH: 34
<212> TYPE: DNA
<213> ORGANISM: Artificial Sequence
<220> FEATURE:
<223> OTHER INFORMATION: N528 primer
<220> FEATURE:
<221> NAME/KEY: misc_feature
<222> LOCATION: (21)..(21)
<223> OTHER INFORMATION: n is a, c, g, or t

<400> SEQUENCE: 94
cttgcaccct ccgtattacc ncggcgctgg cacg                              34

<210> SEQ ID NO 95
<211> LENGTH: 32
<212> TYPE: DNA
<213> ORGANISM: Artificial Sequence
<220> FEATURE:
<223> OTHER INFORMATION: N530 primer
<220> FEATURE:
<221> NAME/KEY: misc_feature

```
<222> LOCATION: (18)..(18)
<223> OTHER INFORMATION: n is a, c, g, or t

<400> SEQUENCE: 95
ttgcaccctc cgtattancg cggctgctgg ca                                32
```

TARGETS FOR THE IDENTIFICATION OF ANTIBIOTICS THAT ARE NOT SUSCEPTIBLE TO ANTIBIOTIC RESISTANCE

RELATED APPLICATIONS

This application is a divisional application of U.S. application Ser. No. 11/914,077, filed Jun. 30, 2008, which is a U.S. national stage application of PCT Patent Application No. PCT/US2006/018320, filed May 11, 2006, which claims the benefit of U.S. Application Ser. No. 60/680,138, filed May 11, 2005, and U.S. Application Ser. No. 60/711,492, filed Aug. 25, 2005, the entire content of each is hereby incorporated herein by reference.

GOVERNMENT SUPPORT

This invention was made with government support under SBIR Grant Number AI060275-01 awarded by the National Institutes of Health. The government has certain rights in the invention.

SEQUENCE LISTING

The instant application contains a Sequence Listing which is identical to the Sequence Listing submitted in the parent application Ser. No. 11/914,077 filed on Jun. 30, 2008 via EFS-Web in ASCII format on Feb. 25, 2011 and is hereby incorporated by reference in its entirety. The ASCII copy was created on Feb. 22, 2011, is entitled "WSS00301.txt" and is 17,322 bytes in size.

BACKGROUND

The increasing emergence of antibiotic resistant bacteria is a global problem. [Fauci, A. S., Touchette, N. A. & Folkers, G. K. (2005). Emerging infectious diseases: a 10-year perspective from the national institute of allergy and infectious diseases. *Emerg Infect Dis* 11, 519-25.] Antibiotic resistant bacteria were responsible for 17 million deaths world-wide in 1996 with an estimated cost of $30 billion dollars in the United States alone. [Levy, S. B. & Marshall, B. (2004). Antibacterial resistance worldwide: causes, challenges and responses. *Nat Med* 10, S122-9.] Funding for new research by major pharmaceutical companies has steadily decreased, as has the development of new antimicrobials. Furthermore, the rapid emergence of resistance to new classes of antimicrobials has limited their use in clinical settings. These trends, if continued, will result in a lack of effective antimicrobials for a majority of bacterial infections in the years to come.

The mechanism of resistance for all currently used therapeutics has been determined. There are several general mechanisms of bacterial resistance: 1) reduction of antibiotic uptake, 2) transport of the antibiotic out of the cell, 3) enzymatic inactivation of the antibiotic, 4) use of an alternative metabolic pathway, 5) titration of the antibiotic by overproduction of the target, and 6) target modification so that it is no longer recognized by the antibiotic. [Laios, E., Waddington, M., Saraiya, A. A., Baker, K. A., O'Connor, E., Pamarathy, D. & Cunningham, P. R. (2004). Combinatorial genetic technology for the development of new anti-infectives. *Arch Pathol Lab Med* 128, 1351-9.] Of these mechanisms, target modification is the most common mechanism of resistance for newly developed antibiotics. The specificity of antibiotic-target binding involves the structure as well as the sequence of the target. Mutations that affect the sequence or structure of the target without effecting function may reduce or eliminate antibiotic binding and result in resistance. For example, aminoglycoside antibiotics target the A-site of bacterial 16 S ribosomal RNA and increase the translational error rate. [Magnet, S. & Blanchard, J. S. (2005). Molecular insights into aminoglycoside action and resistance. *Chem Rev* 105, 477-98.] A single A1408G mutation reduces ribosome function by approximately 30% (unpublished results) but completely disrupts binding of certain aminoglycoside antibiotics. [Recht, M. I., Douthwaite, S., Dahlquist, K. D. & Puglisi, J. D. (1999). Effect of mutations in the A site of 16 S rRNA on aminoglycoside antibiotic-ribosome interaction. *J Mol Biol* 286, 33-43.] Therefore, targeting an antibiotic to all possible mutants of a particular ribosomal region that maintain function would eliminate this mechanism of resistance.

Nearly half of all naturally occurring antibiotics target an aspect of protein synthesis and more specifically the ribosome. The 70 S bacterial ribosome is responsible for the translation of messenger RNA (mRNA) into protein. Ribosome crystal structures and biochemical studies have shown that the RNA is the catalytically active component of the ribosome, therefore, the ribosome is a ribozyme. [Yusupov, M. M., Yusupova, G. Z., Baucom, A., Lieberman, K., Earnest, T. N., Cate, J. H. & Noller, H. F. (2001). Crystal structure of the ribosome at 5.5 A resolution. *Science* 292, 883-96; Wimberly, B. T., Brodersen, D. E., Clemons, W. M., Jr., Morgan-Warren, R. J., Carter, A. P., Vonrhein, C., Hartsch, T. & Ramakrishnan, V. (2000). Structure of the 30S ribosomal subunit. *Nature* 407, 327-39.] The essential nature of the protein synthesis process makes the ribosomal RNA (rRNA) an ideal drug target.

Studies of the rRNA sequences from numerous different organisms have shown that the overall structure of the ribosome is conserved within all three domains of life. Phylogenetic analysis of rRNA sequences has provided much information about pairing interactions and nucleotide conservation. Each of these analyses, however, employs genomic or organelle rRNA sequences. These sequences are constrained by their essential role in protein synthesis. As a result, very little or no sequence variation is observed in rRNA regions believed to be functionally important, since even subtle changes to the structure surrounding critical residues may reduce function and affect fidelity. Additionally, these conserved sites may be structurally important rather than functionally important. Therefore, drugs that target these sites would allow for resistance if the sequence can mutate but maintain the functional structure. An ideal drug would target all possible functional mutations at the target site.

SUMMARY

Another aspect of the present invention relates to a nucleic acid represented by V:

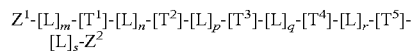
                                                V wherein, independently for each occurrence, $T^1$, $T^2$, $T^3$, $T^4$ and $T^5$ are selected from the group consisting of SEQ ID NO 4, 8, 9, 10, 11, 43, 44, 45, 46, 47, 48, 49, 52, 53, 54, 55, 56, 57, 58 and 59; L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine; $Z^1$ and $Z^2$ are selected from the group consisting of hydrogen, $(C_1-C_5)$alkyl, biotin, fluorescein, tetrachlorofluorescein, hexachlorofluorescein, Cy3 amidite, Cy5 amidite, digoxigenin and resin beads; and m, n, p, q, r and s are integers between 0-40.

BRIEF DESCRIPTION OF THE FIGURES

FIG. 3*a-d* depict four views of a model of the *E. coli* 16 S rRNA crystal structure showing identified regions.

FIG. 8 depicts a tabulation of the target regions in the 16S rRNA along with their known functions.

FIG. 9 depicts a tabulation of the target regions and their sequence identifier numbers.

FIG. 10 depicts organization of target regions into clusters based on spatial proximity and protein binding.

FIG. 2.1 depicts the secondary structure of rrnB 16 S rRNA from *E. coli*. Identification of sequence differences among the ribosomal operons of *E. coli* K-12. The change in nucleotide identity is given within each circle, while the color of the circle corresponds to the operon where the sequence change occurs. A direct change is denoted by a straight line, insertions are denoted by an arrow, and deletions are denoted by a delta (Δ).

FIG. 2.2 depicts the functional differences among the four sequentially different rRNA operons. a) Analysis of function for rRNA operons at 30° C., 37° C., and 42° C. The function of 16 S rRNA from rrnC (first bar), rrnD (second bar), rrnG (third bar), and rrnH (fourth bar) is compared to the function of rrnB under the same growth conditions. b) Analysis of function for rRNA operons at different $Mg^{2+}$ concentrations. Or similar to a). c) Analysis of function for rRNA operons at different pH. Order similar to a). d) Analysis of function for rRNA operons at different ionic concentration. Order similar to a).

FIG. 2.3 depicts the function of rrnG 16 S rRNA unique variations. Single mutations at positions a) 131 and b) 183 were made and assayed for function and given as a percent of rrsB. The wild-type nucleotide is underlined.

FIG. 2.4 depicts the function of rrnH 16 S rRNA unique variations. Unique variations, U855A and the entire helix 33, from the rrnH 16 S rRNA were isolated and cloned into rrsB. The wild-type rrsB (right bar), rrsB with U855A (middle bar), and rrsB with the entire helix 33 (left bar) were assayed for function at 30° C., 37° C. and 42° C. Function is a percent of rrsB grown at 37° C.

FIG. 3.1 depicts the location and conservation of the 530 loop. The 530 loop is located in the central domain. Upper case gray letters indicate universally conserved nucleotides while lower case gray letter indicate nucleotides conserved only within bacteria. Black letters indicate wild-type *E. coli* sequence.

FIG. 3.2 depicts the 530 loop with results of 4N (521-522 and 527-528) interaction. Size of the font indicates the frequency of occurrence of that nucleotide in the pool. Positions that show a significant correlation between level of function and nucleotide identity are boxed.

FIG. 3.3 depicts the 530 loop with results of 6N (505-507 and 524-526) interaction. Size of the font indicates the frequency of occurrence of that nucleotide in the pool. Positions that show a significant correlation between level of function and nucleotide identity are boxed.

FIG. 3.4 depicts the 530 loop with results of 8N (516-519 and 529-532) interaction. Size of the font indicates the frequency of occurrence of that nucleotide in the pool. Positions that show a significant correlation between level of function and nucleotide identity are boxed. Covariation between positions are identified by a solid line with the p-value indicated above the line. Broken lines denote a possible covariation which could not be confirmed due to the absence of adenosine mutants at position 519.

FIG. 3.5*a-c* depicts Table 3.1.a-3.1.c.

FIG. 3.6 depicts Table 3.2.

FIG. 3.7 depicts Table 3.3.

FIG. 3.8 depicts Table 3.5, wherein the oligos lac-L, 16s-Avr II, 16s-Bgl II, 16s-537F, 530-4N, 530-6N, 530-8N, 16s-416F, 16s N527, 16s N528 and 16s N530 have sequence numbers corresponding to SEQ ID NOs: 85-95.

FIG. 4.1 depicts the location of the 970 loop in the 16 S rRNA of *E. coli*. Nucleotides in gray are conserved among the three domain and organelle. Inset contains an expanded view of the 970 loop with functional information as indicated.

FIG. 4.2 depicts the nucleotide frequency in the selected pool. The wild type sequence in indicated in red. The size of the circles indicates the frequency of that nucleotide occurring at that position in the pool. The chi test is a measure of the randomness at each position while the consensus is based on at least a 15% prevalence of that nucleotide in the pool.

FIG. 4.3 depicts the analysis of 970 loop mutants. a) Letter sizes are scaled to reflect the abundance of that nucleotide in the pool at each position. Covariation between nucleotides is indicated by solid lines, unconfirmed covariations are indicated by broken lines. Positions where nucleotide identity significantly correlates with function are boxed. b) Crystal structure of the 970 loop from the *E. coli* 30 S subunit model.

FIG. 4.4 depicts the m²G966 and m⁵ C967 single mutants. The wild type nucleotide is underlined and set at 100%. The average function of each mutant and the standard error is given above each bar. a) $m^2$ G966 single mutants b) $m^5$ C967 single mutants FIG. 4.5 depicts the modeling of the A964G mutation. a) Interaction between the wild type A964 and C970. b) Interaction of the A964G mutant with C970. The N1 of the A964G mutation causes steric clash with the sugar of position 970 which may disrupt the stacking interactions between positions 965, 969 and 970.

FIG. 4.6 depicts Table 4.1.
FIG. 4.7 depicts Table 4.2.
FIG. 4.8 depicts Table 4.3.
FIG. 4.9 depicts Table 4.4.
FIG. 4.10 depicts Table 4.5.
FIG. 5.1 depicts the *E. coli* 16 S rRNA secondary structure showing helix 45 (boxed). Nucleotides in gray are >90 conserved in the three domains and organelles. Nucleotides involved in the formation of intersubunit bridge B2b (●), kasugamycin resistance (■), initiation (▲), and cross-linked to U793 (▼) are indicated. Additionally, the entire helix (positions 1506-1529) has been cross-linked to IF3.

FIG. 5.2 depicts the functional analysis of the 1518:1519 site directed mutants. The size of the dots is proportional to the level of function as compared to the wild type. The mean function (percentage of the wild type) of three GFP assays is provided at the bottom of each box with the standard error.

FIG. 5.3 depicts the functional analysis of the 1512:1523 site directed mutants. The size of the dots is proportional to the level of function as compared to the wild type. The mean function (percentage of the wild type) of three GFP assays is provided at the bottom of each box with the standard error.

FIG. 5.4 depicts the nucleotide distribution at each position in the selected pool. The wild type sequence in indicated in gray. The consensus is based on at least a 10% prevalence of the nucleotide at that position in the selected pool. The Chi-test is a measure of the probability that the observed nucleotide distribution is due to random chance.

FIG. 5.5 depicts the covariation analysis of the selected pool. Positions conserved >90% among the 3 domains and organelles are indicated in gray. The nucleotide font size is proportional to the occurrence of this nucleotide in the selected pool. Covariations identified are shown as solid arrows. Only covariations with p=<0.005 are shown. Additional weak covariations were identified between positions 1513:1515 ($1.8 \times 10^{-2}$), 1515:1522 ($2.8 \times 10^{-2}$), 1518:1520 ($3.1 \times 10^{-2}$), and 1521:1523 ($1.1 \times 10^{-2}$).

FIG. 5.6 depicts the GFP induction curve of helix 45 mutants in DH5 and AAS3. GFP induction curve of helix 45 mutants 100, 115 and the wild type sequence in *E. coli* DH5 or *E. coli* AAS3. An overnight culture was diluted 1:1000 in new LB+Amp 100 media and grown to $OD_{600}$=0.1. The culture was induced with 1 mM IPTG and 500 µL samples taken at different time points. Samples were pelleted and washed twice with 500 µL FIN buffer (20 mM HEPES pH 7.4 and 0.85% NaCl) and resuspended in 500 µL HN buffer. The fluorescence (Ex: 395, Em: 509) and absorbance ($OD_{600}$) were measured. The fluorescence divided by absorbance is plotted against time.

FIG. 5.7 depicts the modeling of mutants 100, 102, and 107. a) All three mutants were modeled using Mfold (Mathews et al., 1999; Zuker, 2003). The calculated ΔG for each mutant is shown below the folded secondary structure. b) The mutants were also modeled using the Homology modeling software developed by Dr. John SantaLucia Jr. (personal communication).

FIG. 5.8 depicts the modeling mutations at positions 1518 and 1519. All possible single mutations at positions 1518 and 1519 were modeled into an energy minimized *E. coli* 16 S rRNA model (Dr. John SantaLucia Jr., personal communication) based on the *T. thermophilus* 30 S crystal structure (Tung et al., 2002). Modeling and energy minimization of substituted nucleotides was performed. a) Pyrimidine mutations at position 1518 do not properly interact with helix 44 due to their smaller size. An A to G substitution causes steric clash between the N2 amino group and helix 44. b) Mutations at position 1519 cause steric hinderance with helix 44 similar to that seen for mutations at position 1518. Mutation at positions 1518 and 1519 disrupting possible interactions with helix.

FIG. 5.9 depicts the formation of a hydrophobic pocket by methyl groups at positions 1516, 1518 and 1519. This hydrophobic pocket contains 793. This interaction may position the 790 loop for additional interactions with helix 44 and 45.

FIG. 5.10 depicts Table 5.1.
FIG. 5.11 depicts Table 5.2.
FIG. 6.1 depicts the *E. coli* 16 S rRNA secondary structure with all conserved positions labeled. A black line shows identified regions and the region number (r1) is given. Junctions (J) in the 16 S rRNA are labeled.

FIG. 6.2 depicts a crystal structure model of the *E. coli* 30 S subunit. A model of the *E. coli* 30 S subunit based on the *T. thermophilus* crystal structure (PDB id 1M5G) was energy minimized by software written by Dr. John SantaLucia Jr. (private communication) and used to identify clusters. a) The 30 S subunit is as viewed from the interface side and parts are labeled. b) Rotated 180° from a)

FIG. 6.3 depicts the clusters identified in the mutation library. Identified clusters are circled and connected to other regions involved in formation of the cluster. The cluster numbering is the same as in Table 6.2.

FIG. 6.4 depicts Table 6.1.
FIG. 6.5 depicts Table 6.2.

DETAILED DESCRIPTION

Figure 1A:
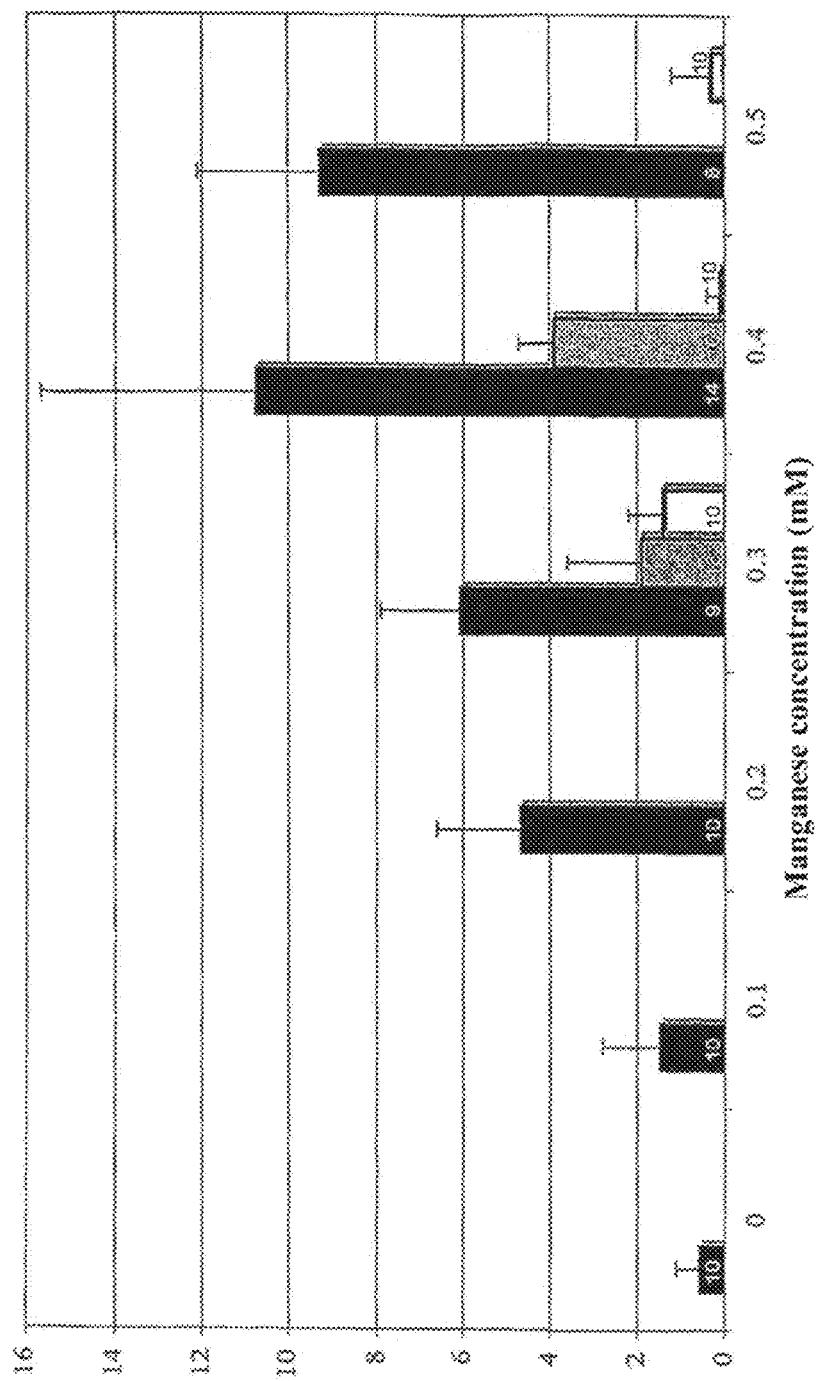
FIG. 1 depicts the determination of optimal mutagenesis conditions. (a) Bar graph of the average number of mutations at each manganese concentration in the absence of chloramphenicol (black), selected at 25 μg/ml (gray), or selected at 50 μg/ml (white) of chloramphenicol. Number of samples analyzed at each concentration is located at the base of the graph. (b) The type of mutations seen in all the mutant clones used to determine the optimal manganese concentration.

The present invention provides novel targets to be used in the identification of pharmaceuticals. Conserved and variable regions of the *E. coli* 16 S rRNA, identified through an instant evolution experiment on the entire 16 S rRNA are provided. These conserved sequences may be used as targets for pharmaceuticals that are taxonomically specific, refractory to the development of drug resistance, or both.

DEFINITIONS

The articles "a" and "an" are used herein to refer to one or more than one (i.e., to at least one) of the grammatical object of the article.

The term "amino acid" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (d) and (l) stereoisomers of such amino acids when the structure of the amino acid admits of stereoisomeric forms. The configuration of the amino acids and amino acid residues herein are designated by the appropriate symbols (d), (l) or (dl), furthermore when the configuration is not designated the amino acid or residue can have the configuration (d), (l) or (dl). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (d) or (l) stereoisomers. D- and L-α-Amino acids are represented by the following Fischer projections and wedge-and-dash drawings. In the majority of cases, D- and L-amino acids have R- and S-absolute configurations, respectively.

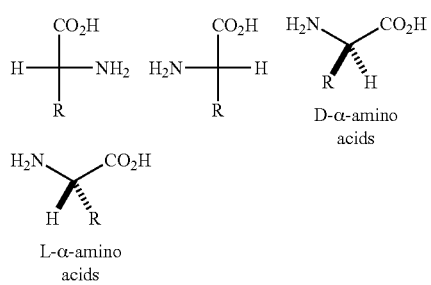

L-α-amino acids

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted religation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "conservative substitutions" refers to changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; valine-leucine-isoleucine-methionine; phenylalanine-tyrosine; phenylalanine-tyrosine-tryptophan; lysine-arginine; and histidine-lysine-arginine.

"Equivalent" when used to describe nucleic acids or nucleotide sequences refers to nucleotide sequences encoding functionally equivalent polypeptides. Equivalent nucleotide sequences will include sequences that differ by one or more nucleotide substitution, addition or deletion, such as an allelic variant; and will, therefore, include sequences that differ due to the degeneracy of the genetic code. For example, nucleic acid variants may include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions.

"Homology" or alternatively "identity" refers to sequence similarity between two peptides or between two nucleic acid molecules. Homology may be determined by comparing a position in each sequence, which may be aligned for purposes of comparison. When a position in the compared sequence is occupied by the same base or amino acid, then the molecules are homologous at that position. A degree of homology between sequences is a function of the number of matching or homologous positions shared by the sequences.

The term "percent identical" refers to sequence identity between two amino acid sequences or between two nucleotide sequences. Identity may be determined by comparing a position in each sequence, which may be aligned for purposes of comparison. When an equivalent position in the compared sequences is occupied by the same base or amino acid, then the molecules are identical at that position; when the equivalent site is occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and may be used with, e.g., default settings. ENTREZ is available through the National Center for Biotechnology Information, National Library of Medicine, National Institutes of Health, Bethesda, Md. In one embodiment, the percent identity of two sequences may be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method may be utilized to align sequences. An alternative search strategy uses MPSRCH software, which runs on a MASPAR computer. MPSRCH uses a Smith-Waterman algorithm to score sequences on a massively parallel computer. This approach improves the ability to pick up distantly related matches, and is especially tolerant of small gaps and nucleotide sequence errors. Nucleic acid-encoded amino acid sequences may be used to search both protein and DNA databases. Databases with individual sequences are described in *Methods in Enzymology*, ed. Doolittle, supra. Databases include Genbank, EMBL, and DNA Database of Japan (DDBJ).

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions, which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: Td=(((((3×#GC)+(2×#AT))×37)−562)/#bp)−5; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10×Denhardt (0.2% Ficoll, 0.2% Polyvinylpyrrolidone, 0.2% bovine serum albumin) and 200 μg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y.; and Tibanyenda, N. et al., Eur. J. Biochem. 139:19 (1984) and Ebel, S. et al., Biochem. 31:12083 (1992).

The term "substantially homologous" when used in connection with a nucleic acid or amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "patient" refers to a mammal in need of a particular treatment. In a preferred embodiment, a patient is a primate, canine, feline, or equine. In another preferred embodiment, a patient is a human.

In the structural formulas found herein, "-" indicates a covalent bond. For example L-T indicates a covalent bond between a nucleic acid and a nucleic acid sequence selected from the group consisting of SEQ ID NO 1-64.

Instant Evolution

An in vivo system has been developed that allows the study of rRNA without affecting host function. [Cunningham et al. WO 2004/003511.] The system comprises a plasmid, pRNA228, which is a derivative of pRNA123. [Lee, K., Holland-Staley, C. A. & Cunningham, P. R. (1996). Genetic analysis of the Shine-Dalgarno interaction: selection of alternative functional mRNA-rRNA combinations. *RNA* 2, 1270-85; Lee, K., Varma, S., SantaLucia, J., Jr. & Cunningham, P. R. (1997). In vivo determination of RNA structure-function relationships: analysis of the 790 loop in ribosomal RNA. *J Mol Biol* 269, 732-43; and Morosyuk, S. V., Lee, K., SantaLucia, J., Jr. & Cunningham, P. R. (2000). Structure and function of the conserved 690 hairpin in *Escherichia coli* 16 S ribosomal RNA: analysis of the stem nucleotides. *J Mol Biol* 300, 113-26.] The pRNA228 plasmid contains the rrnB operon from *E. coli*. In addition, the anti-Shine-Dalgarno of the 16 S rRNA has been modified to a sequence that does not recognize normal host mRNA. [Shine, J. & Dalgarno, L. (1974). The 3'-terminal sequence of *Escherichia coli* 16S ribosomal RNA: complementarity to nonsense triplets and ribosome binding sites. *Proc Natl Acad Sci USA* 71, 1342-6; Hui, A. & de Boer, H. A. (1987). Specialized ribosome system: preferential translation of a single mRNA species by a subpopulation of mutated ribosomes in *Escherichia coli*. *Proc Natl Acad Sci USA* 84, 4762-6; and Hui, A., Jhurani, P. & de Boer, H. A. (1987). Directing ribosomes to a single mRNA species: a method to study ribosomal RNA mutations and their effects on translation of a single messenger in *Escherichia coli*. *Methods Enzymol* 153, 432-52.] The plasmid also contains two reporter genes, chloramphenicol acetyltransferase (CAT) and green fluorescent protein (GFP), both of which contain a modified Shine-Dalgarno sequence complimentary to the anti-Shine-Dalgarno sequence of the 16 S rRNA. Therefore, the plasmid derived 30 S subunit do not translate normal host mRNA and the host ribosomes do not translate the mRNA of the reporter genes.

Figure 1B:
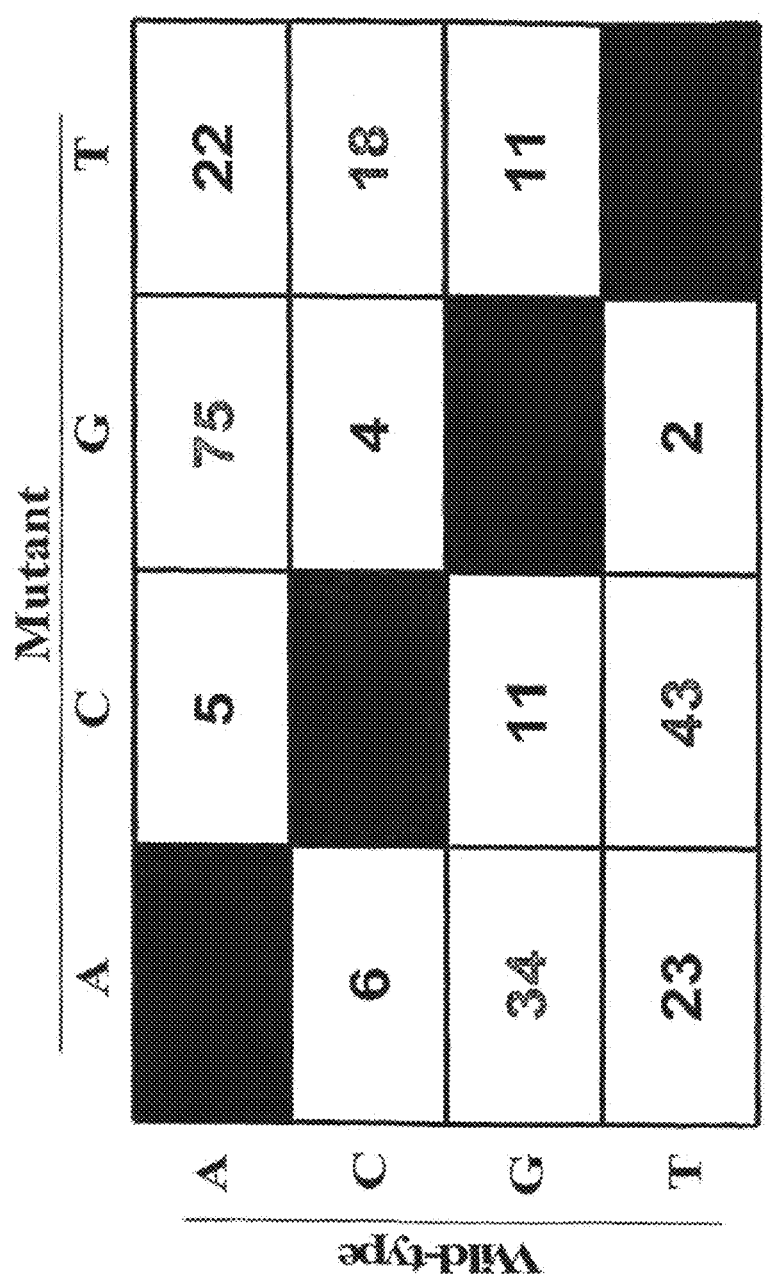

The 16 S rRNA was PCR amplified in the presence of manganese to randomly introduce mutations throughout the product. The concentration of manganese in the PCR reaction is proportional to the number of mutations introduced into the PCR product. To optimize the number of mutations introduced into the 16 S rRNA, the PCR was performed in the presence of a range of $Mn^{2+}$ (0 to 0.5 mM $Mn^{2+}$) concentration. The PCR product from each $Mn^{2+}$ concentration was cloned into pRNA228 (a total of 1484 nucleotides of the 16 S rRNA from position 20 to position 1503), sequenced, and the average number of mutations per clone was analyzed. As expected the average number of mutations increased with the concentration of $Mn^{2+}$ (FIG. 1a). The types of mutations being incorporated into the 16 S rRNA was further characterized. An approximate 2 to 1 ratio between transitions and transversions was observed (FIG. 1b). Insertions and deletions were also identified in the mutant pool but at a much lower rate (data not shown). Mutations were found distributed throughout the 16 S rRNA with no highly mutated regions (data not shown).

Clones from each concentration of $Mn^{2+}$ were then selected for function on chloramphenicol (50 µg/ml) containing medium. Survivors were assayed for function by comparing the level of GFP fluorescence to the wild type GFP fluorescence and sequenced to identify mutations. Analysis of the surviving clones resulted in a decrease in the average number of mutations per clone. At 0.3 mM $Mn^{2+}$, the average number of mutations per clone decreased from 6.1 down to 1.4. The average number of mutations per clone for the 0.4 and 0.5 mM $Mn^{2+}$ concentration decreased to less then zero (0.1 and 0.3 respectively). An average of 1.4 mutations per clone would not provide the number of mutations at each position of the 16 S rRNA in a reasonable number of clones. To increase the number of mutants per sequence, the selection was optimized by reducing the chloramphenicol concentration. The minimum inhibitory concentration (MIC) of chloramphenicol for uninduced wild-type plasmid as well as for a lethal clone was determined to be 15 µg/ml. Therefore, the concentration of chloramphenicol during selection was decreased from 50 µg/ml to 25 µg/ml. This concentration of chloramphenicol allows for the selection of functional clones while still inhibiting the growth of nonfunctional clones. Clones, containing 16 S rRNA mutated with different concentrations of $Mn^{2+}$, were selected at 25 µg/ml of chloramphenicol, sequenced, and assayed for function. Selection at the lower chloramphenicol did not significantly increase the number of mutations per clone at the 0.3 mM $Mn^{2+}$ concentration, however, the number of mutations per clone at the 0.4 mM $Mn^{2+}$ concentration increased from 0.1 to 3.9 (FIG. 1a). Analysis of a larger pool of clones containing 16 S rRNA mutated with 0.4 mM $Mn^{2+}$ and selected at 25 µg/ml of chloramphenicol resulted in a high number of wild type and duplicate clones. To reduce the number of wild type and duplicate samples in the pool, the $Mn^{2+}$ concentration was increased to 0.45 mM $Mn^{2+}$ and the induction time was reduced to 2 hours. These conditions resulted in the optimal balance between number of mutations and function (data not shown).

Figure 2:
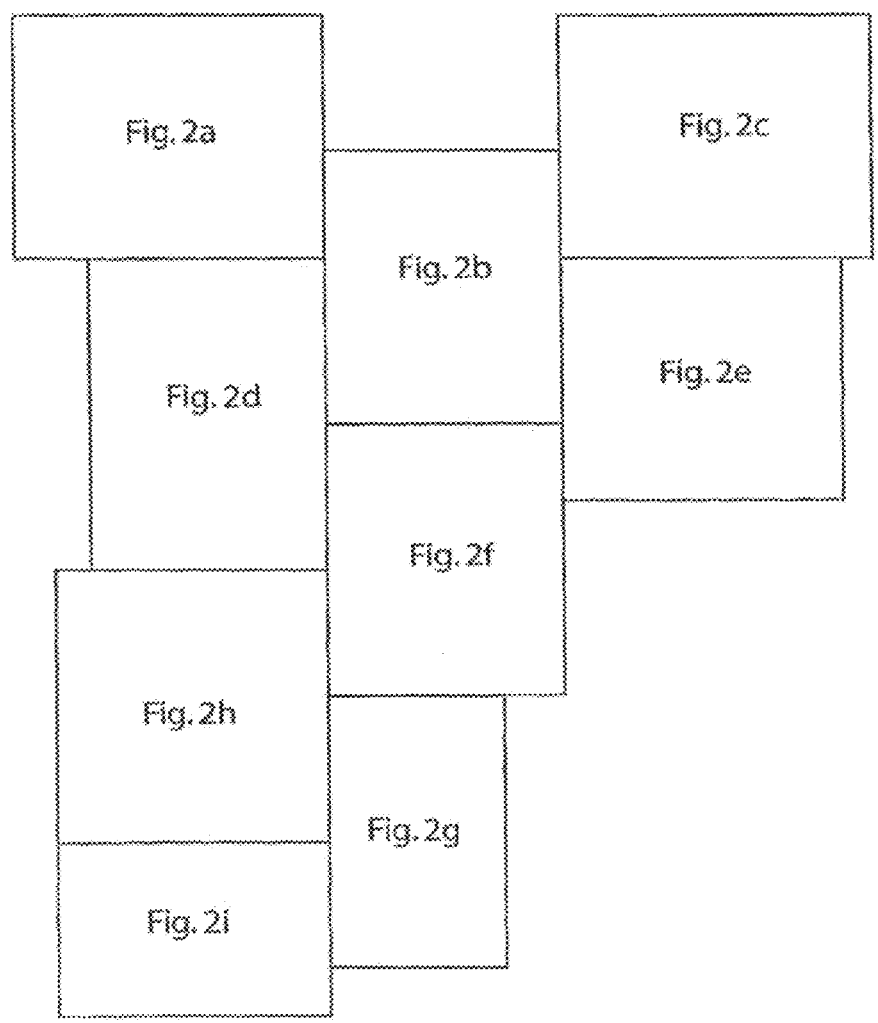
FIG. 2 depicts the secondary structure of 16 S rRNA from *Escherichia coli* (*E. coli*) (SEQ ID NO: 65). Regions identified in the mutation library are shown. Regions of at least 3 sequential nucleotides with 3 or less mutations at each position are shown in red, regions of at least 2 sequential nucleotides with 1 or less mutations at each position are shown in green, and positions with 3 or less mutation separated from a similar position by a single position with 4 or more mutations are shown in orange.
Figure 2A:
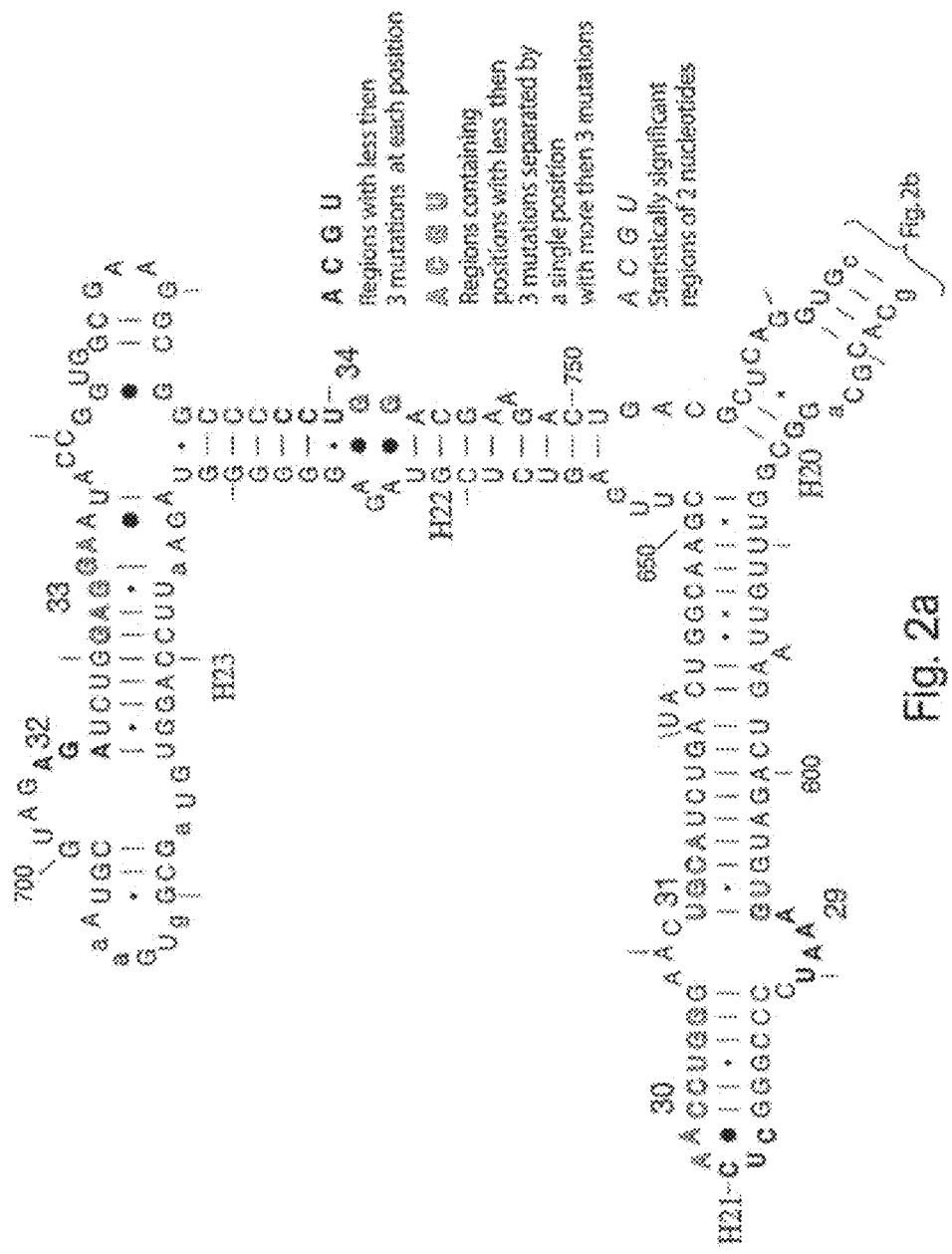
Figure 2B:
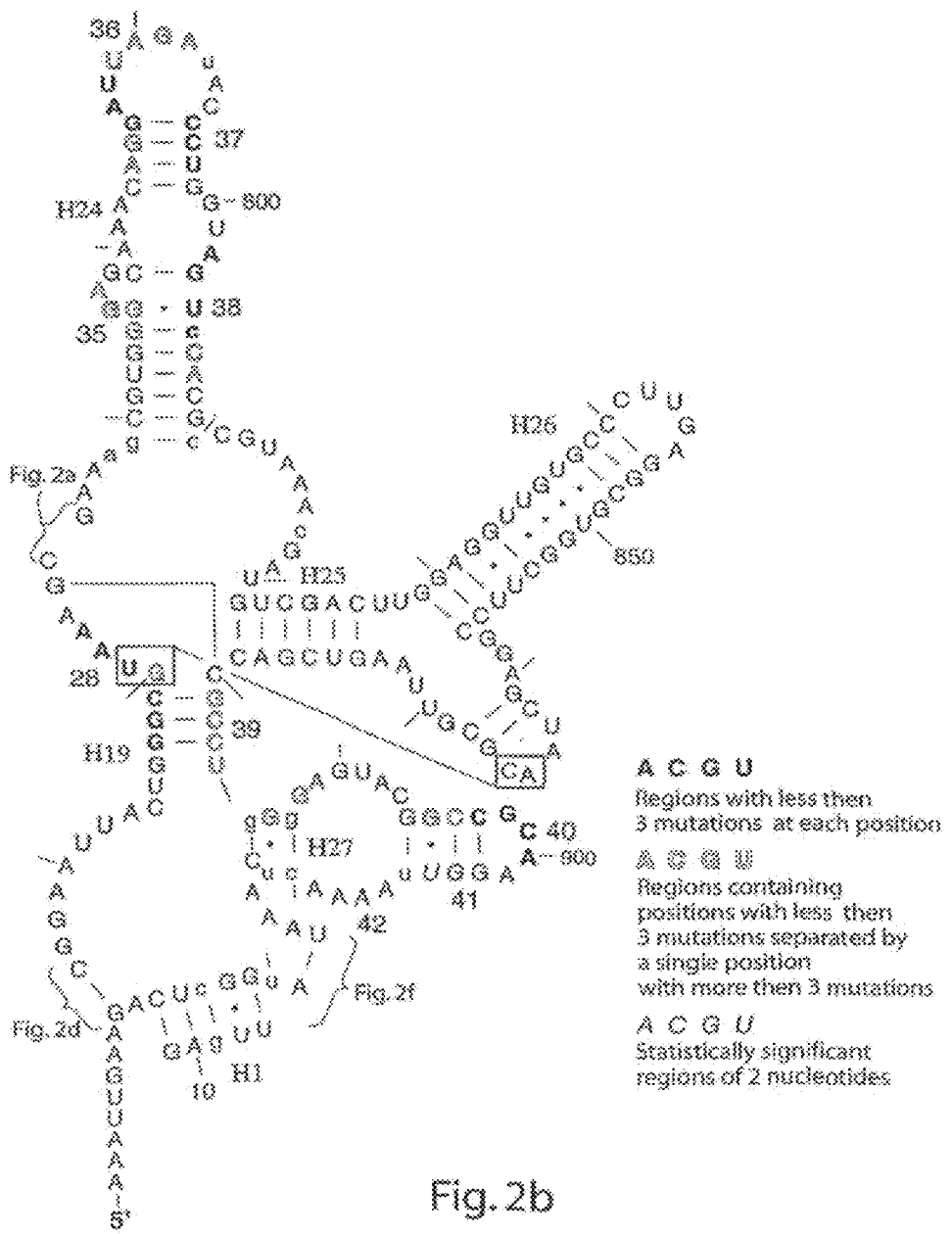
Figure 2D:
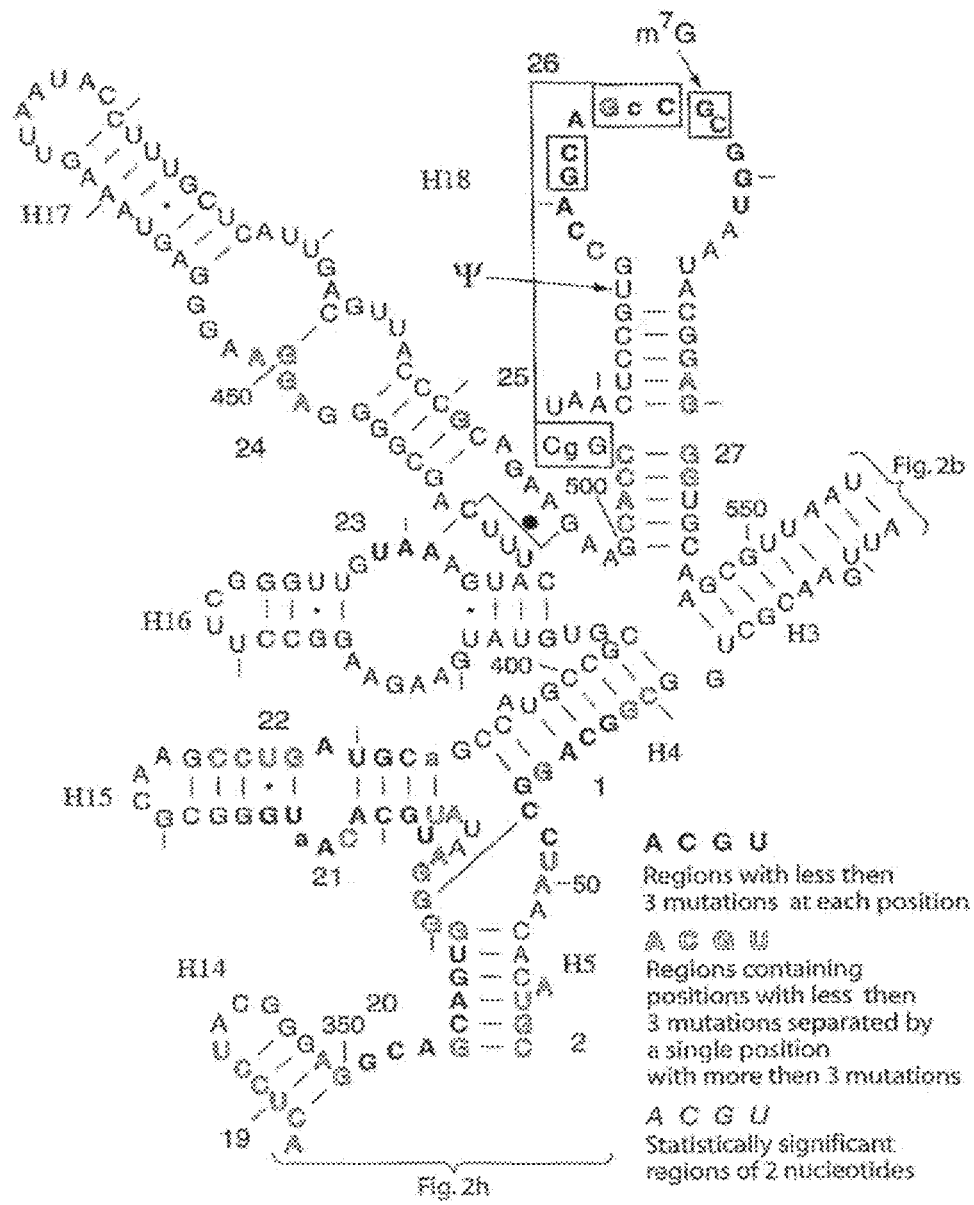
Figure 2E:
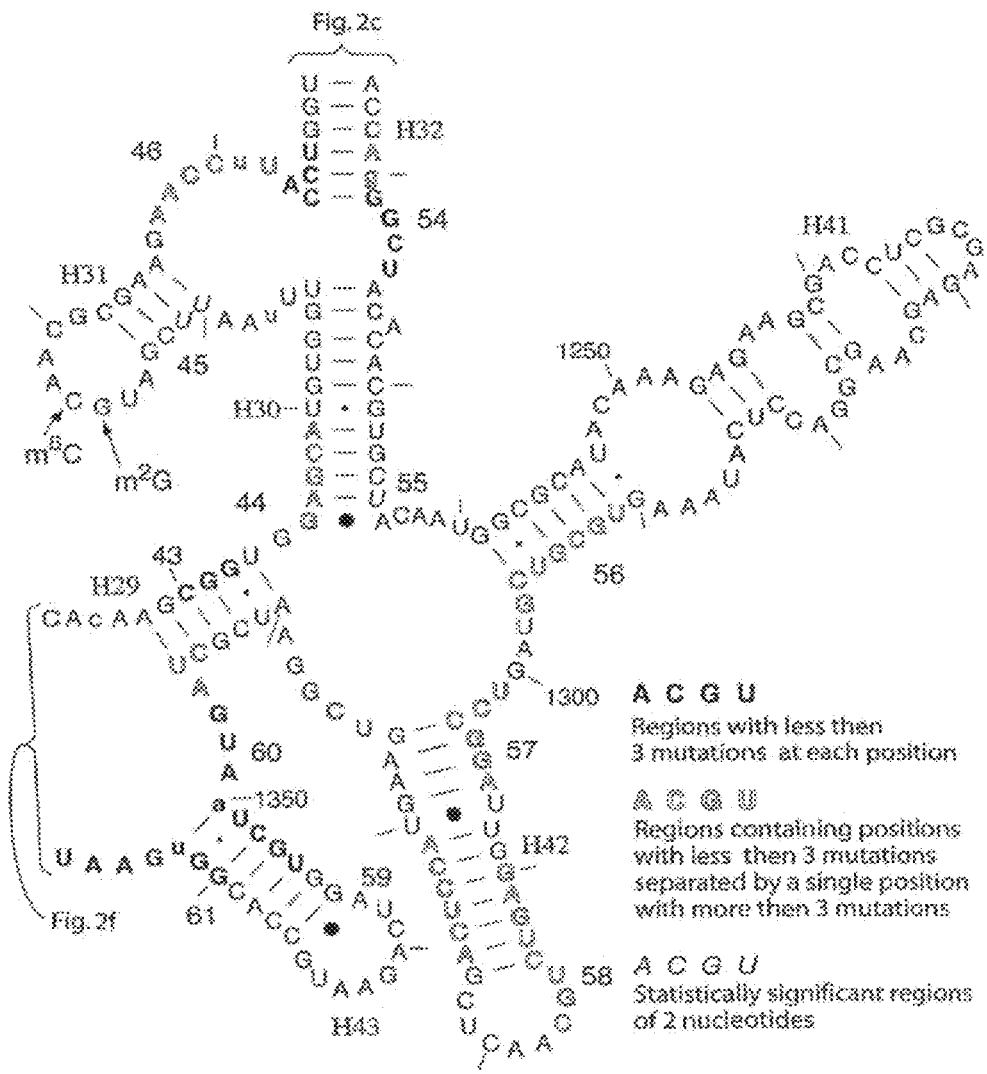
Figure 2F:
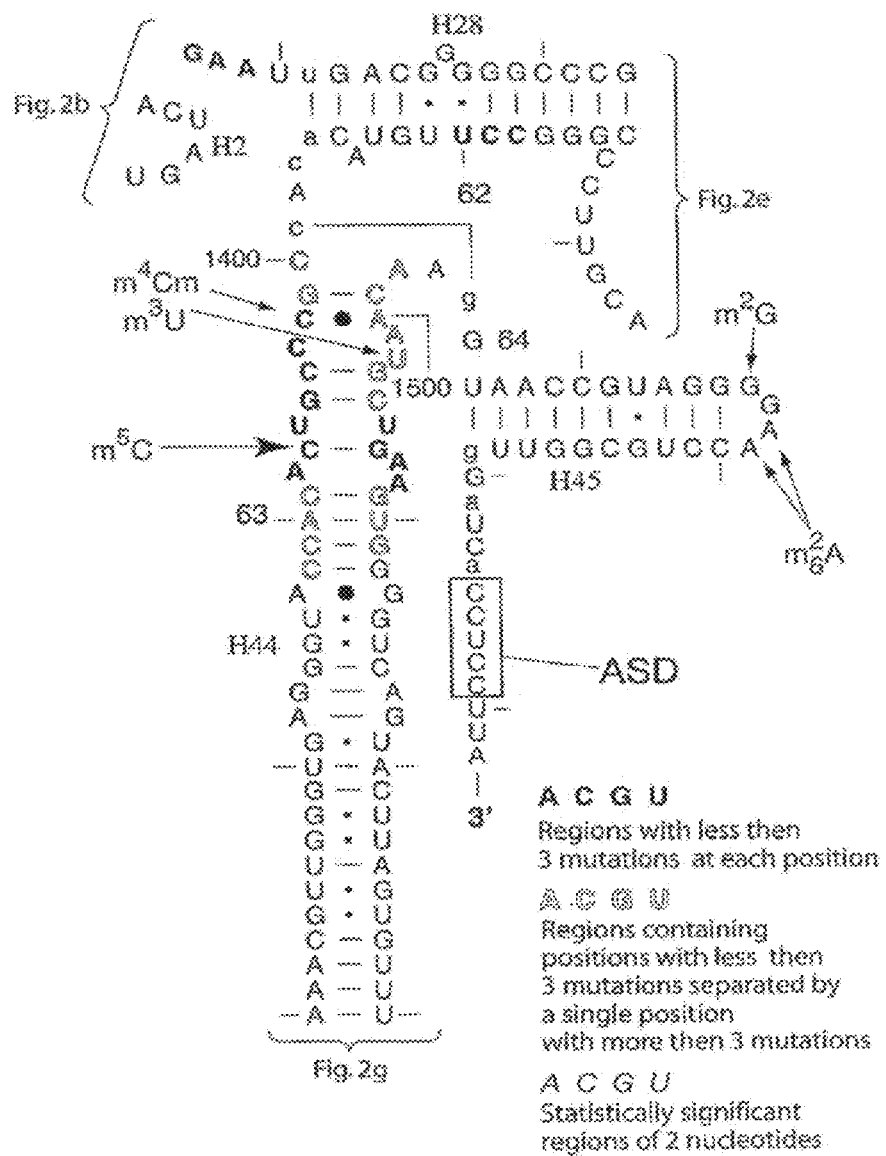
Figure 2G:
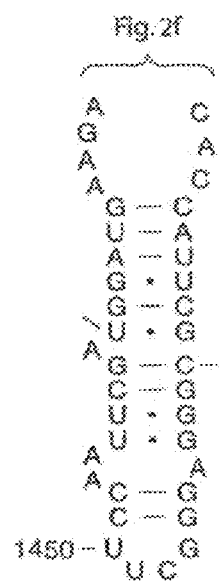
Figure 2H:
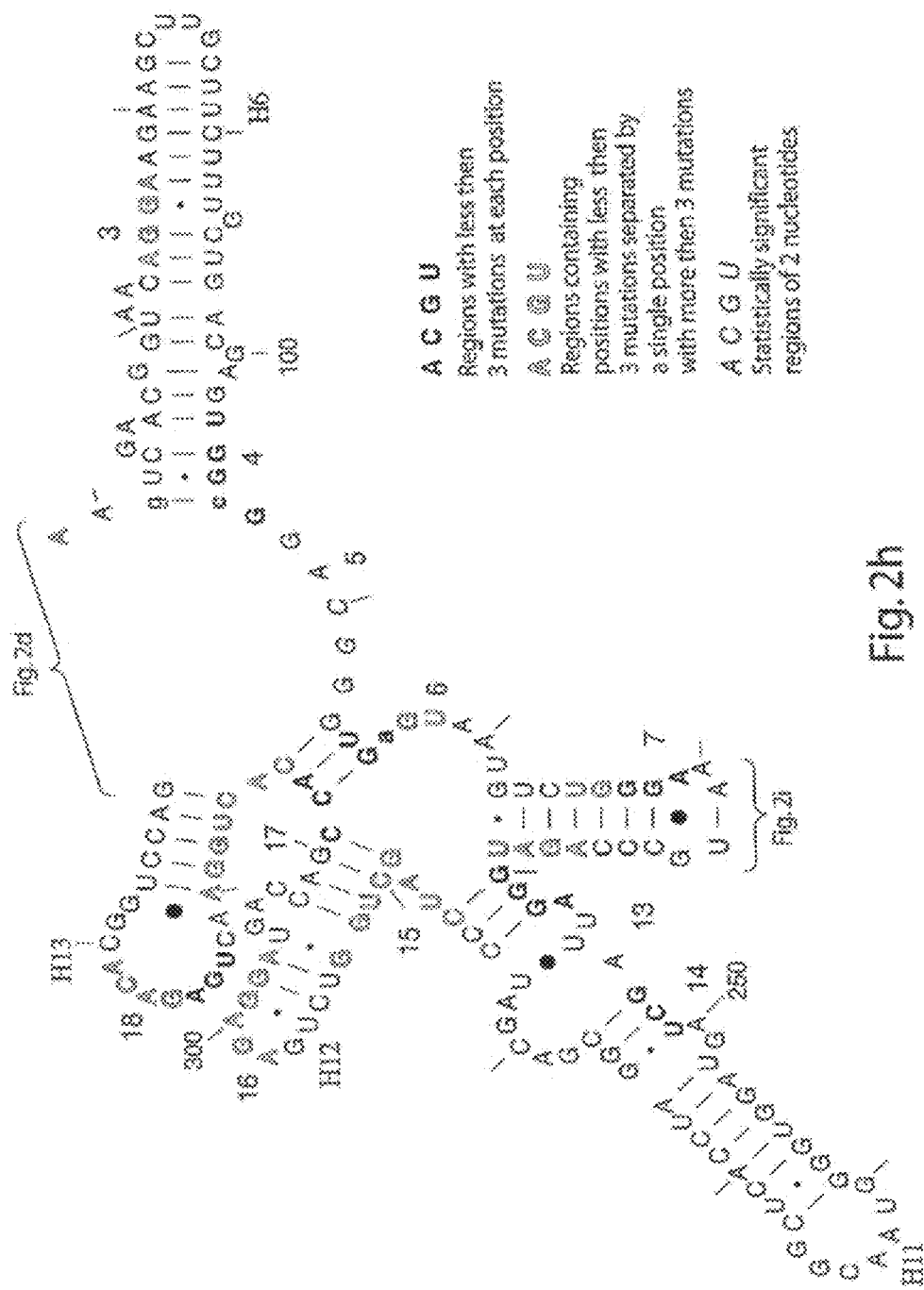
Figure 2I:
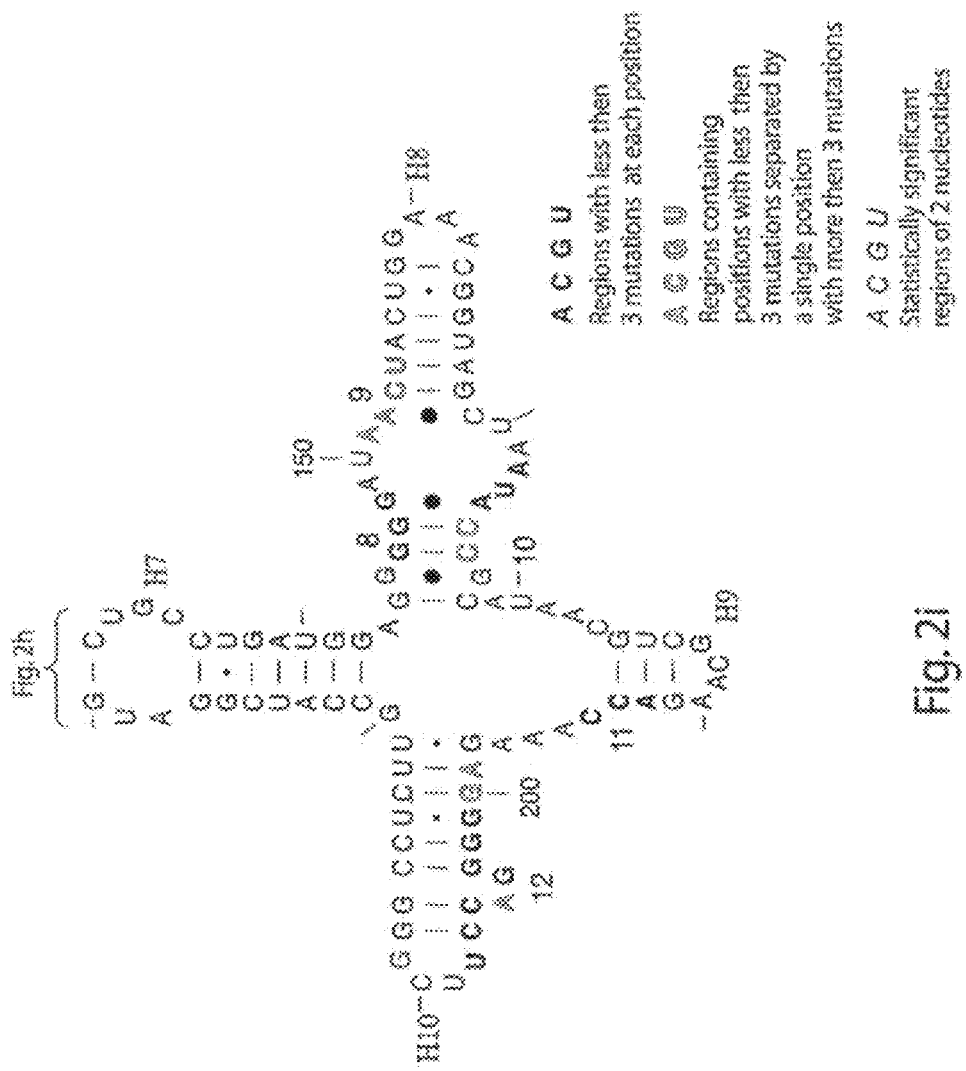
Figure 3B:
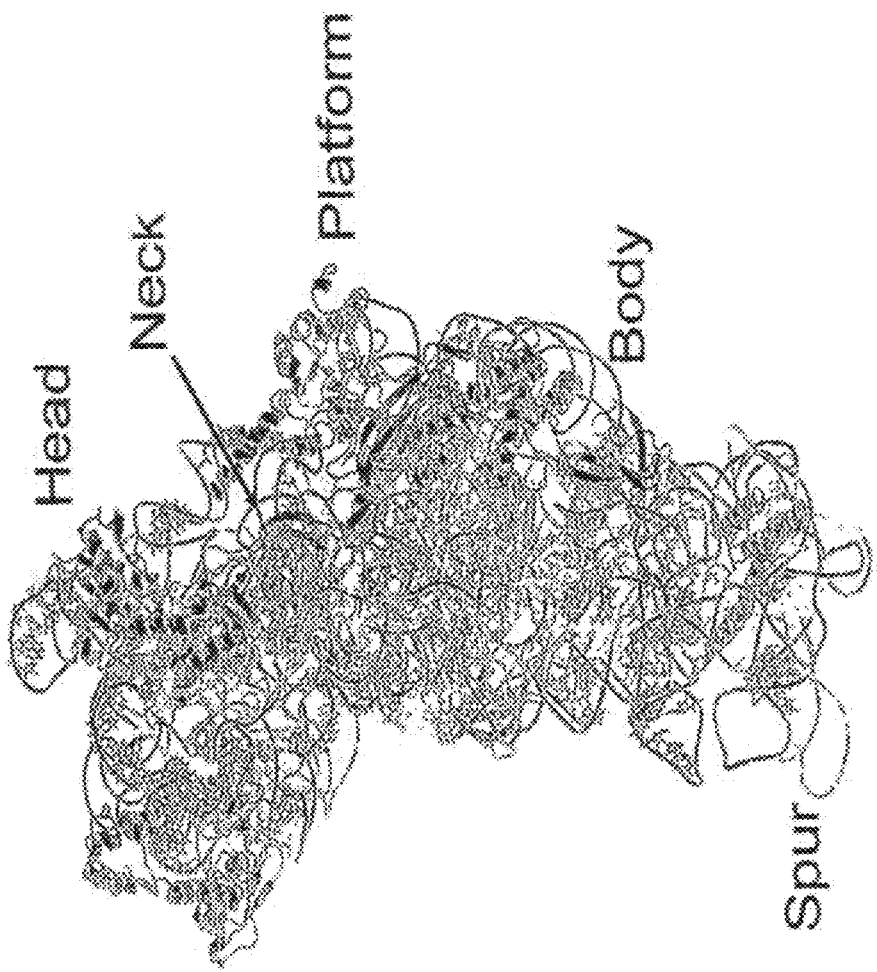
Figure 3C:
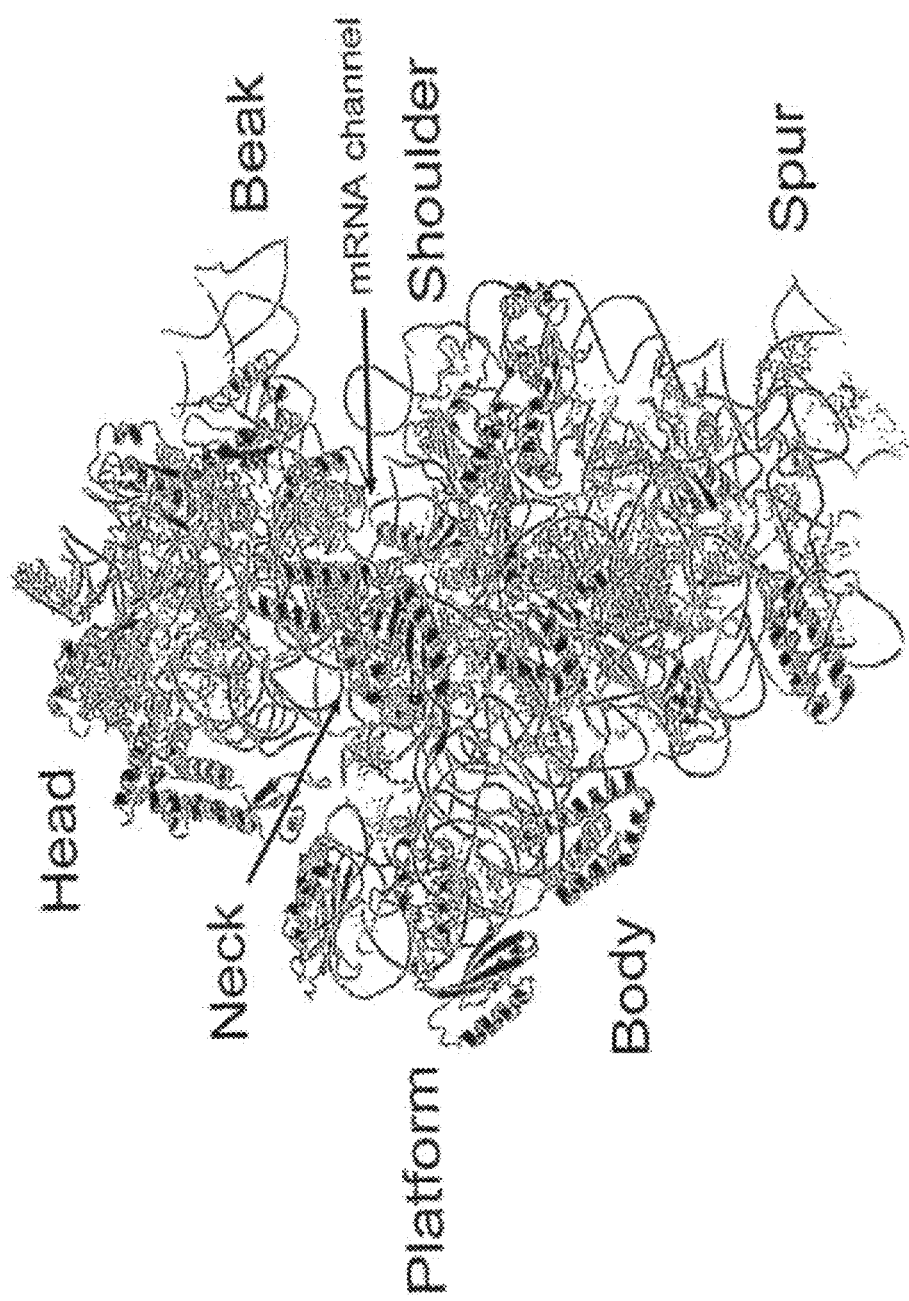
Figure 3D:
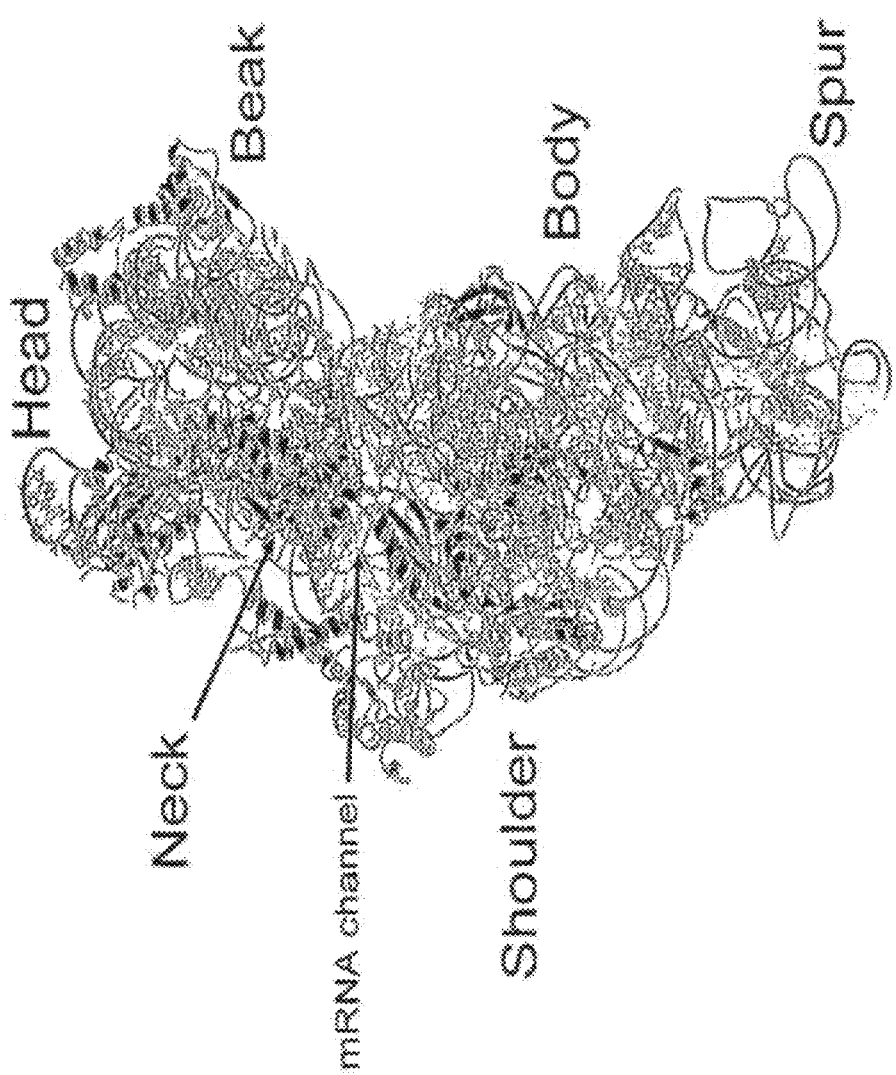

Sequences for a total of 2609 clones were incorporated into a database. The database aligns the sequences, trims the ends, and identifies all the mutations in the sample. These clones contained 10,758 mutations within the 16 S rRNA (positions 20-1503), which translates into an average of 7.3 mutations at each position. The number of mutations at each position ranged from 0 to 38 with a mode of 2 and a median of 6. Regions of 3 or more sequential nucleotides, in the 16 S rRNA, that contain 3 or less mutations are statistically significant, as are regions of 2 or more that contain 0 to 1 mutations. Using these criteria, a total of 47 regions were identified. Single positions with 3 or less mutations separated from other similar positions by a single position with 4 or more mutations were also identified. The identified regions were increased to include positions that contained 3 or less mutations but were separated from previously identified regions by a single position which has more then 4 mutations. This extended previously identified regions and identified previously unisolated regions. Together, a total of 64 conserved regions were identified from the database and mapped onto the 16 S rRNA secondary structure (FIG. 2). The identified conserved regions were compared to the conserved regions identified in the phylogenetic analysis of the 16S rRNA. Identified regions compare well to the conserved regions identified by phylogenetic analysis. An energy minimized model of the *E. coli* 16 S rRNA crystal structure was labeled with these conserved regions to determine their location in three dimensional space. This model was also used to identify any interactions between regions, and identify any interactions with other ribosomal components (FIG. 3).

Targets of the Invention

The 5' Domain.

Figure 4A:
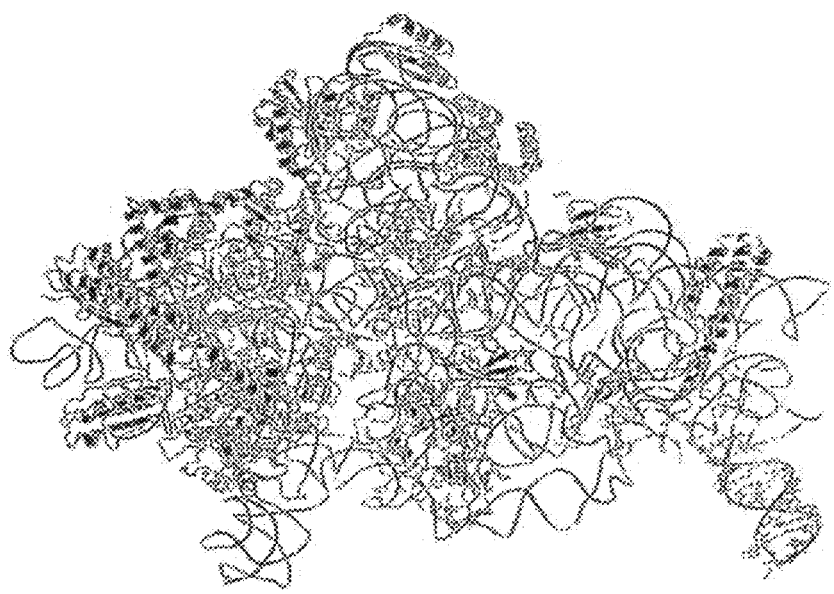
FIG. 4 depicts clusters of conserved regions in the 5' domain. A detailed view of each cluster of conserved regions is shown on the left. The *E. coli* 16 S rRNA modeled crystal structure with proteins with the cluster discussed is shown for reference on the right. A) Helix 6; region 3 B) Helix 10; region 12 C) Helix 16; region 23 D) Helix 18; region 25, 26, and 27 E) Helices 11 and 12; regions 15 and 16 F) Helices 6, 8, and 9; regions 4, 8, 9, 10, and 11 G) Helices 7 and 11; regions 7, 13, and 14 H) Helices 4, 5, 6, 14, 15, and 17; regions 1, 2, 5, 6, 17, 18, 19, 20, 21, 22, and 24.
Figure 4A:
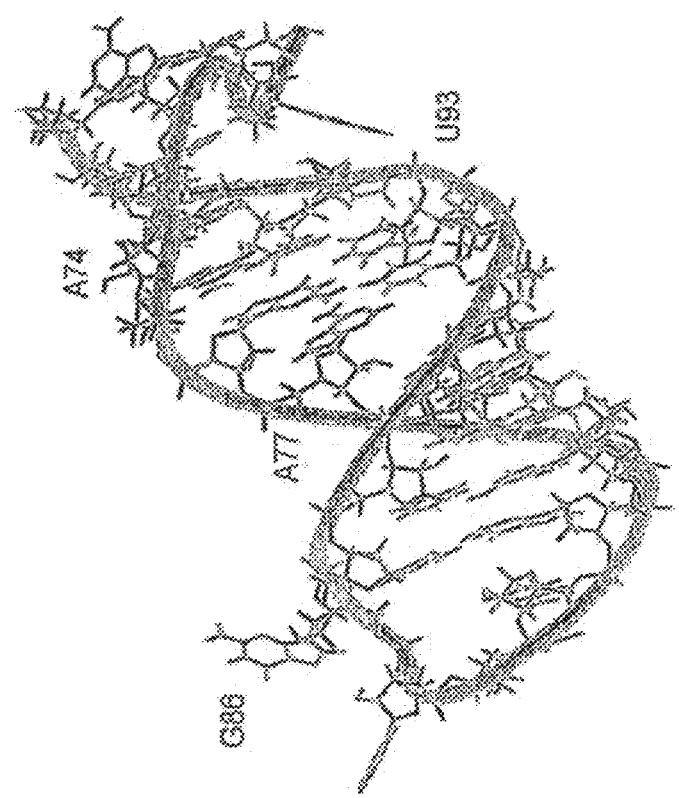

Positions 1 to 560 of the 16 S rRNA are considered to be the 5' domain. In the mutation library, the 5' domain contains 27 conserved regions that are found either as clusters of regions or isolated regions. Region 3 (positions 73-76) is found in helix 6 (H6, notation used throughout the application) and is base paired to positions 93-97 (FIG. 4a). Although all of the residues of region 3 are base paired, position 94 on the opposite strand is flipped out. Position 94 is not known to interact with anything and this helix is not associated with any known function. This helix, however, was reported to mimic P-site bound tRNA during crystal packing but whether this occurs in vivo is unknown.

Figure 4B:
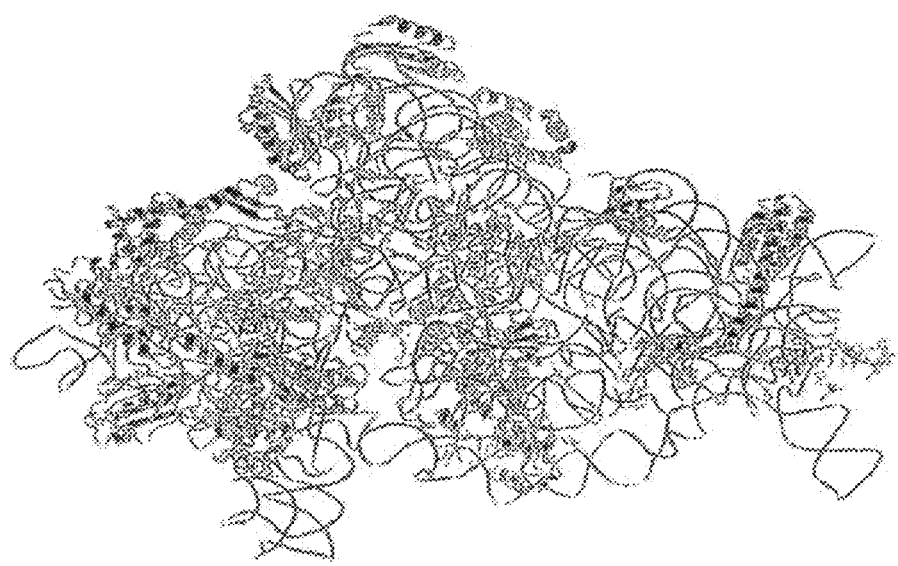
Figure 4B:
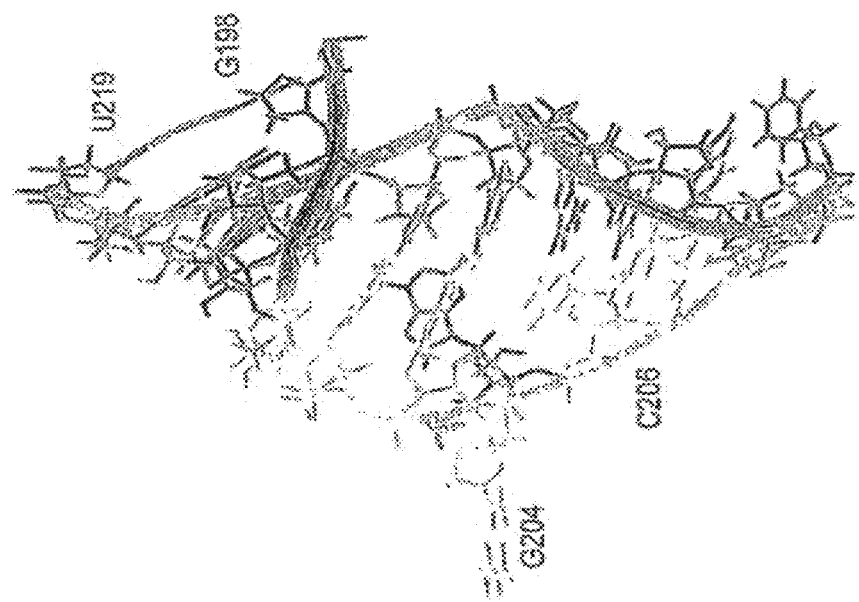

Region 12 (positions 198-207) is found in H10 and is base paired with positions 212-219 (FIG. 4b). As shown in the secondary structure, positions 204 and 205 do not base pair and are flipped out of the helix. Position 205 is positioned in the major groove, disrupting possible interaction with the major grove, while position 204 is completely exposed to solvent. H10 is located on the solvent side of the 30 S subunit and is not known to interact with any of the ribosomal proteins. The function of this helix is unknown.

Figure 4C:
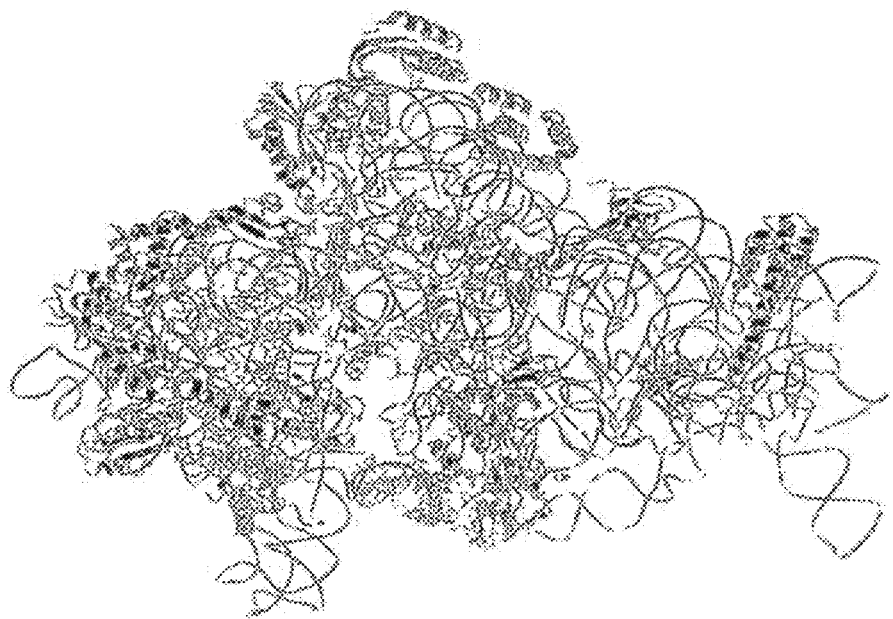
Figure 4C:
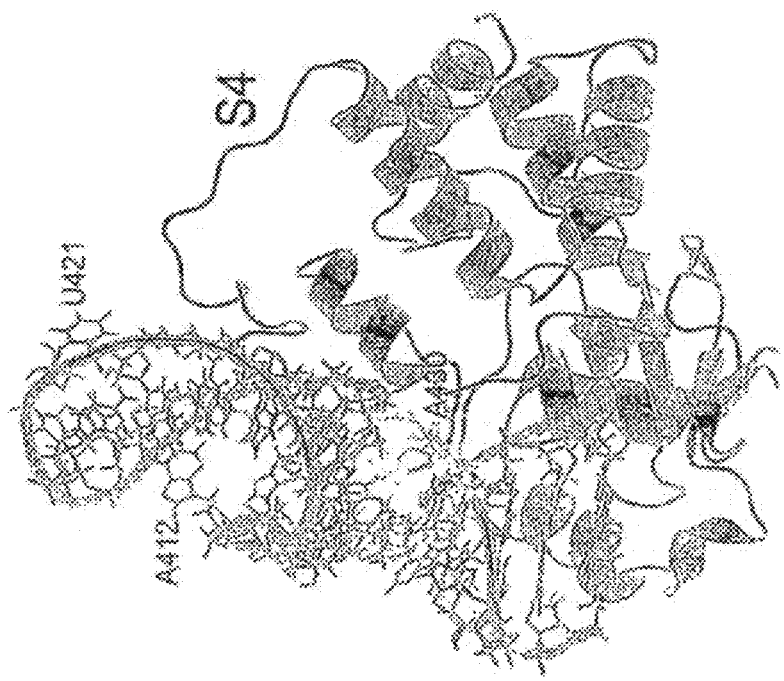

Region 23 (positions 428-430) is found in H16 as part of a bulge loop (FIG. 4c). Ribosomal protein S4 interacts with the backbone of region 23, however, the nucleotides of region 23 are facing into the minor groove. The unique structure of this bulge flips the non-conserved position 412 out of the helix. This region has been shown to be cleaved during directed hydroxyl radical cleavage experiments where Fe(II) was tethered to different positions in elongation factor-G (EF-G) suggesting it be part of a binding site for EF-G. [Wilson, K. S. & Noller, H. F. (1998). Mapping the position of translational elongation factor EF-G in the ribosome by directed hydroxyl radical probing. *Cell* 92, 131-9.]

Figure 4D:
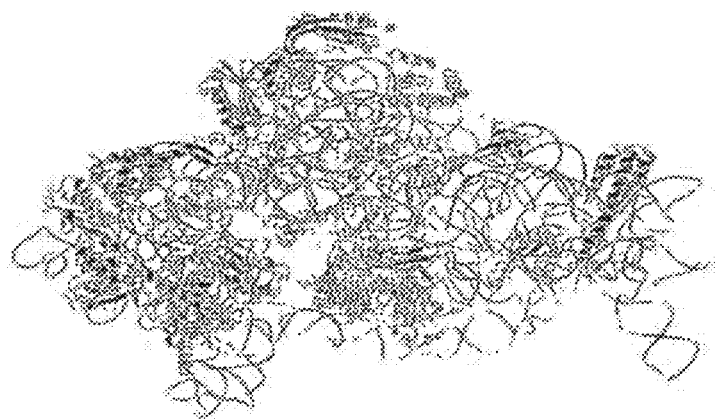
Figure 4D:
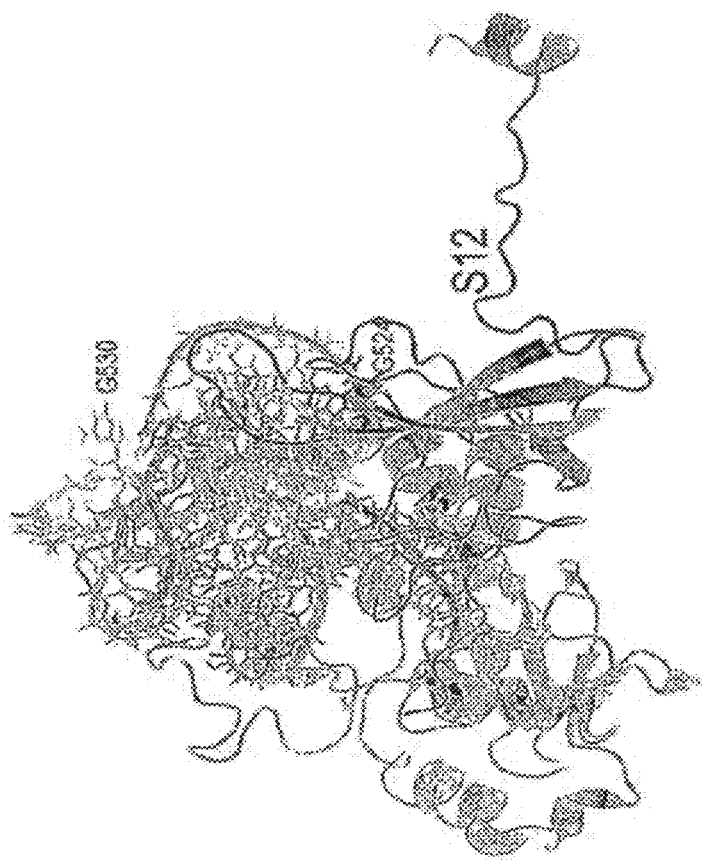

Regions 25 (positions 500-503), 26 (positions 518-530), and 27 (positions 538-541) are located in H18 (FIG. 4d). Regions 25 and 27 are at the base of H18 and help in the formation of the 530 loop structure. Positions 538, 539 and 540 of region 27 interact with positions 511, 512 and 513 while position 541 of region 27 interacts with positions 504. This results in a bulge in the stem that can then form a pseudoknot with the tetraloop at the top of H18. Pseudoknot formation places region 26 in the correct orientation, allowing the functionally important nucleotide at position 530 to be positioned into the A-site. [Yusupov, M. M., Yusupova, G. Z., Baucom, A., Lieberman, K., Earnest, T. N., Cate, J. H. & Noller, H. F. (2001). Crystal structure of the ribosome at 5.5 A resolution. *Science* 292, 883-96; and Ogle, J. M., Brodersen, D. E., Clemons, W. M., Jr., Tarry, M. J., Carter, A. P. & Ramakrishnan, V. (2001).] Recognition of cognate transfer RNA by the 30S ribosomal subunit. *Science* 292, 897-902. Position 530 has been shown to be involved in the discrimination between cognate and near-cognate tRNA. [Ogle, J. M., Brodersen, D. E., Clemons, W. M., Jr., Tarry, M. J., Carter, A. P. & Ramakrishnan, V. (2001). Recognition of cognate transfer RNA by the 30S ribosomal subunit. *Science* 292, 897-902. Region 26 also interacts with initiation factor 1 (IF1), the antibiotic streptomycin, and rprotein S12. Carter, A. P., Clemons, W. M., Jr., Brodersen, D. E., Morgan-Warren, R. J., Hartsch, T., Wimberly, B. T. & Ramakrishnan, V. (2001).

Crystal structure of an initiation factor bound to the 30S ribosomal subunit. *Science* 291, 498-501; and Carter, A. P., Clemons, W. M., Brodersen, D. E., Morgan-Warren, R. J., Wimberly, B. T. & Ramakrishnan, V. (2000). Functional insights from the structure of the 30S ribosomal subunit and its interactions with antibiotics. *Nature* 407, 340-8.] This region as well as the ribosomal components it interacts with have been shown to be important for maintenance of translation fidelity.

Figure 4E:
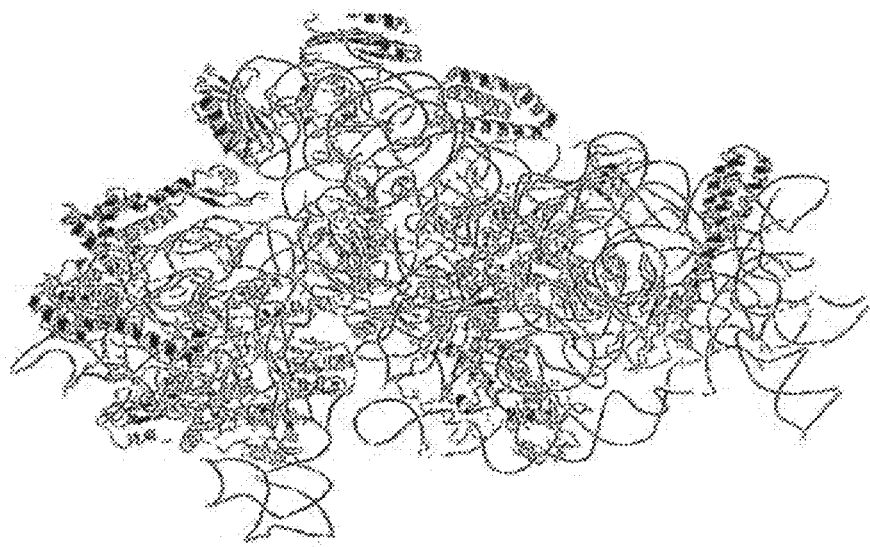
Figure 4E:
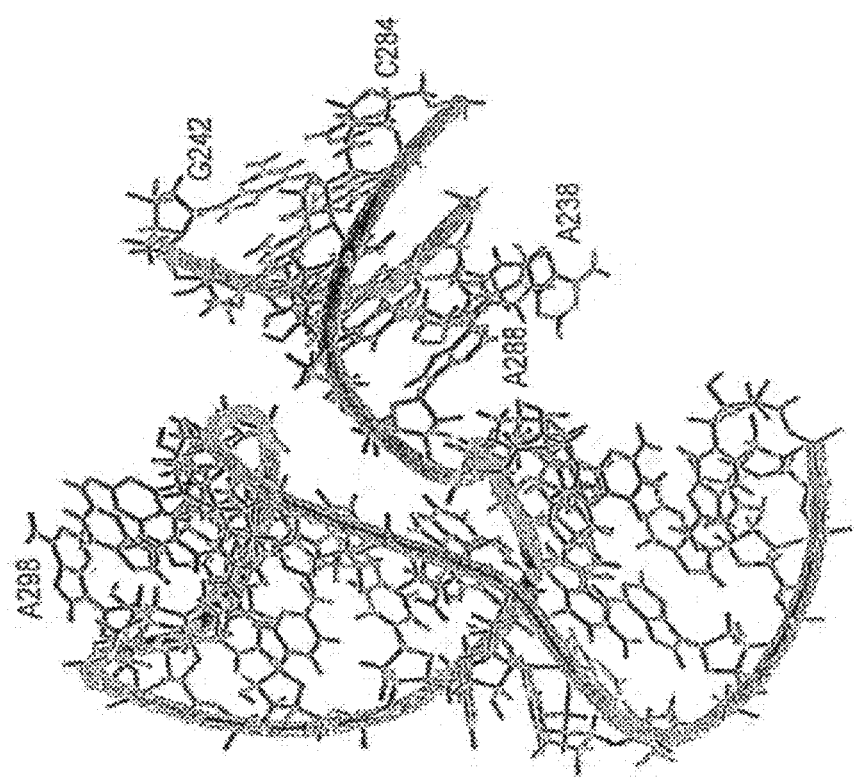

Regions 15 (positions 285-294) and 16 (positions 297-302) are part of H11a and H12 (FIG. 4e). Region 15 is involved in formation of the junction between H11a and H12. Region 16 forms one side of the stem and the GNRA tetraloop of H12. Although no proteins are found to interact with this region, the 5' end of the 16 S rRNA seems to interact with the tetraloop, possibly limiting its mobility. However, no specific function has been associated to this region.

Figure 4F:

The bottom of the ribosome contains 5 regions identified in the mutation library: regions 4 (positions 102-106), 8 (positions 145-147), 9 (positions 150-153), 10 (positions 171-175), and 11 (positions 191-193). With the exception of regions 8 and 9, these regions are involved in the binding of rprotein S20 (FIG. 4f). S20 is a primary binding protein that interacts with both H9 and H44. This interaction stabilizes the bottom of the ribosome and anchors H44 to the body of the ribosome. The anchoring of H44 may be important for the formation of intersubunit bridge sites involving H44 as well as for translational accuracy that occurs at the top of H44. The majority of the interactions with S20, however, are backbone interactions. The bases of these regions are base paired and form helices with other section of the 5' domain. Finally, regions 8 and 9, although not involved in binding to S20, compose the stem and internal loop of H8 with region 10.

Figure 4G:
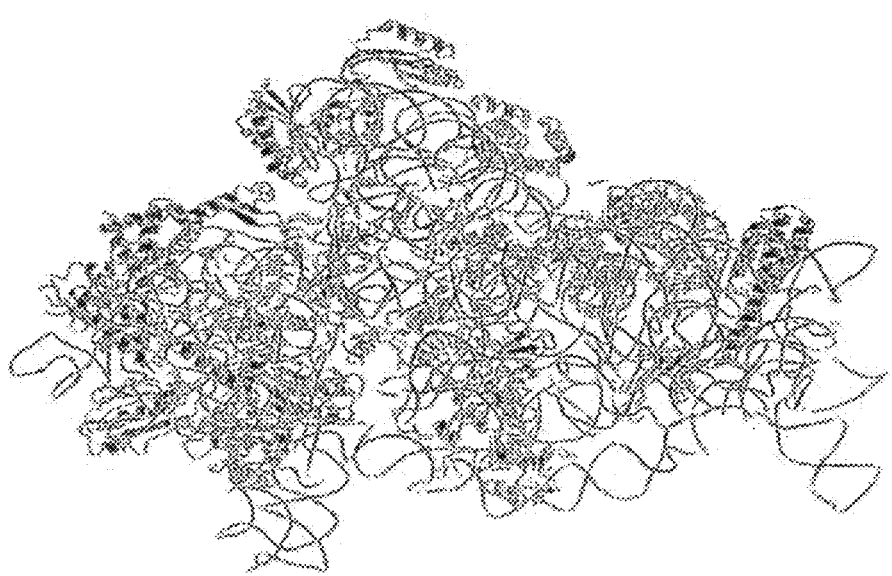
Figure 4G:
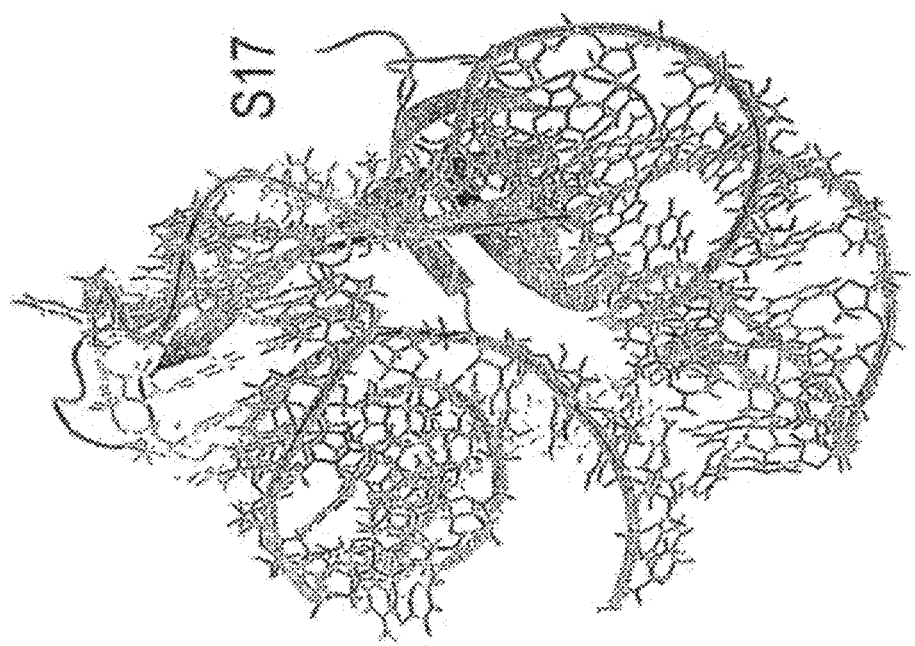

A cluster of three regions, regions 7 (positions 124-128), 13 (positions 235-242), and 14 (positions 246-248) was identified in H7 and H11. Rprotein S17 is a primary binding protein and contacts the backbone of these regions (FIG. 4g). The binding of S17 stabilizes the sharp bend at the H7-H11 junction and aids in the general assembly of the 16 S rRNA. The regions 7 and 14 are base paired and form segments of H7 or H11, respectively. Positions 236-239, of region 13, are involved in base pairing to form H7 while positions 240-242 are involved in base pairing to form H11. Interaction with S17 seems insufficient to explain the conservation of these regions but no other function has been identified.

Figure 4H:
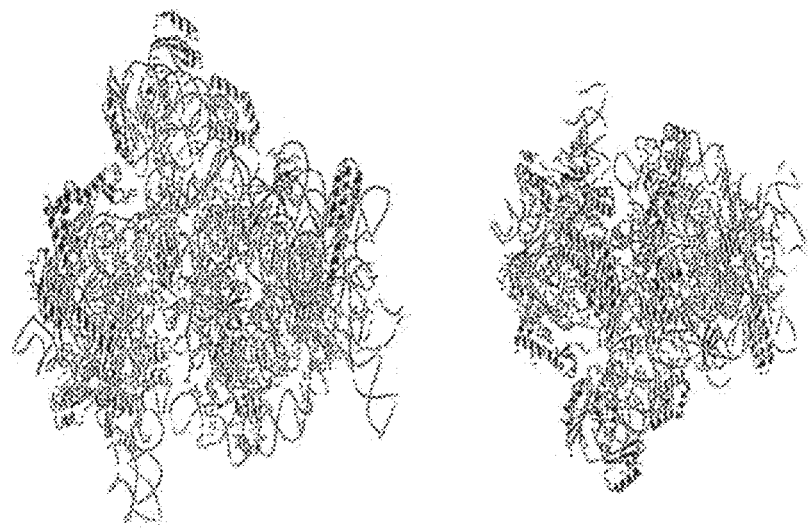
Figure 4H:
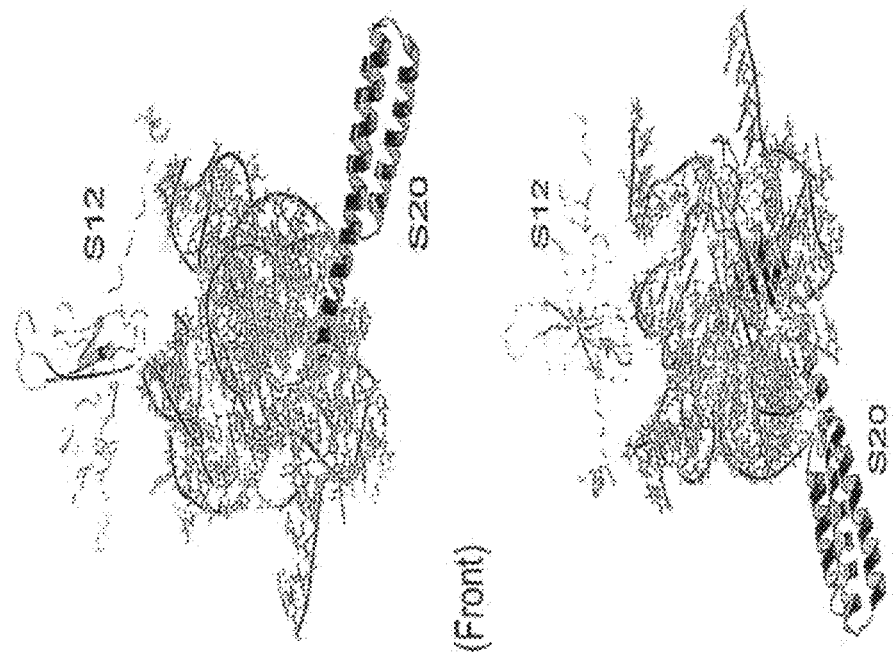

The final clustering of regions in the 5' domain involves regions 1 (positions 39-49), 2 (positions 52-58), 5 (positions 109-110), 6 (positions 113-117), 17 (positions 310-319), 18 (positions 322-328), 19 (positions 337-342), 20 (positions 348-362), 21 (positions 365-375), 22 (positions 384-391), and 24 (positions 447-450). This large cluster of conserved regions is located in the center of the body and makes limited contact with rproteins S12, S16, and S20 (FIG. 4h). The solvent side of this cluster of conserved regions is covered with rRNA and rproteins. The interface side of this cluster though, is exposed to either solvent as a 30 S subunit or to the 50 S subunit when translating. One intersubunit bridge, B8, between positions 343-345 of H14 and rprotein L14, has been identified. However, these positions (343-345) were not identified as being conserved. Regions 19 and 20 create the loop at the end of H14, which may be essential for the formation of intersubunit bridge B8. The function of the other helices in this cluster is not known.

Central Domain.

Figure 5A:
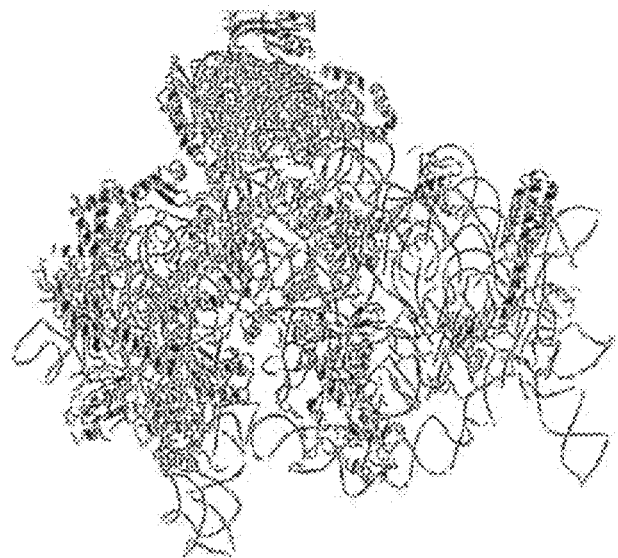
FIG. 5 depicts clusters of conserved regions in the central domain. Image setup similar to FIG. 4. A) Helices 22 and 23; regions 32 and 34 B) Helix 21; regions 29, 30, and 31 C) Helix 24; regions 36 and 37 D) Helix 27; regions 40 and 41 E) Helices 19 and 39; regions 28, 39, and 42 F) Helices 23 and 24; regions 33, 35, and 38.
Figure 5A:
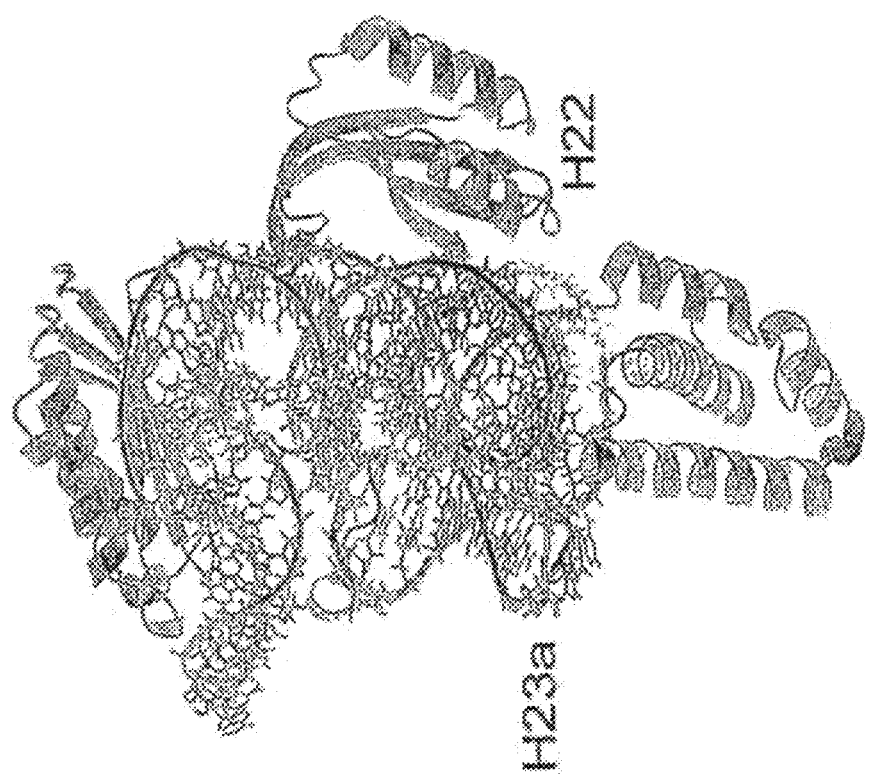

The central domain, positions 561-930, contains 16 conserved regions, that combine into 7 groups. Region 34 (positions 737-741) is located in H22 and is part of an asymmetrical internal loop (FIG. 5a). The backbone of region 34 is involved in an interaction with rproteins S6 and S15 while the bases are paired with positions 664-669. This base paring causes position 665 to be flipped out of the helix. The flipping out of position 665 allows it to interact with position 723 in H23a. This interaction seems to help stabilize H23a so that H22 and H23 can coaxially stack. [Agalarov, S. C., Sridhar Prasad, G., Funke, P. M., Stout, C. D. & Williamson, J. R. (2000). Structure of the S15,S6,S18-rRNA complex: assembly of the 30S ribosome central domain. *Science* 288, 107-13.] The stacking of H22 and H23 is important for the folding of the rRNA and binding of other rproteins.

Region 32 (positions 703-705) is located in the asymmetric internal loop between H23 and H23b (FIG. 5a). Interactions within the loop result in the formation of a pocket containing the nucleotides from region 32. The bases of region 32 interact with rprotein S11 and seem to be its major binding site. S11 helps to stabilize the bent conformation of H23 and the interactions between H23 and H24. Both H23 and H24 have been localized to the E-site, which seems to have a role in the discrimination of tRNA at the A-site.

Figure 5B:
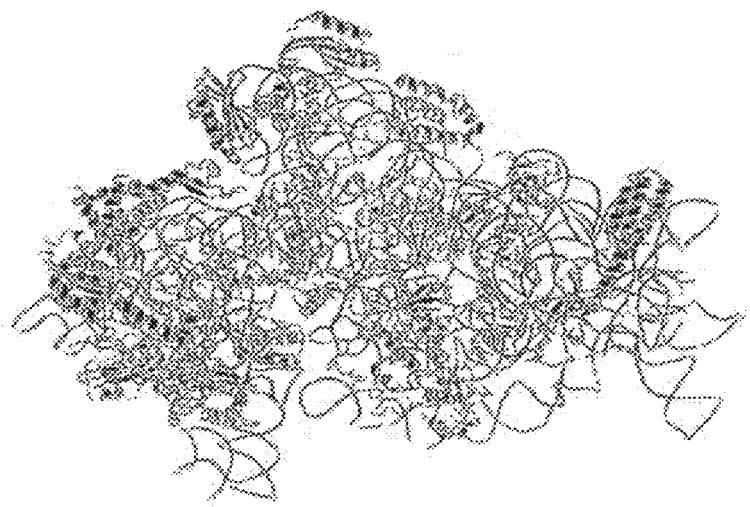
Figure 5B:

The internal loop and pentaloop at the end of H21 was also identified as being conserved in the library. Helix 21 contains regions 29 (positions 604-609), 30 (positions 617-626), and 31 (positions 631-634). The loop of H21 (region 30) makes backbone contacts with rprotein S4 while the rest of region 30 and the backbone of region 29 interacts with S16 (FIG. 5b). Position 621 of region 30 interacts with position 42, part of region 1, so that these regions are brought together. Finally, regions 31 and positions 604-606 of region 29 are base paired. This base pairing may allow for the formation of the internal loop of H21 and flipping positions 607-610 of region 29 out of the helix. Positions 607 and 608 seem to interact with base pairs 291:309 and 292:308, respectively, possibly positioning H21. Finally, positions 609-610 of region 29 are involved in binding to rprotein S4 and S16. H21 is located on the solvent side of a large cluster of regions (regions 1, 2, 5, 6, 17, 18, 19, 20, 21, 22, and 24) identified in the 5' domain. The positioning of this helix may protect this cluster of regions or provide stability for their interaction. Region 30 forms one side of the stem and the loop of H21. Although backbone contacts between region 30 and S16 exist, no other function has been ascribed to this helix.

Figure 5C:
Figure 5C:
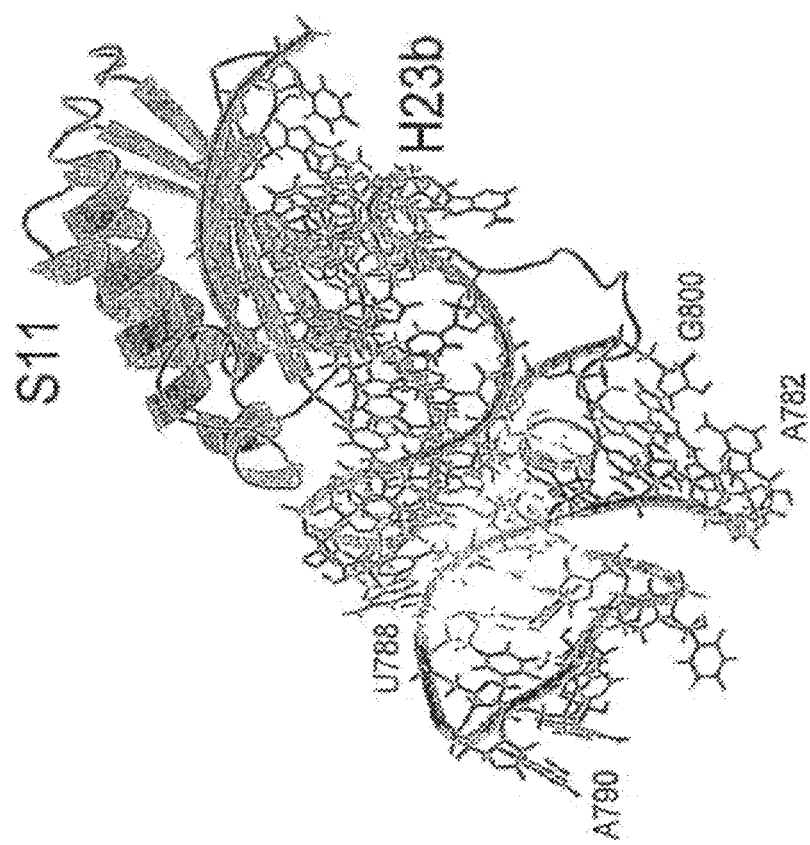

H24a contains regions 36 (positions 783-791) and 37 (positions 795-797) and is commonly termed the 790 loop (FIG. 5c). Region 37 is base paired with positions 785-786 of region 36 to form the stem of the 790 loop. The 690 loop interacts with the stem of the 790 loop to position these two loops together to form part of the E-site. The bottom of the stem also aids in the formation of intersubunit bridge B2b with H69 of the 23 S rRNA. The remainder of region 36 is extended into the loop. The 790 loop (788-789) has been shown to interact with both P-site and E-site bound tRNA. Positions 790 and 791 also interact with the mRNA as it is threaded through the ribosome, stabilizing its orientation. Antibiotics pactamycin and edeine also have binding sites in the 790 loop and affect translational either by inhibiting translocation or accuracy, respectively. These functions of the 790 loop explain its conservation in both the phylogenetic analysis and the mutation library.

Figure 5D:
Figure 5D:
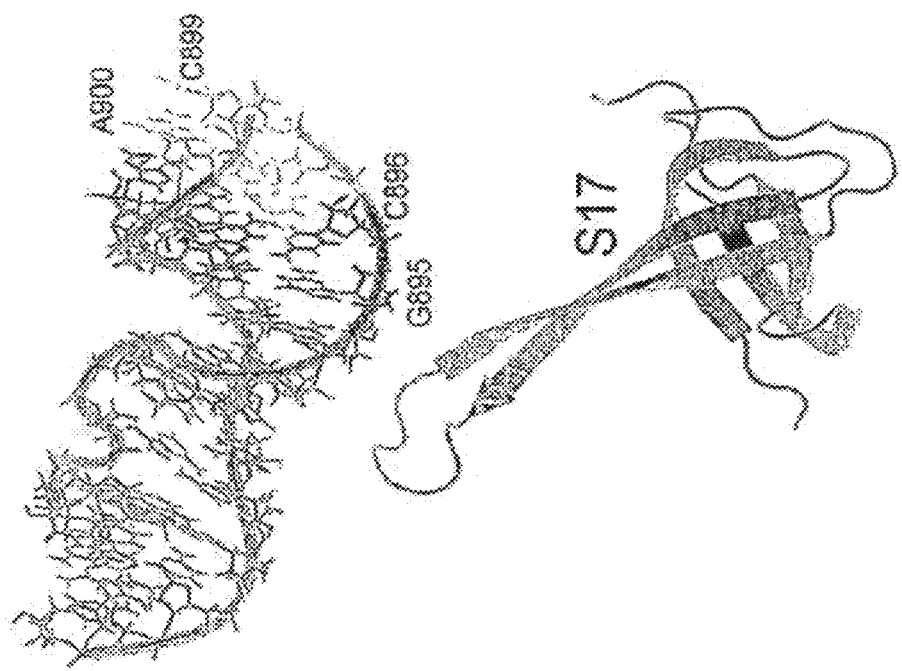

The loop of the switch helix (H27) contains two conserved regions, region 40 (positions 894-899) and region 41 (902-903), that are located on the bottom of the platform and exposed to solvent (FIG. 5d). Region 41 base pairs with positions 896-897 of region 40 to form the stem of H27. Positions 894-897 of region 40 is part of the stem while positions 898-899 form part of a GNRA tetraloop. The tetraloop docks into the base of H24, interacting with positions 796, 770, and 810. Although, H27 has been thought to adjust the accuracy of the ribosome, recent studies has shown that this is not the case. [Lodmell, J. S. & Dahlberg, A. E. (1997). A conformational switch in *Escherichia coli* 16S ribosomal RNA during decoding of messenger RNA. *Science* 277, 1262-7; Gabashvili, I. S., Agrawal, R. K., Grassucci, R., Squires, C. L., Dahlberg, A. E. & Frank, J. (1999). Major rearrangements in the 70S ribosomal 3D structure caused by a conformational switch in 16S ribosomal RNA. *Embo J* 18, 6501-7; and Rodriguez-Correa, D. & Dahlberg, A. E. (2004). Genetic evidence against the 16S ribosomal RNA helix 27 conformational switch model. *Rna* 10, 28-33.]

Figure 5E:
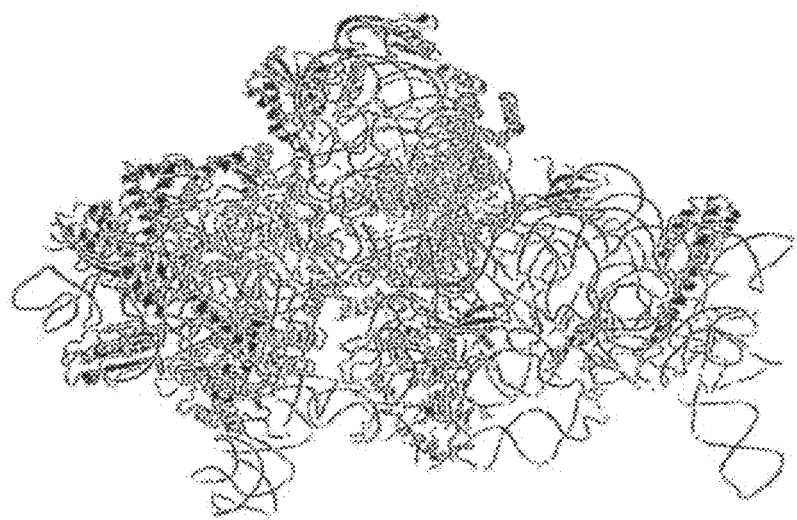
Figure 5E:
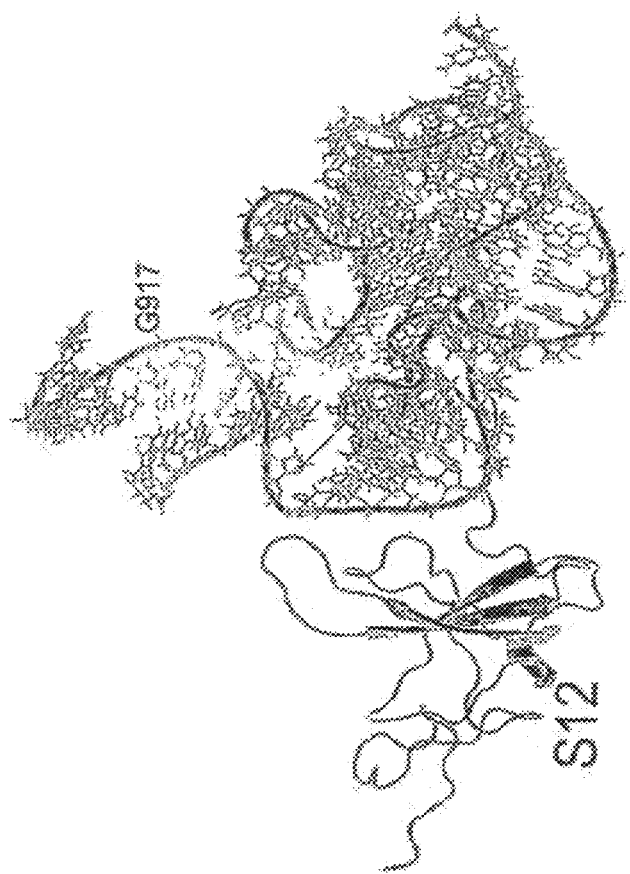

Regions 28 (positions 566-572), 39 (positions 880-887), and 42 (positions 916-918) are located in the central domain and seem to be structural elements (FIG. 5e). Positions 880-884 of region 39 are base paired with positions 566-569 of region 28 to generate H19. H19 separates two large junction loops and is also involved in the binding of the C-terminus of rprotein S12. The rest of region 39 is involved in base pairing to positions 910-912 to form the stem of H27. Position 572 of region 28 form a section of the H19, H20, H24, and H25 junction while positions 570 and 571 base pairing with positions 865 and 866 from the loop of H26a. Pairing of region 42 with positions 17-19, forms H2 and creates the central pseudoknot. Interestingly position 571 interacts with position 18 next to H2, further stabilizing the pseudoknot. The conservation of these regions may be due to their role in structure formation and stabilization.

Figure 5F:
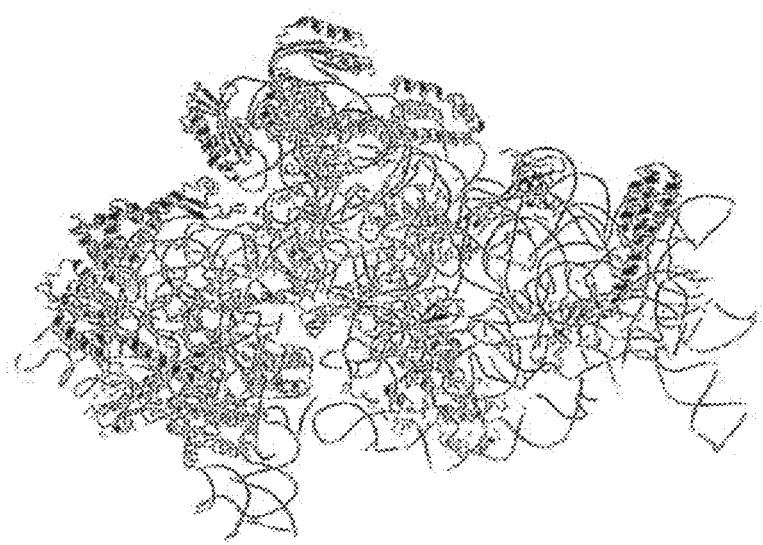
Figure 5F:

The final cluster in the central domain is composed of regions 33 (positions 710-714), (positions 773-776), and 38 (positions 801-806). Region 33 is found in H23 and seems to be involved in the formation of an internal loop (FIG. 5f). Positions 712 and 713 of region 33 are involved in the formation of intersubunit bridge, B7b. Regions 35 and 38 are located in H24. H24 contains a bulge, an internal loop, and the conserved 790 terminal loop. Positions 773 and 774 of region 35 is base paired with positions 805 and 806 of region 38. Contrary to the secondary structure, the G775-U804 wobble pair does not exist in the crystal structure. Instead, position 804 forms a wobble pair with position G778, leaving the bulge as a part of region 35. This bulge in region 35, positions 774-776, also interacts with the 23 S rRNA to form intersubunit bridge B7b. Interestingly, position 777 of region 35 is flipped out of the bulge of H24 and positioned in the minor groove of H23 created by region 33. This may help in positioning H23 and H24 together. Finally, the remaining positions (801-803) of region 38 are part of the closing base pair and first base of the internal loop. A few minor interactions between this cluster and with rproteins S6, S11, and S15 were also identified.

The 3' Domain.

The 3' domain of the 16 S rRNA consists of positions 931 to the 3' end of the rRNA. This domain is further subdivided into the 3' major domain consisting of positions 931-1390 that makes-up the head of the 30 S subunit, and the 3' minor domain which consists of positions 1391-1542 forming helix 44 that runs down the body of the 30 S subunit. It is the 3' minor domain that is mainly responsible for the decoding function ascribed to the 30 S subunit.

Figure 6A:
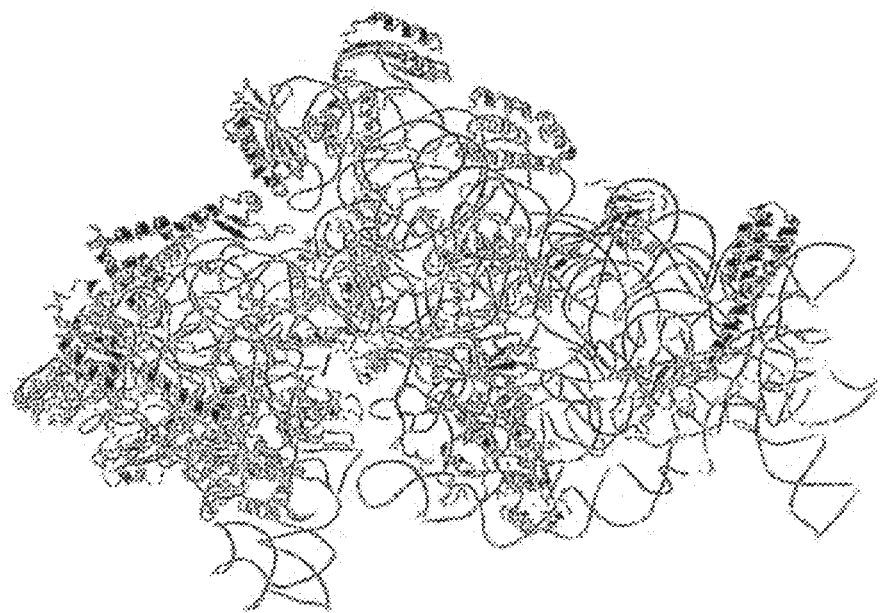
FIG. 6 depicts clusters of conserved regions in the 3' domain. Image setup similar to FIG. 4. A) Helix 39; region 50 B) Helix 40; region 51 C) Helices 29, 30, 41, and 42; regions 43, 44, 55, 56, and 57 D) Helix 43; regions 60 and 61 E) Helices 31, 32, and 42; regions 45, 46, 54, 58, and 59 F) Helices 34 and 35; regions 47, 48, 49, 52, and 53 G) Helices 28 and 44; regions 62, 63, and 64.
Figure 6A:
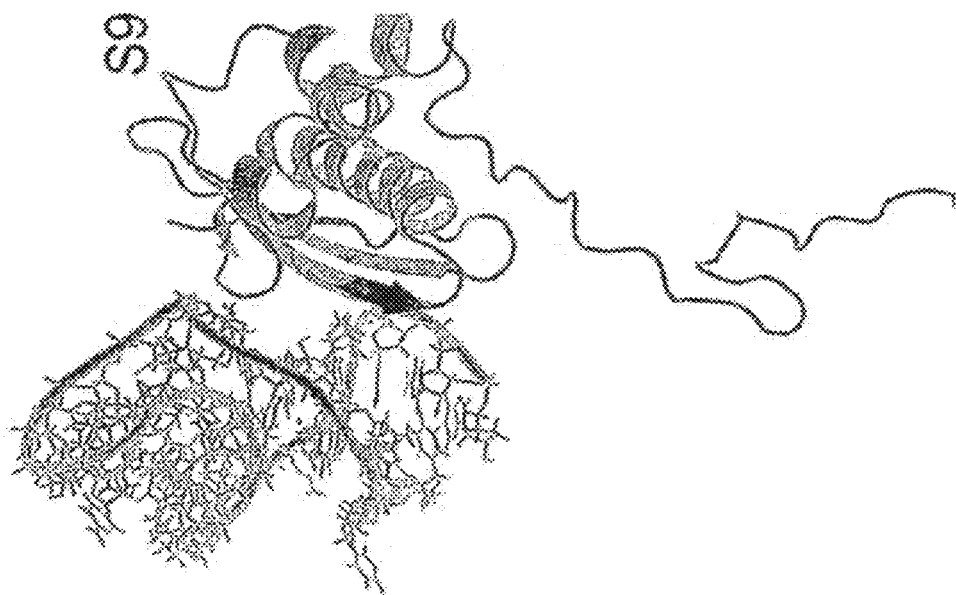

Region 50 (positions 1127-1134) is located in the head of the ribosome as a part of H39. H39 contains an asymmetric internal loop, a bulge, and a pentaloop (FIG. 6a). Region 50 is involved in formation of the bulge and stem before the pentaloop. Positions 1130 and 1131 form the bulge and are excluded from the helix into the minor groove. The remaining positions are base paired and may be responsible for the formation of the bulge and stem before the pentaloop. Although rprotein S9 is involved in some backbone contacts with positions 1128-1131, a specific function has not been associated with this region.

Figure 6B:
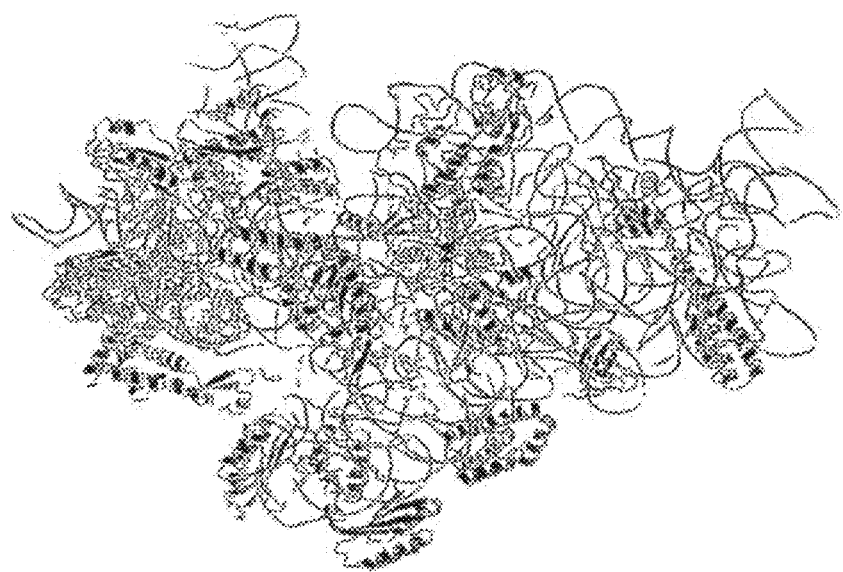
Figure 6B:
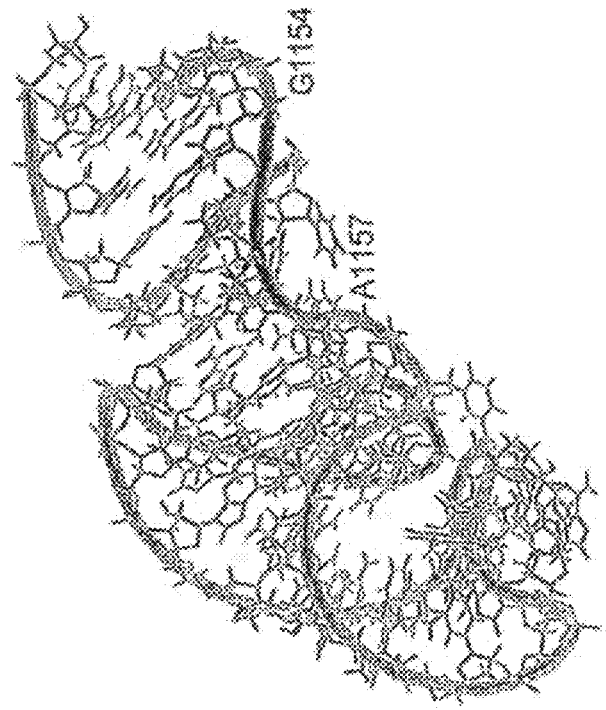

Region 51 (positions 1153-1156) is located in H51 on the solvent side of the ribosome. Region 51 is part of a junction between H38, H39 and H40 (FIG. 6b). Positions 1153-1155 are base paired with positions 1118-1120 as seen in the secondary structure. Position 1156 seems to be interacting with position 1117 and 1179, stabilizing the other side of the bulge so that it is in close proximity. The conservation of this region may be due to it role in formation of this junction.

Figure 6C:
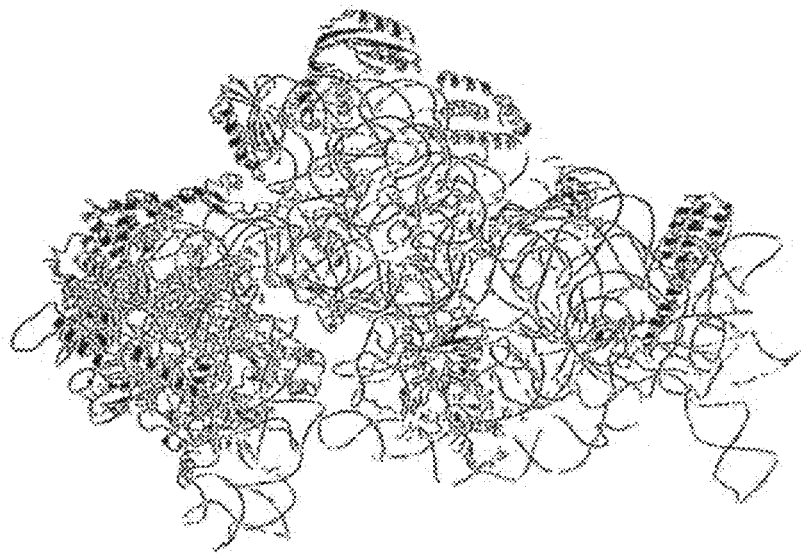
Figure 6C:
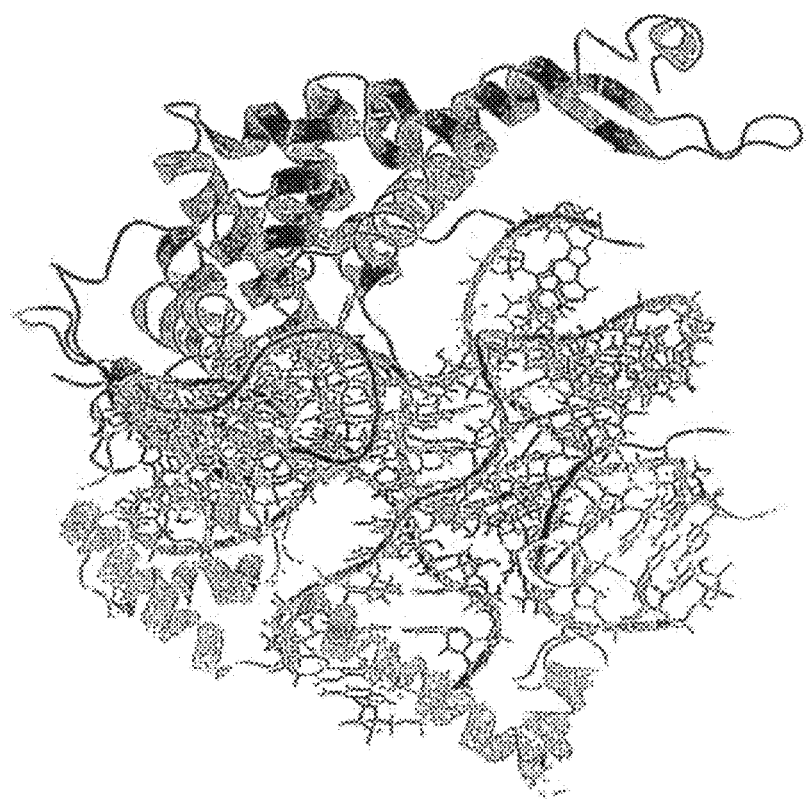

Helices 29, 30, 41, and 42 radiate from a junction in the 3' major domain. Regions 43 (positions 939-941), 44 (positions 944-948), 55 (positions 1233-1234), 56 (positions 1290-1296), and 57 (positions 1300-1305) compose the helices that surround this junction (FIG. 6c). The majority of these regions are located in helices with few positions actually involved in the junction, although, the correct structure of these helices would ensure the proper formation of the junction. Ribosomal proteins S7, S9, and S13 bind to the helices formed by these regions possibly explaining the conservation of these regions.

Figure 6D:
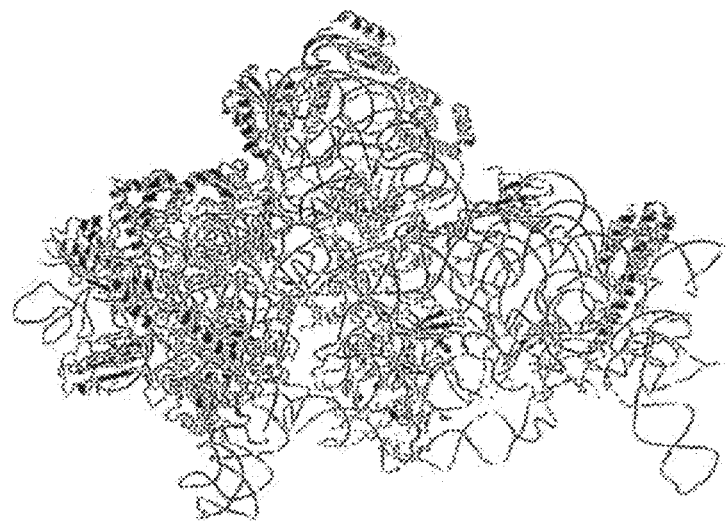
Figure 6D:
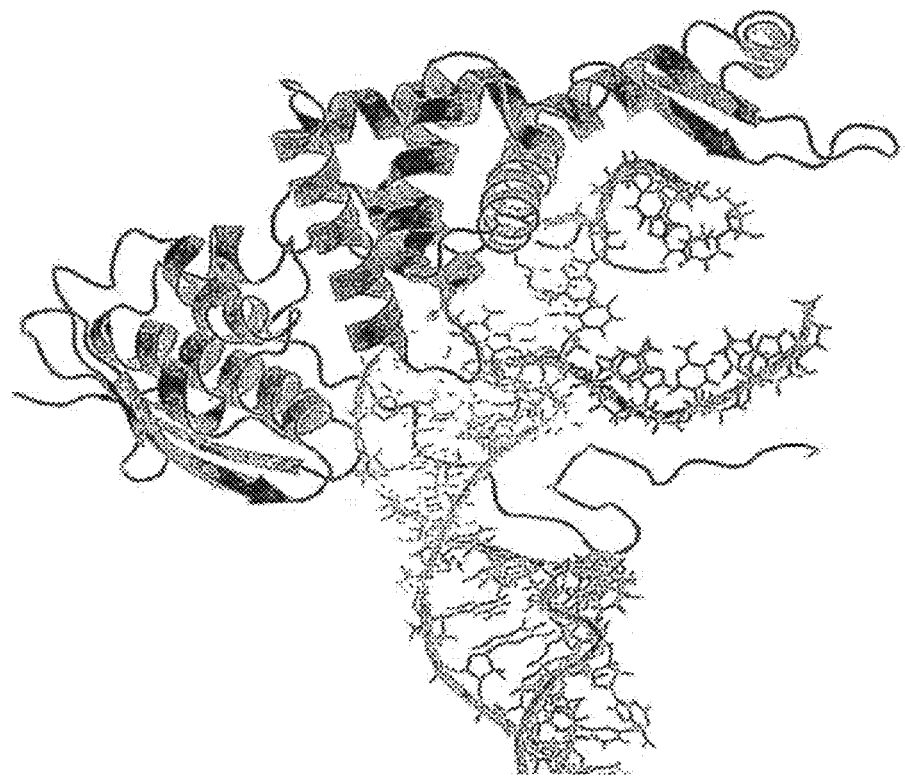

Regions 60 (positions 1343-1353) and 61 (positions 1369-1375) form the junction between H28, H29, and H43 as well as part of the stem of H43 (FIG. 6d). Positions 1350-1353 of region 60 are base paired with positions 1369-1372 of region 61. The remaining positions of both regions form the junction. Rproteins S7 and S9 make extensive contacts with these two regions. S7 is a primary binding protein while S9 is a secondary binding protein. The binding of primary binding proteins is essential for the correct folding of the RNA and binding of subsequent proteins. The conservation of regions 60 and 61 seems to be due to their role in the binding of S7.

Figure 6E:
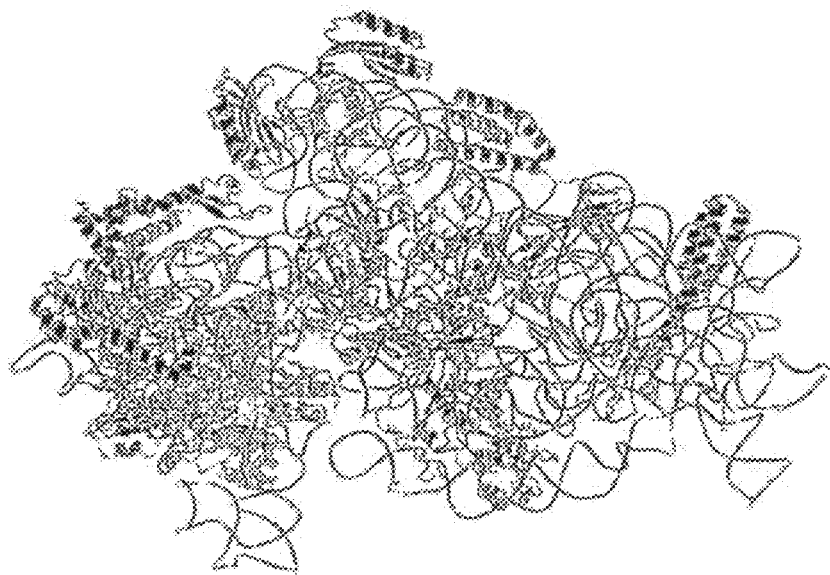
Figure 6E:
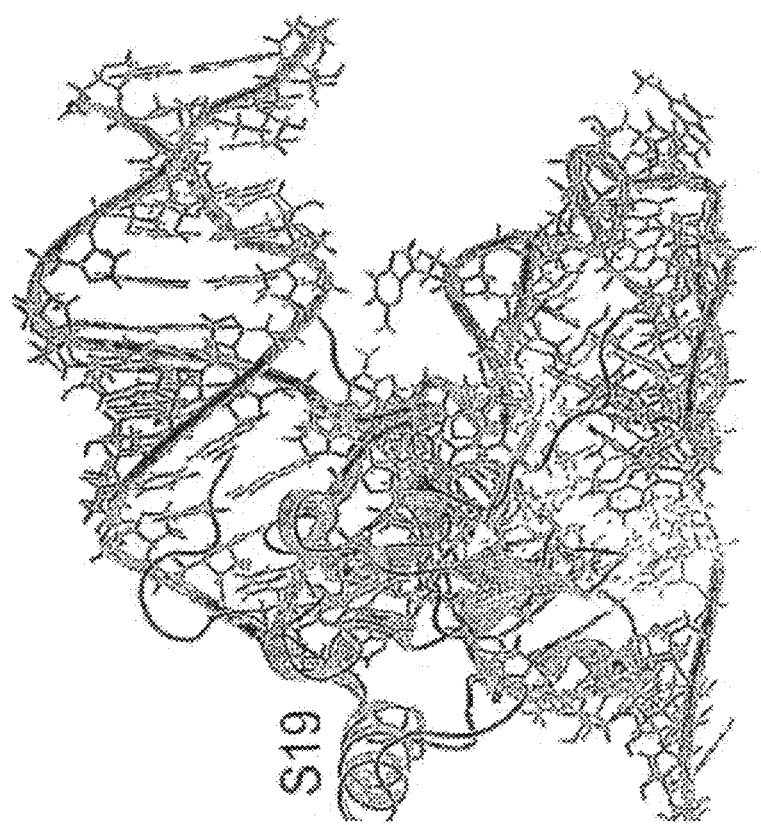

A cluster of 5 conserved regions (45 (positions 958-959), 46 (positions 976-985), 54 (positions 1218-1223), 58 (positions 1309-1316), and 59 (positions 1323-1328)) was identified as forming a major binding site for rprotein S19. These regions are located on the interface side of the 30 S subunit and make extensive contact with S19 but also interacts with several secondary and tertiary binding rproteins, including S13 and S14 (FIG. 6e). Regions 58 and 59 seem to be conserved due to their role in the binding of S19. The loop of H42, formed by regions 58 and 59, interacts with the junction between H30, H31, and H32, the majority of which is formed by regions 45, 46, and 54. The loop of H31 (the 970 loop) is located in the P-site and has been shown to interact with P-site bound tRNA. The binding of S19 would stabilize the interaction between H31 and H43 of the 16 S rRNA and allow positioning of the 970 loop in the P-site.

The path of mRNA through the ribosome has been solved with x-ray crystallography. [Yusupova, G. Z., Yusupov, M. M., Cate, J. H. & Noller, H. F. (2001). The path of messenger RNA through the ribosome. *Cell* 106, 233-41.] The mRNA was shown to thread its way through two channels into and out of the ribosome interface. The upstream channel is an opening created by the head, neck, and shoulder of the ribosome. In the head and neck, the composition of this channel includes regions 47 (positions 1048-1058), 48 (positions 1066-1073), 49 (positions 1102-1106), 52 (positions 1191-1195), and 53 (positions 1203-1208) on the interface side, and ribosomal proteins S2, S3, S4, and S5 on the solvent side (FIG. 6O. The bottom of the channel is bounded by the 530 loop (see central domain section). Regions 48 and 49 form H35, a major binding site for rprotein S2. More importantly, though, may be the formation of H36, which interacts with 55. S5 binds to the solvent side of the ribosome and helps in the formation of the mRNA channel. Position 1068 of region 48 is also involved in interaction with spectinomycin. [Carter, A. P., Clemons, W. M., Brodersen, D. E., Morgan-Warren, R. J., Wimberly, B. T. & Ramakrishnan, V. (2000). Functional insights from the structure of the 30S ribosomal subunit and its interactions with antibiotics. *Nature* 407, 340-8.] Base pairing of regions 47 and 53 form a part of H34. This segment of H34 contains a bulge involving positions 1053-1054. Position 1053 forms a base triple with positions 1057 and 1203 while position 1054 is flipped out into the mRNA channel allowing it to interact with A-site bound tRNA as well as with tetracycline. Previously, position 1054 was shown to interact with the third position of the codon-anticodon interaction in the A-site. The conservation of regions 47 and 53 may be to allow for the flipping out of position 1054. The final region in this area is region 52. The base pairing of this region to the opposite strand results in the formation of a bulge at position 1196, flipping the base out of the helix and allowing this position to interact with tetracyline. Position 1196 is orientated towards the mRNA channel and may serve to position the mRNA down stream of the A-site. This region also contains position 1192, the mutation that confers spectinomycin resistance. [Sigmund, C. D., Ettayebi, M. & Morgan, E. A. (1984). Antibiotic resistance mutations in 16S and 23S ribosomal RNA genes of *Escherichia coli. Nucleic Acids Res* 12, 4653-63.] Spectinomycin inhibits the elongation factor G (EF-G) catalyzed translocation of tRNA from the A-site to the P-site. Although, this region is not involved in EF-G binding, movement of the head seems to be important in aspects of protein synthesis and could be affected by spectinomycin binding. [Peske, F., Savelsbergh, A., Katunin, V. I., Rodnina, M. V. & Wintermeyer, W. (2004). Conformational changes of the small ribosomal subunit during elongation factor G-dependent tRNA-mRNA translocation. *J Mol Biol* 343, 1183-94.] The numerous bulges located in H34 may increase the flexibility and allow for the required movement essential for protein synthesis. Aside from these functions, these regions also interact and position ribosomal proteins S3, S4 and S5 that make up the solvent side of the mRNA channel. Interaction with these proteins is likely the first step in correctly orienting the mRNA for translation.

Figure 6G:
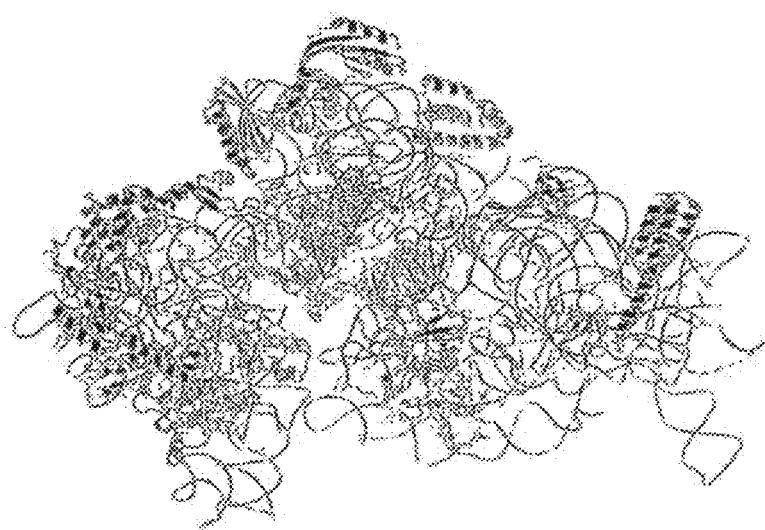
Figure 6G:
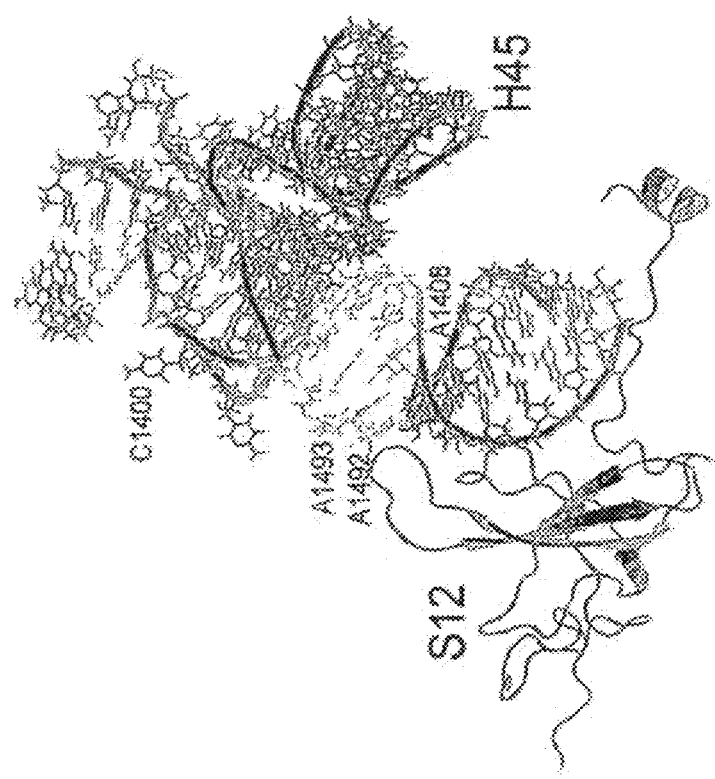
Figure 7:
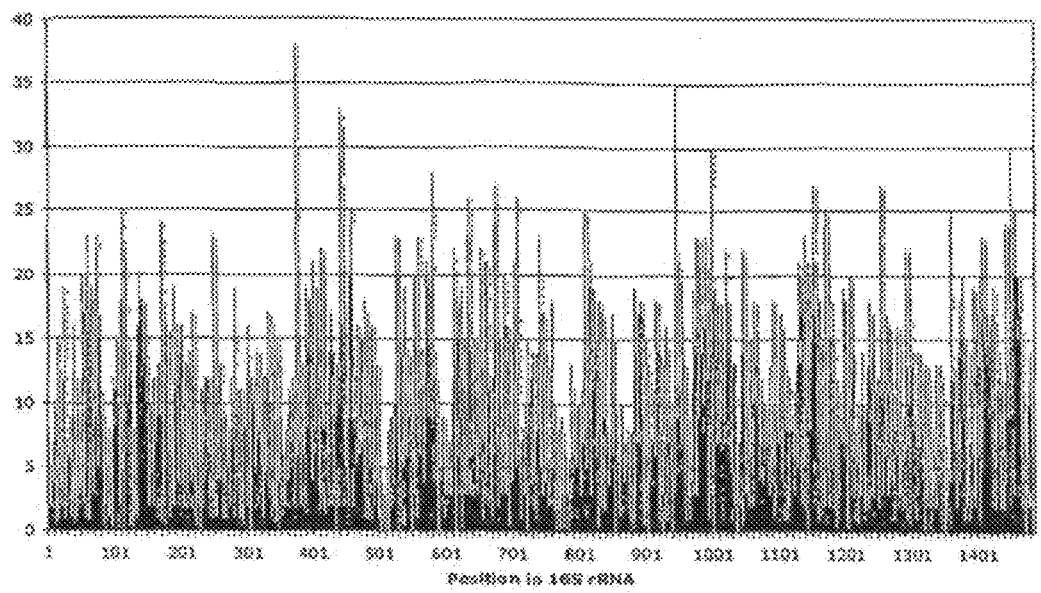
FIG. 7 depicts graphically the results of the "instant evolution" experiment; i.e. the number of mutations at each position in the 16S rRNA.
Figure 7:
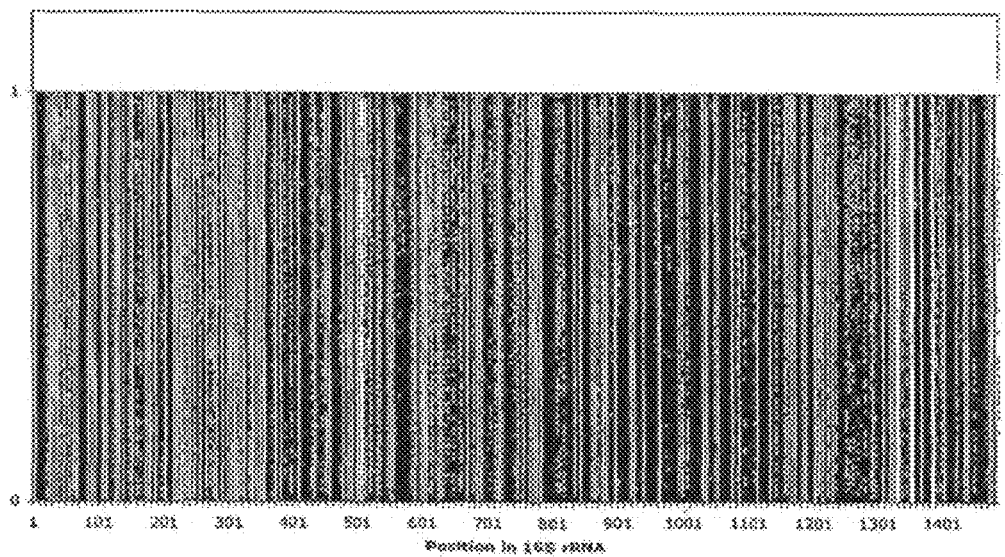

The final cluster of conserved regions is the decoding site. Regions 62 (positions 1387-1389), 63 (positions 1399-1411), and 64 (positions 1488-1501) are located at the top of H44 (FIG. 6g). Region 62 is base paired with positions 928-930 to form part of helix 28. Next to this region is a bulge at position 925 that is flipped out of the helix and stacked on position 1505. This stacking may help stabilize the large change in direction between positions 1505 and 1506. This change in direction positions H45 next to H44 and allows their interaction. Region 63 and 64 have been previously identified in numerous studies as important in ribosome function as the sites of tRNA binding, initiation factor 1 (IF1) binding, aminogylcoside antibiotic binding, and decoding of the mRNA. Positions 1408, 1492, and 1493, in the A-site, are highly conserved as would be expected due to their role in determination of cognate tRNA binding. [Ogle, J. M., Brodersen, D. E., Clemons, W. M., Jr., Tarry, M. J., Carter, A. P. & Ramakrishnan, V. (2001). Recognition of cognate transfer RNA by the 30S ribosomal subunit. *Science* 292, 897-902.] Positions 1400, 1402, 1403, and 1498 were also identified as being important since they are part of the P-site. The intersubunit bridge, B2a, involves positions 1408-1410 and 1494-1495 in regions 63 and 64 and helix 69 from the 23 S rRNA. Additional conserved positions seem to be responsible for formation of the appropriate structure for function.

Analysis of the mutation library has identified numerous regions that are required for function. The identification of known functionally important regions lends credence to the assumption that other identified regions are also important for function. Comparison of the conserved regions from this library to the phylogenetic maps shows a remarkable similarity. However, the regions described herein, are less extensive then those seen in the phylogenetic analysis. One possible explanation for this difference is the reduced functional requirement in the selection. Since the ribosomes are not required to be fully functional, mutations that reduce function and therefore reduce fitness are also represented. These mutations, though, would not survive in the environment and are, therefore, found to be conserved in the phylogenetic analysis. The conserved regions in the mutational library represent those positions that are absolutely required for any function. Conserved regions in all domains of the 16 S rRNA were identified, implying that the rRNA works as a whole to perform its function. It is interesting that it is the internal loops and junctions that appear to be essential for function, rather than terminal loops.

Nucleic Acids of the Invention

One aspect of the present invention relates to a nucleic acid sequence selected from the group consisting of SEQ ID NO 1-64; another aspect of the present invention relates to two nucleic acid sequences selected from the group consisting of SEQ ID NO 1-64 connected by a nucleic acid tether; another aspect of the present invention relates to three nucleic acid sequences selected from the group consisting of SEQ ID NO 1-64 connected by nucleic acid tethers; another aspect of the present invention relates to four nucleic acid sequences selected from the group consisting of SEQ ID NO 1-64 connected by a nucleic acid tethers; another aspect of the present invention relates to five nucleic acid sequences selected from the group consisting of SEQ ID NO 1-64 connected by a nucleic acid tethers; and another aspect of the present invention relates to between five and eleven nucleic acid sequences selected from the group consisting of SEQ ID NO 1-64 connected by nucleic acid tethers. Another aspect of the present invention relates to use of the nucleic acid sequences of FIG. 9, optionally in the combinations shown in FIG. 10. Another aspect of the present invention relates to the clusters shown of FIGS. 4-6.

Another aspect of the present invention relates to a nucleic acid represented by formula I:

$$\{[L]_m\text{-}[T]\}_n\text{-}L_m \qquad\qquad I\,(5'\rightarrow 3')$$

wherein, independently for each occurrence,

T is selected from the group consisting of nucleic acid sequences SEQ ID NO 1-64, or a sequence with greater than or equal to about 85% homology to any one of SEQ ID NO 1-64;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

n is an integer between 1-11; and m is an integer between 0-40.

In certain embodiments, the present invention relates to the aforementioned nucleic acid, wherein L is unsubstituted.

In certain embodiments, the present invention relates to the aforementioned nucleic acid, wherein n is 1, 2, 3 or 5.

In certain embodiments, the present invention relates to the aforementioned nucleic acid, wherein T is selected from the group consisting of nucleic acid sequences SEQ ID NO 1-64, or a sequence with greater than or equal to about 90% homology to any one of SEQ ID NO 1-64.

In certain embodiments, the present invention relates to the aforementioned nucleic acid, wherein T is selected from the group consisting of nucleic acid sequences SEQ ID NO 1-64, or a sequence with greater than or equal to about 95% homology to any one of SEQ ID NO 1-64.

In certain embodiments, the present invention relates to the aforementioned nucleic acid, wherein T is selected from the group consisting of nucleic acid sequences SEQ ID NO 1-64, or a sequence with greater than or equal to about 99% homology to any one of SEQ ID NO 1-64.

In certain embodiments, the present invention relates to the aforementioned nucleic acid, wherein T is selected from the group consisting of SEQ ID NO 1-64.

Another aspect of the present invention relates to a nucleic acid represented by formula II:

$$Z^1\text{-}[L]_m\text{-}[T]\text{-}[L]_n\text{-}Z^2 \qquad \text{II } (5'\rightarrow 3')$$

wherein, independently for each occurrence,

T is selected from the group consisting of SEQ ID NO 3, 12, 23, 50 and 51;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

$Z^1$ and $Z^2$ are selected from the group consisting of hydrogen, $(C_1\text{-}C_5)$alkyl, biotin, fluorescein, tetrachlorofluorescein, hexachlorofluorescein, Cy3 amidite, Cy5 amidite, digoxigenin and resin beads; and m and n are integers between 0-40.

In certain embodiments, the present invention relates to the aforementioned nucleic acid, wherein T is SEQ ID NO 3.

In certain embodiments, the present invention relates to the aforementioned nucleic acid, wherein T is SEQ ID NO 12.

In certain embodiments, the present invention relates to the aforementioned nucleic acid, wherein T is SEQ ID NO 23.

In certain embodiments, the present invention relates to the aforementioned nucleic acid, wherein T is SEQ ID NO 50.

In certain embodiments, the present invention relates to the aforementioned nucleic acid, wherein T is SEQ ID NO 51.

In certain embodiments, the present invention relates to the aforementioned nucleic acid, wherein $Z^1$ is fluorescein.

In certain embodiments, the present invention relates to the aforementioned nucleic acid, wherein $Z^2$ is biotin.

In certain embodiments, the present invention relates to the aforementioned nucleic acid, wherein L is selected from the group consisting of unsubstituted adenosine, cytidine, guanosine and uridine.

In certain embodiments, the present invention relates to the aforementioned nucleic acid, wherein m and n are integers between 0-25.

In certain embodiments, the present invention relates to the aforementioned nucleic acid, wherein m and n are integers between 5-15.

Another aspect of the present invention relates to a nucleic acid represented by III:

$$Z^1\text{-}[L]_m\text{-}[T^1]\text{-}[L]_n\text{-}[T^2]\text{-}[L]_p\text{-}Z^2 \qquad \text{III } (5'\rightarrow 3')$$

wherein, independently for each occurrence, $T^1$ and $T^2$ are selected from the group consisting of SEQ ID NO 15, 16, 32, 34, 36, 37, 40, 41, 56, 57, 60 and 61;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

$Z^1$ and $Z^2$ are selected from the group consisting of hydrogen, $(C_1\text{-}C_5)$alkyl, biotin, fluorescein, tetrachlorofluorescein, hexachlorofluorescein, Cy3 amidite, Cy5 amidite, digoxigenin and resin beads; and m, n and p are integers between 0-40.

In certain embodiments, the present invention relates to the aforementioned nucleic acid, wherein $T^1$ is SEQ ID NO 15; and $T^2$ is SEQ ID NO 16.

In certain embodiments, the present invention relates to the aforementioned nucleic acid, wherein n is 4.

In certain embodiments, the present invention relates to the aforementioned nucleic acid, wherein $T^1$ is SEQ ID NO 32; and $T^2$ is SEQ ID NO 34.

In certain embodiments, the present invention relates to the aforementioned nucleic acid, wherein n is 31.

In certain embodiments, the present invention relates to the aforementioned nucleic acid, wherein $T^1$ is SEQ ID NO 36; and $T^2$ is SEQ ID NO 37.

In certain embodiments, the present invention relates to the aforementioned nucleic acid, wherein n is 3.

In certain embodiments, the present invention relates to the aforementioned nucleic acid, wherein $T^1$ is SEQ ID NO 40; and $T^2$ is SEQ ID NO 41.

In certain embodiments, the present invention relates to the aforementioned nucleic acid, wherein n is 2.

In certain embodiments, the present invention relates to the aforementioned nucleic acid, wherein $T^1$ is SEQ ID NO 60; and $T^2$ is SEQ ID NO 61.

In certain embodiments, the present invention relates to the aforementioned nucleic acid, wherein n is 15.

In certain embodiments, the present invention relates to the aforementioned nucleic acid, wherein $Z^1$ is fluorescein.

In certain embodiments, the present invention relates to the aforementioned nucleic acid, wherein $Z^2$ is biotin.

In certain embodiments, the present invention relates to the aforementioned nucleic acid, wherein L is selected from the group consisting of unsubstituted adenosine, cytidine, guanosine and uridine.

In certain embodiments, the present invention relates to the aforementioned nucleic acid, wherein m and p are integers between 0-25.

In certain embodiments, the present invention relates to the aforementioned nucleic acid, wherein m and p are integers between 5-15.

Another aspect of the present invention relates to a nucleic acid represented by VI:

$$Z^1\text{-}[L]_m\text{-}[T^1]\text{-}[L]_n\text{-}[T^2]\text{-}[L]_p\text{-}[T^3]\text{-}[L]_q\text{-}Z^2 \qquad \text{VI } (5'\rightarrow 3')$$

wherein, independently for each occurrence, $T^1$, $T^2$ and $T^3$ are selected from the group consisting of SEQ ID NO 7, 13, 14, 25, 26, 27, 28, 29, 30, 31, 33, 35, 38, 39, 42, 62, 63, and 64;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

$Z^1$ and $Z^2$ are selected from the group consisting of hydrogen, $(C_1\text{-}C_5)$alkyl, biotin, fluorescein, tetrachlorofluorescein, hexachlorofluorescein, Cy3 amidite, Cy5 amidite, digoxigenin and resin beads; and m, n, p and q are integers between 0-40.

In certain embodiments, the present invention relates to the aforementioned nucleic acid, wherein $T^1$ is SEQ ID NO 25; $T^2$ is SEQ ID NO 26; and $T^3$ is SEQ ID NO 27.

In certain embodiments, the present invention relates to the aforementioned nucleic acid, wherein n is 14.

In certain embodiments, the present invention relates to the aforementioned nucleic acid, wherein p is 7.

In certain embodiments, the present invention relates to the aforementioned nucleic acid, wherein $T^1$ is SEQ ID NO 7; $T^2$ is SEQ ID NO 13; and $T^3$ is SEQ ID NO 14.

In certain embodiments, the present invention relates to the aforementioned nucleic acid, wherein n is 6.

In certain embodiments, the present invention relates to the aforementioned nucleic acid, wherein p is 3.

In certain embodiments, the present invention relates to the aforementioned nucleic acid, wherein $T^1$ is SEQ ID NO 29; $T^2$ is SEQ ID NO 30; and $T^3$ is SEQ ID NO 31.

In certain embodiments, the present invention relates to the aforementioned nucleic acid, wherein n is 7.

In certain embodiments, the present invention relates to the aforementioned nucleic acid, wherein p is 4.

In certain embodiments, the present invention relates to the aforementioned nucleic acid, wherein $T^1$ is SEQ ID NO 28; $T^2$ is SEQ ID NO 39; and $T^3$ is SEQ ID NO 42.

In certain embodiments, the present invention relates to the aforementioned nucleic acid, wherein n is 7.

In certain embodiments, the present invention relates to the aforementioned nucleic acid, wherein p is 28.

In certain embodiments, the present invention relates to the aforementioned nucleic acid, wherein $T^1$ is SEQ ID NO 33; $T^2$ is SEQ ID NO 35; and $T^3$ is SEQ ID NO 38.

In certain embodiments, the present invention relates to the aforementioned nucleic acid, wherein p is 24.

In certain embodiments, the present invention relates to the aforementioned nucleic acid, wherein $T^1$ is SEQ ID NO 62; $T^2$ is SEQ ID NO 63; and $T^3$ is SEQ ID NO 64.

In certain embodiments, the present invention relates to the aforementioned nucleic acid, wherein n is 10.

In certain embodiments, the present invention relates to the aforementioned nucleic acid, wherein $Z^1$ is fluorescein.

In certain embodiments, the present invention relates to the aforementioned nucleic acid, wherein $Z^2$ is biotin.

In certain embodiments, the present invention relates to the aforementioned nucleic acid, wherein L is selected from the group consisting of unsubstituted adenosine, cytidine, guanosine and uridine.

In certain embodiments, the present invention relates to the aforementioned nucleic acid, wherein m and q are integers between 0-25.

In certain embodiments, the present invention relates to the aforementioned nucleic acid, wherein m and q are integers between 5-15.

Another aspect of the present invention relates to a nucleic acid represented by V:

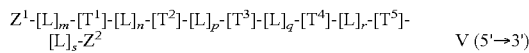

V (5'→3')

wherein, independently for each occurrence, $T^1$, $T^2$, $T^3$, $T^4$ and $T^5$ are selected from the group consisting of SEQ ID NO 4, 8, 9, 10, 11, 43, 44, 45, 46, 47, 48, 49, 52, 53, 54, 55, 56, 57, 58 and 59;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

$Z^1$ and $Z^2$ are selected from the group consisting of hydrogen, ($C_1$-$C_5$)alkyl, biotin, fluorescein, tetrachlorofluorescein, hexachlorofluorescein, Cy3 amidite, Cy5 amidite, digoxigenin and resin beads; and m, n, p, q, r and s are integers between 0-40.

In certain embodiments, the present invention relates to the aforementioned nucleic acid, wherein $T^1$ is SEQ ID NO 4; $T^2$ is SEQ ID NO 8; $T^3$ is SEQ ID NO 9; $T^4$ is SEQ ID NO 10; and $T^5$ is SEQ ID NO 11.

In certain embodiments, the present invention relates to the aforementioned nucleic acid, wherein p is 2.

In certain embodiments, the present invention relates to the aforementioned nucleic acid, wherein q is 17.

In certain embodiments, the present invention relates to the aforementioned nucleic acid, wherein r is 15.

In certain embodiments, the present invention relates to the aforementioned nucleic acid, $T^1$ is SEQ ID NO 43; $T^2$ is SEQ ID NO 44; $T^3$ is SEQ ID NO 55; $T^4$ is SEQ ID NO 56; and $T^5$ is SEQ ID NO 57.

In certain embodiments, the present invention relates to the aforementioned nucleic acid, wherein n is 2.

In certain embodiments, the present invention relates to the aforementioned nucleic acid, wherein r is 3.

In certain embodiments, the present invention relates to the aforementioned nucleic acid, $T^1$ is SEQ ID NO 45; $T^2$ is SEQ ID NO 46; $T^3$ is SEQ ID NO 54; $T^4$ is SEQ ID NO 58; and $T^5$ is SEQ ID NO 59.

In certain embodiments, the present invention relates to the aforementioned nucleic acid, wherein n is 16.

In certain embodiments, the present invention relates to the aforementioned nucleic acid, wherein r is 6.

In certain embodiments, the present invention relates to the aforementioned nucleic acid, $T^1$ is SEQ ID NO 47; $T^2$ is SEQ ID NO 48; $T^3$ is SEQ ID NO 49; $T^4$ is SEQ ID NO 52; and $T^5$ is SEQ ID NO 53.

In certain embodiments, the present invention relates to the aforementioned nucleic acid, wherein n is 7.

In certain embodiments, the present invention relates to the aforementioned nucleic acid, wherein p is 37.

In certain embodiments, the present invention relates to the aforementioned nucleic acid, wherein r is 7.

In certain embodiments, the present invention relates to the aforementioned nucleic acid, wherein $Z^1$ is fluorescein.

In certain embodiments, the present invention relates to the aforementioned nucleic acid, wherein $Z^2$ is biotin.

In certain embodiments, the present invention relates to the aforementioned nucleic acid, wherein L is selected from the group consisting of unsubstituted adenosine, cytidine, guanosine and uridine.

In certain embodiments, the present invention relates to the aforementioned nucleic acid, wherein m and s are integers between 0-25.

In certain embodiments, the present invention relates to the aforementioned nucleic acid, wherein m and s are integers between 5-15.

Target Refinement

The same method ("instant evolution") used to identify the targets set forth above is used to further refine them. One of the advantages of the instant method is that it allows for identification of every target mutation which has the potential to lead to drug resistance, and enables the determination of the critical, structural and non-critical nucleotides before the target is used to isolate new drug leads.

Target Screening

As described herein, libraries of functional target mutations are used to screen compound libraries to discover new drug leads that recognize the wild-type and the viable mutants of the target. First, libraries are screened with the wild-type target. Hits are then counter screened against the corresponding human target to eliminate compounds that would inhibit human ribosomes. Compounds are then screened against pools of viable mutants to select compounds that interact with both wild type and viable mutant sequences, thus selecting for those drugs that should be resistant to target site mutations. Hits identified by this approach should mimic the target's natural ligand (if one exists).

Most small molecule screening approaches are centered on the identification of molecules that bind to proteins. While much can be learned from the study of therapeutics that interact with proteins, the screening described herein requires the use of RNA target-based drug design strategies. One can identify molecules that can bind to critical nucleotides in the RNA targets using RNA-ligand based screening assays, using, for example and without limitation, phage display libraries, synthetic peptide libraries and RNA-binding compounds.

In certain embodiments it may be advantageous to affix the target to a solid support. A large number of immobilization techniques have been used and are well known in the fields of solid phase immunoassays, nucleic acid hybridization assays and immobilized enzymes. [See for example: Hermanson, Greg, T. Bioconjugate Techniques. Academic Press, New York. 1995, 785 pp; Hermanson, G. T., Mallia, A. K. & Smith, P. K. Immobilized Affinity Ligand Techniques. Academic Press, New York, 1992, 454 pp; and Avidin-Biotin Chemistry: A Handbook. D. Savage, G. Mattson, S. Desai, G. Nielander, S. Morgansen & E. Conklin, Pierce Chemical Company, Rockford Ill., 1992, 467 pp.]

Different screening assays have been developed to specifically evaluate RNA-ligand interactions. For example, the "5F assay" developed by Chow et al. [Llano-Sotelo, B., Azucena, E. F., Jr., Kotra, L. P., Mobashery, S. & Chow, C. S. (2002). Aminoglycosides Modified by Resistance Enzymes Display Diminished Binding to the Bacterial Ribosomal Acyl-Transfer Site. *Chemistry & Biology* 9, 455-463.] Therein RNAs are tagged with dye molecules (e.g. fluorescein or a colorimetric tag) and ligand-induced conformational changes in the RNA are monitored. Examples of dye molecules can be found in *Fluorescent and Luminescent Probes for Biological Activity* (Mason, W. T., Ed., Second Edition, Academic Press, 1999) herein incorporated by reference. Importantly, the invention is not limited by the nature of the 5' end label; a wide variety of suitable 5' end labels are known to the art and include, for example, without limitation, biotin, fluorescein, tetrachlorofluorescein, hexachlorofluorescein, Cy3 amidite, Cy5 amidite and digoxigenin The 5F assay is fluorescence based, and has been used to study the conformational changes induced by aminoglycosides at the ribosomal A site. [Fourmy, D., Recht, M. I., Blanchard, S. C. & Puglisi, J. D. (1996). Structure of the A site of *Escherichia coli* 16S Ribosomal RNA Complexed with an Aminoglycoside Antibiotic. *Science* 274, 1367-1371; and Yoshizawa, S., Fourmy, D. & Puglisi, J. D. (1998). Structural Origins of Gentamicin Antibiotic Action. *EMBO J.* 17, 6437-6448.] This assay was used to discover new antibiotics that bind to the A site, as well as to monitor the binding of enzyme-modified aminoglycosides. [Llano-Sotelo, B., Azucena, E. F., Jr., Kotra, L. P., Mobashery, S. & Chow, C. S. (2002). Aminoglycosides Modified by Resistance Enzymes Display Diminished Binding to the Bacterial Ribosomal Acyl-Transfer Site. *Chemistry & Biology* 9, 455-463; and Haddad, J., Kotra, L. P., Llano-Sotelo, Kim, C. A., E. F., Jr., Liu, M. V., S. B., Lee, H. C., C. S. & Mobashery, S. (2002). Design of Novel Antibiotics that Bind to the Ribosomal Acyl transfer Site. *J. Am. Chem. Soc.* 124, 3229-3237.] One of the aminoglycoside analogues exhibited a 45-fold enhancement in binding to 16S rRNA over human 18S rRNA (A1408 vs. G1408), demonstrating that a high specificity of ligand bindings can be achieved, even for RNAs with almost identical sequences. In this assay, the 5' end of the target RNA fragment is tagged with fluorescein or another dye. Alternatively, RNAs can be synthesized chemically with 5'-biotin tags. [Cannone, J. J., Subramanian, S., Schnare, M. N., Collett, J. R., D'Souza, L. M., Du, Y., Feng, B., Lin, N., Madabusi, L. V., Muller, K. M., Pande, N., Shang, Z., Yu, N. & Gutell, R. R. (2002). The Comparative RNA Web (CRW) Site: an online database of comparative sequence and structure information for ribosomal, intron, and other RNAs: Correction. *BMC Bioinformatics* 3, 15.] An advantage of this assay is that only small volumes and concentrations of RNA and ligand are needed (μL, nM-μM), and it can be adapted to a 96- or 384-well plate format.

Another assay which may be used to screen the targets of the instant invention is the "3F-FRET" assay. [Batey, R. T. & Williamson, J. R. (1996). Interaction of the *Bacillus stearothermophilus* ribosomal protein S15 with 16 S rRNA: II. Specificity determinants of RNA-protein recognition. *J Mol Biol* 261, 550-67.] This assay is a three-fluorophore fluorescence resonance energy transfer assay that can detect both the conformational change of RNA fragments in the presence of a ligand and the disruption of a ribosomal protein/rRNA complex by a ligand.

The 3F-FRET assay has been used to screen for small molecule inhibitors of ribosome assembly. During the assembly of the 30S ribosomal subunit, the small subunit proteins bind to the 16S rRNA in a hierarchical manner. S15 is a primary binding ribosomal protein that interacts with a three-way junction in the central domain of 16S rRNA and induces a conformational change. In the assay, the RNA fragment containing the S15 binding site is labeled with two fluorophores and a third fluorophore is attached to the S15 protein. Compounds that bind to the junction and affect conformation can be identified. The assay is highly sensitive and can be performed in 384-well microtiter plates for high throughput screening.

The application of both assays are discussed further in the Exemplification found below.

Compound Libraries

Most compound collections and combinatorial chemistries have been designed around the identification of molecules that bind to proteins. The RNA molecules of the ribosome bind to many proteins, and the process depends on the defined three-dimensional structures of the RNA molecules. The rRNA targets of the present invention may be involved in rRNA/protein interactions. Potential drug leads may alter the functional three-dimensional structure of the nucleic acid so that the interaction with the protein is inhibited, or they may prevent the formation of competent RNA-protein complexes. Hence, while the same compounds used in protein-targeted therapeutics may be screened, compounds that are specifically designed to interact with RNA may also be screened. Since the natural ligands for the rRNA targets are likely to be the RNA binding domains of proteins, the strategy is to use compound libraries containing RNA-binding molecules, together with phage and peptide libraries, to find weak binding hits. These hits are then analyzed together with the targets in structural studies, followed by lead development.

Phage and peptide libraries may be used for screening. Phage-display methodologies offer a convenient way to produce peptide ligands with high affinity for targets, such as rRNA regions, and their functional mutants. This compound class has been chosen because: i) a number of peptides exhibit antibiotic activity; ii) peptides have a proven ability to bind RNA molecules; iii) the level of molecular diversity using only the standard 20 amino acids is enormous; inclusion of 'unnatural' amino acids dramatically increases the diversity still further; iv) the generation of peptides (either through phage display or chemical synthesis) is routine and highly reliable; v) peptide leads can be used as the basis for generating non-peptide ligands and peptidomimetics, and vi) peptides and their derivatives have a history of use as therapeutic agents. [Barrick, J. E. & Roberts, R. W. (2002). Sequence Analysis of an Artificial Family of RNA-Binding Peptides. *Protein Sci.* 11, 2688-2696; Adang, A. E. P., Hermkens, P. H. H., Linders, J. T. M., Ottenheijm, H. C. J. & van Staveren, C. J. (1994). Case Histories of Peptidomimetics: Progression from Peptides to Drugs. *Recl. Trav. Chim. Pays-Bas* 113, 63-78; and Kieber-Emmons, T., Murali, R. & Greene, M. I. (1997). Therapeutic Peptides and Peptidomimetics. *Curr Opin. Biotech.* 8, 435-441.] Importantly, these experiments can be carried out without any prior knowledge of the target's high-resolution structure or information about which region(s) of the target and viable (functional) mutants are structurally similar. Finally, there is precedent that peptides and other organic ligands can be designed to bind RNA regions containing bulged residues and widened and accessible major grooves, structures that may be present in the proposed targets. [Hwang, S., Tamilarasu, N., Ryan, K., Huq, I., Richter, S., Still, W. C. & Rana, T. M. (1999) Inhibition of Gene Expression in Human Cells Through Small-Molecule-RNA Interactions. *Proc. Natl. Acad. Sci. USA* 96, 12997-13002; Mucha, P., Szyk, A., Rekowski, P., Weiss, P. A. & Agris, P. F. (2001). Anticodon Domain Methylated Nucleosides of Yeast tRNA$^{Phe}$ are Significant Recognition Determinants in the Building of a Phage Display Selected Peptide. *Biochemistry* 40, 14191-14199; Mucha, P., Szyk, A., Rekowski, P., Guenther, R. & Agris, P. F. (2002). Interaction of RNA with Phage-Display Selected Peptides Analyzed by Capillary Electrophoresis Mobility Shift Assay. *RNA* 8, 698-704; Wang, Y., Hamasaki, K. & Rando, R. R. (1997). Specificity of Aminoglycoside Binding to RNA Constructs Derived from the 16S rRNA Decoding Region and the HIV-RRE Activator Region. *Biochemistry* 36, 768-779; and Lind, K. E., Du, Z., Fujinaga, K., Peterlin, B. M. & James, T. L. (2002). Structure-Based Computational Database Screening, In vitro Assay, and NMR Assessment of Compounds that Target TAR RNA. *Chem. Biol.* 9, 185-193.]

Once a collection of "hits" is generated, a focused library of compounds is assembled using the structures of the peptides and compounds to guide the selection of new compounds for high throughput screening. These efforts may be assisted by NMR studies of the RNA-ligand complexes, allowing rational decisions to be made, and fine-tuning of the binding interactions through site-specific chemical alterations to each ligand. Commercially available compounds and proprietary collections may be employed in the methods of the present invention.

Structural Studies of Targets and Compounds

Interactions of the hits (peptides and compounds) and drug leads with their *E. coli* rRNA targets are characterized using NMR spectroscopy to determine key functional groups important in the interaction. This data is helpful in modifying the drug leads using rational drug design and medicinal chemistry to improve bioavailability, pharmacodynamics, and to reduce toxicity.

NMR studies provide several types of critical information. First, NMR is used to verify whether the structure of isolated RNA targets taken out of the context of the ribosome resemble their structure in the ribosome and will therefore be valid targets for screening compound libraries. NMR spectroscopy also provides detailed stereochemical information on the mechanism of binding of small-molecule ligands with RNA targets. Lastly, NMR studies reveal crucial differences between the *E. coli* and the human small subunit rRNAs. Comparison of the wild-type and mutant structures will reveal the essential functional groups and structural folds required for ribosome function, thereby focusing the design of drugs to these critical residues. Structural characterization of RNA-ligand complexes will reveal how each compound recognizes the essential target motifs. Further, characterization of RNA dynamics by NMR in the presence and absence of bound drug leads will reveal the role of induced fit in RNA recognition. [Chow, C. S. & Bogdan, F. M. (1997). A Structural Basis for RNA-Ligand Interactions. *Chem. Rev.* 97, 1489-1513.]

Target Validation

Potential drug compounds are tested in eukaryotic and bacterial in vitro protein synthesis assays. Compounds that inhibit wild-type and mutant bacterial ribosomes but not eukaryotic ribosomes are further developed, and allow in vitro validation of the selected targets.

In another embodiment, the functionally important regions identified above are divided into groups based upon whether or not they occur in closely related groups of organisms. For instance, some regions of rRNA are found in all bacteria but not in other organisms. Other areas of rRNA are found only in closely related groups of bacteria, such as all of the members of a particular species, e.g., members of the genus *Mycobacterium* or *Streptococcus*.

In a further embodiment, the regions found in very large groups of organisms, e.g., all bacteria or all fungi, are used to develop broad-spectrum antibiotics that may be used to treat infections from a large number of organisms within that group. The methods of the present invention may be performed on these regions and functional mutant ribosomes identified. These functional mutant ribosomes may be screened, for example, with compound libraries.

In yet another embodiment, regions that are located only in relatively small groups of organisms, such as all members of the genus *Streptococcus* or all members of the genus *Mycobacterium*, may be used to design narrow spectrum antibiotics that will only inhibit the growth of organisms that fall within these smaller groups. The methods of the present invention may be performed on these regions and functional mutant ribosomes identified. These functional mutant ribosomes will be screened with, e.g., compound libraries.

METHODS OF THE INVENTION

One aspect of the present invention relates to a method of identifying an agent which binds to any of the aforementioned nucleic acids, comprising the steps of:

measuring the fluorescence of said nucleic acid, thereby establishing a first fluorescence reading;

contacting a test compound with said nucleic acid, and measuring the resulting fluorescence, thereby establishing a second fluorescence reading;

determining the difference between said first fluorescence reading and said second fluorescence reading; and selecting the compound wherein the difference between said first fluorescence reading and said second fluorescence reading is non-zero, thereby identifying said agent.

In certain embodiments, the present invention relates to the aforementioned method, further comprising the steps of:

modifying the agent identified, thereby forming a modified agent; and contacting said modified agent with said nucleic acid, and measuring the resulting fluorescence, thereby establishing a modified second fluorescence reading;

determining the difference between said first fluorescence reading and said modified second fluorescence reading; and selecting the compound wherein the difference between said first fluorescence reading and said second modified fluorescence reading is non-zero, thereby identifying a modified agent.

Another aspect of the present invention relates to a method of identifying an inhibitor of protein synthesis comprising measuring the fluorescence of the any of the aforementioned nucleic acids, thereby establishing a first fluorescence reading;

contacting a test compound with said nucleic acid, and measuring the resulting fluorescence, thereby establishing a second fluorescence reading;

determining the difference between said first fluorescence reading and said second fluorescence reading;

selecting the compound wherein the difference between said first fluorescence reading and said second fluorescence reading is non-zero, thereby identifying said agent;

assaying the inhibitory properties of the agent by administering it to a cell, a cell extract or purified ribosomes; and detecting protein synthesis; wherein a decrease in protein synthesis indicates that the agent is an inhibitor of protein synthesis.

In certain embodiments, the present invention relates to the aforementioned method, wherein assaying the inhibitory properties of the agent comprises detecting protein synthesis.

In certain embodiments, the present invention relates to the aforementioned method, wherein assaying the inhibitory properties of the agent comprises determining the inhibitor constant for inhibiting mRNA translation.

Another aspect of the present invention relates to a compound obtained any one of the aforementioned methods. Yet another aspect of the present invention relates to a method of administering to a patient in need thereof a compound obtained by any one of the aforementioned methods, wherein said patient is suffering conditions associate with a microbial infection, such as an infection caused by, for example, E. coli, P. aeruginosa, or the like. In certain embodiments said microbial infections is a bacterial infection.

EXEMPLIFICATION

The invention now being generally described, it will be more readily understood by reference to the following examples, which are included merely for purposes of illustration of certain aspects and embodiments of the present invention, and are not intended to limit the invention.

Example #1

Target Selection

Subdomains are selected as potential targets from the 64 RNA "regions of interest" identified herein, using specific selection criteria. Of the targets identified herein, 8 are known antibiotic targets. From the remaining pool of 56 potential drug targets, several of these regions are chosen for further development based on the following criteria: (1) size and complexity, (2) absence of modified nucleotides, (3) known interactions with proteins or other parts of the rRNA, (4) accessibility to solvent, (5) differences from corresponding human sequences, (6) whether the isolated RNA target folds correctly and is amenable to NMR analysis, and (7) whether there is there a known ligand.

After eliminating some of the targets based on sequence composition and similarity to human rRNA, the remaining target RNAs are evaluated for their ability to fold correctly and have the same natural conformation as they do in the complete ribosome. Small samples of each region of interest are synthesized and 1D NMR experiments are performed to determine which regions fold correctly (as compared with the region in the context of the full ribosome), and which give the best NMR spectra and are therefore amenable to NMR structure determination. Targets are also evaluated for changes on exposure to solvents, which tell us if the targets are accessible.

E. coli targets are synthesized using standard phosphoramidite chemistries and can be obtained commercially from Dharmacon. A relatively simple series of experiments confirm the homology structures of the RNAs. For each region of interest, chemical probing experiments are performed on the isolated domains as well as complete 30S ribosome to determine if they have similar reactivity patterns and thus similar structures. Regions that show similar patterns are studied by 1D imino proton NMR and 2D NOESY. The availability of the assignments for the wild-type E. coli domains allow us to match the pattern of NOEs and chemical shifts to determine qualitatively if the structures of the wild-type and isolated regions are similar.

Example #2

Target Refinement

"Instant evolution" is used to identify every mutation that could lead to drug resistance in the RNA subdomains, and NMR spectroscopy and homology modeling are used to determine the essential structural components of the two targets.

Saturation mutagenesis of drug targets and chloramphenicol selection experiments are performed using instant evolution to identify viable mutants. The viable mutants are sequenced, assayed, and analyzed to identify the essential components of each target. GFP production in each mutant is determined by measuring GFP fluorescence in whole cells. The essential sequence and structural motifs identified in the saturation mutagenesis experiments are validated by constructing site-directed mutations that either disrupt or maintain the proposed motif in the target RNA and measuring the effects of the mutations on protein synthesis in vivo.

RNA homology modeling software (e.g. that developed jointly by Dr. John SantaLucia and DNA Software, Inc.) is used to predict the structures of the wild-type targets, viable mutants, and the corresponding human sequences. The software requires the input of a known 3D structure. Next, the software requires a sequence alignment to determine where in the 3D structure substitutions, deletions or insertions will be made. The sequence alignment for each domain may be done with a new alignment program called SBSA (structure based sequence alignment), which automatically performs the sequence alignment subject to the constraint that the paired residues from both secondary structures are in the proper register. The phylogenetically determined secondary structures of the 16S rRNA from E. coli and the human 18S rRNA are available.

Random Mutagenesis and Selection of Viable Mutants.

Saturation mutagenesis is carried out by PCR mutagenesis essentially as described by Higuchi. [Higuchi, R. (1989). Using PCR to engineer DNA. In PCR Technology (Erlich, H.

A., ed.), pp. 61-70, Stockton Press, New York. (Erlich, H. A., ed., Ed.).] Partially randomized mutations are introduced using recombinant PCR, cloned in pRNA123 and used to transform *E. coli* DH5 cells by electroporation. The number of viable mutants of a given target depends on the stringency of the selection and on the functional constraints of the target. To isolate viable mutants, transformants are plated on LB agar containing 100 μg/ml ampicillin, 1 mM IPTG and 50 μg/ml chloramphenicol. This is significantly below the minimum inhibitory concentration (MIC) of chloramphenicol for cells expressing wild-type ribosomes in the system (700 μg/ml) to avoid eliminating mutations with reduced activity that may lead to resistance through the sequential accumulation of second-site complementation mutations. [Bjorkman, J., Nagaev, I., Berg, O. G., Hughes, D. & Andersson, D. I. (2000). Effects of environment on compensatory mutations to ameliorate costs of antibiotic resistance. *Science* 287, 1479-82; and Andersson, D. I., Bjorkman, J. & Hughes, D. (1998). {Antibiotic resistance here to stay? Compensatory mutations restore virulence of resistant bacteria}. *Lakartidningen* 95, 3940, 3943-4.] PCR reactions, restriction enzyme digestions, DNA ligations and electroporations will be performed according to standard procedures. Electroporations will be performed using a BTX high capacity (800 μl) electroporation chamber to provide sufficient transformants for the isolation of viable mutants.

Isolation and characterization is performed for about 300 viable mutants for each target. The final number of mutants analyzed depends upon the initial evaluation of the data from these mutants. Based on the preliminary experiments, 300 mutants is likely in excess of the total number of viable mutants at each site and should be sufficient to allow identification of the components of the targets that are essential for function. Resampling statistics were used to determine the probable total number of viable mutants based on the data from the initial 300 isolates. [Lee, K., Varma, S., SantaLucia, J., Jr. & Cunningham, P. R. (1997). In vivo determination of RNA structure-function relationships: analysis of the 790 loop in ribosomal RNA. *J. Mol. Biol.* 269, 732-43; and Zhang, K. & Zhao, H. (2000). Assessing reliability of gene clusters from gene expression data. *Funct Integr Genomics* 1, 156-73.] If the predicted number of viable mutants is greater than the 300 initial isolates, additional mutants are isolated and characterized to ensure that most of the possible target-site mutants have been isolated. Mutant constructs are sequenced through both external ligation junctions to check for the presence of unprogrammed mutations inserted during the amplification reaction.

GFP Assays.

Overnight cultures are diluted in LB-Amp100 medium and grown at 37° C. with shaking until $OD_{600}$=0.1. The cultures are induced with IPTG (1 mM) and incubated with shaking for an additional three hours. Following incubation, 1 ml of each culture is removed, pelleted, washed twice, and resuspended in buffer. Cell density ($OD_{600}$) is determined and fluorescence (excitation=395 nm, emission=509 nm) measured using a SPECTRAmax GEMINI microplate fluorometer. For each culture, fluorescence is divided by $OD_{600}$ and presented as a percentage of the wild-type *E. coli* construct. Assays for each construct are performed at least three times and the results are averaged.

Homology Modeling.

RNA homology modeling software described earlier is used to predict the structures of the wild-type targets, viable mutants, and human domains. The sequence alignment for each target is done by comparing the known phylogenetically determined structures of the 16S rRNA from *E. coli*, and human 18S. Structures will also be predicted for a number of the functional mutants. The wild-type and mutant structures are superimposed to reveal the functional groups that are conserved in all functional mutants.

Determination of High-Resolution Structures.

The initial focus is on the wild-type targets and human rRNA. This is followed by analysis of the highly functional mutant sequences; two of these mutant structures are solved for each target. NMR is well adapted to solving mutant structures once assignments for a wild-type sequence are known.

NMR Sample Preparation.

NMR samples are synthesized using standard phosphoramidite chemistries or generated using run-off transcription. Highly structured RNAs are often more efficiently transcribed from a linearized plasmid than a single-stranded synthetic template. Synthetic templates are ordered from a commercial source and if yields are not sufficient (particularly if labeled samples are required), then the plasmid are prepared. DNA duplexes corresponding to each of the rRNA sequences to be studied are cloned in the plasmid pWK122. This plasmid contains a T7 Class III promoter and restriction sites that facilitate run-off transcription. [Krzyzosiak, W., Denman, R., Nurse, K., Hellmann, W., Boublik, M., Gehrke, C. W., Agris, P. F. & Ofengand, J. (1987). In vitro synthesis of 16S ribosomal RNA containing single base changes and assembly into a functional 30S ribosome. *Biochemistry* 26, 2353-64. Transcription reactions will be carried out as described previously. Cunningham, P. R., Negre, D., Weitzmann, C., Denman, R., Nurse, K. & Ofengand, J. (1988). The role of 16S RNA in ribosome function: single base alterations and their effect on in vitro protein synthesis. *Arch Biol Med Exp* (Santiago) 21, 393-401]. Transcripts are purified on denaturing polyacrylamide gels and recovered by electroelution. To obtain efficient transcription it is often necessary to mutate the first several nucleotides that form part of the T7 promoter to guanines and cytosines. If this is necessary for the sequence, their biological activities are confirmed by making the same mutants in the whole ribosome encoded on pRNA123, as was done for the studies of the 790 loop. [Lee, K., Varma, S., SantaLucia, J., Jr. & Cunningham, P. R. (1997). In vivo determination of RNA structure-function relationships: analysis of the 790 loop in ribosomal RNA. *J. Mol. Biol.* 269, 732-43.]

Preparation of Labeled NMR Samples.

Uniform $^{13}C$ and $^{15}N$ labeling of RNA are carried out using published methods. [Nikonowicz, E. P., Sin, A., Legault, P., Jucker, F. M., Baer, L. M. & Pardi, A. (1992). Preparation of $^{13}C$ and $^{15}N$ labelled RNAs for heteronuclear multi-dimensional NMR studies. *Nucleic Acids Res.* 20, 4507-4513; Batey, R. T., Inada, M., Kujawinski, E., Puglisi, J. D. & Williamson, J. R. (1992). Preparation of isotopically labeled ribonucleotides for multidimensional NMR spectroscopy of RNA. *Nucleic Acids Res.* 20, 4515-4523.] Uniform labeling facilitates resonance assignments by resolving resonances in multiple dimensions and by relying on through-bond transfers of magnetization. Such labeling also provides significant additional information through heteronuclear J-couplings measured by E. COSY type methods and residual dipolar couplings.

Example #3

Target Screening

Compounds, phage and peptide libraries are screened against the wild type targets and viable mutations of the targets. Compounds with RNA-binding capability and phage libraries are constructed and screened using selection and high-throughput fluorescence assays to isolate lead compounds with high affinity for the wild-type rRNA targets and the viable mutants of these rRNA targets, but low affinity for human ribosomes. The nature of the interaction of the hits with their targets is determined by NMR analysis of lead-target complexes and other biophysical studies. After a collection of initial hits is generated and the sequence information obtained, compound libraries containing RNA-binding molecules are synthesized and accessed from commercial and non-commercial sources. By using a limited set of input building blocks with structural and functional characteristics that resemble the monomers of the initial leads, the binding interactions with the RNA targets are further enhanced and optimized. RNA will be synthesized as described earlier.

The 5F Fluorescence-Based Assay.

Fluorescein-tagged RNAs are synthesized by chemical methods and deprotected by standard procedures as described herein. Fluorescein is added to the 5' end of the RNAs during the last step of the chemical synthesis. Other dyes can be utilized and attached using the corresponding commercial phosphoramidites. Human rRNA sequences and non-specific competitor RNAs is synthesized without any tags. After incubation with the 5F-tagged RNA, compound library beads that fluoresce are selected and assayed as described in the literature. [Hwang, S., Tamilarasu, N., Ryan, K., Huq, I., Richter, S., Still, W. C. & Rana, T. M. (1999) Inhibition of Gene Expression in Human Cells Through Small-Molecule-RNA Interactions. *Proc. Natl. Acad. Sci. USA* 96, 12997-13002; Rothman, J. H. & Still, W. C. (1997). Peptide-Binding Antibiotics: A Solid-Phase Assay for Screening Libraries of Vancomycin Mimics for Selective d-Ala-d-Ala Binding. *Bioorg. Med. Chem. Lett.* 7, 3159-3164; and Lam, K. S., Wade, S., Abdul-Latif, F. & Lebl, M. (1995). Application of a Dual Color Detection Scheme in the Screening of a Random Combinatorial Peptide Library. *J. Immunol. Methods* 180, 219-223.] Specificity is achieved by blocking non-specific-binding compounds with unlabeled RNAs lacking the structural motif of interest. [Hwang, S., Tamilarasu, N., Ryan, K., Huq, I., Richter, S., Still, W. C. & Rana, T. M. (1999). Inhibition of Gene Expression in Human Cells Through Small-Molecule-RNA Interactions. *Proc. Natl. Acad. Sci. USA* 96, 12997-13002.] The library of beads are incubated with F-labeled target wild-type RNAs. A washing step is carried out with either specific or non-specific RNAs ($10^{-25}$ μM). The non-specific RNAs are the duplex regions of the target RNAs in order to select for binding to the internal loops. The level of sensitivity is expected to be about 50 pmoles, therefore binding is detected for compounds with high nM to μM dissociation constants. Higher stringency in the washing steps can be applied in later rounds to select for peptides with higher affinity for the target RNAs. The beads are imaged using a fluorescence microscope equipped with a CCD camera and image processing software; beads that fluoresce are selected and removed from the mixture. Once compound-immobilized beads are identified that bind to the wild-type RNA sequence, competition studies with mutant RNAs are carried out to discover peptides with binding affinity to all of the relevant RNAs. For the human RNA sequences, competition assays are carried out and beads that fluoresce are retained (i.e. select for beads that bind to bacterial RNAs, but not human RNAs). If there is not success with fluorescein-tagged RNAs, there are other applications in the literature with various combinations of dyes that have been successfully applied to bead selection that may be employed. [Hwang, S., Tamilarasu, N., Ryan, K., Huq, I., Richter, S., Still, W. C. & Rana, T. M. (1999) Inhibition of Gene Expression in Human Cells Through Small-Molecule-RNA Interactions. *Proc. Natl. Acad. Sci. USA* 96, 12997-13002; Rothman, J. H. & Still, W. C. (1997). Peptide-Binding Antibiotics: A Solid-Phase Assay for Screening Libraries of Vancomycin Mimics for Selective d-Ala-d-Ala Binding. *Bioorg. Med. Chem. Lett.* 7, 3159-3164; and Lam, K. S., Wade, S., Abdul-Latif, F. & Lebl, M. (1995). Application of a Dual Color Detection Scheme in the Screening of a Random Combinatorial Peptide Library. *J. Immunol. Methods* 180, 219-223.]

The 3F-FRET Assay.

This assay uses the binding of the ribosomal protein S15 to the three way junction (3WJ) formed by helices 20, 21 and 22 in 16S rRNA. [Batey, R. T. & Williamson, J. R. (1996). Interaction of the *Bacillus stearothermophilus* ribosomal protein S15 with 16 S rRNA: II. Specificity determinants of RNA-protein recognition. *J Mol Biol* 261, 550-67; and Serganov, A. A., Masquida, B., Westhof, E., Cachia, C., Portier, C., Garber, M., Ehresmann, B. & Ehresmann, C. (1996). The 16S rRNA binding site of *Thermus thermophilus* ribosomal protein S15: comparison with *Escherichia coli* S15, minimum site and structure. *RNA*, 2, 1124-1138.] This is a key step in the formation of functional bacterial 70S ribosomes in the early stages of 30S subunit assembly. Binding of S15 induces a conformational change in the 16S rRNA at this junction and serves as a prerequisite for subsequent binding events during ribosome assembly. [Orr, J. W., Hagerman, P. J. & Williamson, J. R. (1998). Protein and Mg(2+)-induced conformational changes in the S15 binding site of 16 S ribosomal RNA. *J. Mol. Biol.* 275, 453-464.] Similar conformational changes occur when other ribosomal proteins bind to RNA.

Fluorescence-Based Assays for High Throughput Screening.

The fluorescence assays described above are adapted for use in high-throughput assays with peptide and compound libraries. Once beads that bind to the *E. coli* targets are identified, compounds can be prepared and attached to 96- or 384-well plates and screened with the viable mutants of the target RNAs. Competition assays will be used so that only one F-tagged RNA target needs to be prepared. In this manner, the binding to the viable mutants can be assessed in a high-throughput manner by loss of fluorescence. A fluorescence plate reader is employed, such that many RNAs or compounds can be assessed in a short period of time. Interactions of prospective new compounds are analyzed, and further high-throughput binding assays with selected compound and mutant target sequences is carried out, followed by lead optimization. A dual color assay is employed to make direct comparisons between two specific RNA sequences, such as the wild type *E. coli* and a mutant sequence.

All of the viable target mutants isolated in vivo have chemical and structural properties that are essential for proper interaction of the targets with their ligand(s). Even without knowing what these properties are, the viable mutants are used to identify drug leads that bind specifically to them. One major advantage of this assay is that multiple fluorophores are available such that an RNA target and its functional mutants can be analyzed simultaneously for small-molecule binding. Another key advantage of this screening method is that target-lead interactions can be identified without any prior knowledge of their 3D structures. Screening is continued with new targets and lead compounds through an iterative process until tight-binding molecules (nM or better) are identified.

Phage Display Libraries.

Two commercial phage-display systems are screened, M13 and T7. One is constructed in filamentous phage, M13 (Ph.D.-7, New England Biolabs), which generally contain fewer contaminating bacterial proteins than lytic phage preparations. This is important when screening for RNA-binding peptides due to RNase degradation. [Danner, S. & Belasco, J. G. (2001). T7 phage display: a novel genetic selection system for cloning RNA-binding proteins from cDNA libraries. *Proc Natl Acad Sci USA* 98, 12954-9. The library is cloned into M13KE (a M13mp19 derivative) as an N-terminus fusion to the M13 coat protein, pIII, displaying 5 copies of the peptide. Cha, J., Bishai, W. & Chandrasegaran, S. (1993). New vectors for direct cloning of PCR products. *Gene* 136, 369-70.] The standard heptapeptide library are used in the initial screens. The complexity of the pool is $2.8 \times 10^9$ transformants. This is greater than the number of sequences obtained if 7 amino acids are randomized ($1.28 \times 10^9$). Other M13 libraries are also tried. The Ph.D.-C7C library (New England Biolabs) contains cyclic peptides and will produce tighter binding peptides. Both the linear and the cyclic M13 libraries are screened initially.

The second type of phage-display library is constructed in the lytic phage, T7, (T7Select 415-1, Novagen). Here, the diversity of peptides on the surface of lytic phage is not restricted by their inability to pass through the bacterial membrane. [Castagnoli, L., Zucconi, A., Quondam, M., Rossi, M., Vaccaro, P., Panni, S., Paoluzi, S., Santonico, E., Dente, L. & Cesareni, G. (2001). Alternative bacteriophage display systems. *Comb Chem High Throughput Screen* 4, 121-33.] The library will produce C-terminal fusions to the T7 capsid protein 10B and is present at 415 copies per phage. The 10B protein is normally produced as a frameshift protein of the 10A gene but in this construct the frameshift signals have been removed so that only one type of capsid protein is produced. A strain with the RNase I gene deleted facilitates its use in screening RNA targets.

Screening RNA Targets with Phage Libraries.

The wild-type *E. coli* target sequences are screened first. Phage that bind will be isolated and amplified. The phage pools derived from screening the wild type targets are counter-screened against the corresponding human rRNAs and competitor RNAs with duplex sequences lacking the internal loops or bulges. Phage lacking affinity for the human or competitor RNAs are retained as potential hits and amplified. The amplified pool will then be used to isolate phage that also bind to the viable mutant RNAs. After each binding reaction, the phage are amplified and used to screen the next target. Phage that bind all of the bacterial sequences are retained for further study. The resulting hits should therefore recognize the components of the targets that are essential for viability in bacteria. The target sequences are either synthesized chemically or cloned into a plasmid that facilitates run-off transcription. Each construct is designed so that the transcript forms a stable clamp sequence in the stem with an RNA tail at the 3' end.

RNA targets are annealed with a 5' biotin-linked DNA or synthesized with a 5' biotin tag (for those containing modified nucleotides). Binding reactions with streptavidin-coated beads contain RNA (10-120 nM), phage ($1-5 \times 10^9$ pfu), *E. coli* tRNA, and RNase inhibitor. The beads are recovered by centrifugation and the bound phage (without release from the beads) is used to infect *E. coli* without release from the beads. Plaque assays are performed to titer the phage. After each round of panning, a portion of the phage pool is sequenced and an aliquot of the lysate will be used for the next round of selection.

Compound Libraries.

Compound libraries (either synthetic or natural product libraries) containing molecules that bind to RNA can be used for screening. Functionally diverse organic scaffolds may also be synthesized. By using a limited set of input building blocks with structural and functional characteristics that resemble the monomers of the initial hits, the binding interactions are further enhanced or optimized. The format for the assays, based on streptavidin-coated microtiter plates, requires the compounds to be N-terminally biotinylated. All of the oligomeric ligands used have a free terminal amine moiety that can be coupled to biotin. [Miller, B. T., Collins, T. J., Rogers, M. E. & Kurosky, A. (1997). Peptide Biotinylation with Amine-Reactive Esters: Differential Side Chain Reactivity. *Peptides* 18, 1585-1595.] After a collection of initial hits is generated and the sequence information obtained, small libraries (ca. 10-100 compounds) are collected and screened. Second-generation molecules are designed and accessed or synthesized, based on the structural studies of target-hit complexes. Further optimization of the ligands is undertaken using established methods. [Ahn, J. M., Boyle, N. A., MacDonald, M. T. & Janda, K. D. (2002). Peptidomimetics and Peptide Backbone Modifications. *Mini Rev. Med. Chem.* 2, 463-473.] This effort is greatly assisted by the availability of the NMR structure of the RNA-ligand complexes, allowing rational decisions to be made regarding the 'fine-tuning' of binding interactions through site-specific chemical modifications and alterations to each ligand.

Example #4

Validation of Targets and Compounds

Structural studies of target/hit complexes allows for optimization of hit compounds, and validation of the targets using in vitro protein synthesis assays. Interactions of the drug leads with their *E. coli* rRNA targets are characterized using NMR spectroscopy. This information enables optimization of hits by determining which functional groups of the compounds are essential for binding and which functional groups may be modified using rational drug design and medicinal chemistry to improve bioavailability, pharmacodynamics, and to reduce toxicity. In addition, the compounds isolated above are characterized for their ability to inhibit protein synthesis in vitro. The compounds identified by screening should inhibit protein synthesis of bacterial ribosomes including those with target mutations. To test this hypothesis, peptides and compounds are added to eukaryotic and bacterial in vitro protein synthesis assays. Bacterial protein synthesis assays will be performed using wild-type ribosomes. Several tests of the functional target mutants that are not used in the screen are performed to evaluate the ability of the compounds to recognize all viable target mutations.

Information from the NMR structural studies complements the assays, and is used to improve the design of compounds for pre-clinical development. These functionally and structurally characterized compounds represent starting points for structure-based design approaches to optimize drug leads. [Bursavich, M. G. & Rich, D. H. (2002). Designing Non-Peptide Peptidomimetics in the 21st Century: Inhibitors Targeting Conformational Ensembles. *J. Med. Chem.* 45, 541-558; and Winkler, F. K., Banner, D. W. & Bohm, H. J. (2001). Structure-Based Approaches in Modern Drug Discovery Research. *Ernst Schering Res. Found. Workshop* 34, 123-142.]

Bacterial In Vitro Protein Synthesis Assays.

To determine whether the compounds have the ability to inhibit protein synthesis, they are tested in a bacterial in vitro protein synthesis assay. A commercially available bacterial in vitro protein synthesis assay kit (e.g., *E. coli* S30 Extract System for Linear Templates, Promega) is used. This kit contains an S30 extract of an *E. coli* B strain (F-, hsdS, gal, OmpT, lon, recBCD) that is capable of coupled transcription and translation. [Lesley, S. A., Brow, M. A. & Burgess, R. R. (1991). Use of in vitro protein synthesis from polymerase chain reaction-generated templates to study interaction of *Escherichia coli* transcription factors with core RNA polymerase and for epitope mapping of monoclonal antibodies. *J Biol Chem* 266, 2632-8.] It also contains S30 premix that provides all components (NTP's, tRNA's, ATP regenerating system, IPTG, and salts) except for amino acids; several amino acid mixtures that lack cysteine, methionine, and leucine are needed in the reaction. The provided control DNA of pBESTLuc (Promega) is used as the transcription template. This plasmid contains the firefly luciferase gene under transcriptional control of Ptac and an ampicillin$^r$ marker. To measure inhibition, a series of reactions containing varying amounts of the peptide are incubated and the $^{35}$S-methionine-labeled product is quantified. [Aoki, H., Ke, L., Poppe, S. M., Poel, T. J., Weaver, E. A., Gadwood, R. C., Thomas, R. C., Shinabarger, D. L. & Ganoza, M. C. (2002). Oxazolidinone antibiotics target the P site on *Escherichia coli* ribosomes. *Antimicrob Agents Chemother* 46, 1080-5.] Inhibition is indicated by the loss of product formation in a dose-dependent manner compared to the addition of buffer only.

Bacterial In Vitro Protein Synthesis Assays with Mutant S30 Extracts.

The Shine-Dalgarno sequence of the luciferase gene in pBESTLuc is modified to the same sequence used by CAT and GFP in the specialized ribosome system using site-directed mutagenesis. The new construct is substituted for pBESTLuc in the in vitro protein synthesis assays but is only able to be translated by the mutant specialized ribosomes. Otherwise, the assay is identical to the bacterial protein synthesis assay described above.

Eukaryotic In Vitro Protein Synthesis Assays.

The compounds identified should not inhibit eukaryotic ribosomes. Compounds that inhibit bacterial protein synthesis are tested in eukaryotic in vitro protein synthesis assays. A commercially available rabbit reticulocyte in vitro protein synthesis assay kit (e.g. Proteinscript II Linked Transcription: Translation Kit, Ambion) is used. The transcription and translation reactions are separate. The kit contains all the reagents needed for both transcription and translation including the T7 enzyme and rabbit reticulocyte lysate. [Pelham, H. R. & Jackson, R. J. (1976). An efficient mRNA-dependent translation system from reticulocyte lysates. *Eur J Biochem* 67, 247-56.]

Example #5

Functional Differences Among the *Escherichia coli* Dh5 16 S ribosomalRNA Genes

The *Escherichia coli* DH5 genome contains seven ribosomal operons. The 16 S rRNA sequences from operons rrnA, rrnB, and rrnE are identical. The 16 S rRNA from each of the four other ribosomal operons (rrnC, rrnD, rrnG, and rrnH) contain unique sequence heterogeneities. Thus, there are five different 16 S rRNA sequences in *E. coli*. To determine if these sequence heterogeneities affect protein synthesis, each of the five different sequences were cloned and expressed in a specialized ribosome system as described herein.

Clones expressing the five different 16 S rRNAs were assayed for ribosome function in vivo at different temperatures, pHs, and ionic strength. The 16 S rRNA from operons rrnC and rrnD are functionally identical to rrnB 16 S rRNA under all conditions tested. Under standard growth conditions (37° C., aerobic growth in LB medium), ribosome containing 16 S rRNA from operon rrnG is approximately 20% more active than ribosomes containing the rrnB 16 S rRNA and the rrnH 16 S rRNA is approximately 20% less active. Ribosomes containing 16 S rRNA of rrnG decreased in function with increasing ionic strength or pH while the 16 S rRNA of rrsH increased in function. These data show that the sequence heterogeneities present in *E. coli* rRNA result in different levels of ribosome function in response to changing environmental conditions suggesting a possible evolutionary advantage.

It is known that bacterial genomes often contain multiple ribosomal operons. The similarity of ribosomal operon organization and low levels of sequence heterogeneities has led to the assumption that these operons are functionally identical. Instances of functionally dedicated ribosomal RNA (rRNA) genes, however, have been identified. The parasite, *Plasmodium berghei*, has been shown to express specific 18 S rRNA during the rodent and mosquito steps of its life cycle (Gunderson et al., 1987).

Analysis of the complete genomic sequence of *E. coli* K-12 identified 5 different 16 S rRNA sequences (Acinas et al., 2004). The 16 S rRNA from operons A (rrsA), B (rrsB), and E (rrsE) contained identical sequences while the 16 S rRNA from operons C (rrsC), D (rrsD), G (rrsG), and H (rrsH) exhibited sequence heterogeneities (FIG. 2.1). To determine if the 16 S rRNA from each operon was functionally identical, the 16 S rRNA genes from DH5 were cloned into pRNA123 and assayed for function under different growth conditions.

The rRNA operons of *E. coli* K-12 contain sequence heterogeneities within the 16 S rRNA genes when compared to rrsB (FIG. 2.1). To determine if these sequence variations effected ribosome function, the 16 S rRNA genes from DH5 were amplified by PCR and cloned into the specialized ribosome vector pRNA123 (Lee et al., 1996; Lee et al., 1997; Morosyuk et al., 2001). pRNA123 is a pBR322 derivative containing the rrnB operon under the control of the lacUV5 promoter. The anti-Shine-Dalgarno sequence of the 16 S rRNA has been altered so that plasmid-derived 30S subunits do not translate host mRNA (Lee et al., 1996; Lee et al., 1997). Two reporter genes, chloramphenicol acetyltransferase (CAT) and green fluorescent protein (GFP), with altered Shine-Dalgarno sequences complementary to the altered anti-Shine-Dalgarno sequence of 16S rRNA are also on the plasmid. Only plasmid-derived 30 S subunits are able to translate the reporter mRNA.

Initially the cloned 16 S rRNAs were sequenced to identify the correct operon. Upon sequencing, discrepancies between the 16 S rRNA genes from *E. coli* K-12 and DH5 were identified. These differences involved 16 S rRNA from rrnC, rrnG, and rrnH (FIG. 2.1). The rrsC of *E. coli* DH5 contains an insertion at G903 while rrsG contains a G589U transversion and a deletion between positions 592 and 593. Finally, the rrsH gene of *E. coli* DH5 contained a U855A transversion not found in the rrsH gene of *E. coli* K-12. The 16 S rRNA was recloned and sequenced, confirming the observed differences.

The function of each operon from DH5 was determined under various temperatures, Mg$^{2+}$ concentration, ionic conditions, and pH. GFP analysis of the different 16 S rRNA's (in LB at 37° C.) showed that rrsC and rrsD were functionally identical to rrsB (FIG. 2.2a). rrsG, however, was approximately 20% more functional than rrsB while rrsH was approximately 20% lower in function (FIG. 2.2a). To determine if temperature affected function, all four of the operons were assayed for function at 30° C. and 42° C. At both 30° C. and 42° C., rrsC and rrsD were functionally identical to rrsB. rrsG resulted in approximately 30% more function than rrsB at both temperatures while rrsH resulted in approximately 30% less function at 30° C. and 20% less function at 42° C.

To determine if increasing the level of $Mg^{2+}$ could relieve the differences in function, each 16 S rRNA was assayed at 50 mM and 100 mM $Mg^{2+}$. No change in function was observed at 50 mM $Mg^2$ (FIG. 2.2b). In the presence of 100 mM $Mg^{2+}$, however, all four operons were similar in function. The function of rrsG decreased to 95% while the function of rrsH increased to 108% of rrsB. This suggests that increasing the intercellular concentration of $Mg^{2+}$ may stabilize the ribosome and restore function comparable to rrsB.

The function of 16 S rRNA from the four operons was determined at different pHs between 5.5 and 9.0 (FIG. 2.2c). rrsC had slightly higher function at pH 5.5 but returned to wild-type function at all other pHs tested. The rrsD was also slightly higher in function at pH 5.5. This function dropped to 82% at pH 6.3, but then returned to wild-type levels at all other pH. The most interesting effects were seen in rrsG and rrsH. rrsG had higher function than the wild type at lower pH, but decreased to wild-type levels as the pH was increased (FIG. 2.2c). The opposite was true for rrsH, which had a consistently lower function than the wild-type, but increased to wild type levels at pH 9.0.

Both rrsC and rrsD maintained wild-type function when assayed for function at different ionic strength (FIG. 2.2d). The function of rrsG increased further at low ionic strength but decrease as the ionic strength was increased. The opposite was true for rrsH. As the ionic strength was increased, the level of function increased from 60% to 110% (FIG. 2.2d). Further increasing the ionic strength, however, reduced the function of rrsH.

To determine the sequence variation responsible for the generally greater function of rrsG and the lower function of rrsH, unique differences in each 16 S rRNA when compared to rrsB were identified. The rrnG 16 S rRNA contains two differences, A131G and C183U, not present in the other 16 S rRNAs (FIG. 2.1b). Other variations in the rrnG 16 S rRNA were also present in the rrnC and rrnD 16 S rRNA. The presence of these differences in 16 S rRNA genes with function similar to rrsB was taken to mean that these differences were not responsible for the rrsG phenotype. Single mutations at A131 and C183 were constructed by site directed PCR and cloned into pRNA123. At standard conditions, LB medium at 37° C., mutations either resulted in wild-type function or were non-functional. Single purine mutations at position 183 were non-functional while pyrimidine mutations had wild-type function (FIG. 2.3). At position 131, only G131 and U131 were functional.

The rrnH 16 S rRNA contains the following differences from rrsB, U855A, C1120U, and 9 differences (G1002A, G1006C, U1010C, A1019G, G1020A, A1021U, A1022U, U1023G, and C1038U) in helix 33 (FIG. 2.1b). The C1120U variation was not analyzed because it converts a G-C base pair into a G-U wobble, which maintains the base pair at this position. The U855A variation disrupts a base pair in helix 26 and could potentially be responsible for the observed phenotype. Helix 33 contains a total of 9 differences from the other operons. Of the 9 differences, two of the variations replace the G1002-C1038 base pair with an A-U pair and two other variations replace the U1010-A1019 base pair with a C-G base pair. Three other variations replace the two G-U wobble pairs (G1006-U1023 and U1009-G1020) with standard Watson-Crick pairs (C1006-G1023 and U1009-A1020). Finally, the last two variations replace U-A base pairs (U1007-A1022 and U1008-A1021) with U-U mismatches (U1007-U1022 and U1008-U1021). The U855A and helix 33 variations were individually amplified by PCR, cloned, and assayed for function. At standard conditions, the 16 S rRNA containing just the U855A variation was approximately 92% functional while the 16 S rRNA containing just the helix 33 variation had approximately 107% function of the wild type (FIG. 2.4). Decreasing the growth temperature to 30° C. increases the function of the independent helix 33 to approximately 130% function while the function of just U855A remained constant. Increasing the growth temperature to 42° C. also increased the function of just helix 33 to approximately 130% function, but the function of U855A decreased to approximately 80%.

The 16 S rRNA genes, from E. coli DH5, that had different sequences from rrsB were cloned pRNA123 (Lee et al., 1996; Lee et al., 1997). These clones were then assayed for function under various environmental conditions. The 16 S rRNA from operons rrnC and rrnD were similar in function to rrsB, which was considered to be the wild-type, under all the environmental conditions tested. Therefore, the sequence variations found in the 16 S rRNA from operons rrnC and rrnD do not effect ribosome function under the conditions tested. The 16 S rRNA from operons rrnG and rrnH, however, were functionally different from rrsB. These differences were maintained under the all environmental conditions tested.

The 16S rRNA from rrnG was higher in function than rrsB, except at high $Mg^{2+}$ concentration pH, or ionic strength. In our system, the level of GFP protein is based on the function of the 30 S subunit. The amount of GFP fluorescence produced by a mutant 30 S subunit is then compared to the level of GFP fluorescence produced by the wild type 30 S subunit grown in parallel. Increased levels of GFP fluorescence indicate that rrsG ribosome make more protein then rrsB. The inverse relationship between translation rate and error rate has been know for some time (Allen and Noller, 1989; Allen and Noller, 1991; Dong and Kurland, 1995; Ninio, 1974; Pettersson and Kurland, 1980). rRNA mutations that increase protein synthesis with reduced fidelity have been identified in previous studies (Alksne et al., 1993; O'Connor et al., 1992). The GFP protein, however, is robust and only mutations in the three nucleotide which make up the chromophore would render the GFP protein non-fluorescent (Tsien, 1998).

Positions A131 and C183 are found in regions involved in protein binding (Brodersen et al., 2002). Position A131 is adjacent to the binding site of ribosomal protein (rprotein) S17. S17 is a primary binding protein that is involved in the folding of the 5' domain and the central domain (Brodersen et al., 2002). In the 5' domain, rprotein S17 binds to an asymmetric internal loop at positions 129 and 130 (Brodersen et al., 2002). Position A131 forms a Watson-Crick, closing base paired with U231, below the asymmetric internal loop. Disruption of the internal loop may effect the binding of rprotein S17. With the exception of A131C, which is non-functional, other single mutations did not effect function suggesting that these mutations do not affect S17 binding.

Position 183 is involved in the binding of S20 another primary binding protein. S20 stabilizes the bottom of the 30 S subunit by interacting with helix 9 and helix 44. S20 interacts with the junction loop formed by helices 7, 8, 9, and 10 and with helix 9 (Brodersen et al., 2002). In the *Thermus thermophilus* 30 S subunit crystal structure (Wimberly et al., 2001) the position corresponding to 183 in *E. coli* is a G and is base paired with position 194. In our experimental results, however, mutation of position 183 to a G is lethal. These differences in function may be because the length of helix 9 as well as the length of S20 C-terminus is longer in *T. thermophilus*. In the crystal structure, the C-terminus of S20 lies along the minor groove of helix 9 (Brodersen et al., 2002). This interaction may allow for additional stability between S20 and its binding site. In *E. coli*, however, S20 has a smaller region for interaction and therefore, disruption of a single interaction may have a more significant effect. Binding studies of C-terminal deletion mutants of S20 indicated that deletion of as few as 6 residues resulted in a significant loss of binding (Donly and Mackie, 1988). Additionally, E. coli mutants lacking S20 were found to be defective in subunit association at low $Mg^{2+}$ concentrations (Gotz et al., 1989) as well as defective in translation initiation (Gotz et al., 1990). A decrease or loss of S20 binding would also affect the stability of helix 44 and the bottom of the 30 S subunit. The top of helix 44 is responsible for formation of the A and P-sites while the rest of the helix forms numerous intersubunit contacts with the 50 S subunit suggesting that the increased flexibility of helix 44 may decrease the accuracy of translation.

Single mutations at either site are not sufficient to produce the higher level of function seen in rrsG (FIG. 2.3). Nucleotide changes at both positions 131 and 183 are required to produce higher function and therefore, the change in the binding of both S17 and S20 may be responsible for the increased function. Restoration to rrsB function was seen at high $Mg^{2+}$ concentrations, pH, and ionic strength. Increasing the ionic strength would increase the cation levels in the cell. The same may be true for increasing the pH. The internal pH of E. coli during growth at an external pH range of 5.0 to 9.0 is maintained at 7.4 to 7.8 (Slonczewski and Foster). As the external pH is increased, the cell initiates the SOS response (Taglicht et al., 1987) and the activity of the $Na^+/H^+$ antiport increases, causing a decrease in the cellular pH (Taglicht et al., 1991). The increased concentration of $H^+$ may allow a more stable interaction between the RNA and the rproteins resulting in normal levels of transcription. Under these conditions, the rprotein-RNA interaction may be stabilized and allow restoration to rrsB levels of function.

rrsH has lower function compared to rrsB except under high $Mg^{2+}$ concentration, pH and ionic strength. To further understand these results, two differences (U855A and the entire helix 33) between rrsH and rrsB were isolated and assayed for function. Helix 33 was isolated as a single unit that contains 9 variations specific to the rrsH operon. The isolated helix 33 from rrsH cloned into rrsB is approximately 30% more functional then rrsB at 30° C. and 42° C. and slightly higher at 37° C. Helix 33 composes the beak of the ribosome and interacts with rproteins S19 and S14. S19 makes a specific interaction between Trp34 of S14 and position A1014 in the loop of helix 33 while rprotein S14 makes backbone contacts with positions 1015 and 1016 in the loop of helix 33 (Brodersen et al., 2002). S14 is a secondary binding protein that facilitates the binding of proteins S3 and S10. S3 has been shown to be on the solvent side of the channel by which mRNA enters the ribosome (Yusupova et al., 2001). Additionally, the ribosome has recently been show to have helicase activity and mutations in S3 decrease this activity (Takyar et al., 2005) which may effect translation (Takyar et al., 2005). The substitution of the wild type U-G wobble pairs with Watson-Crick base pairs and the disruption of two Watson-Crick base pairs in helix 33 may disrupt the interaction between helix 33 and proteins S19 and S14 and in turn S3. An increase in temperature may further destabilize this interaction while a decrease in temperature may allow binding at a different site causing changes in function.

A blast search of the rrsH helix 33 sequence identified other bacteria containing this sequence in their ribosomal operons. Horizontal gene transfer event between E. coli DH5 and other bacteria that contain this sequence, may explain how the rrnH 16 S rRNA gene acquired this variant of helix 33. The acquisition of this helix 33 variant would have a drastic effect on the fitness of E. coli. Growth of E. coli DH5 at 37° C. would allow 16 S rRNA containing just helix 33 from rrsH to function relatively normally. E. coli, however, must survive under different temperature conditions and 16 S rRNA containing helix 33 from rrsH translates the GFP mRNA faster when grown at 30° C. or 42° C. Increasing the translation rate increases error rate (Allen and Noller, 1989; Allen and Noller, 1991; Dong and Kurland, 1995; Ninio, 1974; Pettersson and Kurland, 1980). An increased error rate would decrease the fitness of the organism. The U855A variation in rrsB was approximately 90% functional at 30° C. and 37° C. Function of U855A, however, decreased to 80% when grown at 42° C. It is possible that U855A is a compensatory mutation that occurred to decrease translational error rate under suboptimal temperature conditions. Increasing the pH or ionic strength may relieve some of this disruption and allow for normal function.

The 16 S rRNAs that contained sequence differences from rrsB has been cloned. It has been hypothesized that sequence heterogeneity among the seven 16 S rRNA genes of E. coli DH5 may provide functional differences important for survival during different environmental conditions or may be responsible for translation at specific points during the life cycle. Analysis has shown specific functional differences for rrsG and rrsH that responded to changes in $Mg^{2+}$ concentration, pH, and ionic strength. These 16 S rRNAs may play a role in adaption to changing environmental conditions.

Restriction enzymes, ligase, and calf intestine alkaline phosphatase were from New England Biolabs and from Gibco-BRL. Sequencing modified DNA polymerase, nucleotides, and sequencing buffers were from Epicenter Technologies. Oligonucleotides were purchased from Midland Certified Reagent Company (Midland, Tex.) or IDT DNA (Coralville, Iowa). AmpliTaq DNA polymerase and PCR reagents were from Perkin-Elmer-Cetus (Boston, Mass.).

Plasmids and Mutagenesis.

Operons from E. coli DH5 were isolated using polymerase chain reaction (PCR) (Higuchi et al., 1988; Mullis et al., 1986; Mullis and Faloona, 1987) with primers 16S 1F (5'-AAA TTG AAG AGT TTG ATC A-3') and 16S 3' end (5'-CGC GTA AAC GCC TTG CTT TT-3').

Insertion of 16 S rRNA from different operons into pRNA123: Chromosomal DNA from Escherichia coli DH5 was isolated using standard methods. The genomic DNA was used as a template to PCR amplify the 16 S rRNA from all the operons. The PCR product was then cloned into pRNA123 using the BclI and BstEII restriction sites. The ligations was transformed into E. coli DH5 and plated on LB+Amp (100 µg/ml) agar plates. Survivors were sequenced to determine the identity of the 16 S rRNA. Clones were assayed for function using GFP fluorescence.

Construction of rrsG Double Mutants in rrnB 16 S rRNA.

Double mutants were constructed in pASS2-GFP, a pUC19 derivative similar to pRNA123 but containing only the 16S rRNA (Lee et al., 1996; Lee et al., 1997), using site-directed recombinant PCR with primers 16S rrsG 1 (5'-GTT TCC AGT AGT TAT CCC CCT CCA TCA GGC AGN TTC CCA GAC A-3') and lac UV5-74 (5'-GCA GTG AGC GCA ACG CA-3') for PCR1 and 16S rrsG 2 (5'-ATA ACT ACT GGA AAC GGT AGC TAA TAC CGC ATA ANG TCG CAA GAC-3') and 16S H693 (5'-CGG TAT TCC TCC AGA TCT CTA CGC ATT TCA CCG CTA CAC CTG GAA TTC TA-3') for PCR 2. The double mutants were cloned into the 16 S rRNA from rrnB using the BclI and AvrII restriction sites. The ligations was transformed into E. coli DH5 and plated on LB+Amp (100 µg/ml) agar plates. Survivors were sequenced to identify the mutations. Clones were sub-cloned into pRNA123 and assayed for function using GFP fluorescence.

Isolation of rrsH Variation in rrnB 16 S rRNA.

Helix 33 was isolated as an entire unit by digestion with ApaI and XbaI. The fragment was cloned into pRNA272, a derivative of pRNA123 containing a single ApaI site in the rrnB 16 S rRNA, using the ApaI and XbaI restriction sites. The ligations was transformed into E. coli DH5 and plated on LB+Amp (100 μg/ml) agar plates. Survivors were sequenced to confirm the presence of the helix 33 variations. The U855A mutation was constructed using site-directed PCR with primers 16S 1038 rrsH (5'-AGT TCC CGA AGG CAC CAA TC-3') and 16S AvrII (5'-ACG TCG CAA GAC CAA AGA GG-3'). The PCR product was also cloned into pRNA272 using the ApaI and BglII restriction sites. These clones were then transformed into E. coli DH5 cells. The mutant was sequenced to confirm the presence of the U855A mutation and assayed for function using GFP fluorescence.

Bacterial strains and media. All plasmids were maintained and expressed in E. coli DH5 (supE44, hsdR17, recA1, endA1, gyrA96, thi-1, relA1) (Hanahan, 1983). Cultures were maintained in LB medium (Luria and Burrous, 1957) containing 100 μg/ml ampicillin (LB-Ap100). To induce synthesis of plasmid-derived rRNA from the lacUV5 promoter; IPTG (isopropyl-beta-D-thiogalactopyranoside) was added to a final concentration of 1 mM at the times indicated in each experiment. Strains were transformed by electroporation (Dower et al., 1988) using a Gibco-BRL Cell Porator. Unless otherwise indicated, transformants were grown in SOC medium (Hanahan, 1983) for one hour prior to plating on selective medium to allow expression of plasmid-derived genes. High $Mg^{2+}$ medium: Standard LB medium containing 50 mM or a 100 mM Mg2+. GFP assays were performed as described below. Various ionic strength medium: LB media without NaCl, TYE (tryptone 5 g; yeast extract 2.5 g; pH 7), was made for low ionic strength growth. A 3 M KCl solution in TYE medium was used to adjust the ionic strength of the TYE medium to the appropriate concentration. GFP assays were performed as described below. Various pH medium: Standard LB medium was adjusted to different pH using buffers MES (pH 5.5), PIPES (pH 6.3), HEPES (pH 7.4), and AMPSO (pH 9.0). LB containing 100 mM of the appropriate buffer was used to grow the culture at each pH. GFP assays were performed as described below.

Green Fluorescence Protein (GFP) Assay.

Overnight cultures of mutants, as well as a wild type control, were grown in the appropriate medium with Amp100 at 37° C. with shaking for 12-16 hours. The overnight cell cultures were then diluted 1:100, into appropriate medium containing Amp 100 and IPTG (1 mM). The induced culture was grown at 37° C. with shaking for 24 hours. After 24 hours, 500 μL of the culture was aliquoted into 1.7 mL microcentrifuge tubes and centrifuged at approximately 11 g for 1 minute to pellet the cells. The cell pellet was washed twice with 500 μL of HN buffer (20 mM HEPES pH 7.4 and 0.85% NaCl) and resuspended in 500 μL of HN buffer. After cells were resuspended, 100 μL of cell suspension was transferred to a 96 well clear bottom microtiter plate. The cell density (λ=600 nm) was measured using a SPECTRAmax 190 (Molecular Devices, Sunnyvale, Calif.) and fluorescence (excitation=395 nm and emission=509 nm) was measured using a SPECTRAmax GEMINI (Molecular Devices, Sunnyvale, Calif.). For each culture, fluorescence was divided by A600 and presented as a percentage of the wild type. Values represent the average of at least three assays on three separate cultures done on different days.

Example #6

Identification of Interactions within the 530 Loop

The decoding function of the ribosome is thought to involve three regions of the 16 S rRNA: the decoding region (nucleotides 1400-1500), helix 34 (1050/1200 region), and the 530 loop. The 530 loop is a conserved, 45-nucleotide stem-loop structure found in all small subunit ribosomal RNA. Phylogenetic and mutational studies have suggested a requirement for three Watson-Crick interactions within this conserved loop. These interactions are the proposed base pairing between 521-522 and 527-528, the proposed pseudoknot between 505-507 and 524-526, and possible interactions between 516-519 and 529-532. To examine the nature and functional significance of these interactions, three random mutagenesis experiments were conducted in which the nucleotides in each proposed interaction were simultaneously mutated and functional mutants were selected and analyzed.

Analysis of the data showed significant covariation between positions 521-522 and 527-528 as well as between nucleotides 505-507 and 524-526, indicating the importance of base pairing at these positions. The formation of the central pseudoknot is structurally important for ribosome function. Further analysis of the data indicated no sequence specificity besides the ability to base pair. Analysis of nucleotides 516-519 and 529-532 showed significant covariations and sequence specificity, indicating that the identity and interaction of these nucleotides within the loop is important for ribosome function. Positions 516, 518, 519, 529, and 530 showed strong sequence specificity and covariations, indicating that they are functionally important. Mutations at positions 527, 528, and 530 failed to complement mutations at positions 1492 or 1493.

The 16 S ribosomal RNA (rRNA) contains many conserved nucleotides that are believed to play fundamental roles during protein synthesis. One of the most conserved of these regions is commonly referred to as the 530 loop (helix 18, nucleotides 500-540) (FIG. 3.1). The 530 loop has been implicated in transfer RNA (tRNA) binding (Moazed and Noller, 1990; Ogle et al., 2001), translation fidelity (O'Connor et al., 1992; Shen and Fox, 1989), and streptomycin resistance (Melancon et al., 1988; Powers and Noller, 1991; Santer et al., 1993; Santer et al., 1995). Recent crystal structures (Ogle et al., 2001; Wimberly et al., 2000) and numerous biochemical studies (Brimacombe, 1992; Moazed and Noller, 1990; O'Connor et al., 1997) have localized this loop to the decoding region. Chemical protection studies have shown that positions 529, 530, and 531 are protected from chemical modification by A-site bound tRNA while position 532 is protected by P-site bound tRNA (Moazed and Noller, 1990). Mutations at position 530 are lethal (Powers and Noller, 1990) and reconstitution experiments have shown that these mutant ribosomes are deficient in formation of an initiation-dependent peptide bond (Santer et al., 1993) and are rarely found in polysomes (Powers and Noller, 1990; Santer et al., 1993). The crystal structure of the *Thermus thermophilus* 30 S subunit complexed with a U6 oligonucleotide and an anticodon stem loop (ASL) (Ogle et al., 2001) shows position 530 in the A-site with hydrogen-bond contacts to A1492, tRNA, and messenger RNA (mRNA). This crystal structure has led to the proposal that position 530 is involved in monitoring codon-anticodon interaction at the second position and that the 530 loop is involved in translation fidelity (Ogle et al., 2001). Mutations at position 517 resulted in an increased rate of frameshifting and read-through of stop codons when tested in vivo (O'Connor et al., 1992; Shen and Fox, 1989). Mutations in ribosomal proteins S4, S5, and S12 are known to affect translation fidelity (Alksne et al., 1993; Biswas and Gorini, 1972; Rosset and Gorini, 1969) and all three are located in the vicinity of the 530 loop (Brodersen et al., 2002; Capel et al., 1987). Finally, streptomycin resistance, which increases the error rate of translation (Davies et al., 1964; Gorini and Kataja, 1964; Kaji et al., 1966; Pestka, 1967), has been localized to positions 507 (Powers and Noller, 1991), 523 (Melancon et al., 1988), 525 (Powers and Noller, 1991), 529 (Santer et al., 1995), and 530 (Santer et al., 1993) in the 530 loop.

Phylogenetic analysis (Cannone et al., 2002) and crystal structures (Ogle et al., 2001; Wimberly et al., 2000) revealed interesting secondary and tertiary interactions within the 530 loop. Positions 521-522 are base-paired with positions 527-528. This results in the formation of a tetraloop of positions 523-526. Positions 524-526 of the tetraloop interact with positions 505-507 in the stem bulge resulting in the formation of a pseudoknot (Dam et al., 1992; Pleij et al., 1985). It has also been proposed that functionally important base pairs exist between positions 516-519 and 529-532 (Van Ryk and Dahlberg, 1995) though these interactions are not seen in the crystal structure (Ogle et al., 2001; Wimberly et al., 2000).

Focus was given to the interactions identified within the loop (FIG. 3.1), specifically, nucleotides 521-522 and 527-528 (4N), nucleotides 505-507 and 524-526 (6N), and nucleotides 516-519 and 529-532 (8N).

To examine the role of potential interactions within the 530 loop (FIG. 3.1) nucleotides involved in the proposed interactions were randomly mutated using PCR and cloned into pRNA16ST, a derivative of pRNA122 (Lee et al., 1996; Lee et al., 1997). pRNA16ST contains only the 16 S rRNA from the rrnB operon rather then the entire operon. This results in additional unique restriction sites in the 16 S rRNA. In this specialized in vivo system, the chloramphenicol acetyltransferase (CAT) reporter message is translated exclusively by plasmid-derived ribosomes that cannot translate normal cellular messages (Lee et al., 1996; Lee et al., 1997). Thus, the minimal inhibitory concentration (MIC) of chloramphenicol for each mutant is correlated to the level of function of the plasmid-derived ribosomes. This allows for the selection of functional mutants on chloramphenicol containing media. Survivors were then sequenced and assayed for function by determining the MIC for each mutant.

Originally identified through phylogenetic analysis (Woese and Gutell, 1989) the interaction between 521-528 and 522-527 (FIG. 3.1) was tested to confirm the presence of base pairing. A total of 510,000 transformants were obtained to make sure that each of the 256 ($4^4$) mutant sequences was represented in a selected pool (Clarke and Carbon, 1976). Approximately 2.0% of the plated cells survived on 50 μg/ml chloramphenicol containing medium and 53 chloramphenicol-resistant clones were selected and sequenced. A total of 10 unique mutant sequences were identified and further analyzed (Table 3.1a).

Statistical Analysis.

To determine if nucleotide identity at each mutated position in the chloramphenicol-resistant clones was random, the distribution of nucleotides for each position was examined for goodness of fit to an even distribution among possible substitutions. This analysis of isolated mutants revealed non-randomness at all positions except nucleotide 528 (FIG. 3.2). Non-random distribution of nucleotides among the selected functional clones suggests that nucleotide identity within the mutated sequences might affect the level of ribosome function (MIC). To determine if this was the case, the mean activities of all mutants at each position were compared by single-factor analysis of variance (ANOVA) (Lee et al., 1997). Analysis of the ANOVA results show that nucleotide identity within 521-22 and 527-528 had no significant effect on the level of ribosome function at each position. Covariation analysis was not applicable due to the absence of all possible mutations at each position within the pool. Examination of the distribution of Watson-Crick base pairs, wobble base pairs, and mismatches for the proposed interaction, however, shows a marked preference for base pairing between positions 521:528 and 522:527 (Table 3.2).

To identify any potential interactions between C528 and A1492, mutations at positions 527, 528, and 1492 were cloned into pRNA123, a derivative of pRNA122 (Lee et al., 1996; Lee et al., 1997). In this in vivo system, the chloramphenicol acetyltransferase (CAT) and the green fluorescent protein (GFP) reporter messages are translated exclusively by plasmid-derived ribosomes that cannot translate normal cellular messages. Thus, the chloramphenicol minimal inhibitory concentration (MIC) and the GFP fluorescence of each mutant is correlated to the level of function of the plasmid-derived ribosome. Single mutations at positions 527 and 528 resulted in non-functional ribosomes with the exception of $m^7G527U$ or C528U mutants. These two mutations maintained 14% and 24% function respectively when compared to the wild type. Double mutants between 528 and 1492 or 1493 as well as between 527 and 1492 or 1493 were also made. Double mutants between these positions showed no complementation.

505-507 and 524-526 (6N) Interaction.

Also identified through phylogenetic analysis, the interaction involving nucleotides 505-507 and 524-526 (FIG. 3.1) in 16 S rRNA was proposed by Woese and Gutell (1989). A total of 680,000 transformants were plated to make sure that all of the 4096 ($4^6$) mutant sequences were represented in a selected pool with >99.9% confidence (Clarke and Carbon, 1976). Approximately 5.3% of the plated cells survived on medium containing 50 μg/ml chloramphenicol of which 54 chloramphenicol resistant clones were selected and sequenced. A total of 39 unique mutant sequences further analyzed (Table 3.1b).

Statistical Analysis.

Sequence data from the 39 unique mutants was used to statistically determine if a nucleotide preference exists at each position. Although all four nucleotides were found at each position, there was a significant preference for the wild-type nucleotide at each position in the pool (FIG. 3.3).

To determine if nucleotide identity had any effect on ribosome function, an analysis of variance (ANOVA) was performed for each position. With the exception of position 524 ($p<0.05$), there was no significant effect of nucleotide identity on ribosome function. Thus, it appears that identity of the nucleotide at each mutated position, except 524, is not critical in the selection for functional mutants. Therefore, as with the 521:528 and 522:527 interactions, these positions play primarily a structural role.

Since the interaction between these mutated nucleotides may also significantly affect ribosome function in this system, a covariation analysis was performed to examine whether the presence of a particular nucleotide at one position affected nucleotide selection at another mutated position. Significant covariations were only observed between the proposed base-pairing positions ($p<10^{-4}$). These covariations indicate a preference for nucleotides that can form base pairs. Further analysis of the distribution of Watson-Crick base pairs, wobble base pairs, and mismatches for the proposed interaction show a significant preference for base pairing between 505:526 and 506:525, while base pairing between 507:524 is a not as stringent (Table 3.3). These data indicate that the 530 loop is highly constrained.

516-519 and 529-532 (8N) Interaction.

A potential interaction involving nucleotides 516-519 and 529-532 in 16 S rRNA (FIG. 3.1), was proposed by VanRyk and Dahlberg. These eight positions (516-19 and 529-32) were simultaneously mutated and functional mutants were selected, sequenced, and analyzed for ribosome function. A total of 450,000 transformants were obtained to ensure that each of the $4.50 \times 10^5$ ($4^8$) mutant sequences was represented in the selected pool. Approximately 1.90% of plated cells survived on 50 μg/ml chloramphenicol containing media of which 91 chloramphenicol-resistant clones were selected and sequenced. A total of 66 unique mutant sequences were further analyzed (Table 3.1c).

Statistical Analysis.

As shown in FIG. 3.4, significant nucleotide preferences were found for positions 516 ($p=4.7 \times 10^{-13}$), 518 ($p=1.8 \times 10^{-31}$), 519 ($p=4.1 \times 10^{-33}$), 529 ($p=4.4 \times 10^{-30}$), and 530 ($p=1.2 \times 10^{-24}$); whereas the selection of nucleotides at positions 517, 531 and 532 was random ($p>0.1$). Positions that showed a significant effect of nucleotide identity upon the level of ribosome function (ANOVA) were: 516 ($p=8.0 \times 10^{-6}$), 518 ($p=1.3 \times 10^{-3}$), 519 ($p=3.4 \times 10^{-7}$), 529 ($p=6.0 \times 10^{-5}$), and 530 ($p=2.3 \times 10^{-2}$) (Table 3.4). The most significant covariations were observed between positions 518 and 530 ($p=3.8 \times 10^{-8}$) and 518 and 529 ($p=7.5 \times 10^{-8}$). Covariations were identified between position 516 and positions 517 ($p=8.2 \times 10^{-3}$), 518 ($p=5.9 \times 10^{-6}$), 529 ($p=1.2 \times 10^{-5}$), and 530 ($p=6.4 \times 10^{-5}$). Covariations were also identified between positions 529 and 530 ($p=5.2 \times 10^{-4}$) and a weak covariation between positions 531 and 532 ($p=4.1 \times 10^{-2}$). Position 519 covarys with positions 516, 518, 529 within the loop; however, covariation analysis among these positions was not applicable due to the absence of an adenosine mutant at position 519 in the pool. The proposed interactions between positions 516 and 532 and between positions 517 and 531 were not observed.

Complementation Between the 530 Loop and Decoding Region.

Recently, Ogle et al. proposed a model for translational fidelity based on a crystal structure of the 30 S complexed with an oligonucleotide (mRNA) and an anticodon stem loop (ASL) fragment (tRNA). In this model, the 530 loop, and more specifically, nucleotide 530, along with nucleotides 1492 and 1493 in the decoding region, play a direct role in the discrimination between cognate and non-cognate tRNA. Positions G530 and A1492 are proposed to be involved in decoding the second base pair in the codon-anticodon interaction. The nucleotides interact through a hydrogen bond between their N1 positions. Previous studies have shown that any mutations at these positions are lethal (Powers and Noller, 1990; Santer et al., 1993) [this study]. To determine if the lethality of mutations at positions 530 and 1492 were due to the disruption of this interaction, double mutations between G530 and A1492 were constructed and analyzed for restoration of function. No complementation between these positions was observed.

Three separate saturation mutagenesis (Lee et al., 1997) experiments were conducted to examine interactions within the conserved 530 stem loop. These experiments confirm the interaction involving nucleotides 505-507:524-526 and 521-522:527-528 which indicate that the 530 loop is a highly structured and constrained region of the 16 S rRNA. Contrary to phylogenetic analysis, our data indicate that the 530 loop can accommodate sequence variation and retain high ribosomal function as long as the general 530 loop structure is maintained.

521-522 and 527-528 (4N) Interaction.

The data support the hypothesis that base pairing between nucleotides 522 and 527 and between nucleotides 521 and 528 is important for ribosome function. Selection for even low levels of function resulted in the isolation of only mutants that have some ability to base pair. The wild-type nucleotides seemed to be preferred at each position, but mutations at each position were observed. These mutations, however, did not seem to affect function if a complementary mutation that allowed base-pairing was also present. Due to the low number of isolated mutants, covariation interaction or nucleotide preference could not be confirmed. Covariations, however, were identified in the instant evolution of the entire 530 loop (Cho, 1999), confirming the interaction between these nucleotides.

Phylogenetic analysis indicates that the modified nucleotide, m$^7$G527, is conserved. This position was found to be both structurally and functionally important (Cho, 1999). This is consistent with the exemplification provided herein. Although several highly functional mutants contained substitutions at this position, base pairing is maintained. The modification may, however, be involved in disrupting interactions with other regions in the ribosome.

An interaction between G528 and A1492 has been proposed. To study this interaction, single mutants at positions 527, 528, and 1492 were created. Single mutations at positions 527 or 528 resulted in a loss of ribosome function with the exception of m$^7$G527U and C528U mutants. These mutants retained 14% and 24% function, respectively. The simplest explanation for these results is the ability of U to form at least some hydrogen bonds with the other three nucleotides. This explanation is in agreement with the instant evolution results, as well as the phylogenetic data. Single mutants at position 1492 were non-functional. Double mutations between positions 527 and 1492 and between positions 528 and 1492 were also non-functional. This is in agreement with the crystal structure, which shows no interactions between these positions.

505-507 and 524-526 (6N) Interaction.

Analysis of the interaction between 505-507 and 524-526 indicate preferences for wild-type nucleotides, but many mutants that do not violate the constraints of the structure were also highly functional. Covariation analysis of the mutant pool showed strong interactions between 505:526, 506:525, and 507:524 indicating base pairing between these nucleotides (Table 3.3). Requirement for base pairing at these positions was previously shown by Powers and Noller (1991). Several highly functional mutants were identified that did not contain base pairs between all three positions, as well as low functional mutants that did contain base pairs between all three positions. There are several explanations for this discrepancy; base pairing may be facilitated by another ligand, or the sequence, as well as the base pairing, is important for function. The nucleotides involved in this pseudoknot were protected from chemical attack by ribosomal protein S12 (Stern et al., 1988), suggesting an interaction between these 530 loop nucleotides and S12. The recent crystal structures (Ogle et al., 2001; Wimberly et al., 2000) show the N6 position of A523 hydrogen bonded to Asp92 of S12, bringing S12 into close proximity of the pseudoknot. The proximity of S12 to the 530 loop may be responsible for stabilizing this pseudoknot structure (Powers and Noller, 1994). Secondly, nucleotides involved in formation of the pseudoknot are conserved throughout phylogeny. These positions may be conserved for reasons other than just base pairing. In fact, binding of aminoglycoside antibiotics to the decoding region enhanced the reactivity of C525 (Moazed and Noller, 1987) and also induces a conformational change in the 530 loop somewhat similar to the conformational change in the presence of tRNA and mRNA (Ogle et al., 2001). This would imply that the pseudoknot is disrupted at some point during protein synthesis and that the nucleotides involved in pseudoknot formation could interact elsewhere. Furthermore, introduction of single mutations at positions 524-526 showed those at position 524 to be lethal (Powers and Noller, 1991). This is consistent with the ANOVA analysis of the mutant pool, which indicated that nucleotide identity had an effect on function at position 524 ($p=0.01$). Therefore, nucleotide identity as well as ability to form the pseudoknot is important for function.

The 6N and 4N experiments provide information on how the 530 pseudoknot may be formed in vivo. The base pairing between positions 521:528 and 522:527 result in the formation of a AGCC tetraloop at the top of the 530 loop. The AGCC tetraloop is part of a family of conserved AGNN tetraloops. The solution structure of an AGNN (specifically a AGUC) tetraloop was solved using NMR by Lebars et al. (2001). The AGUC tetraloop was stabilized by a hydrogen bond between the first of position (N3 of A) of the loop and the fourth position (N4 of C) of the loop. The phosphodiester backbone turn occurs between the second (G) and third (U) positions and the 5' and 3' nucleotides of the turn are stacked. In the Ogle et al. crystal structure the AGCC tetraloop of the 530 loop does not have the hydrogen bond between the first (A) and fourth (C) position of the loop. The backbone turn occurs between position 523 and 524 with bases 524, 525, and 526 stacked. Finally, position 523 is flipped out to interact with protein S12. This difference between the two structures maybe due to the modification of position $m^7G527$. The modification may disrupt the hydrogen bond within the tetraloop and allow the bases of the loop to interact with the 530 stem to form the pseudoknot.

516-519 and 529-532 (8N) Interaction.

The proposed base-pairing interaction between 516:519 and 529:532 does not seem to exist. There is, however, significant interaction between the two sides of the loop (FIG. 3.4). Five (positions 516, 518, 519, 529, and 530) of the eight nucleotides studied show significant nucleotide preference and seem to be essential for function. Positions 531 and 532 have slightly significant ANOVA P-values, however, no nucleotide preferences were found at these positions. This significance may be due to the small number of mutants analyzed or the significance may indicate a requirement for spacer nucleotides at these positions to be present in the loop for function. Single mutants at these positions did not significantly affect ribosome function (Santer et al., 1993).

Position ψ516 is conserved but is structurally important rather than functionally important. Previous studies in our lab have shown that transition mutations at position 516 were better tolerated then transversion mutations (Lee et al., 2001). This study concluded that the reduction in function for transition mutants was correlated to a reduction in the ability to form the 70 S subunit. The 530 loop does not seem to be involved in any intersubunit bridges (Yusupov et al., 2001) so mutations at position 516 must induce a long range conformational change that inhibits 70 S subunit formation. Transversion mutants also showed a reduction in the ability to form 70 S subunit, but this was not sufficient to explain the loss of function for this type of mutant. It is believed that transversion mutants disrupt some other aspect of protein synthesis as well as reduce the ability to form 70 S subunits. Furthermore, a pseudouridine at position 516 does not seem essential. Deletion of the rsuA gene, which is responsible for formation of ψ516, does not effect growth rate at varying temperatures (Conrad et al., 1999). Therefore, a pseudouridine does not seem to be required for function. Covariations between 516 and other functionally important nucleotides in the loop also indicate a structural role for position 516 (FIG. 3.4). This can be seen in the crystal structure (Ogle et al., 2001) where positions 516, 517, and 531 are stacked and the 516 2'OH forms a hydrogen bond with N3 of C519. Position 516 also shows covariation with positions 529 and 530, although no hydrogen bonds were identified in the crystal structure. The crystal structure is static, interaction between position 516 and positions 529 and 530 may occur during ribosome movement.

Previous studies have shown that mutations at G517 increase translational errors (O'Connor et al., 1992). In our studies, however, several single mutations at position 517 were identified that did not have a significant change in the level of function. In our system, plasmid-derived ribosomes only translate the CAT mRNA and do not translate cellular mRNA. Therefore, an increase in translational error would not affect cell growth. Also, due to the small size of the CAT reporter gene, the reduction of translation fidelity would be difficult to detect by MIC.

Nucleotide identity is strongly conserved at positions 518 and 519. Position 519 forms a hydrogen bond with position 516 as described above and a hydrogen bond between 519 N4 and 529 2'OH. The lack of variation at position 519 may be due to steric hindrance or the requirement of a hydrogen bond between 519 and 529 to stabilize the loop. Position 518 is intercalated between positions 529 and 530, all of which are stacked. This stacking may stabilize position 530 and allow it to interact with position 1492. The N6 of A1492 is also involved in hydrogen bonding to the 2' OH of C518 while the O2 of C518 is involved in a metal-mediated interaction with the 2' OH of the codon in the third base pair of the codon-anticodon helix (Ogle et al., 2001). The O2 of C518 also interacts with the main chain carbonyl of Pro44 (E. coli numbering) of ribosomal protein S12. Consequently, any changes to these positions would affect protein synthesis.

Finally, nucleotide identity at positions 529 and 530 are conserved and are important for ribosome function. Position G529 forms a sheared G-A base pair with A520 and a hydrogen bond between O6 of G530 and Asn49 of ribosomal protein S12. These interactions would be disrupted by mutations at this position. Substitutions of pyrimidines at this position may not reach far enough to make the required contacts, while an adenine would not have the functional groups to interact in a similar manner. Disruption of the 529 interactions may change the structure of the loop or binding of S12, both of which would affect protein synthesis. In the crystal structure (Ogle et al., 2001), position in 530 is shown interacting with the A-site, specifically A1492, and is involved in proofreading at the second and third position of the codon-anticodon helix. The interaction between G530 and A1492 is stabilized by a hydrogen bond between the N1 positions of both nucleotides. The discrimination between cognate, non-cognate, and near-cognate is determined by hydrogen bonds between the 2' OH of the codon to the N3 and the 2' OH of A1492. A similar interaction occurs when the 2' OH of the anticodon hydrogen bonds to the N3 and 2' OH of G530. Lack of variation at this position is probably due to a requirement of the above interactions for accurate translation.

The 530 loop is conserved in sequence and structure throughout phylogeny. The above experiments have confirmed interactions identified through phylogenetic analysis, as well as separate structurally important nucleotides from functionally important nucleotides.

Reagents.

Restriction enzymes, ligase, and calf intestine alkaline phosphatase were from New England Biolabs and from Gibco-BRL. Sequencing modified DNA polymerase, nucleotides, and sequencing buffers were from Epicenter Technologies. Oligonucleotides were either purchased from Midland Certified Reagent Company (Midland, Tex.), IDT DNA (Coralville, Iowa), or synthesized on-site using a Beckman Oligo 1000 DNA synthesizer. AmpliTaq DNA polymerase and PCR reagents were from Perkin-Elmer-Cetus (Boston, Mass.).

Plasmids and Mutagenesis.

All mutagenesis was performed using polymerase chain reaction (PCR) (Higuchi et al., 1988; Mullis et al., 1986; Mullis and Faloona, 1987) and the primers used are listed in Table 5.

Construction of mutations at 530 region in 16S rRNA: All mutations were constructed in pRNA16ST, the construction of which will be described elsewhere. Briefly, this is a pUC19 derivative containing all the features of pRNA122 (Lee et al., 1996; Lee et al., 1997) except that the entire 23S rRNA is deleted. It has advantages over pRNA122 in introducing mutations in 16S rRNA since it provides more unique restriction enzyme sites and larger quantities of plasmid DNA for sequencing. Random mutations were introduced at 6N and 8N positions in 16S rRNA in pRNA16ST by replacing the wild-type sequence between AvrII and BglII with a fragment containing PCR-directed random mutations while EcoRV and BglII were used for the 4N loop by the same methods.

Selection of functional mutants: Transformants were incubated in SOC medium containing 1 mM IPTG for four hours to induce rRNA synthesis and then plated on LB-Amp100-IPTG agar with and without 50 µg/ml chloramphenicol. A total number of about $4.5$-$5.0 \times 10^5$ transformants were obtained for each experiment, yielding approximately 2% chloramphenicol-resistant survivors for 4N and 8N and 5% for 6N. Next, transformants with minimum inhibitory concentrations (MIC) greater than 50 µg/ml were randomly selected and sequenced in statistically significant numbers for each experiment.

Construction of single mutants in 16S rRNA: Single mutants were constructed in pASS2-GFP and then transferred into pRNA123, a derivative of pRNA122 (Lee et al., 1996; Lee et al., 1997) which contains the chloramphenicol acetyltransferase (CAT) and green fluorescence protein (GFP) reporter gene. The ribosome binding sites of the CAT and GFP gene have been modified to match the message binding site of the plasmid-derived ribosome. Therefore, the level of chloramphenicol resistance and GFP fluorescence is directly proportional to the function of plasmid-derived ribosomes. The CAT gene allows for selection of functional mutants while the GFP gene allows for the high throughput screening of mutant function. Each mutant was sequenced to confirm the presence of the mutation and assayed for function using GFP assays.

Construction of double mutants in 16S rRNA: Double mutants were constructed from single mutant constructs in pRNA123. 530 loop single mutant constructs were digested with BglII and XhoI and cloned into pRNA123 containing 1492 or 1493 mutations. These clones were then transformed into E. coli DH5 cells. Each mutant was sequenced to confirm the presence of the mutation and assayed for function using GFP assays.

Bacterial Strains and Media.

All plasmids were maintained and expressed in E. coli DH5 (supE44, hsdR17, recA1, endA1, gyrA96, thi-1, relA1) (Hanahan, 1983). Cultures were maintained in LB medium (Luria and Burrous, 1957) or LB medium containing 100 µg/ml ampicillin (LB-Ap100). To induce synthesis of plasmid-derived rRNA from the lacUV5 promoter; IPTG (isopropyl-beta-D-thiogalactopyranoside) was added to a final concentration of 1 mM at the times indicated in each experiment. Strains were transformed by electroporation (Dower et al., 1988) using a Gibco-BRL Cell Porator. Transformants were grown in SOC medium (Hanahan, 1983) for one hour prior to plating on selective medium to allow expression of plasmid-derived genes.

Minimum Inhibitory Concentration (MIC).

MICs were determined by standard methods in microtiter plates. Overnight cultures grown in LB-Ap100 were diluted and induced in the same medium containing 1 mM IPTG for two to three hours at 37° C. Approximately $10^4$ induced cells were then added to wells containing LB-Ap100+IPTG (1 mM) and chloramphenicol at increasing concentrations. Cultures were grown 24 hours and the lowest concentration of chloramphenicol that completely inhibited growth was designated as the MIC.

Green Fluorescence Protein (GFP) Assay.

Overnight cultures of mutants as well as a wild type control were grown in LB-Amp100 at 37° C. for 12-16 hours. The overnight cell cultures were then diluted 1:1000 and induced in LB-Amp 100+IPTG (1 mM) medium and grown at 37° C. for 24 hours. After 24 hours, 1 mL of the culture was aliquoted and centrifuged at 11,000×g for 1 minute to pellet the cells. The cell pellet was washed twice with 1 mL of FIN buffer (20 mM HEPES pH 7.4 and 0.85% NaCl) and resuspended in 1 ml of HN buffer. After cells were resuspended, 100 µL of cell suspension was transferred to a 96 well clear bottom microtiter plate. The cell density ($\lambda$=600 nm) was measured using a SPECTRAmax 190 (Molecular Devices, Sunnyvale, Calif.) and fluorescence (excitation=395 nm and emission=509 nm) was measured using a SPECTRAmax GEMINI (Molecular Devices, Sunnyvale, Calif.). For each culture, fluorescence was divided by $A_{600}$ and presented as a percentage of the wild type. Values represent the average of at least three assays on three separate cultures done on three different days.

Example #7

Effect of Mutations in the 970 Loop

The 970 loop (helix 31) of Escherichia coli 16 S rRNA contains two modified nucleotides, $m^2G966$ and $m^5C967$. Positions A964, A969 and C970 and the presence of a modified nucleoside at position 966 in helix 31 are conserved across the Bacteria, Archaea and Eukarya. The sequence of the other nucleotides and specific nucleoside modifications in loop, however, are conserved within each of the three Domains. Biochemical and structure studies have placed this loop near the P-site and have shown it to be involved in the decoding process and in binding the antibiotic tetracycline. To identify the functional components of this rRNA hairpin, the eight loop nucleotides of the 970 loop nucleotides of helix 31 were subjected to saturation mutagenesis and 124 unique functional mutants were isolated and analyzed. A non-random nucleotide distribution was found at each mutated position. Nucleotide identity at positions 966, 967, 969, and 970 significantly affects ribosome function. Ribosomes with single mutations of $m^2G966$ or $m^5C967$ produce more protein in vivo than wild-type ribosomes. Over expression of initiation factor 3 (IF3) specifically restored wild-type levels of protein synthesis to the 966 and 967 mutants.

Ribosomes are complexes of ribosomal proteins (rproteins) ribosomal RNA (rRNA), that are responsible for the translation of messenger RNA into protein in all cells. It is well established that the rRNAs perform critical functional roles in each of the partial reactions of the translation process. Ribosomal RNAs contain several modified nucleosides that tend to cluster in regions of the rRNAs known to be functionally important (Brimacombe et al., 1993). Although, their role in protein synthesis remains unclear, these modified nucleotides have been implicated in structural stability (Heus et al., 1983; Meroueh et al., 2000; Rife et al., 1998), subunit assembly (Cunningham et al., 1991), subunit association (Cho, 1999; Lee et al., 2001), and in translational accuracy (Bjork et al., 1999; Urbonavicius et al., 2001).

In *Escherichia coli* 16 S rRNA, the 970 hairpin consists of helix 31 and an eight nucleotide loop (positions 964-971) containing two modified nucleotides at positions 966 ($m^2G$) and 967 ($m^5C$) (FIG. 4.1) (Cannone et al., 2002). The size and sequence of the 970 loop is conserved within the Archaea, Bacteria and Eukarya, but only positions A964, A969, and C970 are conserved among the three Domains. Though a modified nucleoside is present at position 966 in all three domains each Domain is characterized by a specific modification (Kowalak et al., 2000; Maden, 1990). Bacterial 16 S rRNAs contain 2-methyl-guanosine at position 966, while the Eukarya contain 1-methyl-3-(3-amino-3-carboxypropyl) pseudouridine (Maden, 1990), and the Archaea contain 3-(3-amino-3-carboxypropyl) pseudouridine at the corresponding position in their small-subunit rRNAs (Balch et al., 1979; Woese et al., 1984), Involvement of the 970 loop in ribosome function has been suggested by several biochemical, biophysical and genetic studies. Wilms et al. (1997) identified a UV photochemical crosslink between $m^5C967$ and C1400 in the P-site of the decoding region that was disrupted in the presence of initiation factor 3 (IF3) (Ofengand et al., 1982; Shapkina et al., 2000; Wilms et al., 1997). Moazed and Noller showed that $m^2G966$ is protected from chemical probes by P-site bound tRNA and Doring et al., identified a diazirine crosslink between $m^5C966$ and 2-thioC32 of P-site bound tRNA (Brimacombe et al., 1993; Moazed and Noller, 1990; von Ahsen and Noller, 1995). The 70 S crystal structure by Yusupov et al., (2001) also shows a contact between the base of $m^2G966$ and the backbone of position 34 of P-site bound tRNA. These data suggest that the 970 loop may be involved in the proper positioning of tRNA in the ribosomal P site. Using a genetic system in which the rRNA operon is under the control of the lambda promoter PL, Jemiolo et al. found that single nucleotide substitutions at positions 966 and 967 did not affect the growth rate of *E. coli*, but deletion of position 967 resulted in a dominant lethal phenotype (Jemiolo et al., 1991). Crystal structures of *Thermos thermophiles* 30 S subunits (Brodersen et al., 2002) show interactions between the 970 loop and ribosomal proteins S9, S10, and S13. $m^2G966$, $m^5C967$ and A968 make backbone contacts with protein S9, A964 and A969 make backbone contacts with protein S10 (Brodersen et al., 2002), and U965, A969, and C970 make base contacts with protein S13 (Brodersen et al., 2002).

These studies suggest that the 970 loop plays a key functional role in protein synthesis. This notion is supported by structural studies showing that the 970 loop forms part of the primary binding site for tetracycline (Brodersen et al., 2000; Pioletti et al., 2001) and by the recent isolation of a tetracycline-resistant strain of *Helicobacter pylori* that contains three mutations at positions 965, 966 and 967 (Dailidiene et al., 2002). In this study, mutational analyses of the entire 970 loop were performed to identify the sequence and structural motifs that are essential for ribosome function in bacteria and to elucidate the functional roles played by the 970 loop in protein synthesis.

The eight loop nucleotides, 964-971, of helix 31 were subjected to saturation mutagenesis using PCR and cloned in the specialized ribosome expression vector, pRNA123 (Lee et al., 1996; Lee et al., 1997; Morosyuk et al., 2000). In this system, only chloramphenicol acetyltransferase and green fluorescent protein are translated by the plasmid-derived ribosomes. The mutated plasmid pool was then used to transform *E. coli* DH5 cells and functional mutants were selected from the mutant pool by plating transformants on LB medium containing Amp (100 µg/ml), IPTG (1 mM), and chloramphenicol (100 µg/ml). A total of 124 970 loop mutants were isolated, sequenced, and assayed for function (Table 4.1).

Non-random nucleotide distributions ($p<1.4\times10^{-6}$) were observed at all positions in the selected pool (Table 4.2, FIG. 4.2). Although all possible mutations were found at each position, except position 964, a preference for specific nucleotides at each position was observed (FIG. 4.2). Position 964 shows a clear preference for adenosine, guanosine was excluded and pyrimidines were underrepresented. Guanosine was excluded at 965, 968, and 970 ($p<7.6\times10^{-10}$) and uracil was excluded at positions 966 and 971 ($p<1.4\times10^{-6}$) among the functional isolates. Cytosine and adenine were more prevalent than guanosine and uracil at position 967 ($p<2.8\times10^{-6}$). Finally, a preference for purines over pyrimidines was observed at position 969 ($p<6.6\times10^{-23}$). The overall pattern of nucleotide distribution among the functional mutants is similar to that observed when comparing phylogenetic variants (Table 4.2) although as expected, more variation is observed in the mutants.

Nonrandom conservation patterns among the functional mutants may be due to the requirement for specific sequence or structural motifs within the 790 loop. To identify potential nucleotide interactions covariation analysis on all possible pairs of the mutated positions was performed. Weak covariations between positions 964.965 ($p=1.4\times10^{-5}$), 964.966 ($p=3.6\times10^{-3}$), 964.967 ($p=1.2\times10^{-3}$), 967.968 ($p=1.4\times10^{-2}$), and 968.969 ($p=4.4\times10^{-2}$) were observed. The two remaining covariations at position 968 may also indicate a requirement for a structural motif. Only weak covariations between positions 967 and 968 ($1.4\times10^{-2}$) and between positions 968 and 969 ($4.4\times10^{-2}$) were identified (FIG. 4.3). Potential covariations between position 964 and positions 965, 966, and 967 were also identified. These covariations could not be confirmed, however, due to the absence of any guanosines at position 964 among the mutants. An analysis of variance (ANOVA) was performed on the mutant pool to determine if a particular nucleotide present at any position among the mutants specifically affected ribosome function. Statistically significant ANOVAs were obtained at positions 966 ($p<6.1\times10^{-6}$), 967 ($p<3.6\times10^{-2}$), 969 ($p<7.5\times10^{-5}$), and 970 ($p<4.8\times10^{-3}$). These positions are part of two stacked base triples in the 970 loop suggesting that these triples are important for ribosome function.

Site-Directed Mutations.

To better understand the role of the 970 loop in protein synthesis, a series of site-directed mutations were constructed at positions 966 and 967 (FIG. 4.4). Wilms et al. identified a UV crosslink between $m^5C967$ and C1400 (Wilms et al., 1997). To determine if a functional interaction exists between positions $m^5C967$ and C1400, all possible site-directed mutations between position $m^5C967$ and 1400 were also constructed and assayed (Table 4.3).

The m²G966C mutation has little effect on ribosome function (96%±2.1); however, ribosomes containing the m²G966A or the m²G966U mutations produce more GFP than wild-type ribosomes (126% and 127% respectively). Similarly, m⁵C967G mutant is 107% as active as the wild type, whereas activities of the m⁵C967A and m⁵C967U mutants are in 120% and 127%, respectively (FIG. 4.4). Since the rate limiting step of protein synthesis is initiation (Laursen et al., 2005), ways that mutations at positions 966 and 967 might affect initiation were examined. Modeling and UV crosslinking of IF3 have shown interactions with the 970 loop. IF3 was shown to reduce the frequency of UV crosslinks between C967×C1400 (Shapkina et al., 2000). Modeling of the IF3 N-terminus (IF3N) to fit the biochemical data, positioned IF3N in the P-site and interacting with the 970 loop (Pioletti et al., 2001). To determine if mutations at 966 and 967 affected IF3 binding, IF3 was cloned into plasmid the pACYC177 derivative, pKan6, and placed under the control of the inducible AraBAD promoter (Greenfield et al., 1978; Kaplan et al., 1978). When tested with either U966 or U967 (mutants with the most function), over expression of IF3 restored wild-type levels of function for mutations are either U966 or U967 (Table 4.4). Over expression of IF2 or IF1, however, did not restore normal levels of function, suggesting complementation of the U966 and U967 mutations by IF3 is specific. Mutation of C1400 to an A or G resulted in 17% and 15% function, respectively. Ribosomes containing the C1400U mutation, however, produced 23% more GFP than the wild-type ribosomes. In all of the 967/1400 double mutants, ribosome function of the double mutants was approximately the product of the each of the individual mutations suggesting that the effects of the mutations at each site are independent and that m⁵C967 and C1400 do not interact during protein synthesis. The modifications at 966 and 967 were modeled into the *E. coli* 30 S subunit homology model of Tung et al., which was energy minimized by Dr. John SantaLucia Jr. (personal communication) to identify their effect on structure. The m⁵C967 faces back towards the loop while the m²G966 faces the sugar side. Both of these modifications extend the stacking surface and allow greater stability.

The eight nucleotide sequence of the 970 loop of helix 31 is conserved within each domain, but only three nucleotides are conserved among all three domains. The 970 loop contains two modified nucleosides in *E. coli* at positions 966 and 967. Saturation mutagenesis and selection of functional mutants revealed the functionally important sequence and structural motifs of the loop.

Nucleoside Requirements of the 970 Loop.

Nucleotides, with the exception of adenosine, contain charged groups at the N2 position and were selected against at 964 (Table 4.5). Position 964 was the most conserved in the saturation mutagenesis. The smaller size of the pyrimidines would not position the charged group in the same location as a purine, explaining why a small number of pyrimidines, which contain an O2, were found in the functional pool. An electrostatic clash between the O2 of a pyrimidine at 964 and U O4 or G O6 at 965 may explain the underrepresentation of U and G at 965 as well as the covariation seen between these positions. Of the 43 U965 clones identified in the selected pool, no clone with an A964C mutation was identified.

Uracil is underrepresented at position 971 in the functional pool. In the 30 S crystal structure, 971 is flipped out and binds into a pocket formed by the backbone of positions 949, 950, 1363, 1364, and 1365 in 16 S rRNA. The O2 and O4 groups of U would cause increased electrostatic clash with the pocket, disallowing this interaction and decreasing the presence of U at 971 in functional clones.

In the 30 S crystal structure, the remaining six positions form two stacked triples with positions 966, 967, and 968 forming one triple and positions 965, 969, and 970 forming the second triple (FIG. 4.3). Positions 965 and 968 underrepresented purines possibly indicating a steric requirement. In addition, G was strongly selected against, indicating that the positively charged N2 group was detrimental to function. In contrast to positions 965 and 968, positions 966 and 969 prefer purines and underrepresent pyrimidines, which may represent a requirement to contact other ribosomal components. Although, no specific contacts have been identified for position 969, position 966 is known to interact with P-site tRNA, which may explain the requirement for a purine at this position. Also, it is known, that purines stack better then pyrimindines due to a greater surface area. The location of these bases in the stacked triple may guide nucleotide preference for better stacking Positions 967 and 970 prefer A/C while G/U are underrepresented. Rather than a size preference, these two positions require a positively charged group at the N4 or N6 position. The nucleotide requirement of position 1 (966) and 2 (967) in the 966:967:968 stack corresponds to the nucleotide requirement of position 2 (969) and 3 (970) in the 965:969:970 stack.

970 Loop Mutations Effect IF3 Binding.

The N-terminus of IF3 was found to interact with positions 966-968 when modeled into the 30 S crystal structure using available biochemical data (Pioletti et al., 2001). In the saturation mutagenesis, position 966 prefers purines and underrepresent pyrimidines, 967 prefers A/C while G/U are underrepresented, and 968 underrepresented purines (Table 4.5). Site-directed mutations at positions m²G966 and m⁵C967 resulted in higher levels of function when compared to the wild-type indicating an increase in the rate of protein synthesis (FIG. 4.4).

Initiation is the rate limiting step of protein synthesis (Laursen et al., 2005). Biochemical data indicates that IF3 discriminates initiator tRNA from aminoacyl-tRNA during initiation (Hartz et al., 1990). Disruption of IF3 binding may interfere with the discrimination of initiator tRNA, leading to a decrease in the stringency for initiator tRNA and an increased rate of initiation. GFP protein, however, is robust and only specific mutations in the nucleotides that make up the chromophore (Tsien, 1998) would render the GFP protein non-fluorescent. Therefore, in our system, ribosomes that initiate faster would make more GFP protein, and thus, would result in higher fluorescence. All three initiation factors were over expressed in the presence of m²G966U and m⁵C967U to see if wild-type levels of function could be restored.

Over expression of IF3, but not other IF's, along with mutations at position 966 or 967, restores normal levels of function (Table 4.4). This suggests that mutations at positions 966 or 967 interfere with IF3N binding and that this defect can be alleviated by increased production of IF3. It is possible that mutations at these positions disrupt the stacking of positions 966:967:968, which would affect IF3N binding. An increased concentration of IF3 may compensate for the lower binding affinity. The role of the modifications at positions 966 and 967 may be to further stabilize the 966:967:968 stack triple allowing it to function correctly.

Importance of Stacking.

Modeling studies of 25 high function and 25 low function mutants using a program developed by Dr. John SantaLucia Jr., Wayne State University (personal communication) suggested that all functional mutants have the ability to form the stacked triplets. In the selected pool of mutants, only one mutant (10% function) was identified that could form base pairs between both 964:971 and 965:970. Formation of these base pairs may disrupt the formation of the structure seen in the crystal structure and therefore have been selected against. Other mutant that could form base pairs between either 964:971 or 965:970 were also seen in the selected pool. Most of these, however, were A-U base pairs, which can be most easily disrupted.

Stacking at 966, 967, and 968 is Required for Function.

In addition to IF3, positions 966 and 967 have been localized to the P-site by structural and biochemical studies (Doring et al., 1994; Moazed and Noller, 1986; Moazed and Noller, 1990; von Ahsen and Noller, 1995; Yusupov et al., 2001). The base of 966 interacts with the backbone of position 34 P-site tRNA (Yusupov et al., 2001) and in the saturation mutagenesis showed a preference for purines. The positioning of the wild-type $m^2G966$ N2 would be important to avoid interfering with the P-site tRNA or IF3N. In the presence of additional mutations in the loop, the position of the $m^2G966$ N2 may change. In the saturation mutagenesis, an A966 was preferred to the wild-type $m^2G966$. It is possible that A, which lacks a functional group at N2, was preferred over the wild-type G, to avoid interference with the binding of P-site tRNA or IF3N in the presence of additional mutations in the loop. Positions 967 and 968 have not been shown to interact with P-site tRNA and are most likely involved in positioning 966 in the correct location. The nucleotide distribution at 967 suggests a requirement for an N4 or N6, which may be a determinant for IF3 binding. Modeling of the modification at 967 suggests that the $m^5$ C modification extends and stabilizes the stack. Finally, the wild-type A968 was underrepresented in favor of A968U in the selected pool. This may be a consequence of the preference for N4 or N6 at position 967. The U968 O4 allows for a hydrogen bond to the N4 or N6 of 967, increasing the stability of the stack. This interaction would explain the covariation seen between these two positions and suggests the importance of this stacking interaction.

Stacking at 965, 969, and 970 is Required for Function.

Disruption of the 969, 970, and 965 stack is detrimental to ribosome function as indicated by the absence of A964G mutants in the selected pool. In the crystal structure, position 964 is situated above the 965:969:970 stacked triple (FIG. 4.3). Modeling of an A964G mutation into the 30 S crystal showed a steric clash between the N2 of A964G with the sugar of C970, possibly disrupting base stacking (FIG. 4.6). The importance of this stacked triple is not well understood. Analysis of the *Thermus thermophilus* 30 S crystal structure shows interactions between the C-terminus of ribosomal protein S13 and the stacked triplet formed by positions 969, 970, and 965. This interaction involves the final three amino acids of S13 (Brodersen et al., 2002). S13 is phylogenetically conserved and the C-terminus contains several basic side chain which seem to interact with the backbone of P-site bound tRNA between positions 29 and 30 (Hoang et al., 2004). Interestingly, the last seven amino acids of *T. thermophilus* S13 are not present in the *E. coli* S13 (Brodersen et al., 2002). Deletion of the 5 C-terminal amino acids of *E. coli* S13 exhibited only slight growth defects. Further deletions (36 amino acids deleted) of the S13 C-terminus resulted in a defect in tRNA binding (Hoang et al., 2004). In the crystal structure, the C-terminus of S13 contains very little secondary structure; however, this region is responsible for the majority of the interaction with the 16 S rRNA (Brodersen et al., 2002). In *T. thermophilus*, the additional C-terminal amino acids may help stabilize S13 on the ribosome and aid in positioning the tail for its interaction in the P-site.

The binding of IF3N at positions 966-968 limits the space for initiator tRNA binding to the P-site. This may be important during initiation to inhibit binding of non-initiator tRNA at the P-site. IF2 complexed with initiator tRNA positions the initiator in the P-site, requiring the IF3N to move. It is possible that, in the presence of IF2•initiator tRNA, the 965:969:970 triple represents a secondary IF3N binding site. This is suggested by the similarities of nucleotide requirements between positions 966 and 967 (966, 967, 968 stack) and positions 969 and 970 (965, 969, and 970 stack). Additionally, nucleotide identity is important for function at all four of these positions as determined by ANOVA analysis. The role of positions 969, 970, and 965 in the *E. coli* 30 S subunit is still unclear. Two of the three conserved nucleotides, positions 969 and 970 in the 970 loop, are located in this stacked triple. The conservation of these positions suggests some function; however, there is currently no obvious interaction. It is possible that the interaction is transient and therefore has not been identified.

Position 971 Positions the 970 Loop.

The position of A964 in the loop may be responsible for flipping out G971 as well as helping form the triplet involving positions U965, A969, and C970. Position 971 makes six hydrogen bonds within a pocket formed by positions 949, 950, 1363, 1364, and 1365 in 16 S rRNA. This extensive hydrogen bonding with the exposed nucleotide, 971, may serve to limit the mobility of the 970 loop and to connect the movement of the 970 loop to the movement of the ribosome during protein synthesis. The ribosome is known to undergo conformational changes during translation (Frank and Agrawal, 2000; Ogle et al., 2002; Valle et al., 2003; VanLoock et al., 2000). G971 may maintain the positioning of the 970 loop and coordinate its movement with the ribosome.

Reagents.

Restriction enzymes, ligase, and calf intestine alkaline phosphatase were from New England Biolabs and from Gibco-BRL. Sequencing modified DNA polymerase, nucleotides, and sequencing buffers were from Epicenter Technologies. Oligonucleotides were either purchased from Midland Certified Reagent Company (Midland, Tex.) or IDT DNA (Coralville, Iowa). AmpliTaq DNA polymerase and PCR reagents were from Perkin-Elmer-Cetus (Boston, Mass.).

Plasmids and Mutagenesis.

This plasmid contains the *E. coli* rrnB operon, with the 16 S rRNA containing an altered anti-Shine-Dalgarno (ASD) sequence, under the control of a lacUV5 promoter. The plasmid also contains the chloramphenicol acetyltransferase (CAT) and green fluorescence protein (GFP) reporter genes with Shine-Dalgarno (SD) sequences complimentary to the ASD sequence (Hui and de Boer, 1987; Hui et al., 1987; Lee et al., 1996; Shine and Dalgarno, 1974) of the plasmid 16 S rRNA. Therefore, the CAT and GFP mRNAs are specifically translated by the plasmid-encoded 30S subunits. The plasmid-encoded 30S subunits cannot translate normal host mRNAs, so mutations within 16S rRNA only affect translation of the reporter genes and do not affect cell viability. The CAT gene can be used to select clones with sub-optimal function, while the GFP can be used for high throughput functional assays.

All mutagenesis was performed using a recombinant polymerase chain reaction (PCR) (Higuchi et al., 1988; Mullis et al., 1986; Mullis and Faloona, 1987) with primers 970 loop mut (5'-GGA TGT CAA GAC CAG GTA AGG TTC TTC GNN NNN NNN CGA ATT AAA CCA CAT GCT CCA CCG-3') and 16S AvrII (5'-ACG TCG CAA GAC CAA AGA GG-3') for PCR 1 and 970 loop R (5'-CCT GGT CTT GAC ATC CAC GG-3') and 16S XbaI (5'-GGT CGG CGA CTT TCA CTC AC-3') for PCR 2.

Construction of mutations at 970 region in 16 S rRNA: All mutations were constructed in a modified version of pRNA123 containing a lethal mutation at the 970 loop (964-UCCCCCGU-971). Random mutations were introduced in the 16 S rRNA of pRNA123 by replacing the wild type sequence between the BglII and BstEII cut sites with a fragment containing PCR directed random mutations.

Selection of Functional Mutants.

Transformants were incubated at 37° C. with shaking in SOC medium for one hour to allow for the expression of the $Amp^R$ gene. A sample of the culture was plated on LB+Amp 100 plates to determine the transformation efficiency. IPTG (isopropyl-β-D-thiogalactopyranoside) was then added to the remaining culture to a concentration of 1 mM and incubated at 37° C. with shaking for an additional three hours to induce rRNA synthesis. The culture was then plated on LB-Amp100-IPTG agar with 100 µg/ml chloramphenicol. A survivor rate of approximately 10% was observed. Survivors were randomly selected and sequenced in statistically significant numbers.

Construction of Single Mutants in 16S rRNA.

Single mutants were constructed in pRNA272, a derivative of pRNA123 (Lee et al., 1996; Lee et al., 1997), the construction of which will be described later. The pRNA272 construct contains a unique ApaI site in the 16 S rRNA. Single mutants at positions 966 and 967 were made using site directed PCR and cloned into pRNA272 using ApaI and RsrII restriction enzymes. Mutations at position 1400 were made using site directed PCR and cloned into pRNA272 using XbaI and BsrGI restriction enzymes. Each mutant was sequenced to confirm the presence of the mutation and assayed for function using GFP assays.

Construction of Double Mutants in 16S rRNA.

Double mutants were constructed from single mutant constructs in pRNA272. Both the 1400 and 967 single mutants were digested with RsrII and XhoI. Fragments containing the single mutations were ligated together to form the double mutants. These clones were then transformed into *E. coli* DH5 cells. Each mutant was sequenced to confirm the presence of the mutation and assayed for function using GFP assays.

Bacterial Strains and Media.

All plasmids were maintained and expressed in *E. coli* DH5 (supE44, hsdR17, recA1, endA1, gyrA96, thi-1, relA1) (Hanahan, 1983). Cultures were maintained in LB medium (Luria and Burrous, 1957) or LB medium containing 100 µg/ml ampicillin (LB-Ap100). To induce synthesis of plasmid-derived rRNA from the lacUV5 promoter; IPTG (isopropyl-beta-D-thiogalactopyranoside) was added to a final concentration of 1 mM at the times indicated in each experiment. Strains were transformed by electroporation (Dower et al., 1988) using a Gibco-BRL Cell Porator. Unless otherwise indicated, transformants were grown in SOC medium (Hanahan, 1983) for one hour prior to plating on selective medium to allow expression of plasmid-derived genes.

Green Fluorescence Protein (GFP) Assay.

Overnight cultures of mutants, as well as a wild type control, were grown in LB-Amp100 at 37° C. with shaking for 12-16 hours. The overnight cell cultures were then diluted 1:100, induced in LB-Amp 100+IPTG (1 mM) medium, and grown at 37° C. with shaking for 24 hours. After 24 hours, 500 µL of the culture was aliquoted into 1.7 mL microcentrifuge tubes and centrifuged at approximately 11,000×g for 1 minute to pellet the cells. The cell pellet was washed twice with 500 µL of HN buffer (20 mM HEPES pH 7.4 and 0.85% NaCl) and resuspended in 500 µL of HN buffer. After cells were resuspended, 100 µL of cell suspension was transferred to a 96 well clear bottom microtiter plate. The cell density (λ=600 nm) was measured using a SPECTRAmax 190 (Molecular Devices, Sunnyvale, Calif.) and fluorescence (excitation=395 nm and emission=509 nm) was measured using a SPECTRAmax GEMINI (Molecular Devices, Sunnyvale, Calif.). For each culture, fluorescence was divided by $A_{600}$ and presented as a percentage of the wild type. Values represent the average of at least three assays on three separate cultures done on different days.

Example #8

The Role of Helix 45 in 16S Ribosomal RNA

Helix 45 of *Escherichia coli* 16 S rRNA contains three modified nucleotides, $m^2$G1516, $m_2^6$A1518, and $m_2^6$A1519. The dimethyladenosines at positions 1518 and 1519 are conserved in all organisms with few exceptions. Deletion of the KsgA methylase, which methylates positions 1518 and 1519, has only a slight effect on growth rate as well as conferring resistance to the antibiotic kasugamycin. Biochemical and structural studies have shown helix 45 interacting with the decoding region, forming intersubunit bridge B2b, and binding to initiation factor 3. To study the role of helix 45 (positions 1512-1523) a saturation mutagenesis was performed and 116 functional mutants were isolated and analyzed. A non-random nucleotide distribution was observed at all positions except 1515 and 1520. Six functional mutations at positions 1518 and 1519 were isolated in the selected pool indicating that compensatory changes in the helix may reduce the nucleotide constraint at these positions. To see the effect of mutations at just positions 1518 and 1519, single and double mutations were made. All single and double mutants exhibited a total loss of function. A ksgA strain was constructed to determine if loss of methylation effected the function of mutations in helix 45. The loss of the KsgA methylase resulted in a reduced initiation rate.

Ribosomal RNA (rRNA) plays a major role in the catalytic functions attributed to ribosomes during protein synthesis. Phylogenetic analysis of the numerous rRNA sequences available has provided much information about the conservation of RNA sequences and structures. Helix 45, in 16 S rRNA, is conserved among the three domains (Cannone et al., 2002) (FIG. 5.1). In *Escherichia coli*, the stem of helix 45 contains a conserved U1512:G1523 wobble base pair and a A1513:U1522 Watson-Crick base pair while the loop contains three conserved nucleotides at positions 1517, 1518, and 1519. The loop also contains three modified nucleotides: an N2-methylguanosine ($m^2$G) and two adjacent N6,N6-dimethyladenosines ($m_2^6$A) at positions 1516, 1518, and 1519 respectively (Cannone et al., 2002) (FIG. 5.1). The stem mismatch has been proposed to be a recognition factor for the KsgA methylase (Formenoy et al., 1994) while the loop nucleotides are involved in ribosome subunit association (Yusupov et al., 2001), IF3 binding (Ehresmann et al., 1986; Pioletti et al., 2001), and resistance to the antibiotic kasugamycin (Helser et al., 1971; Helser et al., 1972; Van Buul et al., 1983) (FIG. 5.1).

The methylase, responsible for dimethylation of positions 1518 and 1519, is encoded by the ksgA gene in *E. coli* and comparative homologs have been identified in bacteria (Housen et al., 1997; Van Buul et al., 1983) and eukaryotes (Lafontaine et al., 1994; Seidel-Rogol et al., 2003) while putative homologs have been identified in archaea (O'Farrell et al., 2004). In ksgA mutants, an increase in doubling time, an increased need for initiation factor 3 (IF3), decreased translational fidelity, and resistance to kasugamycin (Igarashi et al., 1981; Poldermans et al., 1979; van Buul et al., 1984b) was seen. The ksgA ortholog in yeast (dim1), however, is essential for function (Lafontaine et al., 1994). In yeast, Dim1 has two known functions, methylation of positions 1518 and 1519 and processing of 18 S rRNA (Lafontaine et al., 1995). Mutations in Dim1 that uncouple the two functions and retain only the rRNA processing function are still viable and show no apparent growth defects implying that dimethylation was not required for function (Lafontaine et al., 1998). So, KsgA and the methylations at positions 1518 and 1519 are not essential for function.

The U1512:G1523 wobble base pair is an important recognition site for KsgA. Mutation of this wobble base pair results in a 20-80% decrease in methylation of positions 1518 and 1519, but not a complete inhibition of methylation (Formenoy et al., 1994). Therefore, the methylase may recognize a structure formed by this wobble pair rather then the nucleotides.

The nucleotide identity and methylation of positions 1518 and 1519 are universally conserved. To date, only three exceptions have been identified: *Saccharomyces cerevisiae* mitochondrial 12 S rRNA that does not contain any methyl groups on the two adenosines (Klootwijk et al., 1975) and the *Euglena gracilis* chloroplast rRNA and the archaea *Sulfolobus solfataricus* 16 S rRNA both of which contain only one dimethylated adenosine (Noon et al., 1998; Schnare et al., 1992; Steege et al., 1982; Van Buul et al., 1984a). In vitro mutational studies of 1518 and 1519 have resulted in little effect on ribosome reconstitution, but most activity was partially decreased (Cunningham et al., 1990). Although, no activity was completely abolished, initiation-dependent formation of the first peptide bond was inhibited by two thirds in the 1518 mutants (Cunningham et al., 1990). Using a system in which all chromosomal rRNA operons have been deleted (Asai et al., 1999), Vila-Sanjurjo et al. (1999) found that a mutation at position 1519 not only confers a kasugamycin resistance phenotype, but does not significantly effect ribosome function. In yeast, however, A1518G and A1519G mutations allowed proper processing of the rRNA, but did not support growth (Lafontaine et al., 1995).

The loop nucleotides of helix 45 (1516-1519) form intersubunit bridge B2b and interact with the stem of the 1915 loop (helix 69; 1919-1920) in the 23 S rRNA (Yusupov et al., 2001). Ehresmann et al. (1986) identified a cross-link between positions 1506-1529 and IF3 using trans-diamminedichloroplatinum(II). A recent crystal structure by Pioletti et al., however, showed that the IF3 C-terminus was in contact with positions 1532-1534. Although, it is not a direct contact with helix 45, this contact may affect the mobility of helix 45, inhibiting the formation of bridge B2b and preventing subunit association (Pioletti et al., 2001).

To understand the role of helix 45 modifications in protein synthesis, a saturation mutagenesis experiment on nucleotides 1512-1523 was performed either in the presence or absence of the KsgA methylase.

A saturation mutagenesis experiment was performed on 12 nucleotides in helix 45 (positions 1512-1523). All mutations were introduced by PCR and cloned into the plasmid pRNA123 (Lee et al., 1996; Lee et al., 1997). This plasmid contains the *E. coli* rrnB operon under the control of a lacUV5 promoter. The anti-Shine-Dalgarno (ASD) sequence of the 16 S rRNA has been altered so that normal host mRNA no longer binds. The plasmid also contains the chloramphenicol acetyltransferase (CAT) and green fluorescence protein (GFP) reporter genes with Shine-Dalgarno (SD) sequences complimentary to the altered ASD sequence (Lee et al., 1996) of the plasmid 16 S rRNA. The CAT and GFP mRNAs are specifically translated by the plasmid-encoded 30 S subunits. The plasmid-encoded 30 S subunits cannot translate normal host mRNAs, so mutations within 16 S rRNA only affect translation of the reporter genes and do not affect cell viability.

Unselected clones were sequenced to confirm that each mutated position was random (data not shown). Clones were then selected for function by plating on LB media containing Amp (100 μg/mL), IPTG (1 mM), and chloramphenicol (150 μg/mL). A total of 116 unique clones were isolated, sequenced, and assayed for function (Table 1).

Statistical Analysis.

A non-random nucleotide distribution was observed for all positions except 1515 and 1520 in the selected pool (FIG. 5.4). All possible mutations were found for each position except for positions 1512, 1517, 1518, and 1519. With the exception of positions 1517, 1518, and 1519 greater variability than in the phylogenetic analysis was found at each position. Despite the increased variability seen, nucleotide preference was still evident in the selection (FIG. 5.4). Positions 1512 and 1523 preferred the wild-type uridine and guanosine, respectively. Positions 1513, 1514, 1516 and 1522 also preferred the wild-type sequence, but show increased variability from the phylogenetic analysis. Finally, positions 1515, 1520 and 1521 demonstrated a random nucleotide distribution indicating that nucleotide identity was not essential for function at these positions.

To identify nucleotide interactions in helix 45, a covariation analysis was performed. Very strong covariations between positions 1513:1522 ($p=2.3\times10^{-18}$), 1514:1521 ($p=4.1\times10^{-25}$), and 1515:1520 ($p=2.8\times10^{-20}$) were seen, indicating base pairing (FIG. 5.5). Weaker covariations were identified between positions 1512 and 1523 ($p=7.0\times10^{-4}$), 1513 and 1515 ($p=1.8\times10^{-2}$), 1515 and 1522 ($p=2.8\times10^{-2}$), and 1521 and 1523 ($p=1.1\times10^{-2}$). Covariations between position 1517 and positions 1516 ($p=4.8\times10^{-3}$), 1518 ($p=7.5\times10^{-6}$), and 1523 ($p=1.3\times10^{-3}$) as well as between positions 1518 and positions 1520 ($p=2.5\times10^{-3}$) and 1521 ($p=3.1\times10^{-2}$) were also identified.

Of the 116 selected mutants, a subset of 57 mutants with more than 30% function of the wild-type were subjected to statistical analysis. This subset of higher functional mutants showed a slight reduction in variability at some positions, but this reduced variability did not appear to be significant. Covariation analysis of just the highly functional mutants retained the strong covariation between positions 1513:1522 ($p=8.4\times10^{-10}$), 1514:1521 ($p=1.4\times10^{-9}$), and 1515:1520 ($p=1.5\times10^{-8}$). The weak covariations between positions 1517 and 1523 ($p=2.2\times10^{-5}$), between positions 1517 and 1518 ($p=9.6\times10^{-4}$), and between positions 1518 and 1520 ($p=4.2\times10^{-3}$) were also maintained. The remaining covariations (between 1513: 1515, 1515:1522, 1516:1517, 1518:1521, and 1521:1523) identified in the entire pool were not seen possibly due to the small sample size. This subset of mutants maintain the requirement for formation of the stem. Furthermore, the covariations between the loop and stem of helix 45 may indicate a role for the stem in positioning of the loop.

Although rare, 6 mutations at positions 1518 and 1519 were found in the selected pool. Of these six mutations, four were A1518G mutations that ranged in function from ~35-90%. All four of these clones, however, also contain a C1520A mutation. Surprisingly, the highest functional clone (92% function) contained two mutations: A1518G and C1520A. The remaining two mutations were A1519G (73% function of wild type) and A1519U (12% function of wild type). Both of the A1519 mutants had additional mutations in the closing base pair of the loop. Although single mutations at positions 1518 and 1519 are lethal, it appears that compensatory mutations in the stem can restore function.

KsgA Methylase.

To determine the effect of methylation on mutations in helix 45, an isogenic ksgA strain was constructed using a P1 transduction between DH5 and JM101 ksgA19. This ksgA strain (AAS3) was used to repeat the saturation mutagenesis of helix 45. The number of survivors in the ksgA strain was significantly reduced from the ksgA$^+$ strain when selected at 150 µg/ml chloramphenicol (concentration used to select in ksgA$^+$ strain). To increase the number of survivors, the chloramphenicol concentration was decreased to 50 µg/ml. The decrease in chloramphenicol did not significantly increase the number of survivors. To understand the cause of the reduced survivor rate, survivors of the selection in the ksgA$^+$ strain were transformed into the ksgA strain. GFP assays were performed with these mutants in both the ksgA$^+$ and ksgA strain (Table 5.2). Of the 12 mutants tested, 9 showed a slight increase in function. Therefore, the majority of the mutants selected in the ksgA$^+$ stain are functional in the absence of the KsgA methylase despite the low survival rate seen during the selection. The three remaining mutants, however, resulted in a significant loss of function. These three clones contain adenosines at positions 1518 and 1519, but contain other mutations in the stem.

The ΔG and secondary structure for each clone was calculated using Mfold (Mathews et al., 1999; Zuker, 2003). Clones that were non-functional in the ksgA strain had an average calculated ΔG of 2.3 (FIG. 5.7), while the average calculated ΔG of functional clones is −0.86. In addition to the decreased stability, the structure of clone 102 incorporates position 1519 into a base pair that would not be possible in the presence of methyl groups at this position (FIG. 5.7). The mutations were also modeled using software developed by Dr. John SantaLucia Jr., Wayne State University. Modeling of these mutants resulted in changes in the helix which may be responsible for the loss of function. This suggests that mutations in the stem, in the absence of the methylation, may cause the formation of unstable, non-functional structures.

To resolve the inconsistencies between the survivor rate in the ksgA strain and the function of ksgA$^+$ selected mutants in the ksgA strain, a GFP induction curve was performed. Induction of a growing culture with IPTG (1 mM) at $OD_{600}$=0.1 should produce a sigmoidal curve of GFP fluorescence as plasmid derived ribosomes are produced and translate the GFP mRNA. The difference in fluorescence between the two strains at the start of the curve indicates the difference in the rate of initiation, while the slope of the curve indicates the elongation rate. As shown in FIG. 5.6, in the absence of the methylase, there is a reduction in the rate of initiation and a reduction in the elongation rate. This reduction in initiation and elongation rates is seen even in the AAS3 strain with the wild type helix 45 sequence, implying that it is the loss of methylation, specifically, that is responsible for the growth defect. Mutations in helix 45, in the absence of the KsgA methylase, may compound this defect. This defect may be responsible for the low survivor rate observed during selection. Cultures for GFP assays are allowed to grow for 24 hours before assaying for fluorescence allowing the ribosomes ample time to initiate protein synthesis. During selection, though, the culture is only induced for 3 hours before being plated on chloramphenicol containing medium. At 3 hours after induction, there is a 25% difference in protein synthesis between the ksgA$^+$ and the ksgA strains (FIG. 5.6). Consequently, three hours may not be enough time to produce enough CAT protein to provide resistance to chloramphenicol during the selection and no survivors would be observed.

Site-Directed Mutations.

Positions 1512, 1523, 1518, and 1519 were targeted for study because of their almost universal conservation and the lack of variability. Single and double mutants between positions 1518 and 1519 and between positions 1512 and 1523 were constructed. All of the double mutations between positions 1512 and 1523 resulted in a 0-80% function of the wild-type (FIG. 5.2). The most deleterious effect was observed with the U1512A:G1523A double mutant (1.8% function). A significant reduction in function was also observed with the U1512A:G1523C (7.6% function), U1512G:G1523A (23.1% function), and U1512U:G1523U (13.1% function) mutants. Other double mutants resulted in functions ranging from 30 to 80% function of the wild-type. The highest functional mutant (81% function) was a U1512C single mutant while the second highest functional mutant was U1512G:G1523C (62% function). Therefore, the ability to form a Watson-Crick base pair is an important, but not the only determinant for function. A slight preference for pyrimidines was noticed at position 1512, while position 1523 showed no preference. Any single mutation at position 1523, however, reduced function by approximately 45%. All single and double mutations at positions 1518 and 1519, however, were lethal (FIG. 5.3).

Helix 45 contains seven conserved nucleotides and three modified nucleotides. Helix 45 has been cross-linked to initiation factor 3 (IF3), the 790 loop of helix 24, shown to affect tRNA binding and selectivity, and cross-linked to the 1915 loop of helix 69 in the 23 S rRNA forming intersubunit bridge B2b. Mutations were made to identify the structurally and functionally important nucleotides in this helix.

Positions 1514:1521 and positions 1515:1520 are involved in base pairing as suggested by the phylogenetic analysis. Nucleotide identity is not conserved, but the ability to base pair is maintained and is important for function. Positions 1513 and 1522 also seem to be base paired, but nucleotide identity is conserved. Although, the role of 1513:1522 is unclear, this base pair may be part of the KsgA methylase recognition site or may help stabilize the U1512:G1523 wobble base pair. Covariation analyses indicate that these base pairs may allow for the correct positioning of the loop.

Nucleotide identity at positions 1512 and 1523 is conserved in the phylogenetic analysis as well as in our mutagenesis analysis. Mutations at the U1512:G1523 wobble pair, show a preference for pyrimidines at position 1512 and a preference for guanosine at position 1523. Pyrimidine-pyrimidine or pyrimidine-purine pairings were generally more functional than purine-purine pairings, suggesting that this type of interaction results in a conformational change that interferes with function. The nucleotide preferences seen in the double mutants were also seen in the mutagenesis of helix 45. Covariations between position 1523 and positions 1517 and 1521 indicate some interaction with the U:G wobble pair and helix 45. The conservation of the U1512:G1523 wobble pair may be due to the unique properties of the U:G wobble pair. The U:G wobble pair allows for several unique characteristics: 1) unique functional groups are exposed into the major and minor groove 2) its thermodynamic stability approaches that of Watson-Crick base pairs and 3) helixes containing U:G wobble pairs are more flexible then Watson-Crick base pairs and may allow for recognition by induced fit (Allain and Varani, 1995; Varani and McClain, 2000). Analysis of the change in ΔG between the wild-type sequence and the mutants did not indicate any correlation between free energy and function implying that structure is more important than stability (data not shown). Of the double mutants, the C1512: G1523 mutant retained the highest function. This mutation maintains the structure of the helix but decreases its flexibility. Therefore, the U:G wobble pair may provide the necessary structure and flexibility required for optimal function of this helix.

The conservation of positions 1517, 1518, and 1519 are probably due to their interaction with positions in helix 44, connecting these two helices together. These three stacked bases interact with the minor groove formed by positions 1404-1406 and positions 1496-1497 of helix 44 (FIG. 5.8). Adenosine is the only base without a functional group on the sugar side of the base, substitution of adenosine with any other base would place a functional group into the minor groove of helix 44 causing either a conformational change in one or both helices or a disruption of binding. Therefore, as seen in the single and double mutants at positions 1518 and 1519, mutations at these positions are lethal. These results are consistent with mutations at these positions in yeast but in contrast to the results of Vila-Sanjurjo et al. (1999) who found that mutations at position 1519 had only minor effects on cell growth. A1518G mutations, however, were identified in the selected pool. All A1518G mutations also contained a C1520A mutation resulting in a G1518, A1519 and A1520 sequence. Formation of alternate loop structures may allow these two adenosines to interact with helix 44 in a similar manner to the wild type sequence. Mutations A1519G and A1519U were also identified in the selected pool. These clones contained additional mutations in the closing base pair (1515:1520) of the loop, resulting in a C:U mismatch for the U1519 clone (12%) and a G:A mismatch for the G1519 clone (73%). A mismatch in the closing base pair of the loop would decrease loop constraints and allow greater flexibility of the loop possibly allowing partial function. This suggests that mutations at positions 1518 and 1519 may be tolerated in the presence of compensatory mutations in helix 45.

The conservation of methylation at positions 1518 and 1519 may be due to their stabilizing effects on formation of the tetraloop. Loss of these methyl groups may result in reduced stability of the loop and the formation of non-functional structures. In fact, mutant 102 when modeled with Mfold (Mathews et al., 1999; Zuker, 2003) showed that the most stable secondary structure involves a base pair between positions 1514 and 1519 (FIG. 5.7), inhibiting the formation of the loop. In the presence of methylation at position 1519, this base pair would not be allowed, possibly allowing the formation of the tetraloop.

Position $m^2$ G1516 is one of the modified nucleotides found in the GNRA tetraloop at helix 45. Unlike the conserved dimethyadenosines at positions 1518 and 1519, the $m^2$ G1516 is not conserved in the phylogenetic analysis, although a preference for guanosine at this position was observed in the selected mutant pool. Thermodynamic studies have shown that in the absence of the dimethyl adenosines at positions 1518 and 1519, an $m^2$ G is iso-energetic to G within a GNRA tetraloop and did not have an effect on stability (Rife et al., 1998). Nucleotide identity at positions 1517, 1518, and 1519 is conserved as are the modifications at positions 1518 and 1519. The crystal structures (Ogle et al., 2001; Wimberly et al., 2000; Yusupov et al., 2001) of the 30 S subunit show these three positions as being stacked and interacting with helix 44 as well as with helices 69 and 71 of the 50 S subunit to form intersubunit bridge B2b. Modeling studies of the loop, including the modified nucleotides, suggests that the dimethyl groups may aid in stabilizing the stacking of positions 1517, 1518, and 1519. The modification at position 1516 allows for a hydrophobic interaction with position 1519, providing stability to the loop as well as adding to the hydrophobic region on the minor groove side of the loop.

The hydrophobic region on the minor groove side of the dimethyl loop caused by the five methyl groups is covered by position 793 of the 790 loop (FIG. 5.9). This hydrophobic interaction may help position the 790 loop for additional interactions with helix 44 and 45. Although the hydrophobic interaction between position 793 and the dimethyl adenosine loop may be important for positioning of the 790 loop, other interactions between the 790 loop and helix 44 and 45 would probably still occur in the absence of this interaction. These additional interactions to position these two regions together may explain why methylation at these sites is not essential for function. Removal of the KsgA methylase, which is responsible for the dimethylation of positions 1518 and 1519 result in a slight defect in initiation and elongation. The observed growth defects agree with previous work that identified defects in initiation (Poldermans et al., 1979) and an increase in translational fidelity (van Buul et al., 1984b) in the absence of KsgA. The loss of methylation may alter the stability or conformation of the 790 loop-helix 45-helix 44 complex resulting in a change in IF3 binding and consequently a change in initiation. Binding of IF3 has been shown to inhibit a 793:1517 cross-link indicating that binding of IF3 changes the structure of helix 45 and the 790 loop, that presumably would be required to reform into the original structure during elongation. The loss of methylation may affect the restructuring of this region after initiation and therefore affect the elongation process.

In the 30 S crystal structure, helix 45 is tightly packed between the 790 loop and helix 44. The 790 loop is involved in tRNA binding in the P-site and the E-site as well as interacting with the 690 loop. The 690 and 790 loops are important for E-site tRNA binding in the 30 S subunit, which has been shown to be allosterically connected to the A-site. Helix 45 helps form and stabilize the interaction between the 790 loop and helix 44. The coupling of these two regions may be important for information exchange about the state of the A and E sites as well as the coordinated movement of the subunit explaining the conservation of helix 45 throughout phylogeny.

Reagents.

Restriction enzymes, ligase, and calf intestine alkaline phosphatase were from New England Biolabs and from Gibco-BRL. Sequencing modified DNA polymerase, nucleotides, and sequencing buffers were from Epicenter Technologies. Oligonucleotides were either purchased from Midland Certified Reagent Company (Midland, Tex.) or IDT DNA (Coralville, Iowa). AmpliTaq DNA polymerase and PCR reagents were from Perkin-Elmer-Cetus (Boston, Mass.).

Plasmids and Mutagenesis.

All mutagenesis was performed using the polymerase chain reaction (PCR) (Higuchi et al., 1988; Mullis et al., 1986; Mullis and Faloona, 1987).

Construction of Helix 45 Mutations in 16 S rRNA.

All mutations were constructed in pRNA123. Helix 45 was randomly mutated using site directed PCR with primers DMA mut12 (5'-ACT GGG GTG AAG TCG TAA CAA GGT AAC CGN NNN NNN NNN NNC GGT TGG ATC ATG GGA TTA-3') and 16S XbaI (5'-GGT CGG CGA CTT TCA CTC AC-3'). Random mutations were introduced in the 16 S rRNA of pRNA123 by replacing the wild type sequence between the XbaI and BstEII cut sites with a fragment containing PCR directed random mutations.

Selection of Functional Mutants.

Transformants were incubated at 37° C. with shaking in SOC medium for one hour to allow for the expression of the Amp$^R$ marker. A sample of the culture was plated on LB+Amp (100 µg/ml) plates to determine the transformation efficiency. IPTG (isopropyl-β-D-thiogalactopyranoside) was then added to the remaining culture to a final concentration of 1 mM and incubated at 37° C. with shaking for an additional three hours to induce rRNA synthesis. The culture was then plated on LB+Amp (100 µg/ml)+IPTG (1 mM) agar with 150 µg/ml chloramphenicol. Survivors were randomly selected and sequenced in statistically significant numbers.

Construction of Double Mutants in 16S rRNA:

Single and double mutants were constructed in pRNA123 (Lee et al., 1996; Lee et al., 1997). All possible mutations between positions 1512 and 1523 and between positions 1518 and 1519 were made using site directed PCR using 16S DMA N1512/N1523 (5'-ACT GGG GTG AAG TCG TAA CAA GGT AAC CGN AGG GGA ACC TNC GGT TGG ATC ATG GGA TTA-3') and 16S DMA N1518/N1519 (5'-ACT GGG GTG AAG TCG TAA CAA GGT AAC CGT AGG GGN NCC TGC GGT TGG ATC ATG GGA TTA-3') as the forward primers and 16S XbaI as the reverse primer for both PCR reactions. The products were cloned into pRNA123 using the BstEII and XbaI restriction enzymes. Each mutant was sequenced to confirm the presence of the mutation and assayed for function using GFP assays.

Bacterial Strains and Media.

All plasmids were maintained and expressed in *E. coli* DH5 (supE44, hsdR17, recA1, endA1, gyrA96, thi-1, relA1) (Hanahan, 1983) or *E. coli* AAS3 (supE44, hsdR17, recA1, endA1, gyrA96, thi-1, relA1, ksgA).

Construction of a DH5 ksgA Strain.

A P1 lysate grown on MC86 thr::tn10 was transduced into ksgA strains JM101 ksgA19 using standard methods. A P1 lysate grown on the resulting JM101 ksgA19 thr::tn10 strain was then used to transduce into the a DH5 strain containing the plasmid pMAS53 (recA$^+$) and plated on agar containing 1× Medium E, 0.4% glucose, 0.1% CAA, 0.2×LB, 5 µg/ml thiamine, 40 µg/ml chloramphenicol, and 50 µg/ml tetracycline. The disruption of the ksgA gene, in the new strain (AAS3), was confirmed by PCR. To confirm that the ksgA methylase was inactivated, the strain was grown on kasugamycin to determine the level of resistance. The 16 S rRNA from the stain was also digested into nucleosides and run through HPLC to confirm the lack of dimethyladenosines.

Cultures were maintained in LB medium (Luria and Burrous, 1957) containing 100 µg/ml ampicillin (LB-Ap100). To induce synthesis of plasmid-derived rRNA from the lacUV5 promoter; IPTG (isopropyl-beta-D-thiogalactopyranoside) was added to a final concentration of 1 mM at the times indicated in each experiment. Strains were transformed by electroporation (Dower et al., 1988) using a Gibco-BRL Cell Porator. Unless otherwise indicated, transformants were grown in SOC medium (Hanahan, 1983) for one hour prior to plating on selective medium to allow expression of plasmid-derived genes.

Green Fluorescence Protein (GFP) Assay.

Overnight cultures of mutants, as well as a wild type control, were grown in LB-Amp100 at 37° C. with shaking for 12-16 hours. The overnight cell cultures were then diluted 1:100, induced in LB-Amp 100+IPTG (1 mM) medium, and grown at 37° C. with shaking for 24 hours. After 24 hours, 500 µL of the culture was aliquoted into 1.7 mL microcentrifuge tubes and centrifuged at approximately 11,000×g for 1 minute to pellet the cells. The cell pellet was washed twice with 500 µL of HN buffer (20 mM HEPES pH 7.4 and 0.85% NaCl) and resuspended in 500 µL of HN buffer. After the cells were resuspended, 100 µL of the cell suspension was transferred to a 96 well clear bottom microtiter plate. The cell density (λ=600 nm) was measured using a SPECTRAmax 190 (Molecular Devices, Sunnyvale, Calif.) and fluorescence (excitation=395 nm and emission=509 nm) was measured using a SPECTRAmax GEMINI (Molecular Devices, Sunnyvale, Calif.). For each culture, fluorescence was divided by $A_{600}$ and presented as a percentage of the wild type. Values represent the average of at least three assays on three separate cultures done on different days.

Example #9

Identification of Functionally Important Nucleotides in the *E. Coli* 16S rRNA

To identify all functionally important nucleotides in the *Escherichia coli* 16 S ribosomal RNA, a mutational library was created using error-prone PCR and selected for sub-optimal function. Approximately 2600 clones, with an average of four mutations per clone, were analyzed, which resulted in an average of seven mutations at each mutated position of the 16 S ribosomal RNA (positions 20-1503). Positions where nucleotide identity is important for function result in sites with zero or few mutations. Comparison with known functionally important nucleotides was used to test the ability of the library to identify these sites. The mutation library identified known as well as previously unknown functional nucleotides. A model of the *E. coli* 30 S subunit was used to identify interactions between conserved positions.

Ribosomes are a responsible for translation of messenger RNA (mRNA) into protein. The *Escherichia coli* 70 S bacterial ribosome can be disassociated into two asymmetrical subunits, a small (30 S) subunit, composed of 16 S ribosomal RNA (rRNA) and 21 ribosomal proteins (rproteins), and a large subunit (50 S), composed of 23 S rRNA, 5 S rRNA, and 34 rproteins. The small subunit is responsible for decoding and maintaining the accuracy of the tRNA-mRNA interaction while the large subunit contains the peptidyl transferase center, the site of peptide bond formation. Biochemical studies (Green and Noller, 1997; Noller et al., 1992) and the ribosome crystal structures (Nissen et al., 2000; Wimberly et al., 2000; Yusupov et al., 2001) have shown that the RNA is the catalytically active component of the ribosome; therefore, the ribosome is a ribozyme.

Comparative sequence analysis of rRNA sequences from numerous different organisms has shown that the overall secondary structure of the rRNA is conserved within all domains of life. Additionally, analysis of these rRNA sequences has identified conserved nucleotides that are believed to important for ribosome function. This analysis, however, employs genomic or organelle rRNA sequences. These sequences are constrained by their essential role in protein synthesis. As a result, very little or no sequence variation is observed in rRNA regions believed to be functionally important, since even subtle changes to the structure surrounding critical residues may reduce function, affect fidelity, and reduce fitness. Additionally, these conserved sites may be structurally important rather than functionally important, serving to position functionally important groups in the correct orientation. Mutations at these sites may not be lethal, but may result in a ribosome with partial function. This results in a loss of fitness and therefore would not be identified in the phylogenetic analysis. Analysis of rRNA sequences with sub-optimal function would allow for greater variability and allow for identification of positions that are truly essential for function.

To address this issue, the 16 S rRNA from *Escherichia coli* was randomly mutated using error-prone PCR and selected for mutants with suboptimal function. A total of 2593 functional mutants with an average of 4.1 mutations per sample were used to create a mutation library. This translated to an average of seven mutations at each mutated position of the 16 S rRNA. A range from 0 to 37 mutations per position with a mode of 2 and a median of 6 was observed in the library. From this mutation library, 67 conserved regions of the 16 S rRNA were identified that come together in the crystal structure to form 16 functionally important clusters.

The *E. coli* 16 S rRNA was PCR amplified in the presence of manganese (0.45 mM) to randomly introduce mutations throughout the product and cloned into the pRNA228 vector. pRNA228 is a derivative of pRNA123 (Lee et al., 1996; Lee et al., 1997; Morosyuk et al., 2001) that contains the rrnB operon from *Escherichia coli* under the control of the inducible lacUV5 promoter. The anti-Shine-Dalgarno of the 16 S rRNA has been altered to a sequence that does not recognize and therefore does not translate normal host mRNA (Hui and de Boer, 1987; Hui et al., 1987; Shine and Dalgarno, 1974). The pRNA228 plasmid also contains two reporter genes, chloramphenicol acetyltransferase (CAT) and green fluorescent protein (GFP), both of which contain an altered Shine-Dalgarno sequence complimentary to the altered anti-Shine-Dalgarno sequence of the 16 S rRNA. The plasmid-derived 30 S subunit does not translate normal host mRNA and the host ribosomes do not translate the mRNA of the reporter genes. The CAT gene allows for selection of sequences with partial function, while the GFP gene allows for high throughput assays of mutant function.

Clones were transformed into *E. coli* DH5 (supE44, hsdR17, recA1, endA1, gyrA96, thi-1, relA1) (Hanahan, 1983) and plated on medium containing 25 μg/ml chloramphenicol to select functional mutants. Survivors were spotted on medium containing 25 μg/ml chloramphenicol and sequenced.

Sequences for a total of 2593 clone were incorporated into a mutation library. These clones contained 10,736 total mutations within the 16 S rRNA (positions 20-1503), which is an average of 7.2 mutations at each mutated position. The number of mutations at each position ranged from 0 to 37 with a mode of 2 and a median of 6. A series of three or more sequential nucleotides where each position contained three or less mutations is statistically significant. Two or more sequential nucleotides where each position contains zero or one mutation was also found to be statistically significant. Using these criteria, 40 different, nucleotide groupings were identified and are referred to as regions. These criteria were broadened to also include three or more positions, with three or less mutations, separated from each other by a single position with four or more mutations. These sequences were also identified as regions. A total of 67 conserved regions were identified in the library (Table 6.1). All positions with 3 or less mutations are shown on the *E. coli* 16 S rRNA secondary structure in FIG. 6.1. The conserved regions identified in this study were compared to conserved regions identified by phylogenetic analysis of the 16 S rRNA. Compared with bacterial conservation, a significant decrease of conserved nucleotides was observed in the mutation library (FIG. 6.1). Conserved nucleotides identified in this study, however, show a greater similarity to the conserved nucleotides identified by phylogenetic analysis of all three domains and organelles (3D2O) (FIG. 6.1) (Cannone et al., 2002). Difference between the mutation library and phylogenetic conservation were also seen. Specifically, helices (H) H8, H9, H10, H12, H13, and H21 contained conserved regions in the mutation library but these helices are not conserved in the 3D2O phylogenetic conservation. These differences may be due to specific *E. coli* requirements for ribosomal function. Additional conserved nucleotides that did not fall into a region were also seen in the library. Some of these conserved positions interact with identified regions explaining their conservation. It is unclear if the remaining conserved positions identified in the library are functionally important or a product of random chance.

An *E. coli* 30 S subunit model, based on the *Thermus thermophilus* 30 S subunit crystal structure has been published (Tung et al., 2002). An energy minimized version of this model (Dr. John SantaLucia Jr., personal communication) was used to determine the location of conserved positions in three dimensional space (FIG. 6.2). This model was used to identify interactions between regions (FIG. 6.3). Regions that come together in the tertiary structure to form functionally important units were termed clusters. A total of 16 clusters (figures of all clusters are given in the Appendix) were identified (Table 6.2).

Clusters.

Due to the modular nature of the ribosome, isolated clusters were localized to specific domains, although, two clusters with interactions in different domains were identified. The 5' domain (positions 1-560) contains 4 clusters, the central domain (positions 561-922) contains 5 clusters, while the 3' domain (positions 923-1542) contain 7 clusters.

The 5' Domain.

Cluster 1 includes regions 1, 2, 20, 21, 22, and 23 in the 5' domain as well as region 31 located in the central domain (FIGS. 6.1 and 6.3). Regions 1, 2, 21, 22, and 23 form junction 3 (see FIG. 6.1 for junction numbering), which connects H4, H5, and H15. Regions 20 and part of region 21 form the stem of H14, while region 31 forms the stem and loop of H21. Viewed from the interface, this cluster forms the left side of the ribosome body and interacts with ribosomal proteins S4 and S16 (Appendix). S16 makes significant contacts with the regions in the 5' domain as well as region 31 in the central domain bringing these two domains together. There are only a few contacts between cluster 1 and S4 (Brodersen et al., 2002), implying that cluster 1 is not a major determinant for the binding of S4. Aside from the binding of proteins S4 and S16, cluster 1 also contains H14, which has been identified as a part of intersubunit bridge B8. Intersubunit bridge B8 is an RNA-protein bridge between positions 345-347 and the large subunit protein L146 (Yusupov et al., 2001). The lack of conservation in the H14 loop suggests that bridge B8 involves backbone interactions. The conservation of the stem, however, indicates that positioning of the loop is important for formation of the intersubunit bridge.

Junctions are RNA structural features that allow positioning of helices in the tertiary structure. Regions 7, 8, 14, 16, and 18, in the 5' domain, form junction 5, which connects H7, H11, and H12. This junction along with regions 30 and 32, from the central domain, form cluster 2 (FIGS. 6.1 and 6.3). Cluster 2 interacts with rproteins S16 and S17 in the center of the body (Appendix). S17 is a primary binding protein involved in bringing together the 5' domain and the central domain (Brodersen et al., 2002). S16 is a secondary binding protein with a role similar to that of S17, bringing together the 5' and central domains. The conservation of cluster 2 may be due to the requirement for the formation of binding sites for S16 and S17. Additionally, the conservation of this junction may maintain functionally important positioning of H7, H11, and H12. It is interesting to note that helices separating two closely spaced junctions seem to be specifically conserved (see H5 between junctions 3 and 4, H19 between junctions 1 and 7, H29 between junctions 11 and 12, etc.).

Cluster 3 (FIG. 6.3), composed of regions 3, 5, 6, 9, 10, 11, 12, and 19 (FIG. 6.1), is involved in the binding of S20, a primary binding protein located at the bottom on the 30 S subunit. The majority of the conserved nucleotide in cluster 3 are involved in formation of the S20 binding site rather than direct interaction with the protein (Appendix). In addition to cluster 3, the bottom of H44 also interacts with S20 (Culver and Noller, 1998; Wimberly et al., 2000). The major role of S20 is anchoring the bottom of H44. The bottom of H44, however, was not identified as a region and not included in cluster 3. Although not lethal, the loss of S20 results in defects in subunit assembly (Dabbs, 1979; Ryden-Aulin et al., 1993), translation fidelity (Gotz et al., 1990), and subunit association (Gotz et al., 1989). The top of H44 is known as the decoding region and is the site of translation while the length of H44 is involved in the formation of multiple intersubunit bridges, responsible for holding the 30 S and 50 S subunits together during translation. During translocation, the top of H44 has been shown to move approximately 12 Å (VanLoock et al., 2000). The bottom of H44, however, does not move (Van-Loock et al., 2000), probably due to the anchoring by S20. In the absence of S20, the bottom of H44 is free to move, which may be responsible for the observed defects in translation fidelity and subunit association. Finally, S20, as the only protein located at the bottom of the 30 S subunit, is responsible for nucleating the folding of this region.

The final cluster, cluster 4 (FIG. 6.3), in the 5' domain is composed of regions 25, 26, 27, and 28, which form H18 and the 530 loop (FIG. 6.1). The 530 loop is located in the shoulder of the 30 S subunit and is involved in maintaining the accuracy of translation (O'Connor et al., 1997; Santer et al., 1993; Santer et al., 1995), binding of initiation factor 1 (IF1) (Carter et al., 2001; Dahlquist and Puglisi, 2000), and rprotein S12 (Ogle et al., 2001; Wimberly et al., 2000). Consistent with its multiple roles, the 530 loop is conserved in both the phylogenetic analysis and in the mutation library. The 530 loop is not just functionally conserved, but is also structurally conserved. Specifically, position 530 along with position 1492 (see cluster 16) monitors the second position of the codon-anticodon interaction (Ogle et al., 2001) (FIG. 1.13). To position G530 in the decoding region, H18 forms a pseudoknot structure (Appendix). Base pairing between regions 25, 26 and 28, forms the stem of H18, which causes a bulge of positions 505-510. In the loop, base pairing of 521:528 and 522:527 results in a tetraloop (positions 523-526) which folds to base pair with positions 505-507 to form a pseudoknot (see Chapter 3). Additionally, other conserved nucleotides in the loop aid in positioning and stabilizing G530 for its functional role.

The central domain. H22, containing regions 33, 34, and 37 (FIG. 6.1), forms cluster 5 (FIG. 6.3). Junction 8 connects H20, H21, and H22 to form the binding site for, the primary binding protein, S15 (Appendix). The binding of S15 initiates the folding and structuring of the central domain. Region 33 and conserved positions 748, 750, and 754 base pair and form the bottom of H22 adjacent to the junction. The conservation of these positions is probably due to their role in the formation of the S15 binding site. At the top of H22, conserved position 732 interacts with position 667, in region 34, to pack H23a against H22. This packing interaction allows H22 and H23 to co-axially stack, continuing the folding of the central domain (Agalarov et al., 2000). Regions 34 and 37, at the top of H22, help form the binding site for the S6/S18 dimer.

Clusters 6 and 7 (FIG. 6.3) are formed by interactions between H23 and H24 (FIG. 6.1) and between the functionally important 690 and 790 loops. Cluster 6 is composed of regions 39 and 40 while cluster 7 is composed of regions 36, 38, and 41. The conservation of cluster 7 is most likely due to the interaction between H23 and H24. The interaction between these helices (Appendix) may stabilize the 690 and 790 loops. Although, S6 has a few interactions with region 36, it does not have a major role in stabilizing the interaction between H23 and H24 (Brodersen et al., 2002). S11, however, binds specifically to the K-turn motif formed by H23 and stabilizes this sharp turn (Klein et al., 2001). The C-terminal domain of S11 is extended and interacts with both H23 and H24 at cluster 7, stabilizing this interaction (Brodersen et al., 2002).

The 690 loop is involved in E-site tRNA binding (Doring et al., 1994; Yusupocv et al., 2001) while the 790 loop is involved in both P-site and E-site tRNA binding (Moazed and Noller, 1986; Morosyuk et al., 2001; Yusupov et al., 2001). The 790 loop was conserved in both the phylogentic analysis of the three Domains and two organelles (3D2O) and in this library. The 690 loop, however, was only conserved in the 3D2O phylogenetic analysis. Only position U697 was conserved in the mutational library. Previous saturation mutagenesis studies of the 690 loop, in our lab, has shown that nucleotide identity was important at positions 690, 691, 692, 696, and 697 (Morosyuk et al., 2001). Although the 690 loop is not conserved in the mutation library when considering only positions with three or less mutations, an analysis of the type of mutations found in the library did identify some nucleotide requirements. Positions G691 (6 mutations), A694 (27 mutations), and A695 (17 mutations) had all possible nucleotide substitutions; however, positions G690 (12 mutations) and G693 (7 mutations) excluded C while position U692 (18 mutations) excluded G. Finally, position A696 (7 mutations) only contained purines. The differences between these studies may be due to the fact that the Morosyuk et al. (2001) study was done solely on the 690 loop while keeping the remaining 16 S rRNA constant, excluding the possibility of compensatory mutations. Additionally, these mutants were selected for higher function (selected at a higher chloramphenicol concentration) than in the mutation library.

The role of the 690 loop in the binding of E-site tRNA (Doring et al., 1994; Yusupocv et al., 2001), which is probably mediated through backbone interactions, requires the formation of a functional structure rather then a specific nucleotide interaction. The two conserved nucleotides identified in the 690 loop, positions 697 and 698, are involved in interactions with the 790 loop, implying that interaction with the 790 loop is the reason for their conservation. In addition to its role in the binding of P and E-site tRNA (Doring et al., 1994; Yusupov et al., 2001), the 790 loop also stabilizes mRNA exiting the ribosome (Yusupova et al., 2001), forms an intersubunit bridge B2b with H69 of the 23 S rRNA (Yusupov et al., 2001; Lee et al., 1997), and binds the antibiotics pactamycin and edeine (Dins et al., 2004). The functions of the 790 loop explain its conservation in the mutation library.

Cluster 8 (FIG. 6.3), composed of regions 29, 42, and 45, is located in the center of the 30 S subunit. Regions 29 and 42 form H19, which connects two major junctions, junction 7 connecting H19, H20, H24, and H25 and junction 1 connecting H2, H3, H19, and H27 (FIG. 6.1). Junction 7 orients the major helices in the central domain while the junction 1 orients the entire 5' domain. Although the junctions are not conserved, the formation of H19 may be important to maintain two separate junctions. The structure of H19 is further stabilized by the C-terminal extension of rprotein S12, which makes contacts with the base of H19 and H27 (Appendix). Finally, region 45 forms a pseudoknot with positions 17-19 in the loop of H1. Position 572 of region 29 folds down to interacts with position 19, further stabilizing this pseudoknot.

H27 contains two conserved regions, region 43 and 44 (FIG. 6.1), that form cluster 9 (FIG. 6.3). When viewed from the interface side, cluster 9 is located on the bottom of the platform. Positions 899-900 of the loop dock with the base of H24 (positions 768-770 and 809-811) (Belanger et al., 2002) while positions 900-901 are involved in the formation of intersubunit bridge B2c (Yusupov et al., 2001). It is interesting to note that although positions 898 and 899 in the loop are conserved, the docking site at the base of H24, with the exception of position 769, is not conserved. This is surprising considering that interfering with the tetraloop-receptor binding was shown to effect translational fidelity and subunit association (Belanger et al., 2002). Additionally, the nucleotides in the 900 loop believed to be involved in formation of intersubunit bridge B2c are also not conserved. The stem and the closing base pair, however, are conserved suggesting that formation and positioning of the loop is important for function and that docking into the base of H24 and intersubunit bridge B2c are probably backbone mediated interactions.

The 3' Domain.

The 3' domain forms the head of the 30 S subunit. Although only a third of the total volume of the subunit, this domain contains about half of the rproteins (Brodersen et al., 2002). As a consequence, many of the clusters identified in the 3' domain are protein binding sites. Regions 46, 63, and 64 form two of the three helices (H28, H29, and H43) connected by junction 11 (FIG. 6.1), to compose cluster 10 (FIG. 6.3). Junction 11 forms binding sites for the primary binding protein S7 and the secondary binding protein S9. The binding of S7 is essential for the binding of the remaining rproteins in the head in order to form the functional 3' domain (Brodersen et al., 2002). The conservation of this cluster is also seen in the phylogenetic analysis underlining the importance of this cluster and the S7 binding site. The globular domain of S9 is located close to S7 while an extended C-terminal domain interacts with H38, H43, H31, and H29 (Brodersen et al., 2002) (Appendix). The S9 C-terminus ends at the P-site and interacts with P-site bound tRNA. Deletion of as few as 3 amino acids from the C-terminus of S9, resulted in a decreased affinity for non-initiator tRNA (Hoang et al., 2004). Positions 1250 and 1287 in H41 interact with the minor groove of H43 at positions 1353 and 1370 to bring the two helices together. This interaction along with H42, forms a pocket that, in *Thermus thermophilus*, is the binding site of the rprotein THX (Brodersen et al., 2002). The extreme natural environment of *T. thermophilus* may require THX binding to maintain the structure. Although THX is not found in *E. coli*, the conservation of positions involved in the formation of this structure strongly advocates its importance in ribosome function.

Cluster 11 (FIG. 6.3) involves H29, H30, H41, and H42, that connect to junction 12 and contain regions 47, 58, 59, and 62 (FIG. 6.1). Although, the N-terminal domain of S9 has limited contact (see cluster 10), cluster 11 is the major binding site for rprotein S13. S13 is secondary binding protein with a globular N-terminus located at the top of the 30 S subunit and an extended C-terminal domain that wraps around H42 and then penetrates the 30 S subunit to end near the P-site (Brodersen et al., 2002; Hoang et al., 2004). S13 forms intersubunit bridge B1a and B1b (Yusupov et al., 2001). Although, not essential, ribosomes lacking S13 are defective in subunit association and translational fidelity (Cukras and Green, 2005; Cukras et al., 2003). The hairpin at the end of H42, containing two regions (regions 60 and 61) (FIG. 6.1), was designated as cluster 15 (FIG. 6.3). The stem of H42 has S13 contacts while the loop of H42 binds rprotein S19 (Brodersen et al., 2002). S19, a secondary binding protein, has been shown to interact with RimM, a protein involved in maturation of the 30 S subunit head (Lovgren et al., 2004).

In addition to the loop of H42, S19 also interacts with region 57 (FIG. 6.1). Regions 57, 48, and 49 form cluster 12 (FIG. 6.3), which, in addition to S19, binds rprotein S14. In *T. thermophilus*, S14 binds a zinc ion through the coordination of 4 cysteine residues. These residues, however, are not found in *E. coli* (Tsiboli et al., 1998). The role of this protein, aside from stabilization of rRNA, is unclear. The conservation of clusters 10, 11, 12, and 15 as rprotein binding sites may be to position clusters 13 and 14.

Clusters 13 and 14 (FIG. 6.3) are formed by H34 and H35, respectively.

These two clusters, along with clusters 4 (see 5' domain) and 16 (see below), form the channel where mRNA enters the ribosome (Yusupova et al., 2001). When viewed from the interface side, clusters 4 (the 530 loop) and 16 (the decoding regions) form the bottom and right side of the downstream mRNA channel while clusters 13 and 14 form the top and left side. Clusters 4 and 16 monitor the codon-anticodon interaction to maintain translational fidelity while clusters 13 and 14 bind and orient the incoming mRNA (Yusupova et al., 2001). Clusters 13 and 14, in addition to binding and orienting the incoming mRNA, are the binding sites for rproteins S5 and S3, respectively. These rproteins along with S4 line the mRNA channel on the solvent side. It has been suggested that these proteins are involved in removing mRNA secondary structure, translational processivity, and maintenance of the reading frame (Takyar et al., 2005; Yusupova et al., 2001). The final cluster, cluster 16 (FIG. 6.3), is the decoding site, composed of regions 66 and 67 (FIG. 6.1). Regions 66 and 67 have been previously identified in numerous studies as important in ribosome function as the sites of A and P-site tRNA binding, initiation factor 1 (IF1) binding, aminoglycoside antibiotic binding, and decoding of the mRNA (Carter et al., 2001; Ogle et al., 2001; Vicens and Westhof, 2003). Positions 1492, and 1493, in the A-site, are conserved as would be expected due to their role in translational fidelity (Ogle et al., 2001). As part of the P-site, positions 1399 and 1401 were conserved. Position 1400, however, was not conserved (9 mutations) in the mutation library in spite of being involved in the P-site (Moazed and Noller, 1990; Yusupov et al., 2001) and crosslinked to position 967 (Wilms et al., 1997). Position 1400 contained no C1400G and only two C1400A mutations in the library suggesting that a purine is highly detrimental. This was also seen in site-directed mutations at 1400 where purines resulted in an 80% decrease in ribosome function (Chapter 4). The intersubunit bridge, B2a, involves positions 1408-1410 and 1494-1495 and H69 from the 23 S rRNA (Yusupov et al., 2001). Of these five positions, only two positions (positions 1409 and 1494) were conserved. The non-conserved positions, however, showed a nucleotide preference for each position. All mutations at position 1408 (7 mutations) were A to G transitions while position 1410 (13 mutations) excluded C and position 1495 (6 mutations) excluded G. Additional conserved positions seem to be responsible for formation of the appropriate structure for function. The formation of this structure is the binding site for IF1 and aminoglycoside antibiotics.

Intersubunit Bridges.

Intersubunit bridges are dynamic interactions that allow communication between the subunits during protein synthesis. These interactions, hold the large and small subunits together during protein synthesis, and have been identified at near atomic resolution in the 70 S crystal structure of *T. thermophilus* (Yusupov et al., 2001). A total of eight intersubunit bridges have been identified with the majority of the RNA-RNA bridges (interaction between RNA from both the 30 S and 50 S subunits) located in the center and RNA-protein bridges (interaction between RNA from one subunit and protein from the other subunit) located on the periphery (Yusupov et al., 2001). A comparative analysis of rRNA sequences, from all Domains, used to model the minimal ribosome, found a conservation of all intersubunit bridges (Mears et al., 2002). Addition of organelle rRNA sequences to the analysis resulted in a conservation of only bridges B2a, B2c, B3, and B7b (Mears et al., 2002). Analysis of the mutation library identified nucleotides involved in the formation of intersubunit bridges B2a, B2b, and B7b as being part of conserved regions. Other intersubunit bridges have conserved nucleotides, but these nucleotides were not identified as part of a region. It is unclear whether these isolated, conserved positions are functionally important or were not mutated as often as other positions because of random chance. Bridges B2a and B2b are located in the center of the ribosome close to the catalytic center and are involved in tRNA binding, translocation, and subunit association. Intersubunit bridge B7b, is a RNA-protein bridge between regions 33 and 35 in the 16 S rRNA and large subunit protein 2 (L2). The conservation of this bridge may be due to the role of L2 in tRNA binding to the A and P-sites and its role in peptidyl transferase activity (Diedrich et al., 2000; Uhlein et al., 1998). Our results are surprisingly consistent with the modeling study and suggest that intersubunit bridges do not interact through direct base pairing.

tRNA Binding.

The interactions between tRNA and 16 S rRNA have been identified using biochemical methods and recently by crystallography studies (Moazed and Noller, 1990; Yusupov et al., 2001). Most of the interactions between tRNA and rRNA are backbone-backbone interactions (Yusupov et al., 2001) as would be expected given the number of different tRNA's required to bind to each site, therefore, specific base conservation is unlikely. Comparison of the known tRNA-16 S rRNA interactions with conserved regions identified in the mutation library shows limited conservation of the 16 S rRNA at the P and E-site interactions. The P-site bound tRNA positions 40 and 41 interact with conserved positions 1339 and 1338 (region 62), respectively (Yusupov et al., 2001). Position 38 of P-site tRNA interacts with the backbone of position 790 from region 39 (Yusupov et al., 2001). Position 790 (8 mutations) is not conserved but a C mutation was excluded from this position. Conserved positions 789 (region 39) and 1339 (region 62) interact with positions 38 and 35 of E-site bound tRNA, respectively (Yusupov et al., 2001). Although nucleotide identity is not conserved at the site of tRNA interaction, nucleotides surrounding the binding site are conserved suggesting that positioning of the backbone is important. In contrast, the majority of the interactions between 16 S rRNA and A-site bound tRNA are conserved. Positions 530 (region 26), 1054 (region 47), and 1492-1493 (region 64) of the 16 S rRNA interact with A-site tRNA at positions 34-36, 34, and 38, respectively (Yusupov et al., 2001). These contacts, however, are responsible for discrimination between cognate and near-cognate tRNA by monitoring the codon-anti-codon interaction and are universally conserved in the phylogenetic analysis as well as in the mutational library (Cannone et al., 2002; Ogle et al., 2001).

mRNA Binding

During translation, mRNA is wrapped around the neck of the ribosome, entering and exiting through two discrete tunnels (Yusupova et al., 2001) (FIG. 6.2). The upstream tunnel, between the head and platform of the ribosome, is formed by S7, the 690 loop, the 790 loop, the base of H45, and H28 (Yusupova et al., 2001). Only the 790 loop (region 39) and a small section of H28 (region 65) were identified as a conserved components of the upstream mRNA tunnel, although the base of H45 cannot be ruled out since it was not part of the mutagenesis. The minor groove side of the 790 loop (region 36) interacts directly with the mRNA, suggesting that it has a role in positioning of the mRNA.

Four conserved clusters (clusters 4, 13, 14, and 16) form the downstream tunnel (Yusupova et al., 2001) (FIG. 6.2). When viewed from the interface side, clusters 4 (see 5' domain) and 16 (see 3' domain) form the bottom and right side of the tunnel while clusters 13 and 14 form the top and left side. The interface side of the tunnel is composed of RNA, while proteins S3, S4, and S5 surround the tunnel on the solvent side (Yusupova et al., 2001). Clusters 13 and 14 that form binding sites for rproteins S3 and S5, respectively while S4 binds through interactions with S5 and cluster 4. These ribosomal proteins on the solvent side of the tunnel appears to position the mRNA and unwind the mRNA (Yusupova et al., 2001). Recently, purified ribosomes were shown to have helicase activity which is decreased by mutations in S3 and S4 (Takyar et al., 2005). In addition to binding rproteins, clusters 13 and 14 also contain positions important for positioning and decoding the mRNA. This may allow the mRNA to interact correctly with the incoming tRNA at the A-site.

Protein Binding.

The 21 ribosomal proteins, of the *E. coli* 30 S subunit, are separated into three categories based on the order of binding: primary binding proteins (S4, S7, S8, S15, S17 and S20) which bind first directly to the rRNA, secondary binding proteins (S9, S12, S13, S16, S18, and S19) which bind to structures formed after primary protein binding, and tertiary binding proteins (S2, S3, S5, S6, S10, 511, S14, and S21) which bind to secondary binding proteins forming the functional 30 S subunit (Grondek and Culver, 2004; Held et al., 1973) (FIG. 1.4). The binding of ribosomal proteins, unlike other RNA binding proteins, is mainly through salt-bridges between polypeptide backbone amide and carbonyl groups and phosphate oxygen atoms of the rRNA rather than base specific contact (Allers and Shamoo, 2001). Therefore, structure and charge of the rRNA is of greater importance than sequence for most rprotein binding (Brodersen et al., 2002).

Only seven rproteins (S7, S9, S11, S12, S13, S19, and S20) had direct base contacts at four or more conserved positions, while the remaining rproteins had between 0-3 base specific contacts at conserved positions. Interestingly, only two of the proteins with 4 or more direct base contacts with conserved regions are primary binding proteins. The interactions between rproteins and the rRNA occur through backbone interactions (Brodersen et al., 2002). Nucleotide identity conservation, therefore, is not essential for protein binding and so many protein binding sites were not identified as conserved regions. The use of backbone and structure for rprotein binding allows for the use of the base in other reactions and may allow mutations to occur without affecting rprotein binding.

Factor Binding.

The process of protein synthesis is aided by factors. In bacteria initiation involves three initiation factors, IF1, IF2, and IF3. The crystal structure of IF1 bound to the 30 S subunit (Carter et al., 2001) and the C-terminal domain of IF3 (IF3C) bound to the subunit has been solved (Pioletti et al., 2001). In the crystal structure, IF1 binds to the backbone of H44 (cluster 16) and the 530 loop (cluster 4) as well as to rprotein S12 (Carter et al., 2001). Although a crystal structure of IF2 bound to the 30 S subunit has not been solved, it has been shown to bind to initiator tRNA and its affinity to the ribosome is increased in the presence of IF1 (Zucker and Hershey, 1986). It has been proposed that IF2 binds over IF1 in the A-site and aids in positioning initiator tRNA in the P-site (Roll-Mecak et al., 2000). Finally, the location of IF3 is still under debate. Biochemical and cryo-electron microscopy (cryo-EM) studies have placed the C-terminal domain of IF3 (IF3C) on the interface side of the platform with contacts to H23, H24 and H45 (Dallas and Noller, 2001; McCutcheon et al., 1999), while the crystal structure places the IF3C on the solvent side of the platform with contacts to H23, H26, and H45 (Pioletti et al., 2001). Of the four binding sites, helices 23 and 24 form clusters 6 and 7, H26 was not conserved and H45 was not included in the mutation library. The majority of the binding sites for elongations factors, EF-G and EF-Tu have been located on the 50 S subunit by structural and biochemical studies (Agrawal et al., 1998; Stark et al., 1997; Valle et al., 2003; Wilson and Noller, 1998). The same data suggests that EF-Tu and EF-G contact similar regions of the 30 S subunit (Agrawal et al., 1998; Stark et al., 1997b; Valle et al., 2003; Wilson and Noller, 1998). For EF-G, these interactions include the base of the 530 loop, the 790 loop, position 1400, and around positions 1210 and 1230 (Wilson and Noller, 1998). With the exception of regions around 1210 and 1230, the remaining binding sites are conserved in the mutation library. These contact sites are similar for the EF-Tu•tRNA complex, although these contacts probably occur between the tRNA and the rRNA rather then with EF-Tu.

The termination of protein synthesis requires two classes of release factors to release the nascent protein and to dissociate the termination complex. A stop codon, in the A-site are recognized by class I release factors, RF1 and RF2. In the 30 S subunit, these release factors mimic the binding of tRNA and interact with H44 (cluster 16), H18 (cluster 4), and rprotein S12 (Klaholz et al., 2003). After release of the nascent protein, class II release factor, RF3, mediates the release of the class I release factor from the ribosome by competing for the same binding site (Zavialov et al., 2001). The binding of RF3 is similar to the binding of EF-G and EF-Tu with additional contacts to H5, H16, and H17 (Klaholz et al., 2004).

Ribosomal factors play essential roles in the process of protein synthesis and interact with conserved sites in the 16 S rRNA. These conserved sites, however, have other functions associated with them in addition to factor binding, explaining their conservation in the mutation library.

Antibiotic Binding.

The ribosome as the sole source of protein synthesis in the cell is an ideal target for antibiotics. Numerous naturally occurring antibiotics bind to functionally important sites and disrupt protein synthesis. Resistance to many of these antibiotics, however, is accomplished through target modification suggesting that, though the sites of action for these antibiotics are at functionally important regions, these sites can still tolerate some variation and retain function (Beauclerk and Cundliffe, 1987; Dailidiene et al., 2002; Sigmund et al., 1984; Spangler and Blackburn, 1985). For example, aminoglycoside antibiotics bind to the A-site and contact positions A1408, G1491, A1492, and A1493 (Brodersen et al., 2000; Fourmy et al., 1996; Fourmy et al., 1998a; Fourmy et al., 1998b; Schroeder et al., 2000). An A1408G mutation decreases function by 30% (unpublished results), while a transverse mutation results in a greater decrease in function. Mutations at position 1408, however, inhibit the binding of aminoglycoside antibiotics (Beauclerk and Cundliffe, 1987; Harris et al., 1989). In the mutation library, position 1408 is not conserved and contains seven mutations, all of which are A1408G transitions. Analysis of the mutation library has identified the sites of action for spectinomycin, pactamycin, edeine and aminoglycosides as being conserved. In addition, further analysis of the mutation library, has identified known mutations that provide resistance to the antibiotic while maintaining function (Beauclerk and Cundliffe, 1987; Sigmund et al., 1984). Identification of sites of action for known antibiotics implies that the other conserved regions found in the mutational library may be good targets for the development of new antimicrobials.

Analysis of the mutation library has identified numerous regions that are required for function. The identification of known functionally important regions lends credence to the assumption that other identified regions are also important for function. Comparison of the conserved regions from our library to the phylogenetic maps shows a remarkable similarity. The regions described herein, however, are less extensive then those seen in the phylogenetic analysis. One possible explanation for this difference may be the reduced functional requirement during our selection. Since our ribosomes are not required to be fully functional, mutations that reduce function and therefore reduce fitness are also represented. These mutations, though, would not survive in the environment and are, therefore, found to be conserved in the phylogenetic analysis. The conserved regions in the mutational library represent those positions that are absolutely required for any function. Conserved regions in all domains of the 16 S rRNA have been identified, implying that the rRNA works as a whole to perform its function.

Reagents.

Restriction enzymes, ligase, and calf intestine alkaline phosphatase were from New England Biolabs and from Fermentas. Sequencing modified DNA polymerase, nucleotides, and sequencing buffers were from Epicenter Technologies. Oligonucleotides were either purchased from Midland Certified Reagent Company (Midland, Tex.) or IDT DNA (Coralville, Iowa). AmpliTaq DNA polymerase and PCR reagents were from Perkin-Elmer-Cetus (Boston, Mass.).

Plasmids and Mutagenesis.

All mutagenesis was performed using the polymerase chain reaction (PCR) (Higuchi et al., 1988; Mullis et al., 1986; Mullis and Faloona, 1987). Construction of 16 S rRNA mutation library: All mutations were constructed in pRNA228. The 16 S rRNA was mutated using error-prone PCR with primers lac UV5-74 (5'-GCA GTG AGC GCA ACG CA-3') and 23S 20R (5'-GTA CGC TTA GTC GCT TAA CC-3'). The 16 S rRNA was cloned into pRNA228 by replacing the wild type sequence between the BclI and BstEII cut sites. Ligations were transformed into E. coli DH5 using a Gibco-BRL Cell Porator.

Selection of Functional Mutants.

Transformants were incubated at 37° C. with shaking in SOC medium for half an hour to allow for the expression of the $Amp^R$ marker. A sample of the culture was plated on LB+Amp (100 μg/ml) plates to determine the transformation efficiency. IPTG (isopropyl-β-D-thiogalactopyranoside) was then added to the remaining culture to a final concentration of 1 mM and incubated at 37° C. with shaking for an additional 1.5 hours to induce rRNA synthesis. The culture was then plated on LB+Amp (100 μg/ml)+IPTG (1 mM) agar with 25 μg/ml chloramphenicol. Survivors were randomly selected and spotted onto LB+Amp (100 μg/ml)+IPTG (1 mM) agar with 25 μg/ml chloramphenicol and incubated at 37° C. for 24 hours. These plates were then sent to SeqWright Inc. for sequencing.

Bacterial Strains and Media.

All plasmids were maintained and expressed in E. coli DH5 (supE44, hsdR17, recA1, endA1, gyrA96, thi-1, relA1) (Hanahan, 1983). Cultures were maintained in LB medium (Luria and Burrous, 1957) containing 100 μg/ml ampicillin (LB-Ap100). To induce synthesis of plasmid-derived rRNA from the lacUV5 promoter; IPTG (isopropyl-beta-D-thiogalactopyranoside) was added to a final concentration of 1 mM at the times indicated in each experiment. Strains were transformed by electroporation (Dower et al., 1988) using a Gibco-BRL Cell Porator. Unless otherwise indicated, transformants were grown in SOC medium (Hanahan, 1983) for one hour prior to plating on selective medium to allow expression of plasmid-derived genes.

Numerous biochemical studies and the high-resolution crystal structures of both subunits have been used to determine the general mechanism of protein synthesis. The mechanism of protein synthesis on a molecular lever, however, is still mostly unknown. Here, I have used a genetic system that allows mutagenesis of rRNA, in vivo, without affecting normal cellular function to determine the effect of mutations at discrete regions and throughout the 16 S rRNA. Saturation mutagenesis of the 530 loop, 970 loop, and helix 45 identified both structural and functional nucleotides that are important for the decoding function of the ribosome. Creation of the mutation library identified nucleotide required for ribosome function.

The 970 loop is important for initiation of protein synthesis as shown by the increased levels of function seen when positions 966 and 967 are mutated. This change in function can be complimented by over expression of IF3. G530 is involved in maintaining fidelity of the codon-anti-codon interaction. The remainder of the loop is involved in positioning of G530. Finally, helix 45 is involved in positioning helix 44 and the 790 loop close together in the crystal structure. Helix 44 and the 790 loop is involved in the A and P-sites. Helix 45 may be involved in transmitting information between the A and P-sites.

The mutation library was used to identify conserved nucleotides that are required for ribosome function. Comparison of the conserved nucleotides identified in the mutation library with those identified in the phylogenetic analysis of the three Domain and two organelles found a remarkable similarity suggesting that the molecular mechanism of protein synthesis involves the same nucleotides in all organisms. Differences, however, were identified that may be Domain specific but these results still have to be verified.

Information resulting from the saturation mutagenesis and mutational library can be used to identify new targets for the development of antimicrobials. The saturation mutagenesis data has provided insight into molecular interactions required for translational accuracy. Disruption of these interactions will affect protein synthesis and in fact, the site of action for naturally occurring antibiotics, tetracycline, aminoglycosides, and kasugamycin involve interactions with the 970 loop, the decoding region, and helix 45, respectively. These and other sites of action for other naturally occurring antibiotics (spectinomycin, pactamycin, and edeine) were also identified in the mutational library. The identification of known antibiotic sites of action in the mutation library suggest that other conserved sites found in the library may be good targets for the development of new antimicrobials.

REFERENCES

Acinas, S. G., Marcelino, L. A., Klepac-Ceraj, V., and Polz, M. F. (2004). Divergence and Redundancy of 16S rRNA Sequences in Genomes with Multiple rrn Operons. J Bacteriol 186, 2629-2635.

Agalarov, S. C., Sridhar Prasad, G., Funke, P. M., Stout, C. D., and Williamson, J. R. (2000). Structure of the S15,S6,S18-rRNA complex: assembly of the 30S ribosome central domain. Science 288, 107-113.

Agrawal, R. K., Penczek, P., Grassucci, R. A., and Frank, J. (1998). Visualization of elongation factor G on the Escherichia coli 70S ribosome: the mechanism of translocation. Proc Natl Acad Sci USA 95, 6134-6138.

Agrawal, R. K., Spahn, C. M., Penczek, P., Grassucci, R. A., Nierhaus, K. H., and Frank, J. (2000). Visualization of tRNA movements on the Escherichia coli 70S ribosome during the elongation cycle. J Cell Biol 150, 447-460.

Alksne, L. E., Anthony, R. A., Liebman, S. W., and Warner, J. R. (1993). An accuracy center in the ribosome conserved over 2 billion years. Proc Natl Acad Sci USA 90, 9538-9541.

Allain, F. H., and Varani, G. (1995). Divalent metal ion binding to a conserved wobble pair defining the upstream site of cleavage of group I self-splicing introns. Nucleic Acids Res 23, 341-350.

Allen, P. N., and Noller, H. F. (1989). Mutations in ribosomal proteins S4 and S12 influence the higher order structure of 16 S ribosomal RNA. J Mol Biol 208, 457-468.

Allen, P. N., and Noller, H. F. (1991). A single base substitution in 16S ribosomal RNA suppresses streptomycin dependence and increases the frequency of translational errors. Cell 66, 141-148.

Allers, J., and Shamoo, Y. (2001). Structure-based analysis of protein-RNA interactions using the program ENTANGLE. J Mol Biol 311, 75-86.

Apirion, D., Neil, J., and Watson, N. (1976). Consequences of losing ribonuclease III on the Escherichia coli cell. Mol Gen Genet 144, 185-190.

Asai, T., Zaporojets, D., Squires, C., and Squires, C. L. (1999). An Escherichia coli strain with all chromosomal rRNA operons inactivated: complete exchange of rRNA genes between bacteria. Proc Natl Acad Sci USA 96, 1971-1976.

Bakin, A., Lane, B. G., and Ofengand, J. (1994). Clustering of pseudouridine residues around the peptidyltransferase center of yeast cytoplasmic and mitochondrial ribosomes. Biochemistry 33, 13475-13483.

Balch, W. E., Fox, G. E., Magrum, L. J., Woese, C. R., and Wolfe, R. S. (1979). Methanogens: reevaluation of a unique biological group. Microbiol. Rev 43, 260-296.

Ban, N., Nissen, P., Hansen, J., Capel, M., Moore, P. B., and Steitz, T. A. (1999). Placement of protein and RNA structures into a 5 A-resolution map of the 50S ribosomal subunit. Nature 400, 841-847.

Barta, A., Kuechler, E., Branlant, C., Sri Widada, J., Krol, A., and Ebel, J. P. (1975). Photoaffinity labelling of 23 S RNA at the donor-site of the Escherichia coli ribosome. FEBS Lett 56, 170-174.

Batey, R. T., Rambo, R. P., and Doudna, J. A. (1999). Tertiary Motifs in RNA Structure and Folding. Angew Chem Int Ed Engl 38, 2326-2343.

Beauclerk, A. A., and Cundliffe, E. (1987). Sites of action of two ribosomal RNA methylases responsible for resistance to aminoglycosides. J Mol Biol 193, 661-671.

Belanger, F., Leger, M., Saraiya, A. A., Cunningham, P. R., and Brakier-Gingras, L. (2002). Functional studies of the 900 tetraloop capping helix 27 of 16S ribosomal RNA. J Mol Biol 320, 979-989.

Bergemann, K., and Nierhaus, K. H. (1983). Spontaneous, elongation factor G independent translocation of Escherichia coli ribosomes. J Biol Chem 258, 15105-15113.

Biswas, D. K., and Gorini, L. (1972). Restriction, de-restriction and mistranslation in missense suppression. Ribosomal discrimination of transfer RNA's. J Mol Biol 64, 119-134.

Bjork, G. R., Durand, J. M., Hagervall, T. G., Leipuviene, R., Lundgren, H. K., Nilsson, K., Chen, P., Qian, Q., and Urbonavicius, J. (1999). Transfer RNA modification: influence on translational frameshifting and metabolism. FEBS Lett 452, 47-51.

Boublik, M. (1975). Proceedings: Structural analysis of ribosomes by electron microscopy. J Ultrastruct Res 52, 135-136.

Bowman, C. M., Dahlberg, J. E., Ikemura, T., Konisky, J., and Nomura, M. (1971). Specific inactivation of 16S ribosomal RNA induced by colicin E3 in vivo. Proc Natl Acad Sci USA 68, 964-968.

Breitmeyer, J. B., and Noller, H. F. (1976). Affinity labeling of specific regions of 23 S RNA by reaction of N-bromoacetyl-phenylalanyl-transfer RNA with *Escherichia coli* ribosomes. J Mol Biol 101, 297-306.

Brimacombe, R. (1992). Structure-function correlations (and discrepancies) in the 16S ribosomal RNA from *Escherichia coli*. Biochimie 74, 319-326.

Brimacombe, R., Mitchell, P., Osswald, M., Stade, K., and Bochkariov, D. (1993). Clustering of modified nucleotides at the functional center of bacterial ribosomal RNA. Faseb J 7, 161-167.

Brodersen, D. E., Clemons, W. M., Jr., Carter, A. P., Morgan-Warren, R. J., Wimberly, B. T., and Ramakrishnan, V. (2000). The structural basis for the action of the antibiotics tetracycline, pactamycin, and hygromycin B on the 30S ribosomal subunit. Cell 103, 1143-1154.

Brodersen, D. E., Clemons, W. M., Jr., Carter, A. P., Wimberly, B. T., and Ramakrishnan, V. (2002). Crystal structure of the 30 S ribosomal subunit from *Thermus thermophilus*: structure of the proteins and their interactions with 16 S RNA. J Mol Biol 316, 725-768.

Brosius, J., Dull, T. J., Sleeter, D. D., and Noller, H. F. (1981a). Gene organization and primary structure of a ribosomal RNA operon from *Escherichia coli*. J Mol Biol 148, 107-127.

Brosius, J., Ullrich, A., Raker, M. A., Gray, A., Dull, T. J., Gutell, R. R., and Noller, H. F. (1981b). Construction and fine mapping of recombinant plasmids containing the rrnB ribosomal RNA operon of *E. coli*. Plasmid 6, 112-118.

Cannone, J. J., Subramanian, S., Schnare, M. N., Collett, J. R., D'Souza, L. M., Du, Y., Feng, B., Lin, N., Madabusi, L. V., uuml, et al. (2002). The Comparative RNA Web (CRW) Site: an online database of comparative sequence and structure information for ribosomal, intron, and other RNAs. BMC Bioinformatics 3, 2.

Capel, M. S., Engelman, D. M., Freeborn, B. R., Kjeldgaard, M., Langer, J. A., Ramakrishnan, V., Schindler, D. G., Schneider, D. K., Schoenborn, B. P., Sillers, I. Y., and et al. (1987). A complete mapping of the proteins in the small ribosomal subunit of *Escherichia coli*. Science 238, 1403-1406.

Carter, A. P., Clemons, W. M., Jr., Brodersen, D. E., Morgan-Warren, R. J., Hartsch, T., Wimberly, B. T., and Ramakrishnan, V. (2001). Crystal structure of an initiation factor bound to the 30S ribosomal subunit. Science 291, 498-501.

Caskey, C. T., Forrester, W. C., Tate, W., and Ward, C. D. (1984). Cloning of the *Escherichia coli* release factor 2 gene. J Bacteriol 158, 365-368.

Cate, J. H., Gooding, A. R., Podell, E., Zhou, K., Golden, B. L., Kundrot, C. E., Cech, T. R., and Doudna, J. A. (1996a). Crystal structure of a group I ribozyme domain: principles of RNA packing Science 273, 1678-1685.

Cate, J. H., Gooding, A. R., Podell, E., Zhou, K., Golden, B. L., Szewczak, A. A., Kundrot, C. E., Cech, T. R., and Doudna, J. A. (1996b). RNA tertiary structure mediation by adenosine platforms. Science 273, 1696-1699.

Cate, J. H., Yusupov, M. M., Yusupova, G. Z., Earnest, T. N., and Noller, H. F. (1999). X-ray crystal structures of 70S ribosome functional complexes. Science 285, 2095-2104.

Celano, B., Pawlik, R. T., and Gualerzi, C. O. (1988). Interaction of *Escherichia coli* translation-initiation factor IF-1 with ribosomes. Eur J Biochem 178, 351-355. Cho, H. D. (1999) Genetic analysis of the decoding region in *Escherichia coli* 16S ribosomal RNA, Wayne State University, Detroit, Mich.

Clarke, L., and Carbon, J. (1976). A colony bank containing synthetic Col E1 hybrid plasmids representative of the entire *E. coli* genome. Cell 9, 91-99.

Condon, C., French, S., Squires, C., and Squires, C. L. (1993). Depletion of functional ribosomal RNA operons in *Escherichia coli* causes increased expression of the remaining intact copies. Embo J 12, 4305-4315.

Condon, C., Philips, J., Fu, Z. Y., Squires, C., and Squires, C. L. (1992). Comparison of the expression of the seven ribosomal RNA operons in *Escherichia coli*. Embo J 11, 4175-4185.

Conrad, J., Niu, L., Rudd, K., Lane, B. G., and Ofengand, J. (1999). 16S ribosomal RNA pseudouridine synthase RsuA of *Escherichia coli*: deletion, mutation of the conserved Asp102 residue, and sequence comparison among all other pseudouridine synthases. Rna 5, 751-763.

Conrad, J., Sun, D., Englund, N., and Ofengand, J. (1998). The rluC gene of *Escherichia coli* codes for a pseudouridine synthase that is solely responsible for synthesis of pseudouridine at positions 955, 2504, and 2580 in 23 S ribosomal RNA. J Biol Chem 273, 18562-18566.

Correll, C. C., and Swinger, K. (2003). Common and distinctive features of GNRA tetraloops based on a GUAA tetraloop structure at 1.4 A resolution. Rna 9, 355-363.

Costa, M., and Michel, F. (1995). Frequent use of the same tertiary motif by self-folding RNAs. Embo J 14, 1276-1285.

Cukras, A. R., and Green, R. (2005). Multiple effects of S13 in modulating the strength of intersubunit interactions in the ribosome during translation. J Mol Biol 349, 47-59.

Cukras, A. R., Southworth, D. R., Brunelle, J. L., Culver, G. M., and Green, R. (2003). Ribosomal proteins S12 and S13 function as control elements for translocation of the mRNA:tRNA complex. Mol Cell 12, 321-328.

Culver, G. M., and Noller, H. F. (1998). Directed hydroxyl radical probing of 16S ribosomal RNA in ribosomes containing Fe(II) tethered to ribosomal protein S20. Rna 4, 1471-1480.

Cummings, H. S., and Hershey, J. W. (1994). Translation initiation factor IF1 is essential for cell viability in *Escherichia coli*. J Bacteriol 176, 198-205.

Cunningham, P. R., Negre, D., Weitzmann, C., Denman, R., Nurse, K., and Ofengand, J. (1988). The role of 16S RNA in ribosome function: single base alterations and their effect on in vitro protein synthesis. Arch Biol Med Exp (Santiago) 21, 393-401.

Cunningham, P. R., Weitzmann, C. J., Nurse, K., Masurel, R., Van Knippenberg, P. H., and Ofengand, J. (1990). Site-specific mutation of the conserved m6(2)A m6(2)A residues of *E. coli* 16S ribosomal RNA. Effects on ribosome function and activity of the ksgA methyltransferase. Biochim Biophys Acta 1050, 18-26.

Cunningham, P. R., Richard, R. B., Weitzmann, C. J., Nurse, K., and Ofengand, J. (1991). The absence of modified nucleotides affects both in vitro assembly and in vitro function of the 30S ribosomal subunit of *Escherichia coli*. Biochimie 73, 789-796.

Dabbs, E. R. (1979). Selection for *Escherichia coli* mutants with proteins missing from the ribosome. J Bacteriol 140, 734-737.

Dabbs, E. R. (1991). Mutants lacking individual ribosomal proteins as a tool to investigate ribosomal properties. Biochimie 73, 639-645.

Dabrowski, M., Spahn, C. M., Schafer, M. A., Patzke, S., and Nierhaus, K. H. (1998). Protection patterns of tRNAs do not change during ribosomal translocation. J Biol Chem 273, 32793-32800.

Dahlquist, K. D., and Puglisi, J. D. (2000). Interaction of translation initiation factor IF1 with the E. coli ribosomal A site. J Mol Biol 299, 1-15.

Dailidiene, D., Bertoli, M. T., Miciuleviciene, J., Mukhopadhyay, A. K., Dailide, G., Pascasio, M. A., Kupcinskas, L., and Berg, D. E. (2002). Emergence of tetracycline resistance in *Helicobacter pylori*: multiple mutational changes in 16S ribosomal DNA and other genetic loci. Antimicrob Agents Chemother 46, 3940-3946.

Dallas, A., and Noller, H. F. (2001). Interaction of translation initiation factor 3 with the 30S ribosomal subunit. Mol Cell 8, 855-864.

Dam, E., Pleij, K., and Draper, D. (1992). Structural and functional aspects of RNA pseudoknots. Biochemistry 31, 11665-11676.

Davies, J., Gilbert, W., and Gorini, L. (1964). Streptomycin, Suppression, And The Code. Proc Natl Acad Sci USA 51, 883-890.

Decatur, W. A., and Fournier, M. J. (2002). rRNA modifications and ribosome function. Trends Biochem Sci 27, 344-351.

Diedrich, G., Spahn, C. M., Stelzl, U., Schafer, M. A., Wooten, T., Bochkariov, D. E., Cooperman, B. S., Traut, R. R., and Nierhaus, K. H. (2000). Ribosomal protein L2 is involved in the association of the ribosomal subunits, tRNA binding to A and P sites and peptidyl transfer. Embo J 19, 5241-5250.

Dinos, G., Wilson, D. N., Teraoka, Y., Szaflarski, W., Fucini, P., Kalpaxis, D., and Nierhaus, K. H. (2004). Dissecting the ribosomal inhibition mechanisms of edeine and pactamycin: the universally conserved residues G693 and C795 regulate P-site RNA binding. Mol Cell 13, 113-124.

Dong, H., and Kurland, C. G. (1995). Ribosome mutants with altered accuracy translate with reduced processivity. J Mol Biol 248, 551-561.

Donly, B. C., and Mackie, G. A. (1988). Affinities of ribosomal protein S20 and C-terminal deletion mutants for 16S rRNA and S20 mRNA. Nucleic Acids Res 16, 997-1010.

Doring, T., Mitchell, P., Osswald, M., Bochkariov, D., and Brimacombe, R. (1994). The decoding region of 16S RNA; a cross-linking study of the ribosomal A, P and E sites using tRNA derivatized at position 32 in the anticodon loop. Embo J 13, 2677-2685

Dower, W. J., Miller, J. F., and Ragsdale, C. W. (1988). High efficiency transformation of *E. coli* by high voltage electroporation. Nucleic Acids Res 16, 6127-6145.

Dunn, J. J., and Studier, F. W. (1973). T7 early RNAs and *Escherichia coli* ribosomal RNAs are cut from large precursor RNAs in vivo by ribonuclease 3. Proc Natl Acad Sci USA 70, 3296-3300.

Ehresmann, C., Moine, H., Mougel, M., Dondon, J., Grunberg-Manago, M., Ebel, J. P., and Ehresmann, B. (1986). Cross-linking of initiation factor IF3 to *Escherichia coli* 30S ribosomal subunit by trans-diamminedichloroplatinum(II): characterization of two cross-linking sites in 16S rRNA; a possible way of functioning for IF3. Nucleic Acids Res 14, 4803-4821.

Ellwood, M., and Nomura, M. (1982). Chromosomal locations of the genes for rRNA in *Escherichia coli* K-12. J Bacteriol 149, 458-468.

Formenoy, L. J., Cunningham, P. R., Nurse, K., Pleij, C. W., and Ofengand, J. (1994). Methylation of the conserved A1518-A1519 in *Escherichia coli* 16S ribosomal RNA by the ksgA methyltransferase is influenced by methylations around the similarly conserved U1512.G1523 base pair in the 3' terminal hairpin. Biochimie 76, 1123-1128.

Fourmy, D., Recht, M. I., Blanchard, S. C., and Puglisi, J. D. (1996). Structure of the A site of *Escherichia coli* 16S ribosomal RNA complexed with an aminoglycoside antibiotic. Science 274, 1367-1371.

Fourmy, D., Recht, M. I., and Puglisi, J. D. (1998a). Binding of neomycin-class aminoglycoside antibiotics to the A-site of 16 S rRNA. J Mol Biol 277, 347-362.

Fourmy, D., Yoshizawa, S., and Puglisi, J. D. (1998b). Paromomycin binding induces a local conformational change in the A-site of 16 S rRNA. J Mol Biol 277, 333-345.

Frank, J., Verschoor, A., Li, Y., Zhu, J., Lata, R. K., Radermacher, M., Penczek, P., Grassucci, R., Agrawal, R. K., and Srivastava, S. (1995a). A model of the translational apparatus based on a three-dimensional reconstruction of the *Escherichia coli* ribosome. Biochem Cell Biol 73, 757-765.

Frank, J., Zhu, J., Penczek, P., Li, Y., Srivastava, S., Verschoor, A., Radermacher, M., Grassucci, R., Lata, R. K., and Agrawal, R. K. (1995b). A model of protein synthesis based on cryo-electron microscopy of the *E. coli* ribosome. Nature 376, 441-444.

Freistroffer, D. V., Pavlov, M. Y., MacDougall, J., Buckingham, R. H., and Ehrenberg, M. (1997). Release factor RF3 in *E. coli* accelerates the dissociation of release factors RF1 and RF2 from the ribosome in a GTP-dependent manner. Embo J 16, 4126-4133.

Gavrilova, L. P., and Spirin, A. S. (1971). Stimulation of "non-enzymic" translocation in ribosomes by p-chloromercuribenzoate. FEBS Lett 17, 324-326.

Gegenheimer, P., and Apirion, D. (1981). Processing of procaryotic ribonucleic acid. Microbiol Rev 45, 502-541.

Gegenheimer, P., and Apirion, D. (1980). Precursors to 16S and 23S ribosomal RNA from a ribonuclear III-strain of *Escherichia coli* contain intact RNase III processing sites. Nucleic Acids Res 8, 1873-1891.

Gegenheimer, P., Watson, N., and Apirion, D. (1977). Multiple pathways for primary processing of ribosomal RNA in *Escherichia coli*. J Biol Chem 252, 3064-3073.

Gorini, L., and Kataja, E. (1964). Phenotypic Repair By Streptomycin Of Defective Genotypes In *E. coli*. Proc Natl Acad Sci USA 51, 487-493.

Gotz, F., Dabbs, E. R., and Gualerzi, C. O. (1990). *Escherichia coli* 30S mutants lacking protein S20 are defective in translation initiation. Biochim Biophys Acta 1050, 93-97.

Gotz, F., Fleischer, C., Pon, C. L., and Gualerzi, C. O. (1989). Subunit association defects in *Escherichia coli* ribosome mutants lacking proteins S20 and L11. Eur J Biochem 183, 19-24.

Gourse, R. L., Stark, M. J., and Dahlberg, A. E. (1982). Site-directed mutagenesis of ribosomal RNA. Construction and characterization of deletion mutants. J Mol Biol 159, 397-416.

Green, R., and Noller, H. F. (1997). Ribosomes and translation Annu Rev Biochem 66, 679-716.

Grondek, J. F., and Culver, G. M. (2004). Assembly of the 30S ribosomal subunit: positioning ribosomal protein S13 in the S7 assembly branch. Rna 10, 1861-1866.

Grunberg-Manago, M., Dessen, P., Pantaloni, D., Godefroy-Colburn, T., Wolfe, A. D., and Dondon, J. (1975). Light-scattering studies showing the effect of initiation factors on the reversible dissociation of *Escherichia coli* ribosomes. J Mol Biol 94, 461-478.

Gunderson, J. H., Sogin, M. L., Wollett, G., Hollingdale, M., de la Cruz, V. F., Waters, A. P., and McCutchan, T. F. (1987). Structurally distinct, stage-specific ribosomes occur in *Plasmodium*. Science 238, 933-937.

Hanahan, D. (1983). Studies on transformation of *Escherichia coli* with plasmids. J Mol Biol 166, 557-580.

Harris, E. H., Burkhart, B. D., Gillham, N. W., and Boynton, J. E. (1989). Antibiotic resistance mutations in the chloroplast 16S and 23S rRNA genes of *Chlamydomonas reinhardtii*: correlation of genetic and physical maps of the chloroplast genome. Genetics 123, 281-292.

Hartz, D., Binkley, J., Hollingsworth, T., and Gold, L. (1990). Domains of initiator tRNA and initiation codon crucial for initiator tRNA selection by *Escherichia coli* IF3. Genes Dev 4, 1790-1800.

Held, W. A., Mizushima, S., and Nomura, M. (1973). Reconstitution of *Escherichia coli* 30 S ribosomal subunits from purified molecular components. J Biol Chem 248, 5720-5730.

Helser, T. L., Davies, J. E., and Dahlberg, J. E. (1971). Change in methylation of 16S ribosomal RNA associated with mutation to kasugamycin resistance in *Escherichia coli*. Nat New Biol 233, 12-14.

Helser, T. L., Davies, J. E., and Dahlberg, J. E. (1972). Mechanism of kasugamycin resistance in *Escherichia coli*. Nat New Biol 235, 6-9.

Heus, H. A., Van Kimmenade, J. M., van Knippenberg, P. H., and Hinz, H. J. (1983). calorimetric measurements of the destabilisation of a ribosomal RNA hairpin by dimethylation of two adjacent adenosines. Nucleic Acids Res 11, 203-210.

Higuchi, R., Krummel, B., and Saiki, R. K. (1988). A general method of in vitro preparation and specific mutagenesis of DNA fragments: study of protein and DNA interactions. Nucleic Acids Res 16, 7351-7367.

Hirashima, A., and Kaji, A. (1970). Factor dependent breakdown of polysomes. Biochem Biophys Res Commun 41, 877-883.

Hirashima, A., and Kaji, A. (1972). Factor-dependent release of ribosomes from messenger RNA. Requirement for two heat-stable factors. J Mol Biol 65, 43-58.

Hoang, L., Fredrick, K., and Noller, H. F. (2004). Creating ribosomes with an all-RNA 30S subunit P site. Proc Natl Acad Sci USA 101, 12439-12443.

Housen, I., Demonte, D., Lafontaine, D., and Vandenhaute, J. (1997). Cloning and characterization of the K1DIM1 gene from *Kluyveromyces lactis* encoding the m2(6)A dimethylase of the 18S rRNA. Yeast 13, 777-781.

Howard-Flanders, P., and Theriot, L. (1966). Mutants of *Escherichia coli* K-12 defective in DNA repair and in genetic recombination. Genetics 53, 1137-1150. Huang, L., Ku, J., Pookanjanatavip, M., Gu, X., Wang, D., Greene, P. J., and Santi, D. V. (1998). Identification of two *Escherichia coli* pseudouridine synthases that show multisite specificity for 23S RNA. Biochemistry 37, 15951-15957.

Hui, A., and de Boer, H. A. (1987). Specialized ribosome system: preferential translation of a single mRNA species by a subpopulation of mutated ribosomes in *Escherichia coli*. Proc Natl Acad Sci USA 84, 4762-4766.

Hui, A., Jhurani, P., and de Boer, H. A. (1987). Directing ribosomes to a single mRNA species: a method to study ribosomal RNA mutations and their effects on translation of a single messenger in *Escherichia coli*. Methods Enzymol 153, 432-452.

Igarashi, K., Kishida, K., Kashiwagi, K., Tatokoro, I., Kakegawa, T., and Hirose, S. (1981). Relationship between methylation of adenine near the 3' end of 16-S ribosomal RNA and the activity of 30-S ribosomal subunits. Eur J Biochem 113, 587-593.

Jemiolo, D. K., Taurence, J. S., and Giese, S. (1991). Mutations in 16S rRNA in *Escherichia coli* at methyl-modified sites: G966, C967, and G1207. Nucleic Acids Res 19, 4259-4265.

Jinks-Robertson, S., Gourse, R. L., and Nomura, M. (1983). Expression of rRNA and tRNA genes in *Escherichia coli*: evidence for feedback regulation by products of rRNA operons. Cell 33, 865-876.

Kaji, H., Suzuka, I., and Kaji, A. (1966). Binding of specific soluble ribonucleic acid to ribosomes. Binding of soluble ribonucleic acid to the template-30 S subunits complex. J Biol Chem 241, 1251-1256.

Karimi, R., Pavlov, M. Y., Buckingham, R. H., and Ehrenberg, M. (1999). Novel roles for classical factors at the interface between translation termination and initiation. Mol Cell 3, 601-609.

King, T. C., Sirdeshmukh, R., and Schlessinger, D. (1984). RNase III cleavage is obligate for maturation but not for function of *Escherichia coli* pre-23S rRNA. Proc Natl Acad Sci USA 81, 185-188.

Klaholz, B. P., Myasnikov, A. G., and Van Heel, M. (2004). Visualization of release factor 3 on the ribosome during termination of protein synthesis. Nature 427, 862-865.

Klaholz, B. P., Pape, T., Zavialov, A. V., Myasnikov, A. G., Orlova, E. V., Vestergaard, B., Ehrenberg, M., and van Heel, M. (2003). Structure of the *Escherichia coli* ribosomal termination complex with release factor 2. Nature 421, 90-94.

Klein, D. J., Schmeing, T. M., Moore, P. B., and Steitz, T. A. (2001). The kink-turn: a new RNA secondary structure motif. Embo J 20, 4214-4221.

Klootwijk, J., Klein, I., and Grivell, L. A. (1975). Minimal post-transcriptional modification of yeast mitochondrial ribosomal RNA. J Mol Biol 97, 337-350.

Kowalak, J. A., Bruenger, E., Crain, P. F., and McCloskey, J. A. (2000). Identities and phylogenetic comparisons of posttranscriptional modifications in 16 S ribosomal RNA from *Haloferax volcanii*. J Biol Chem 275, 24484-24489.

Krzyzosiak, W., Denman, R., Nurse, K., Hellmann, W., Boublik, M., Gehrke, C. W., Agris, P. F., and Ofengand, J. (1987). In vitro synthesis of 16S ribosomal RNA containing single base changes and assembly into a functional 30S ribosome. Biochemistry 26, 2353-2364.

Krzyzosiak, W. J., Denman, R., Cunningham, P. R., and Ofengand, J. (1988). An efficiently mutagenizable recombinant plasmid for in vitro transcription of the *Escherichia coli* 16 S RNA gene. Anal Biochem 175, 373-385.

Lafontaine, D., Delcour, J., Glasser, A. L., Desgres, J., and Vandenhaute, J. (1994). The DIM1 gene responsible for the conserved m6(2)Am6(2)A dimethylation in the 3'-terminal loop of 18 S rRNA is essential in yeast. J Mol Biol 241, 492-497.

Lafontaine, D., Vandenhaute, J., and Tollervey, D. (1995). The 18S rRNA dimethylase Dim1p is required for pre-ribosomal RNA processing in yeast. Genes Dev 9, 2470-2481.

Lafontaine, D. L., Preiss, T., and Tollervey, D. (1998). Yeast 18S rRNA dimethylase Dim1p: a quality control mechanism in ribosome synthesis? Mol Cell Biol 18, 2360-2370.

Lake, J. A. (1976). Ribosome structure determined by electron microscopy of *Escherichia coli* small subunits, large subunits and monomeric ribosomes. J Mol Biol 105, 131-139.

Lee, K., Holland-Staley, C. A., and Cunningham, P. R. (1996). Genetic analysis of the Shine-Dalgarno interaction: selection of alternative functional mRNA-rRNA combinations. Rna 2, 1270-1285.

Lee, K., Holland-Staley, C. A., and Cunningham, P. R. (2001). Genetic approaches to studying protein synthesis: effects of mutations at Psi516 and A535 in *Escherichia coli* 16S rRNA. J Nutr 131, 2994S-3004S.

Lee, K., Varma, S., SantaLucia, J., Jr., and Cunningham, P. R. (1997). In vivo determination of RNA structure-function relationships: analysis of the 790 loop in ribosomal RNA. J Mol Biol 269, 732-743.

Lovgren, J. M., Bylund, G. O., Srivastava, M. K., Lundberg, L. A., Persson, O. P., Wingsle, G., and Wikstrom, P. M. (2004). The PRC-barrel domain of the ribosome maturation protein RimM mediates binding to ribosomal protein S19 in the 30S ribosomal subunits. Rna 10, 1798-1812.

Luria, S. E., and Burrous, J. W. (1957). Hybridization between *Escherichia coli* and *Shigella*. J Bacteriology 74, 461-476.

Maden, B. E. (1990). The numerous modified nucleotides in eukaryotic ribosomal RNA. Prog Nucleic Acid Res Mol Biol 39, 241-303.

Mathews, D. H., Sabina, J., Zuker, M., and Turner, D. H. (1999). Expanded sequence dependence of thermodynamic parameters improves prediction of RNA secondary structure. J Mol Biol 288, 911-940.

McCutcheon, J. P., Agrawal, R. K., Philips, S. M., Grassucci, R. A., Gerchman, S. E., Clemons, W. M., Jr., Ramakrishnan, V., and Frank, J. (1999). Location of translational initiation factor IF3 on the small ribosomal subunit. Proc Natl Acad Sci USA 96, 4301-4306.

Mears, J. A., Cannone, J. J., Stagg, S. M., Gutell, R. R., Agrawal, R. K., and Harvey, S. C. (2002). Modeling a minimal ribosome based on comparative sequence analysis. J Mol Biol 321, 215-234.

Melancon, P., Gravel, M., Boileau, G., and Brakier-Gingras, L. (1987). Reassembly of active 30S ribosomal subunits with an unmethylated in vitro transcribed 16S rRNA. Biochem Cell Biol 65, 1022-1030.

Melancon, P., Lemieux, C., and Brakier-Gingras, L. (1988). A mutation in the 530 loop of *Escherichia coli* 16S ribosomal RNA causes resistance to streptomycin. Nucleic Acids Res 16, 9631-9639.

Meroueh, M., Grohar, P. J., Qiu, J., SantaLucia, J., Jr., Scaringe, S. A., and Chow, C. S. (2000). Unique structural and stabilizing roles for the individual pseudouridine residues in the 1920 region of *Escherichia coli* 23S rRNA. Nucleic Acids Res 28, 2075-2083.

Merryman, C., Moazed, D., Daubresse, G., and Noller, H. F. (1999a). Nucleotides in 23S rRNA protected by the association of 30S and 50S ribosomal subunits. J Mol Biol 285, 107-113.

Merryman, C., Moazed, D., McWhirter, J., and Noller, H. F. (1999b). Nucleotides in 16S rRNA protected by the association of 30S and 50S ribosomal subunits. J Mol Biol 285, 97-105.

Moazed, D., and Noller, H. F. (1986). Transfer RNA shields specific nucleotides in 16S ribosomal RNA from attack by chemical probes. Cell 47, 985-994.

Moazed, D., and Noller, H. F. (1987). Interaction of antibiotics with functional sites in 16S ribosomal RNA. Nature 327, 389-394.

Moazed, D., and Noller, H. F. (1989). Intermediate states in the movement of transfer RNA in the ribosome. Nature 342, 142-148.

Moazed, D., and Noller, H. F. (1990). Binding of tRNA to the ribosomal A and P sites protects two distinct sets of nucleotides in 16 S rRNA. J Mol Biol 211, 135-145.

Morosyuk, S. V., Lee, K., SantaLucia, J., Jr., and Cunningham, P. R. (2000). Structure and function of the conserved 690 hairpin in *Escherichia coli* 16 S ribosomal RNA: analysis of the stem nucleotides. J Mol Biol 300, 113-126.

Morosyuk, S. V., SantaLucia, J., Jr., and Cunningham, P. R. (2001). Structure and function of the conserved 690 hairpin in *Escherichia coli* 16 S ribosomal RNA. III. Functional analysis of the 690 loop. J Mol Biol 307, 213-228.

Mullis, K., Faloona, F., Scharf, S., Saiki, R., Horn, G., and Erlich, H. (1986). Specific enzymatic amplification of DNA in vitro: the polymerase chain reaction. Cold Spring Harb Symp Quant Biol 51, 263-273.

Mullis, K. B., and Faloona, F. A. (1987). Specific synthesis of DNA in vitro via a polymerase-catalyzed chain reaction. Methods Enzymol 155, 335-350.

Murphy, F. L., and Cech, T. R. (1994). GAAA tetraloop and conserved bulge stabilize tertiary structure of a group I intron domain. J Mol Biol 236, 49-63.

Nierhaus, K. H. (1990). The allosteric three-site model for the ribosomal elongation cycle: features and future. Biochemistry 29, 4997-5008.

Nikolaev, N., Silengo, L., and Schlessinger, D. (1973). Synthesis of a large precursor to ribosomal RNA in a mutant of *Escherichia coli*. Proc Natl Acad Sci USA 70, 3361-3365.

Ninio, J. (1974). A semi-quantitative treatment of missense and nonsense suppression in the strA and ram ribosomal mutants of *Escherichia coli*. Evaluation of some molecular parameters of translation in vivo. J Mol Biol 84, 297-313.

Nissen, P., Hansen, J., Ban, N., Moore, P. B., and Steitz, T. A. (2000). The structural basis of ribosome activity in peptide bond synthesis. Science 289, 920-930.

Noller, H. F. (1991). Ribosomes. Drugs and the RNA world. Nature 353, 302-303.

Noller, H. F., Hoffarth, V., and Zimniak, L. (1992). Unusual resistance of peptidyl transferase to protein extraction procedures. Science 256, 1416-1419.

Noller, H. F., and Woese, C. R. (1981). Secondary structure of 16S ribosomal RNA. Science 212, 403-411.

Nomura, M., Gourse, R., and Baughman, G. (1984). Regulation of the synthesis of ribosomes and ribosomal components. Annu Rev Biochem 53, 75-117. Nomura, M. (1987). The role of RNA and protein in ribosome function: a review of early reconstitution studies and prospects for future studies. Cold Spring Harb Symp Quant Biol 52, 653-663.

Noon, K. R., Bruenger, E., and McCloskey, J. A. (1998). Posttranscriptional modifications in 16S and 23S rRNAs of the archaeal hyperthermophile *Sulfolobus solfataricus*. J Bacteriol 180, 2883-2888.

O'Connor, M., Goringer, H. U., and Dahlberg, A. E. (1992). A ribosomal ambiguity mutation in the 530 loop of *E. coli* 16S rRNA. Nucleic Acids Res 20, 4221-4227.

O'Connor, M., Thomas, C. L., Zimmermann, R. A., and Dahlberg, A. E. (1997). Decoding fidelity at the ribosomal A and P sites: influence of mutations in three different regions of the decoding domain in 16S rRNA. Nucleic Acids Res 25, 1185-1193.

O'Farrell, H. C., Scarsdale, J. N., and Rife, J. P. (2004). Crystal structure of KsgA, a universally conserved rRNA adenine dimethyltransferase in *Escherichia coli*. J Mol Biol 339, 337-353.

Ogle, J. M., Brodersen, D. E., Clemons, W. M., Jr., Tarry, M. J., Carter, A. P., and Ramakrishnan, V. (2001). Recognition of cognate transfer RNA by the 30S ribosomal subunit. Science 292, 897-902.

Pape, T., Wintermeyer, W., and Rodnina, M. (1999). Induced fit in initial selection and proofreading of aminoacyl-tRNA on the ribosome. Embo J 18, 3800-3807.

Paul, B. J., Ross, W., Gaal, T., and Gourse, R. L. (2004). rRNA transcription in *Escherichia coli*. Annu Rev Genet 38, 749-770.

Peske, F., Savelsbergh, A., Katunin, V. I., Rodnina, M. V., and Wintermeyer, W. (2004). Conformational changes of the small ribosomal subunit during elongation factor G-dependent tRNA-mRNA translocation. J Mol Biol 343, 1183-1194.

Pestka, S. (1969). Studies on the formation of transfer ribonucleic acid-ribosome complexes. VI. Oligopeptide synthesis and translocation on ribosomes in the presence and absence of soluble transfer factors. J Biol Chem 244, 1533-1539.

Pestka, S. (1967). The action of streptomycin on protein synthesis in vitro. Bull N Y Acad Med 43, 126-148.

Pettersson, I., and Kurland, C. G. (1980). Ribosomal protein L7/L12 is required for optimal translation. Proc Natl Acad Sci USA 77, 4007-4010.

Piepersberg, W., Bock, A., and Wittmann, H. G. (1975). Effect of different mutations in ribosomal protein S5 of *Escherichia coli* on translational fidelity. Mol Gen Genet 140, 91-100.

Pioletti, M., Schlunzen, F., Harms, J., Zarivach, R., Gluhmann, M., Avila, H., Bashan, A., Bartels, H., Auerbach, T., Jacobi, C., et al. (2001). Crystal structures of complexes of the small ribosomal subunit with tetracycline, edeine and IF3. Embo J 20, 1829-1839.

Pleij, C. W., Rietveld, K., and Bosch, L. (1985). A new principle of RNA folding based on pseudoknotting. Nucleic Acids Res 13, 1717-1731.

Poldermans, B., Goosen, N., and Van Knippenberg, P. H. (1979). Studies on the function of two adjacent N6,N6-dimethyladenosines near the 3' end of 16 S ribosomal RNA of *Escherichia coli*. I. The effect of kasugamycin on initiation of protein synthesis. J Biol Chem 254, 9085-9089.

Powers, T., and Noller, H. F. (1990). Dominant lethal mutations in a conserved loop in 16S rRNA. Proc Natl Acad Sci USA 87, 1042-1046.

Powers, T., and Noller, H. F. (1991). A functional pseudoknot in 16S ribosomal RNA. Embo J 10, 2203-2214.

Powers, T., and Noller, H. F. (1994). Selective perturbation of G530 of 16 S rRNA by translational miscoding agents and a streptomycin-dependence mutation in protein S12. J Mol Biol 235, 156-172.

Ramakrishnan, V. (2002). Ribosome structure and the mechanism of translation. Cell 108, 557-572.

Raychaudhuri, S., Conrad, J., Hall, B. G., and Ofengand, J. (1998). A pseudouridine synthase required for the formation of two universally conserved pseudouridines in ribosomal RNA is essential for normal growth of *Escherichia coli*. Rna 4, 1407-1417.

Raychaudhuri, S., Niu, L., Conrad, J., Lane, B. G., and Ofengand, J. (1999). Functional effect of deletion and mutation of the *Escherichia coli* ribosomal RNA and tRNA pseudouridine synthase RluA. J Biol Chem 274, 18880-18886.

Rife, J. P., Cheng, C. S., Moore, P. B., and Strobel, S. A. (1998). N2-methylguanosine is iso-energetic with guanosine in RNA duplexes and GNRA tetraloops. Nucleic Acids Res 26, 3640-3644.

Rife, J. P., and Moore, P. B. (1998). The structure of a methylated tetraloop in 16S ribosomal RNA. Structure 6, 747-756.

Rodnina, M. V., Savelsbergh, A., Katunin, V. I., and Wintermeyer, W. (1997). Hydrolysis of GTP by elongation factor G drives tRNA movement on the ribosome. Nature 385, 37-41.

Rodnina, M. V., Savelsbergh, A., and Wintermeyer, W. (1999). Dynamics of translation on the ribosome: molecular mechanics of translocation. FEMS Microbiol Rev 23, 317-333.

Roll-Mecak, A., Cao, C., Dever, T. E., and Burley, S. K. (2000). X-Ray structures of the universal translation initiation factor IF2/eIF5B: conformational changes on GDP and GTP binding. Cell 103, 781-792.

Rosenberger, R. F., and Hilton, J. (1983). The frequency of transcriptional and translational errors at nonsense codons in the lacZ gene of *Escherichia coli*. Mol Gen Genet 191, 207-212.

Rosset, R., and Gorini, L. (1969). A ribosomal ambiguity mutation. J Mol Biol 39, 95-112.

Rozenski, J., Crain, P. F., and McCloskey, J. A. (1999). The RNA Modification Database: 1999 update. Nucleic Acids Res 27, 196-197.

Ryden-Aulin, M., Shaoping, Z., Kylsten, P., and Isaksson, L. A. (1993). Ribosome activity and modification of 16S RNA are influenced by deletion of ribosomal protein S20. Mol Microbiol 7, 983-992.

Sancar, A., Hack, A. M., and Rupp, W. D. (1979). Simple method for identification of plasmid-coded proteins. J Bacteriol 137, 692-693.

Santer, M., Santer, U., Nurse, K., Bakin, A., Cunningham, P., Zain, M., O'Connell, D., and Ofengand, J. (1993). Functional effects of a G to U base change at position 530 in a highly conserved loop of *Escherichia coli* 16S RNA. Biochemistry 32, 5539-5547.

Santer, U. V., Cekleniak, J., Kansil, S., Santer, M., O'Connor, M., and Dahlberg, A. E. (1995). A mutation at the universally conserved position 529 in *Escherichia coli* 16S rRNA creates a functional but highly error prone ribosome. Rna 1, 89-94.

Schmitt, E., Guillon, J. M., Meinnel, T., Mechulam, Y., Dardel, F., and Blanquet, S. (1996). Molecular recognition governing the initiation of translation in *Escherichia coli*. A review. Biochimie 78, 543-554.

Schnare, M. N., Yepiz-Plascencia, G. M., Copertino, D. W., Hallick, R. B., and Gray, M. W. (1992). 5'- and 3'-terminal sequences of the chloroplast 16S and 23S ribosomal RNAs of *Euglena gracilis*. Nucleic Acids Res 20, 1421.

Schroeder, R., Waldsich, C., and Wank, H. (2000). Modulation of RNA function by aminoglycoside antibiotics. Embo J 19, 1-9.

Schwartz, I., Gordon, E., and Ofengand, J. (1975). Photoaffinity labeling of the ribosomal A site with S-(p-azidophenacyl)valyl-tRNA. Biochemistry 14, 2907-2914.

Seidel-Rogol, B. L., McCulloch, V., and Shadel, G. S. (2003). Human mitochondrial transcription factor B1 methylates ribosomal RNA at a conserved stem-loop. Nat Genet 33, 23-24.

Senior, B. W., and Holland, I. B. (1971). Effect of colicin E3 upon the 30S ribosomal subunit of *Escherichia coli*. Proc Natl Acad Sci USA 68, 959-963.

Shapkina, T. G., Dolan, M. A., Babin, P., and Wollenzien, P. (2000). Initiation factor 3-induced structural changes in the 30 S ribosomal subunit and in complexes containing tRNA (f)(Met) and mRNA. J Mol Biol 299, 615-628.

Shen, L. X., Cai, Z., and Tinoco, I., Jr. (1995). RNA structure at high resolution. Faseb J 9, 1023-1033.

Shen, Z. H., and Fox, T. D. (1989). Substitution of an invariant nucleotide at the base of the highly conserved '530-loop' of 15S rRNA causes suppression of yeast mitochondrial ochre mutations. Nucleic Acids Res 17, 4535-4539.

Shine, J., and Dalgarno, L. (1974). The 3'-terminal sequence of *Escherichia coli* 16S ribosomal RNA: complementarity to nonsense triplets and ribosome binding sites. Proc Natl Acad Sci USA 71, 1342-1346.

Shine, J., and Dalgarno, L. (1975). Determinant of cistron specificity in bacterial ribosomes. Nature 254, 34-38.

Sigmund, C. D., Ettayebi, M., and Morgan, E. A. (1984). Antibiotic resistance mutations in 16S and 23S ribosomal RNA genes of *Escherichia coli*. Nucleic Acids Res 12, 4653-4663.

Slonczewski, J. L., and Foster, J. W. pH-Regulated Genes and Survival at Extreme pH, pp. Chapter 96.

Spangler, E. A., and Blackburn, E. H. (1985). The nucleotide sequence of the 17S ribosomal RNA gene of Tetrahymena thermophila and the identification of point mutations resulting in resistance to the antibiotics paromomycin and hygromycin. J Biol Chem 260, 6334-6340.

Sprinzl, M., and Vassilenko, K. S. (2005). Compilation of tRNA sequences and sequences of tRNA genes. Nucleic Acids Res 33, D139-140.

Stark, H., Mueller, F., Orlova, E. V., Schatz, M., Dube, P., Erdemir, T., Zemlin, F., Brimacombe, R., and van Heel, M. (1995). The 70S *Escherichia coli* ribosome at 23 A resolution: fitting the ribosomal RNA. Structure 3, 815-821.

Stark, H., Orlova, E. V., Rinke-Appel, J., Junke, N., Mueller, F., Rodnina, M., Wintermeyer, W., Brimacombe, R., and van Heel, M. (1997a). Arrangement of tRNAs in pre- and posttranslocational ribosomes revealed by electron cryomicroscopy. Cell 88, 19-28.

Stark, H., Rodnina, M. V., Rinke-Appel, J., Brimacombe, R., Wintermeyer, W., and van Heel, M. (1997b). Visualization of elongation factor Tu on the *Escherichia coli* ribosome. Nature 389, 403-406.

Stark, M. J., Gourse, R. L., and Dahlberg, A. E. (1982). Site-directed mutagenesis of ribosomal RNA. Analysis of ribosomal RNA deletion mutants using maxicells. J Mol Biol 159, 417-439.

Steege, D. A., Graves, M. C., and Spremulli, L. L. (1982). *Euglena gracilis* chloroplast small subunit rRNA. Sequence and base pairing potential of the 3' terminus, cleavage by colicin E3. J Biol Chem 257, 10430-10439.

Stern, S., Powers, T., Changchien, L. M., and Noller, H. F. (1988). Interaction of ribosomal proteins S5, S6, S11, S12, S18 and S21 with 16 S rRNA. J Mol Biol 201, 683-695.

Taglicht, D., Padan, E., Oppenheim, A. B., and Schuldiner, S. (1987). An alkaline shift induces the heat shock response in *Escherichia coli*. J Bacteriol 169, 885-887.

Taglicht, D., Padan, E., and Schuldiner, S. (1991). Overproduction and purification of a functional Na+/H+ antiporter coded by nhaA (ant) from *Escherichia coli*. J Biol Chem 266, 11289-11294.

Takyar, S., Hickerson, R. P., and Noller, H. F. (2005). mRNA helicase activity of the ribosome. Cell 120, 49-58.

Tapprich, W. E., Goss, D. J., and Dahlberg, A. E. (1989). Mutation at position 791 in *Escherichia coli* 16S ribosomal RNA affects processes involved in the initiation of protein synthesis. Proc Natl Acad Sci USA 86, 4927-4931.

Tapprich, W. E., and Hill, W. E. (1986). Involvement of bases 787-795 of *Escherichia coli* 16S ribosomal RNA in ribosomal subunit association. Proc Natl Acad Sci USA 83, 556-560.

Tsiboli, P., Triantafillidou, D., Franceschi, F., and Choli-Papadopoulou, T. (1998). Studies on the Zn-containing S14 ribosomal protein from *Thermus thermophilus*. Eur J Biochem 256, 136-141.

Tsien, R. Y. (1998). The green fluorescent protein. Annu Rev Biochem 67, 509-544.

Tuerk, C., Gauss, P., Thermes, C., Groebe, D. R., Gayle, M., Guild, N., Stormo, G., d'Aubenton-Carafa, Y., Uhlenbeck, O. C., Tinoco, I., Jr., and et al. (1988). CUUCGG hairpins: extraordinarily stable RNA secondary structures associated with various biochemical processes. Proc Natl Acad Sci USA 85, 1364-1368.

Tung, C. S., Joseph, S., and Sanbonmatsu, K. Y. (2002). All-atom homology model of the *Escherichia coli* 30S ribosomal subunit. Nat Struct Biol 9, 750-755.

Uhlein, M., Weglohner, W., Urlaub, H., and Wittmann-Liebold, B. (1998). Functional implications of ribosomal protein L2 in protein biosynthesis as shown by in vivo replacement studies. Biochem J 331 (Pt 2), 423-430.

Urbonavicius, J., Qian, Q., Durand, J. M., Hagervall, T. G., and Bjork, G. R. (2001). Improvement of reading frame maintenance is a common function for several tRNA modifications. Embo J 20, 4863-4873.

Valle, M., Zavialov, A., Li, W., Stagg, S. M., Sengupta, J., Nielsen, R. C., Nissen, P., Harvey, S. C., Ehrenberg, M., and Frank, J. (2003). Incorporation of aminoacyl-tRNA into the ribosome as seen by cryo-electron microscopy. Nat Struct Biol 10, 899-906.

van Acken, U. (1975). Proteinchemical studies on ribosomal proteins S4 and S12 from ram (ribosomal ambiguity) mutants of *Escherichia coli*. Mol Gen Genet 140, 61-68.

Van Buul, C. P., Damm, J. B., and Van Knippenberg, P. H. (1983). Kasugamycin resistant mutants of *Bacillus stearothermophilus* lacking the enzyme for the methylation of two adjacent adenosines in 16S ribosomal RNA. Mol Gen Genet 189, 475-478.

Van Buul, C. P., Hamersma, M., Visser, W., and Van Knippenberg, P. H. (1984a). Partial methylation of two adjacent adenosines in ribosomes from *Euglena gracilis* chloroplasts suggests evolutionary loss of an intermediate stage in the methyl-transfer reaction. Nucleic Acids Res 12, 9205-9208.

van Buul, C. P., Visser, W., and van Knippenberg, P. H. (1984b). Increased translational fidelity caused by the antibiotic kasugamycin and ribosomal ambiguity in mutants harbouring the ksgA gene. FEBS Lett 177, 119-124.

Van Ryk, D. I., and Dahlberg, A. E. (1995). Structural changes in the 530 loop of *Escherichia coli* 16S rRNA in mutants with impaired translational fidelity. Nucleic Acids Res 23, 3563-3570.

VanLoock, M. S., Agrawal, R. K., Gabashvili, I. S., Qi, L., Frank, J., and Harvey, S. C. (2000). Movement of the decoding region of the 16 S ribosomal RNA accompanies tRNA translocation. J Mol Biol 304, 507-515.

Varani, G., and McClain, W. H. (2000). The G×U wobble base pair. A fundamental building block of RNA structure crucial to RNA function in diverse biological systems. EMBO Rep 1, 18-23.

Vasiliev, V. D. (1974). Morphology of the ribosomal 30S subparticle according to electron microscopic data. Acta Biol Med Ger 33, 779-793.

Vicens, Q., and Westhof, E. (2003). Molecular recognition of aminoglycoside antibiotics by ribosomal RNA and resistance enzymes: an analysis of x-ray crystal structures. Biopolymers 70, 42-57.

Vila-Sanjurjo, A., Squires, C. L., and Dahlberg, A. E. (1999). Isolation of kasugamycin resistant mutants in the 16 S ribosomal RNA of Escherichia coli. J Mol Biol 293, 1-8.

von Ahsen, U., and Noller, H. F. (1995). Identification of bases in 16S rRNA essential for tRNA binding at the 30S ribosomal P site. Science 267, 234-237.

Weiel, J., and Hershey, J. W. (1981). Fluorescence polarization studies of the interaction of Escherichia coli protein synthesis initiation factor 3 with 30S ribosomal subunits. Biochemistry 20, 5859-5865.

Weiss, R. B., Murphy, J. P., and Gallant, J. A. (1984). Genetic screen for cloned release factor genes. J Bacteriol 158, 362-364.

Wilms, C., Noah, J. W., Zhong, D., and Wollenzien, P. (1997). Exact determination of UV-induced crosslinks in 16S ribosomal RNA in 30S ribosomal subunits. Rna 3, 602-612.

Wilson, D. N., Blaha, G., Connell, S. R., Ivanov, P. V., Jenke, H., Stelzl, U., Teraoka, Y., and Nierhaus, K. H. (2002). Protein synthesis at atomic resolution: mechanistics of translation in the light of highly resolved structures for the ribosome. Curr Protein Pept Sci 3, 1-53.

Wilson, K. S., and Noller, H. F. (1998). Mapping the position of translational elongation factor EF-G in the ribosome by directed hydroxyl radical probing. Cell 92, 131-139.

Wimberly, B. T., Brodersen, D. E., Clemons, W. M., Jr., Morgan-Warren, R. J., Carter, A. P., Vonrhein, C., Hartsch, T., and Ramakrishnan, V. (2000). Structure of the 30S ribosomal subunit. Nature 407, 327-339.

Wimberly, B. T., Guymon, R., McCutcheon, J. P., White, S. W., and Ramakrishnan, V. (1999). A detailed view of a ribosomal active site: the structure of the L11-RNA complex. Cell 97, 491-502.

Wittmann, H. G. (1983). Architecture of prokaryotic ribosomes. Annu Rev Biochem 52, 35-65.

Woese, C. R., Gupta, R., Hahn, C. M., Zillig, W., and Tu, J. (1984). The phylogenetic relationships of three sulfur dependent archaebacteria. Syst Appl Microbiol 5, 97-105.

Woese, C. R., and Gutell, R. R. (1989). Evidence for several higher order structural elements in ribosomal RNA. Proc Natl Acad Sci USA 86, 3119-3122.

Woese, C. R., Winker, S., and Gutell, R. R. (1990). Architecture of ribosomal RNA: constraints on the sequence of "tetra-loops". Proc Natl Acad Sci USA 87, 8467-8471.

Yarian, C., Townsend, H., Czestkowski, W., Sochacka, E., Malkiewicz, A. J., Guenther, R., Miskiewicz, A., and Agris, P. F. (2002). Accurate translation of the genetic code depends on tRNA modified nucleosides. J Biol Chem 277, 16391-16395.

Yusupov, M. M., Yusupova, G. Z., Baucom, A., Lieberman, K., Earnest, T. N., Cate, J. H., and Noller, H. F. (2001). Crystal structure of the ribosome at 5.5 A resolution. Science 292, 883-896.

Yusupova, G. Z., Yusupov, M. M., Cate, J. H., and Noller, H. F. (2001). The path of messenger RNA through the ribosome. Cell 106, 233-241.

Zavialov, A. V., Buckingham, R. H., and Ehrenberg, M. (2001). A posttermination ribosomal complex is the guanine nucleotide exchange factor for peptide release factor RF3. Cell 107, 115-124.

Zuker, M. (2003). Mfold web server for nucleic acid folding and hybridization prediction. Nucleic Acids Res 31, 3406-3415.

Zucker, F. H., and Hershey, J. W. (1986). Binding of Escherichia coli protein synthesis initiation factor IF1 to 30S ribosomal subunits measured by fluorescence polarization. Biochemistry 25, 3682-3690.

INCORPORATION BY REFERENCE

All of the references including, without limitation, U.S. patents, U.S. patent application publications, published international applications and journal articles cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A nucleic acid represented by formula V:

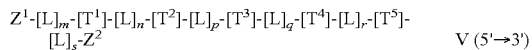   V (5'→3')

wherein, independently for each occurrence, $T^1$, $T^2$, $T^3$, $T^4$ and $T^5$ are selected from the group consisting of SEQ ID NOs: 4, 8, 9, 10, 11, 43, 44, 45, 46, 47, 48, 49, 52, 53, 54, 55, 56, 57, 58 and 59;

L is a nucleic acid selected from the group consisting of adenosine, cytidine, guanosine and uridine; optionally substituted with one substituent selected from the group consisting of biotin, fluorescein, tetrachlorofluorescein, hexachlorofluorescein, Cy3 amidite, Cy5 amidite, digoxigenin, TEXAS RED® maleimide and tetramethylrhodamine;

$Z^1$ and $Z^2$ are selected from the group consisting of biotin, fluorescein, tetrachlorofluorescein, hexachlorofluorescein, Cy3 amidite, Cy5 amidite, digoxigenin and resin beads; and m, n, p, q, r and s are independently an integer from 0 to 40.

2. The nucleic acid of claim 1, wherein $T^1$ is SEQ ID NO 4; $T^2$ is SEQ ID NO 8; $T^3$ is SEQ ID NO 9; $T^4$ is SEQ ID NO 10; and $T^5$ is SEQ ID NO 11.

3. The nucleic acid of claim 2, wherein p is 2, q is 17, r is 15, $Z^1$ is fluorescein, $Z^2$ is biotin, and each L is, independently for each occurrence, selected from the group consisting of unsubstituted adenosine, unsubstituted cytidine, unsubstituted guanosine and unsubstituted uridine.

4. The nucleic acid of claim 1, wherein $T^1$ is SEQ ID NO 43; $T^2$ is SEQ ID NO 44; $T^3$ is SEQ ID NO 55; $T^4$ is SEQ ID NO 56; and $T^5$ is SEQ ID NO 57.

5. The nucleic acid of claim 4, wherein n is 2, r is 3, $Z^1$ is fluorescein, $Z^2$ is biotin, or each L is, independently for each occurrence, selected from the group consisting of unsubstituted adenosine, unsubstituted cytidine, unsubstituted guanosine and unsubstituted uridine.

6. The nucleic acid of claim 4, wherein n is 2, r is 3, $Z^1$ is fluorescein, $Z^2$ is biotin, and each L is, independently for each occurrence, selected from the group consisting of unsubstituted adenosine, unsubstituted cytidine, unsubstituted guanosine and unsubstituted uridine.

7. The nucleic acid of claim 1, wherein $T^1$ is SEQ ID NO 45; $T^2$ is SEQ ID NO 46; $T^3$ is SEQ ID NO 54; $T^4$ is SEQ ID NO 58; and $T^5$ is SEQ ID NO 59.

8. The nucleic acid of claim 7, wherein n is 16, r is 6, $Z^1$ is fluorescein, $Z^2$ is biotin, or each L is, independently for each occurrence, selected from the group consisting of unsubstituted adenosine, unsubstituted cytidine, unsubstituted guanosine and unsubstituted uridine.

9. The nucleic acid of claim 7, wherein n is 16, r is 6, $Z^1$ is fluorescein, $Z^2$ is biotin, and each L is, independently for each occurrence, selected from the group consisting of unsubstituted adenosine, unsubstituted cytidine, unsubstituted guanosine and unsubstituted uridine.

10. The nucleic acid of claim 1, wherein $T^1$ is SEQ ID NO 47; $T^2$ is SEQ ID NO 48; $T^3$ is SEQ ID NO 49; $T^4$ is SEQ ID NO 52; and $T^5$ is SEQ ID NO 53.

11. The nucleic acid of claim 10, wherein n is 7, p is 37, r is 7, $Z^1$ is fluorescein, $Z^2$ is biotin, or each L is, independently for each occurrence, selected from the group consisting of unsubstituted adenosine, unsubstituted cytidine, unsubstituted guanosine and unsubstituted uridine.

12. The nucleic acid of claim 10, wherein n is 7, p is 37, r is 7, $Z^1$ is fluorescein, $Z^2$ is biotin, and each L is, independently for each occurrence, selected from the group consisting of unsubstituted adenosine, unsubstituted cytidine, unsubstituted guanosine and unsubstituted uridine.

13. The nucleic acid of claim 1, wherein $Z^1$ is fluorescein.

14. The nucleic acid of claim 1, wherein $Z^2$ is biotin.

15. The nucleic acid of claim 1, wherein each L is, independently for each occurrence, selected from the group consisting of unsubstituted adenosine, unsubstituted cytidine, unsubstituted guanosine and unsubstituted uridine.

16. The nucleic acid of claim 1, wherein m and s are integers between 0-25.

17. The nucleic acid of claim 1, wherein m and s are integers between 5-15.

18. A method of identifying an inhibitor of protein synthesis comprising measuring the fluorescence of the nucleic acid of claim 1, thereby establishing a first fluorescence reading;

contacting a test compound with said nucleic acid, and measuring the resulting fluorescence, thereby establishing a second fluorescence reading;

determining the difference between said first fluorescence reading and said second fluorescence reading;

selecting the compound wherein the difference between said first fluorescence reading and said second fluorescence reading is non-zero, thereby identifying said agent;

assaying the inhibitory properties of the agent by administering it to a cell, a cell extract or purified ribosomes; and detecting protein synthesis; wherein a decrease in protein synthesis indicates that the agent is an inhibitor of protein synthesis.

19. The method of claim 18, wherein assaying the inhibitory properties of the agent comprises detecting protein synthesis.

20. The method of claim 18, wherein assaying the inhibitory properties of the agent comprises determining the inhibitor constant for inhibiting mRNA translation.

21. The method of identifying an agent which binds to the nucleic acid of claim 1, comprising the steps of:

measuring the fluorescence of said nucleic acid, thereby establishing a first fluorescence reading;

contacting a test compound with said nucleic acid, and measuring the resulting fluorescence, thereby establishing a second fluorescence reading;

determining the difference between said first fluorescence reading and said second fluorescence reading; and selecting the compound wherein the difference between said first fluorescence reading and said second fluorescence reading is non-zero, thereby identifying said agent.

* * * * *